(12) United States Patent
Broadhurst et al.

(10) Patent No.: US 6,239,151 B1
(45) Date of Patent: May 29, 2001

(54) COMPOUNDS AS INHIBITOR OF TUMOR NECROSIS FACTOR ALPHA RELEASE

(75) Inventors: Michael John Broadhurst, Royston; William Henry Johnson, Bodmin; Daryl Simon Walter, Knebworth, all of (GB)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/332,809

(22) Filed: Jun. 14, 1999

(30) Foreign Application Priority Data

Jun. 26, 1998 (GB) .................................. 9813919
Dec. 2, 1998 (GB) .................................. 9826491

(51) Int. Cl.[7] ...................... A61K 31/445; C07D 211/26
(52) U.S. Cl. .......................... 514/331; 514/359; 514/396; 514/482; 546/231; 548/261; 548/335.5; 564/151; 564/153
(58) Field of Search ..................... 514/331, 359, 514/396, 482; 546/231; 548/261, 335.5; 564/151, 153

(56) References Cited

U.S. PATENT DOCUMENTS

| | | | |
|---|---|---|---|
| 5,304,549 | 4/1994 | Broadhurst et al. | 514/80 |
| 5,399,589 | 3/1995 | Rentzea et al. | 514/615 |
| 5,614,625 | * 3/1997 | Broadhurst | 540/480 |

FOREIGN PATENT DOCUMENTS

| | | |
|---|---|---|
| 497 192 | 8/1992 | (EP) . |
| WO 99/01428 | 1/1999 | (WO) . |
| WO 99/40063 | 8/1999 | (WO) . |

OTHER PUBLICATIONS

Broadhurst et al. "Hydrazine derivatives" CA 2000:384147, 2000.*
Chemical Abstracts, vol. 104, No. 9, Abstract No. 61519p, Mar. 3, 1986.
Abstract WPIDS 1999–479413 (1999).
Coffey, R.J. et al., Nature (1987) 328, pp. 817–820.
Karashima, T. et al., Dermatol. Sci. (1996) 12, pp. 246–254.
Olanrian A. et al., Arch. Dermatol. Sci. (1995) 287, pp. 231–236.
Chemical Abstr., General Substances Index, vol. 11th Collective, 1982–1986, p. 14, 583 CS, Compound with RN 87362–025 which is 2–(phenylsulfonyl)hydrazide.
Chernyk et al., "Biologically Active Substances in Hydrazide Derivatives of Succinic Heterylamides", Khimiko–farmatsevticheskii Zhurnal, vol. 23, No. 7, pp. 825–828 (1989).
Kratasyuk et al., "The Effect of Succinic Acid Sulfoderivatives on Bacterial Luminescence", Prikl. Biokhim. Mikrobiol., vol. 27(1): 127–133 (1991).

* cited by examiner

Primary Examiner—Ceila Chang
(74) Attorney, Agent, or Firm—George W. Johnston; William H. Epstein; F. Aaron Dubberley

(57) ABSTRACT

The invention provides hydrazine derivatives of the formula

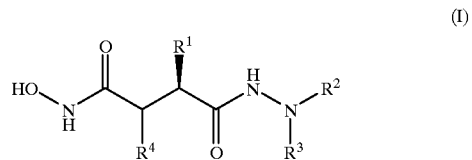

(I)

wherein $R^1$ is lower alkyl, lower alkenyl, lower cycloalkyl, lower cycloalkyl-lower alkyl, aryl or aryl-lower alkyl; $R^2$ is an acyl group derived from an α-, β-, γ- or δ-(amino, hydroxy or thiol)carboxylic acid in which the amino, hydroxy or thiol group is optionally lower alkylated or the amino group is optionally acylated, sulphonylated or amidated and in which any functional group present in a side-chain is optionally protected, or a group of the formula $Het(CH_2)_mCO$; $R^3$ is hydrogen, lower alkyl, halo-lower alkyl, cyano-lower alkyl, amino-lower alkyl, hydroxy-lower alkyl, lower alkoxy-lower alkyl, lower alkoxycarbonyl-lower alkyl, lower cycloalkyl-lower alkyl, aryl-lower alkyl, heterocyclyl-lower alkyl, heterocyclylcarbonyl-lower alkyl, lower alkenyl, lower alkynyl, lower cycloalkyl, aryl-lower alkenyl, aryl or heterocyclyl; $R^4$ is lower alkyl, lower alkenyl, lower cycloalkyl, lower cycloalkyl-lower alkyl or a grouping of the formula X-aryl, X-heteroaryl or $-(CH_2)_n-CH=CR^5R^6$; $R^5$ and $R^6$ together are lower alkylene in which one $CH_2$ group is optionally replaced by a hetero atom; Het is heterocyclyl; X is a spacer group; m is 0, 1, 2, 3 or 4; and n is 1 or 2; and their pharmaceutically acceptable salts inhibit the release of tumour necrosis factor alpha (TNF-α) from cells. They can be used as medicaments, especially in the treatment of inflammatory and autoimmune diseases, osteoarthritis, respiratory diseases, tumours, cachexia, cardiovascular diseases, fever, haemorrhage and sepsis.

22 Claims, No Drawings

COMPOUNDS AS INHIBITOR OF TUMOR NECROSIS FACTOR ALPHA RELEASE

BACKGROUND OF THE INVENTION

Release of such cytokines as tumor necrosis factor a (TNF-α) and transforming growth factor α (TGF-α) can cause adverse reactions ranging from psoriasis to sepsis. Many of these reactions are related to inflammation or autoimmune conditions, such as psoriasis and arthritis.

Hydroxamic acid derivatives are known to have some inhibitory effect against certain cytokines, however they also inhibit matrix metalloproteinase enzymes (MPPs) such as collagenases, stromolysins, and gelatinases, leading to undesirable side effects. Thus it is desirable to find compounds capable of inhibiting TNF-α and TGF-α which do not have these side effects. In contrast to structurally related hydroxamic acid derivatives, the hydrazine derivatives provided by the present invention show only weak inhibitory activity against the matrix metalloproteinase (MMP) family of enzymes, such as collagenases, stromelysins and gelatinases.

SUMMARY OF THE INVENTION

The hydrazine derivatives provided by the present invention are compounds of the formula

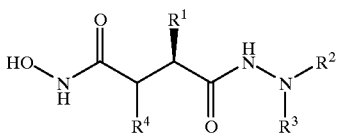

(I)

wherein
- $R^1$ represents lower alkyl, lower alkenyl, lower cycloalkyl, lower cycloalkyl-lower alkyl, aryl or aryl-lower alkyl;
- $R^2$ represents an acyl group derived from an α-, β-, γ- or δ-(amino, hydroxy or thiol)carboxylic acid in which the amino, hydroxy or thiol group is optionally lower alkylated or the amino group is optionally acylated, sulphonylated or amidated and in which any functional group present in a side-chain is optionally protected, or a group of the formula Het(CH$_2$)$_m$CO—;
- $R^3$ represents hydrogen, lower alkyl, halo-lower alkyl, cyano-lower alkyl, amino-lower alkyl, hydroxy-lower alkyl, lower alkoxy-lower alkyl, lower alkoxycarbonyl-lower alkyl, lower cycloalkyl-lower alkyl, aryl-lower alkyl, heterocyclyl-lower alkyl, heterocyclylcarbonyl-lower alkyl, lower alkenyl, lower alkynyl, lower cycloalkyl, aryl-lower alkenyl, aryl or heterocyclyl;
- $R^4$ represents lower alkyl, lower alkenyl, lower cycloalkyl, lower cycloalkyl-lower alkyl or a grouping of the formula X-aryl, X-heteroaryl or —(CH$_2$)$_n$—CH=CR$^5$R$^6$;
- $R^5$ and $R^6$ together represent lower alkylene in which one CH$_2$ group is optionally replaced by a hetero atom;
- Het represents heterocyclyl;
- X represents a spacer group;
- m stands for 0, 1, 2, 3 or 4; and
- n stands for 1 or 2;

and pharmaceutically acceptable salts thereof.

The hydrazine derivatives provided by the present invention are inhibitors of tumour necrosis factor alpha (TNF-α) release from cells. TNF-α has been associated with various cellular processes including inflamrnatory and cytotoxic processes. In particular TNF-α has been associated with inflammatory and autoimmune diseases (such as rheumatoid arthritis[1], inflammatory bowel disease[2], psoriasis[16,17]), osteoarthritis[5,6], respiratory diseases (such as chronic obstructive pulmonary disease[7,8] and asthmas[8,9]), tumour growth and angiogenesis[10], cachexia[11,12], cardiovascular diseases (such as congestive heart failure[13,14]), dermatological diseases (such as graft-versus-host-disease[15] and), fever[18,19], haemorrhage[20,21] and sepsis[22]. Therefore the compounds of formula I are useful in treating the TNF-α dependent cellular processes associated with these diseases.

DETAILED DESCRIPTION OF THE INVENTION

As used herein, the term "lower alkyl", alone or in combination as in, for example, "halo-lower alkyl" or "lower cycloalkyl-lower alkyl", means a straight-chain or branched-chain alkyl group containing up to 8, preferably up to 4, carbon atoms, e.g. methyl, ethyl, n-propyl, isopropyl, n-butyl, isobutyl, sec.butyl, tert-butyl, n-pentyl and n-hexyl.

The term "halo-lower alkyl" means a lower alkyl group as defined earlier which carries one or more halogen atoms. Examples of halo-lower alkyl groups are chloromethyl, trifluoromethyl and 2,2,2-trifluoroethyl.

The term "lower alkoxy", alone or in combination as in "lower alkoxycarbonyl", means a lower alkyl group as defined above which is bonded via an oxygen atom, e.g. methoxy, ethoxy, n-propoxy, isopropoxy, n-butoxy, isobutoxy and tert-butoxy. Methoxycarbonyl, ethoxycarbonyl and the like are examples of lower alkoxycarbonyl groups.

The term "lower cycloalkyl", alone or in combination as in "lower cycloalkyl-lower alkyl", means a cycloalkyl group containing 3 to 7 carbon atoms, i.e. cyclopropyl, cyclobutyl, cyclopentyl, cyclohexyl and cycloheptyl. Cyclopropylmethyl, 2-cyclobutyl-ethyl and 3-cyclohexyl-propyl are examples of lower cycloalkyl-lower alkyl groups.

The term "lower alkenyl", alone or in combination as in "aryl-lower alkenyl", means an alkenyl group containing from 2 to 7 carbon atoms, e.g. allyl, vinyl and butenyl.

The term "lower alkylene" means an alkylene group containing from 2 to 6 carbon atoms, e.g. dimethylene, trimethylene, tetramethylene etc. Thus, $R^5$ and $R^6$ together with the carbon atom to which they are attached can represent, for example, a cyclopentane or cyclohexane ring. One CH$^2$ group may optionally be replaced by a heteroatom selected from N(H), S, or O wherein the hydrogen in the N(H) group may optionally be substituted by a lower alkyl group. For example, where $R^5$ and $R^6$ together with the carbon atom to which they are attached form a tetrahydropyrane ring.

The term "lower alkynyl" means an alkynyl group containing from 2 to 7 carbon atoms, e.g. propanyl or butynyl.

The term "aryl", alone or in combination as in "aryl-lower alkyl", means phenyl or naphthyl optionally substituted by halogen, i.e. fluorine, chlorine, bromine or iodine, lower alkyl, lower alkoxy, trifluoromethyl, hydroxy, lower alkoxycarbonyl, nitro, phenyl or the like, e.g. phenyl, 1-naphthyl, 2-methylphenyl, 4-methoxyphenyl, 2,4-difluorophenyl, 4-nitrophenyl and 4-methoxycarbonylphenyl. Benzyl, 4-chlorobenzyl, 4-bromobenzyl, 3-hydroxybenzyl, 4-methoxybenzyl, 4-nitrobenzyl, 2-phenylethyl, 3,4-dimethoxyphenethyl and the like are typical examples of aryl-lower alkyl groups and benzyloxy, 4-chlorobenzyloxy and 4-nitrobenzyloxy are typical examples of aryl-lower alkoxy groups. 2-Phenylvinyl and 3-phenylallyl can be mentioned as examples of aryl-lower alkenyl groups.

The term "heterocyclyl", alone or in combination as in "heterocyclyl-lower alkyl", means a 4-, 5-, 6- or 7-membered saturated or partially unsaturated or 5- or 6-membered aromatic heterocyclic ring which is bonded via a C atom or secondary N atom (i.e. —NH—), which contains one or more hetero atoms selected from nitrogen, sulphur and oxygen and/or a SO or $SO_2$ group and which is optionally substituted at any ring atom by up to four substituents, e.g. halogen, lower alkyl, lower alkoxy, oxo, thioxo and/or imino, and/or optionally benz-fused. Preferably the heterocyclyl group contains from 1 to 4 heteroatoms. Examples of such heterocyclyl groups are pyrrolidinyl, pyrrolinyl, pyrazolinyl, piperidinyl, N-methylpiperidinyl, morpholinyl, thiamorpholinyl, thiamorpholinyl S,S-dioxide, tetrahydropyranyl, tetrahydrothiopyranyl, hexahydroazepinyl, furyl, thienyl, thiazolyl, oxazolyl, isoxazolyl, oxetanyl, imidazolidinyl, dioxolanyl, pyrrolyl, pyridyl, pyrimidinyl, benzofuranyl, benzothienyl, benzthiazolyl, 1,2,3,6-tetrahydro-2,6-dioxo-4-pyrimidinyl, 2-thioxo-4-oxo-5-thiazolidinyl, 1-methyl-3-pyrrolyl, indolyl, isoindolyl, e.g. phthalimido, quinolyl, and isoquinolyl.

The term "heterocyclylcarbonyl" means a heterocyclyl group as previously defined which is bonded to C(O) via a secondary N atom. Morpholinocarbonyl is a typical example of such a heterocyclylcarbonyl group.

The term "heteroaryl" means an aromatic heterocyclic group within the definition of "heterocyclyl".

The term "halo" means fluoro, chloro, bromo or iodo unless specifically indicated to the contrary.

An acyl group $R^2$ can be derived from a L-, D- or racemic amino-, hydroxy- or thiolcarboxylic acid when such an acid contains a chiral centre. Thus, $R^2$ can represent an acyl group derived from an α-aminocarboxylic acid such as glycine, L- or D-alanine, L- or D-valine, L- or D-leucine, L- or D-lysine, L- or D-serine, L- or D-phenylalanine, 2-amino-n-butanoic acid or 2-amino-n-pentanoic acid. β-Alanine, 3-aminobutanoic acid and 3-amino-2-methylpropanoic acid are examples of β-aminocarboxylic acids from which an acyl group $R^2$ can be derived. The amino moiety of an acyl group $R^2$ can be optionally mono- or di-lower alkylated as in the case of e.g. N-methylglycyl, N,N-dimethylglycyl, N,N-diethylglycyl, N-methyl-alanyl, or acylated as in the case of e.g. N-acetylglycyl or N-acetyl-alanyl, or amidated, e.g. as in the case of N-aminocarbonylglycyl and N-aminocarbonylalanyl. When $R^2$ represents an acyl group derived from an α-, β-, γ- or δ-hydroxycarboxylic acid, the latter can be, for example, an α-, β-, γ- or δ-hydroxyalkanecarboxylic acid, such as e.g. hydroxyacetic acid, 2-hydroxypropionic acid and the like. The hydroxy group of an acyl group derived from an α-, β-, γ-, or δ-hydroxycarboxylic acid can be lower alkylated as in the case of e.g. methoxyacetyl. Further, when $R^2$ represents an acyl group derived from an α-, β-, γ- or δ-thiolcarboxylic acid, the latter can be, for example, an α-, β-, γ- or δ-thiolalkanecarboxylic acid, e.g. mercaptoacetic acid. Here again, the thiol group can be lower alkylated, e.g. in the case of methylthioacetic acid. Moreover, the acyl group $R^2$ can be derived from a carboxylic acid of the formula $R^a$—COOH, wherein $R^a$ represents 3–7C cycloalkyl which is substituted by amino, hydroxy or thiol in the 1-, 2-, 3- or 4-position, preferably by amino in the 1-position (α-amino). Examples of such carboxylic acids are 1-amino-1-cyclopropanecarboxylic acid, 1-amino-1-cyclopentanecarboxylic acid, 1-amino-1-cyclohexanecarboxylic acid, 4-aminocyclohexanecarboxylic acid.

Preferably, $R^2$ represents an acyl group derived from an α- or β-(amino, hydroxy or thiol)carboxylic acid in which the amino, hydroxy or thiol group is optionally lower alkylated or the amino group is optionally acylated, amidated or sulphonylated, preferably acylated or amidated, and in which any functional group present in a side-chain is optionally protected, or a group of the formula $Het(CH_2)_m$ CO in which m stands for 0, 1 or 2.

In particular, $R^2$ represents an acyl group $R^8CO$, wherein $R^8$ is an α-, β-, γ- or δ-(amino, hydroxy or thiol) substituted lower alkyl, lower cycloalkyl or side-chain of a natural amino acid, in which the amino, hydroxy or thiol group is optionally lower alkylated or the amino group is optionally acylated, sulphonylated or amidated and in which any functional group present in a side-chain is optionally protected, or a group of the formula $Het(CH_2)_m$, in which m stands for 0, 1, 2, 3 or 4. In one preferred example, $R^8$ represents an α- or β-(amino, hydroxy or thiol) substituted lower alkyl, lower cycloalkyl or side chain of a natural amino acid, in which the amino, hydroxy or thiol group is optionally lower alkylated or the amino group is optionally acylated, amidated or sulphonylated, preferably acylated or amidated, and in which any functional group present in a side-chain is optionally protected, or a group of the formula $Het(CH_2)_m$ in which m stands for 0, 1 or 2. In another preferred example, $R^8$ represents a 3–7C cycloalkyl which is substituted by amino, hydroxy or thiol in the 1-, 2-, 3- or 4-position, preferably by amino in the 1-position (α-amino). In other preferred examples, $R^8$ represents an α-amino-substituted lower alkyl, an α-amino-substituted side chain of a natural amino acid, an α-amino-substituted lower cycloalkyl, an α-hydroxy-substituted lower alkyl or an α-hydroxy-substituted side chain of a natural amino acid.

In general, in accordance with this invention a protecting group means any conventional protecting group such as a hydroxy protecting group, amino protecting group, carboxy protecting group, or mercapto protecting group. The cleavage of such protecting groups is also conventional and can be utilized in accordance with this invention. Accordingly, a functional (i.e. reactive) group present in a side-chain of an acyl group denoted by $R^2$ may be protected, with the protecting group being any protecting group in the field of peptide chemistry. For example, an amino group can be protected using any conventional amino protecting group, including for example, a tert.-butoxycarbonyl, formyl, trityl, benzyloxycarbonyl, 9-fluorenylmethyloxycarbonyl (Fmoc), trifluoroacetyl, 2-(biphenylyl)isopropoxycarbonyl or isobornyloxycarbonyl group or in the form of a phthalimido group. A carboxy group can be protected using any conventional carboxy protecting group, including for example, an ester such as the methyl, ethyl, tert.-butyl or benzyl ester. A hydroxy group can be protected using any conventional hydroxy protecting group, for example in the form of an ether, e.g. the methyl, tert.-butyl, benzyl or tetrahydropyranyl ether, or in the form of an ester, e.g. the acetate. A mercapto group can be protected using any conventional mercapto protecting group, for example, by a tert.-butyl or benzyl group.

The spacer group denoted by X can be, for example, a grouping of the formula —$(CH_2)_p$—$(Y)_z$—$(CH_2)_q$— in which p and q each independently stand for 0, 1, 2, 3, 4 or 5; z stands for 0 or 1; and Y represents —CH═CH—, —C≡C—, —S—, —O—, —NH—, —NHCO—, —CONH—, —SO$_2$—, —NHSO$_2$—, —SO$_2$NH—, —NHCONH— or —NHSO$_2$NH—. Preferably p and q each independently stand for 0, 1, 2 or 3. Typical examples of such spacer groups are —(CH$_2$)$_p$—, —CH$_2$—CH =CH—, —CH$_2$—C≡C—, —CH$_2$NHCO—, —(CH$_2$)$_n$NHCONH—, —(CH$_2$)$_p$—S—, —S—, —CH$_2$NHSO$_2$—, —CH$_2$NHCH$_2$—, —(CH$_2$)$_p$—O— and —O—(CH$_2$)$_q$—, wherein n has the significance given earlier.

Compounds of formula I which are acidic form pharmaceutically acceptable salts with bases such as alkali metal hydroxides, e.g. sodium hydroxide and potassium hydroxide, alkaline earth metal hydroxides, e.g. calcium hydroxide, barium hydroxide and magnesium hydroxide, and the like. Those compounds of formula I which are basic can form pharmaceutically acceptable salts with inorganic acids, e.g. with hydrohalic acids such as hydrochloric acid and hydrobromic acid, sulphuric acid, nitric acid and phosphoric acid, and with organic acids, e.g. with acetic acid, tartaric acid, succinic acid, fumaric acid, maleic acid, malic acid, salicylic acid, citric acid methanesulphonic acid and p-toluenesulphonic acid.

It will be appreciated that, although the formulae presented herein show the respective compounds in their absolute stereochemistry, the invention embraces not only the depicted stereoisomers, but also the corresponding racemates and diastereoisomeric mixtures. The stereochemistry of the hydrazine derivatives of the present invention depends on the stereochemistry of the starting material of formula m from which it is made. Such starting materials can be made as in Example 1(iii); or in Beckett et al, Synlett 1993, 137; Larcheveque and Petit, Synthesis, 1991, 162; Bashiardes, et al., J. Organomet. Chem., 1989, 364, C29; Bashiardes et al., J. Chem. Soc. Perkin 1, 1989, 1162; or Fadel, et al., Tetrahedron Letts. 1988, 29, 6257–6260. The 1(S) compound is the preferred product or, in other terms, which are independent from the R or S terminology, it means that it is preferred that R$^4$ in a compound of formula (I) is "down" of the paper plane. Further, when the spacer group denoted by X contains an olefinic double bond, as in —CH$_2$—CH=CH—, this can have the (E) or (Z) configuration, preferably the (E) configuration.

Preferred compounds of formula I are those in which R$^1$ represents lower alkyl, especially isobutyl, or lower cycloalkyl-lower alkyl, especially cyclobutylmethyl or cyclopentylmethyl. R$^2$ preferably represents an acyl group derived from an α-aminocarboxylic acid or from an α-hydroxycarboxylic acid or a group of the formula Het (CH$_2$)$_m$CO, especially where m stands for 0 or 1. R$^3$ preferably represents lower alkyl, especially isobutyl, halolower alkyl, lower cycloalkyl-lower alkyl, aryl-lower alkyl, aryl or heterocyclyl. R$^4$ preferably represents a grouping of the formula X-aryl, especially a grouping of the formula —CH$_2$—CH=CH—Ph in which Ph represents unsubstituted phenyl.

Particularly preferred compounds of formula I are:
(E)-2'-(D-Alanyl)-2(R)-[1(S)-(hydroxycarbamoyl)-4-phenyl-3-butenyl]-2'-isobutyl-4-methylvalerohydrazide;
(E)-2(R)-[1(S)-(hydroxycarbamoyl)-4-phenyl-3-butenyl]-2'-(2(R)-hydroxypropionyl)-2'-isobutyl-4-methylvalerohydrazide;
(E)-2(R)-[1(S)-(hydroxycarbamoyl)-4-phenyl-3-butenyl]-2'-[2-(1-imidazolyl)acetyl]-2'-isobutyl-4-methylvalerohydrazide;
(E)-2(R)-[1(S)-(hydroxycarbamoyl)-4-phenyl-3-butenyl]-2'-isobutyl-4-methyl-2'-[(4-piperidinyl)carbonyl]valerohydrazide;

and pharmaceutically acceptable salts thereof.
Another preferrred compound of formula I is 2'-Benzyl-2(R)-[1(S)-(hydroxycarbamoyl)-4-phenylbutyl]-4-methyl-2'-[2-(1H-1,2,3-triazol-1-yl)acetyl]valerohydrazide or the pharmaceutically acceptable salt thereof.

According to the process provided by the present invention, the novel hydrazine derivatives defined earlier are manufactured by cleaving off the protecting group denoted by R$^7$ and, as required, any protecting group(s) present in R$^{20}$ and/or R$^{30}$ from a compound of the formula

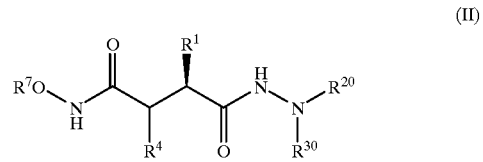

(II)

wherein R$^1$, and R$^4$ have the significances given earlier, R$^7$ represents a protecting group and R$^{20}$ has the same significance as R$^2$ hereinbefore, provided that in the case of an acyl group the amino, hydroxy or thiol group (when not lower alkylated, acylated, sulphonylated, or amidated as specified under R$^2$) is optionally protected and any functional group present in a side-chain is optionally protected and R$^{30}$ has the same significance as R$^3$ hereinbefore provided that any amino or hydroxy group present therein is optionally protected, and, if desired, converting a compound of formula I obtained into a pharmaceutically acceptable salt.

The protecting group denoted by R$^7$ in a compound of formula II can be any conventional protecting group, preferably tetrahydropyranyl, benzyl, 4-methoxybenzyl or tri (lower alkyl)silyl, especially tert-butyldimethylsilyl. Likewise, any protecting group present in R$^{20}$ can be a conventional protecting group; examples of such groups have been discosed earlier in connection with the protection of functional groups in R$^2$.

The cleavage of the protecting group denoted by R$^7$ from a compound of formula II is carried out according to methods known per se. For example, the tetrahydropyranyl group can be cleaved off by treatment with acid, e.g. hydrogen chloride in dioxan or a sulphonic acid, e.g. a lower alkanesulphonic acid such as methanesulphonic acid or an aromatic sulphonic acid such as p-toluenesulphonic acid, in a lower alkanol, e.g. methanol. Cleavage of the benzyl group can be effected by hydrogenolysis in the presence of a catalyst, e.g. palladium, and in a lower alkanol, e.g. methanol. A tri(lower alkyl)silyl protecting group can be cleaved off by subjecting the respective protected compound to the action of water or low pH.

Any protecting group(s) present in R$^{20}$ and/or R$^{30}$ can be cleaved off according to conventional methods known for the cleavage of the respective protecting group. Thus, for example, a tert-butoxycarbonyl group can be cleaved off by treatment with acid and a 9-fluorenylmethoxycarbonyl group can be cleaved off by treatment with piperidine. Cleavage of phthaloyl can be effected by treatment with hydrazine hydrate.

When the amino, hydroxy or thiol group in R$^{20}$ is protected and/or an amino or hydroxy group in R$^{30}$ is protected, then, depending on the choice of protecting group(s), the cleavage of such protecting group(s) can be carried out before, simultaneously with or after the cleavage of the protecting group denoted by R$^7$. Further, when it is desired to manufacture a compound of formula I in which a side-chain of the acyl group contains a protected functional group, then the protecting groups and cleavage conditions will be chosen such that the protecting group in the side-chain is retained while the protecting group denoted by $R^7$ and any protecting group(s) in $R^{20}$ and/or $R^{30}$ is/are cleaved off cleaved off.

The conversion of a compound of formula I obtained into a pharmaceutically acceptable salt is effected by treatment with an appropriate acid or base in a known manner.

The compounds of formula II used as starting materials in the foregoing process are novel and form a further object of the invention. They can be prepared by a variety of routes as illustrated in the Reaction Schemes A, B, C and D hereinafter in which $R^1$, $R^4$, $R^7$, $R^{20}$ and $R^{30}$ have the significances given earlier, $^tBu$ represents tert-butyl, Me represents methyl and M represents an alkali metal, especially sodium.

0° C. to about room temperature. Halogenated hydrocarbons, e.g. dichloromethane, are suitable solvents and tri(lower alkyl)amines, e.g. triethylamine, pyridine, 4-dimethylaminopyridine etc. are suitable solvents. When the base is a liquid under the reaction conditions, it may be used in excess and in this case it can serve both as the base and as the solvent.

In the next step a compound of formula VI is deprotected using trifluoroacetic acid (TFA) to give a carboxylic acid of formula VII. The deprotection is carried out in a manner known per se, e.g. in an organic solvent which is inert under the conditions of the reaction, such as a halogenated hydrocarbon, e.g. dichloromethane, at about room temperature.

Condensation of a carboxylic acid of formula VII with an O-protected hydroxylamine of formula VIII in the subse-

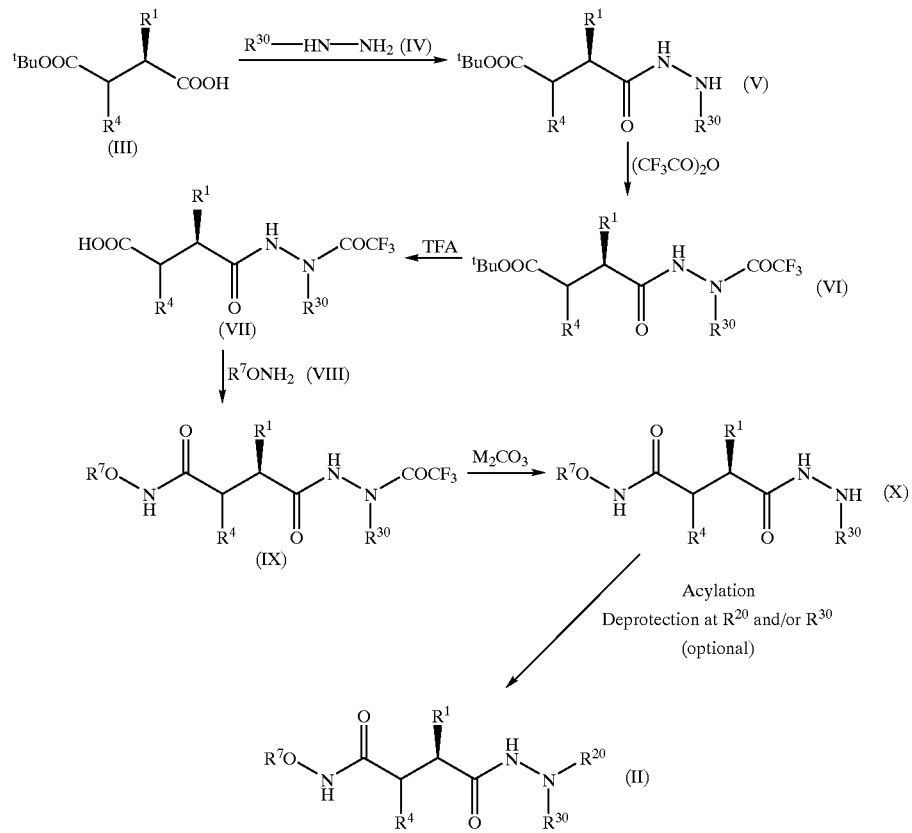

Reaction Scheme A

Having regard to Reaction Scheme A, in the first step a compound of formula III is condensed with hydrazine or a substituted hydrazine of formula IV to give a hydrazide of formula V. This condensation is carried out under the known conditions of peptide coupling reactions using coupling reagents known per se for such couplings, e.g. 1-hydroxybenzotriazole in the presence of 1-ethyl-3-(3-dimethylaminopropyl)carbodiimide and N-methylmorpholine.

A hydrazide of formula V is reacted in the second step with trifluoroacetic anhydride to give a compound of formula VI. This reaction is carried out in a known manner, e.g. in an organic solvent which is inert under the conditions of the reaction and in the presence of an organic base at about quent step gives a compound of formula (IX). This condensation is carried out in a manner known per se for peptide coupling reactions, e.g. in the presence of 1-ethyl-3-(3-dimethylaminopropyl)carbodiimide hydrochloride, and in an organic solvent which is inert under the conditions of the reaction, e.g. dimethylformamide.

In the next step the trifluoroacetyl protecting group is cleaved off from a compound of formula IX by treatment with an alkali metal carbonate, e.g. sodium carbonate or potassium carbonate, to give a compound of formula X. This treatment is conveniently carried out by dissolving the compound of formula IX in a lower alkanol, e.g. methanol, ethanol, etc., adding an aqueous alkali metal carbonate solution and holding the mixture at about room temperature until the cleavage is complete.

Subsequently, a compound of formula X is acylated. The acylation can be carried out in a manner known per se. For example, a compound of formula X can be reacted with an acid of the formula $R^{20}OH$ (XI), wherein $R^{20}$ has the significance given earlier, in the presence of a coupling reagent such as 1-ethyl-3-(3-dimethylaminopropyl)-carbodiimide hydrochloride in an organic solvent which is inert under the reaction conditions, e.g. dimethylformamide, at about 0° C. to about room temperature. An acid of formula XI can be converted into the corresponding acid fluoride or acid chloride and, in this case, the reaction is conveniently effected in an organic solvent which is inert under the conditions of the reaction, e.g. a halogenated hydrocarbon such as dichloromethane, and in the presence of a base, e.g. a tri(lower alkyl)amine such as triethylamine, pyridine, 4-dimethylaminopyridine etc., at about room temperature. Further, a compound of formula X can be acylated with a reactive derivative of an acid of formula XI in which $R^{20}$ represents a group of the formula $Het(CH_2)_mCO$, wherein Het and m have the significances given earlier, in a conventional manner, e.g. in an organic solvent which is inert under the reaction conditions, such as a halogenated hydrocarbon, e.g. dichloromethane, and in the presence of a base such as a tri(lower alkyl)amine, e.g. triethylamine, at a low temperature, e.g. about 0–10° C.

Finally, when the acylation product contains a protected acyl group $R^{20}$, the protecting group(s) can be cleaved off in a manner analogous to that described earlier. Also, when $R^{30}$ in the acylation product contains a protected amino or protected hydroxy group, then the respective protecting group can be cleaved off as described earlier.

The compounds of formula III used in Reaction Scheme A, insofar as they are not known compounds or analogues of known compounds, can be prepared as described in the following Examples or in analogy thereto. In addition, the compounds of formula III can be prepared by methods disclosed in EP-497192-A; EP-574758-A; EP-684240-A; Beckett et al, Synlett 1993, 137; and Pratt et al, Synlett 1998, 531. The compounds of formulae IV, VIII and XI, likewise used in Reaction Scheme A, are known compounds or analogues of known compounds. Compounds of formula IV were obtained from commercial suppliers or prepared by the method of Zwierzak, Synthesis 1987, 485. Compounds of formula VIII were obtained from commercial suppliers or prepared by the method of Teodozyl et al, Rocz. Chem 1976, 50(2), 367 (CAN 85:62908). Compounds of formula XI were obtained from commercial suppliers or prepared by adapting methods found in the following: WO 9843968-A1; EP 314060-A2, DE 19503827-A1; Pestic. Chem., Pro. Int. Congr. Pestic. Chem., 2nd (1972), 5,209; U.S. Pat. No. 4,684,483-A; J. Med. Chem., 1971, 14, 990; Chem. Lett., 1974, 8,859; Bioorg. Med. Chem., 1994, 2, 305; Bioorg. Med. Chem. Lett., 1992, 2, 1717.

Reaction Scheme B

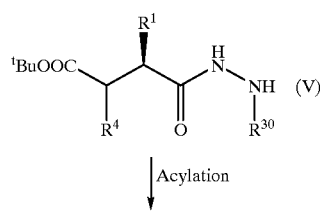

Acylation

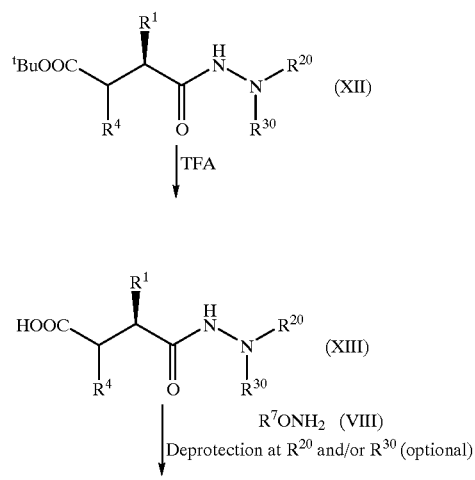

TFA

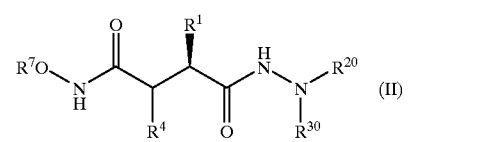

$R^7ONH_2$ (VIII)

Deprotection at $R^{20}$ and/or $R^{30}$ (optional)

Having regard to Reaction Scheme B, the respective steps, i.e. the acylation of a compound of formula V to a compound of formula XII, the deprotection of the latter with TFA and the condensation of a resulting compound of formula VIII with an O-protected hydroxylamine of formula VIII, are carried out in an analogous manner to that described earlier in connection with the corresponding steps in Reaction Scheme A, i.e. the acylation of a compound of formula X, the deprotection of a compound of formula VI and the condensation of a compound of formula VII with an O-protected hydroxylamine of formula VIII. When the product resulting from the condensation of a compound of formula XIII with an O-protected hydroxylamine of formula VIII contains a protected acyl group $R^{20}$ and/or a protecting group in $R^{30}$, the protecting group(s) can be cleaved off in a manner analogous to that described earlier.

If desired, certain compounds occurring in Reaction Scheme B may be interconverted. Thus, for example, a compound of formula V in which $R^4$ represents —$CH_2CH=CH_2$ can be reacted with an aryl or heteroaryl iodide in the presence of $Pd(OAc)_2$ and a tri(lower alkyl) amine, e.g. triethylamine, to give a corresponding compound of formula V in which $R^4$ represents —$(CH_2)_3$-(aryl or heteroaryl). Again, for example, a compound of formula XII in which $R^4$ represents phthalimido-lower alkyl can be treated with hydrazine hydrate, conveniently in an organic solvent which is inert under the reaction conditions, e.g. a lower alkanol such as methanol or ethanol, at about room temperature, and the resulting product, a compound corresponding to formula XII, but in which $R^4$ represents amino-lower alkyl. The amino group can subsequently be substituted in a conventional manner to generate a desired group $R^4$, e.g. by reaction with an appropriate (hetero)aromatic carboxylic acid or reactive derivative thereof, such as a corresponding carboxylic acid halide.

Reaction Scheme C

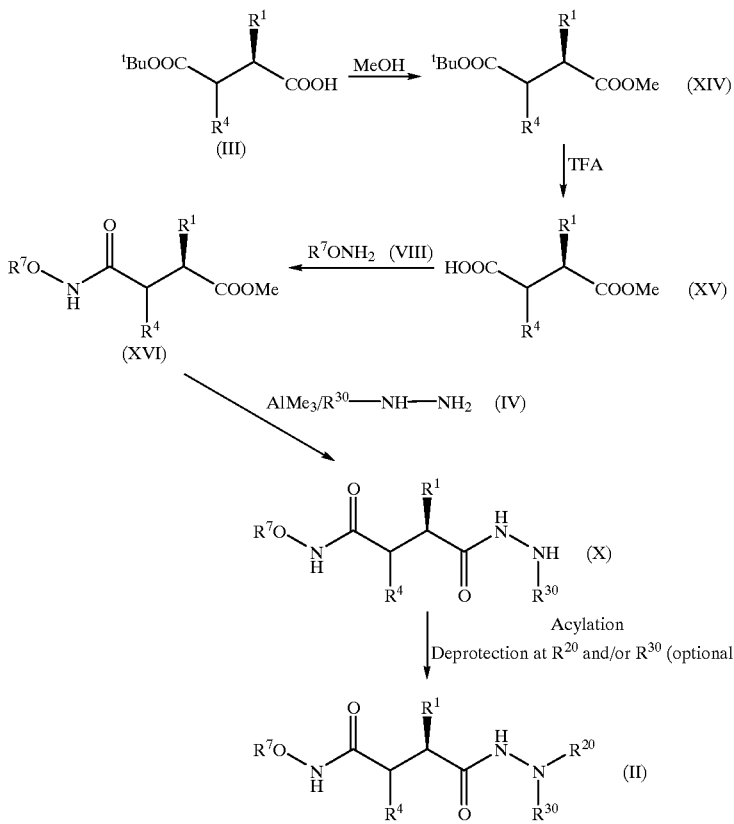

Having regard to Reaction Scheme C, the first step involves the conversion of a carboxylic acid of formula m into the corresponding methyl ester of formula XIV. This is carried out in a known manner, e.g. by reaction with methanol in the presence of a tertiary organic base such as 4-dimethylaminopyridine and a condensation agent such as 1-ethyl-3-(3-dimethylaminopropyl)carbodiimide.

The next two steps of Reaction Scheme C, i.e. the deprotection of a compound of formula XIV with TFA and the condensation of the resulting acid of formula XV with an O-protected hydroxylamine of formula VIII, are carried out in an analogous manner to that described in Reaction Scheme A in connection with the deprotection of a compound of formula VI and the condensation of the resulting acid of formula VII with an O-protected hydroxylaamine of formula VIII.

In the next step a resulting compound of formula XVI is converted into a compound of formula X by reaction with trimethylaluminium and hydrazine or a substituted hydrazine of formula IV. This reaction is suitably carried out in an organic solvent which is inert under the reaction conditions, e.g. a halogenated hydrocarbon such as dichloromethane, and at a temperature between about room temperature and about 60° C.

Subsequently, a compound of formula X is acylated and, when the acylation product contains a protected acyl group $R^{20}$ and/or a protecting group in $R^{30}$ the protecting group(s) are optionally cleaved off. This acylation and optional deprotection are carried out in a manner analogous to that described earlier in connection with Reaction Scheme A.

Reaction Scheme D

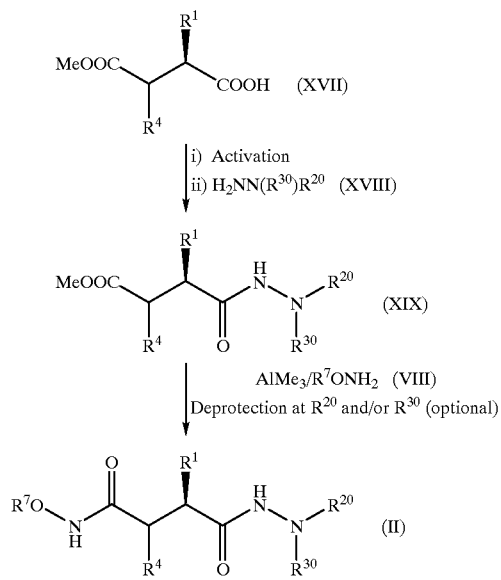

In the first step or Reaction Scheme D a carboxylic acid of formula XVII is activated, conveniently using oxalyl chloride, and then reacted with a substituted hydrazine of formula XVIII to give a compound of formula XIX. This reaction is expediently carried out in the presence of a base, e.g. a tertiary organic amine such as triethylamine, and in an organic solvent which is inert under the reaction conditions, e.g. a halogenated hydrocarbon such as dichloromethane, at about 0° C.

The desired starting material of formula II is then obtained by reacting a compound of formula XIX with trimethylaluminium and an O-protected hydroxylamine of formula VIII followed by optional deprotection of any protected acyl group present in the reaction product. Conveniently, the reaction can be carried out in an organic solvent which is inert under the reaction conditions, e.g. a halogenated hydrocarbon such as dichloromethane, at about room temperature to about 60° C., while the deprotection can be carried out in a manner analogous to that described earlier.

The carboxylic acids of formula XVII and the substituted hydrazines of formula XVIII used in Reaction Scheme D are known compounds or analogues of known compounds which can be prepared in an analogous manner to the known compounds.

As mentioned earlier, the hydrazine derivatives provided by the present invention inhibit the release of TNF-α from mammalian cells. This can be demonstrated using the in vitro test procedure described hereinafter:

THP1 cells were cultivated in RPMI 1640 medium supplemented with antibiotics and 10% foetal calf serum, harvested by centrifugation and diluted to $5 \times 10^5$ cells/ml in the above medium supplemented with 20 mM HEPES buffer. Aliquots (200 ml) of the cell suspension were plated out on 96 well culture plates and incubated for 0.5 hour at 37° C. prior to the addition of the test compounds. The latter were dissolved in dimethyl sulphoxide (DMSO) to a stock concentration of 1.2 mM which was diluted with phosphate buffered saline/10% DMSO solution to provide test compounds in final concentrations of $10^{-9}$ to $10^{-5}$ M, with each concentration being tested in duplicate. The cells were incubated with the test compounds for 0.5 hour at 37° C., LPS (bacterial lipopolysaccharide) was then added to a concentration of 2 mg/ml and incubation was continued for 3 hours at 37° C. in an atmosphere containing 5% $CO_2$ and at 95% relative humidity. After centrifugation at 260 g for 10 minutes an aliquot of each supernatant was removed and the amount of TNF-α was estimated by ELISA (R & D Systems Europe Ltd., Abingdon, England). The concentration of test compound which brings about 50% inhibition of LPS-induced TNF-α release ($IC_{50}$) was computed from the dose-response curve.

The results obtained in the foregoing test with representative compounds of formula I are compiled in the following Table.

TABLE

| Compound | $IC_{50}$ (nMol) |
| --- | --- |
| A | 303 |
| B | 589 |
| C | 201 |
| D | 345 |

Compounds:
A = (E)-2'-(D-Alanyl)-2(R)-[1(S)-(hydroxycarbamoyl)-4-phenyl-3-butenyl]-2'-isobutyl-4-methylvalerohydrazide.
B = (E)-2(R)-[1(S)-(Hydroxycarbamoyl)-4-phenyl-3-butenyl]-2'-(2(RS)-hydroxy-propionyl)-2'-isobutyl-4-methylvalerohydrazide.
C = (E)-2(R)-[1(S)-(Hydroxycarbamoyl)-4-phenyl-3-butenyl]-2'-[2-(1-imidazolyl)acetyl]-2'-isobutyl-4-methylvalerohydrazide.
D = (E)-2(R)-[1(S)-(Hydroxycarbamoyl)-4-phenyl-3-butenyl]-2'-isobutyl-4-methyl-2'-[(4-piperidinyl)carbonyl]valerohydrazide.

The hydrazine derivatives provided by the present invention (i.e. the compounds of formula I and their pharmaceutically acceptable salts) can be used as medicaments, for example in the form of pharmaceutical preparations. The pharmaceutical preparations can be administered orally, e.g. in the form of tablets, coated tablets, dragées, hard and soft gelatine capsules, solutions, emulsions or suspensions. However, they can also be administered rectally, e.g. in the form of suppositories, or parenterally, e.g. in the form of injection solutions.

For the manufacture of pharmaceutical preparations the hydrazine derivatives can be formulated with therapeutically inert, inorganic or organic carriers. Lactose, corn starch or derivatives thereof, talc, stearic acid or its salts can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active ingredient no carriers are, however, generally required in the case of soft gelatine capsules. Suitable carriers for the manufacture of solutions and syrups are, for example, water, polyols, saccharose, invert sugar, glucose and the like. Suitable carriers for the manufacture of injection solutions are, for example, water, alcohols, polyols, glycerine, vegetable oils and the like. Natural and hardened oils, waxes, fats, semi-liquid polyols and the like are suitable carriers for the manufacture of suppositories.

The pharmaceutical preparations can also contain preservatives, stabilizers, wetting agents, emulsifiers, sweeteners, colorants, flavorants, salts for adjustment of the osmotic pressure, buffers, masking agents or antioxidants. They may also contain other therapeutically active substances.

Medicaments containing an aforementioned hydrazine derivative and a therapeutically acceptable carrier as well as a process for the manufacture of such medicaments are also objects of the present invention. This process comprises bringing a compound of formula I or a pharmaceutically acceptable salt thereof into a galenical administration form together with a therapeutically inert carrier material and, if desired, one or more additional therapeutically active substances.

A further object of the invention comprises the use of the hydrazine derivatives provided by the invention in the treatment of illnesses, especially in the treatment of inflammatory and autoimmune diseases (e.g. rheumatoid arthritis, inflammatory bowel disease, multiple sclerosis and psoriasis), osteoarthritis, respiratory diseases (e.g. asthma and chronic obstructive pulmonary disease), tumours, cachexia, cardiovascular diseases (e.g. congestive heart failure), fever, haemorrhage and sepsis. The dosage can vary within wide limits and will, of course, be adjusted to the individual requirements in each particular case. In general, in the case of administration to adults, a daily dosage of about 1–20 mg/kg, preferably about 3–5 mg/kg, should be appropriate, although the upper limit may be exceeded when this is found to be expedient. The daily dosage can be administered as a single dosage or in divided dosages.

The contents of British Patent Application Nos. 9813919.9, filed Jun. 26, 1998, and 9826491.4, filed Dec. 2, 1998 are incorporated herein by reference.

The following Examples illustrate, but do not limit, the invention disclosed herein.

EXAMPLE 1

(E)-2(R)-[1(S)-(Hydroxycarbamoyl)-4-phenyl-3-butenyl]-2'-isobutyl-2'-(D-prolyl)-4-methylvalerohydrazide hydrochloride A solution of 0.656 g of (E)-2(R)-[1(S)-[(tetrahydro-2(RS)-pyranyloxy)carbamoyl]-4-phenyl-3-butenyl]-2'- isobutyl-2'-(N-tert.-butoxycarbonyl-D-prolyl)-4-methylvalerohydrazide in 8 ml of dioxan was treated with 4 ml of 4M hydrogen chloride in dioxan. The mixture was stirred for 2 hours at room temperature and diluted with diethyl ether. The solid was filtered off, washed with diethyl ether and dried to give 0.367 g of (E)-2(R)-[1(S)-(hydroxycarbamoyl)-4-phenyl-3-butenyl]-2'-isobutyl-2'-(D-prolyl)-4-methylvalerohydrazide hydrochloride in the form of a white solid.

MS: 473 (M+H)$^+$. HPLC: Gradient elution using solvent A containing 20% solvent B for 5 minutes increasing to 60% solvent B from 5 minutes to 20 minutes; flow rate 1 ml per minute. Retention time: 15.585 minutes. Solvent A: $H_2O$/ 0.1% TFA; solvent B: $CH_3CN$/0.085% TFA. Column type: HYPERPEP 300A.

The (E)-2(R)-[1(S)-[(tetrahydro-2(RS)-pyranyloxy)carbamoyl]-4-phenyl-3-butenyl]-2'-isobutyl-2'-(N-tert.-butoxycarbonyl-D-prolyl)-4-methylvalerohydrazide used as the starting material was prepared as follows:

(i) A solution of 253.3 g of 4-tert-butyl hydrogen 2(R)-isobutylsuccinate in 2 l of dry tetrahydrofuran was cooled to −70° C. while stirring under nitrogen. 1.2 l of a 2M solution of lithium diisopropylamide in tetrahydrofuran were added dropwise and the mixture was stirred at −70° C. for 30 minutes. A solution of 282 g of cinnamyl bromide in 2 l of dry tetrahydrofuran was then added dropwise and the mixture was left to come to room temperature gradually. After stirring overnight, the tetrahydrofuran was evaporated and the residue was partitioned between ethyl acetate and 2M hydrochloric acid solution. The ethyl acetate layer was washed with a further portion of 2M hydrochloric acid solution, water and saturated sodium chloride solution and then dried over anhydrous magnesium sulphate. The solvent was evaporated to give a gum-like solid which was suspended in 2 l of hexane. The product was removed by filtration (crop 1: 77.3 g). The hexane solution was treated with 109 g of cyclohexylamine and the mixture was left to stand for 1 hour at room temperature and for 16 hours at 4° C. The solid which formed was collected by filtration and dissolved in 2.5 l of methyl tert.butyl ether and 1.5 l of 2M hydrochloric acid to give a clear solution. The separated organic phase was washed twice with water and saturated sodium chloride solution and subsequently dried over anhydrous magnesium sulphate. After evaporation of the solvent there were obtained 189.8 g of a solid (crop 2). The two crops were combined and dried to give 267.1 g of (E)-2(R)-[1(R)-(tert-butoxycarbonyl)-4-phenyl-3-butenyl]-4-methylvaleric acid in the form of a pale cream colored solid.

(ii) The (E)-2(R)-[1(R)-(tert-butoxycarbonyl)-4-phenyl-3-butenyl]-4-methylvaleric acid obtained in part (i) was dissolved in 2.5 l of dry tetrahydrofuran, the solution was cooled to −78° C. while stirring and 860 ml of a 2M solution of lithium diisopropylamide in tetrahydrofuran were added dropwise over 2 hours. After stirring for 0.5 hour at −78° C., 330 ml of methanol were added dropwise. The mixture was left to come to room temperature gradually and was then stirred overnight. The tetrahydrofuran was evaporated and the residue was partitioned between ethyl acetate and 2M hydrochloric acid solution. The ethyl acetate phase was washed in succession with two portions of hydrochloric acid solution, two portions of water and saturated sodium chloride solution and then dried over magnesium sulphate. After evaporation, there was obtained an orange colored oil which contained a mixture of the 1(S),2(R) and 1(R),2(R) isomers of E-2-[1-(tert-butoxycarbonyl)-4-phenyl-3-butenyl]-4-methylvaleric acid. The above epimerization procedure was repeated three times to give a mixture substantially enriched in the 1(S),2(R) isomer. The crude product was dissolved in 2500 ml of hexane and the solution was treated with 89 ml of tert.butylamine. After leaving to stand at 4° C., the precipitated salt was filtered off and dried. There were obtained 210.3 g of a pale cream colored solid which was converted into the free acid by the procedure described above to give of (E)-2(R)-[1(S)-(tert-butoxycarbonyl)-4-phenyl-3-butenyl]-4-methylvaleric acid in the form of a yellow solid.

(iii) A solution of 4.05 kg of (E)-2(R)-[1(S)-(tert-butoxycarbonyl)-4-phenyl-3-butenyl]-4-methylvaleric acid in 12 l of dimethylformanide was cooled to 4° C., treated with 1.97 kg of hydroxybenzotriazole hydrate and 2.466 kg of 1-ethyl-3-(3-dimethylaminopropyl)carbodiimide hydrochloride and stirred for 2 hours at 4° C. 3.895 kg of isobutylhydrazine ditosylate salt were added followed by 2.36 l of N-methyl-morpholine. The mixture was stirred for 2 hours at 4° C. and for 50 hours at room temperature, diluted with 12 l of 2M hydrochloric acid and 12 l of methyl tert.butyl ether and the organic layer was separated. The organic phase was washed with water, saturated sodium hydrogen carbonate solution and water and then evaporated to give a dark cream colored solid. Recrystallization from hexane gave 2.47 kg of (E)-2(R)-[1(S)-(tert-butoxycarbonyl)-4-phenyl-3-butenyl]-2'-isobutyl-4-methylvalerohydrazide in the form of a cream colored solid.

MS: 417 (M+H)$^+$.

(iv) A solution of 40.0 g of (E)-2(R)-[1(S)-(tert-butoxycarbonyl)-4-phenyl-3-butenyl]-2'-isobutyl-4-methylvalerohydrazide and 11.2 ml of pyridine in 400 ml of dichloromethane was stirred under a nitrogen atmosphere. 16.3 ml of trifluoroacetic anhydride were added and the mixture was stirred for 10 minutes at room temperature and then evaporated. The residue in ethyl acetate was washed with 5% sodium hydrogen carbonate solution, water, 2M aqueous hydrochloric acid and water. The ethyl acetate phase was dried over anhydrous magnesium sulphate and the solvent was evaporated to yield 55.0 g of (E)-2(R)-[1(S)-(tert-butoxycarbonyl)-4-phenyl-3-butenyl]-2'-isobutyl-2'-(trifluoroacetyl)-4-methylvalerohydrazide in the form of a dark orange colored gum.

MS: 513 (M+H)$^+$.

(v) The crude tert.butyl ester obtained in part (iv) was dissolved in 250 ml of a 40% solution of trifluoroacetic acid in dichloromethane and the solution was stirred at room temperature for 2.5 hours. The solvents were evaporated and traces of trifluoroacetic acid were removed by the addition and evaporation of toluene (2×30 ml). The residue was triturated with hexane to give 39.1 g of (E)-2(R)-[1(S)-(carboxy)-4-phenyl-3-butenyl]-2'-isobutyl-2'-(trifluoroacetyl)-4-methylvalerohydrazide in the form of an off-white solid.

(vi) The carboxylic acid prepared in part (v) was dissolved in 90 ml of dimethylformamide and the solution was cooled to 0° C. and treated in succession with 50.0 g of O-(tetrahydro-2H-pyran-2(RS)-yl)hydroxylamine and 18.0 g of 1-ethyl-3-(3-dimethylaminopropyl)carbodiimide hydrochloride. The mixture was left to come to room temperature and was stirred overnight. The solvent was evaporated and the residue was partitioned between ethyl acetate and water. The ethyl acetate phase was washed with water until neutral, dried over anhydrous magnesium sulphate and evaporated. The resulting solid was triturated with hexane and filtered off to give 37.6. g of (E)-2(R)-[1(S)-[(tetrahydro-2(RS)-pyranyloxy)carbamoyl]-4-phenyl-3-butenyl]-2'-isobutyl-2'-(trifluoroacetyl)-4-methylvalerohydrazide in the form of a white solid.

(vii) The (E)-2(R)-[1(S)-[(tetrahydro-2(RS)-pyranyloxy) carbamoyl]-4-phenyl-3-butenyl]-2'-isobutyl-2'-(trifluoroacetyl)-4-methylvalerohydrazide obtained in part (v) was dissolved in 200 ml of methanol and the solution was treated with a solution of 18.7 g of potassium carbonate in 50 ml of water for 16 hours at room temperature. Removal of the methanol by evaporation gave a solid which was washed with water and dried in vacuo over solid sodium hydroxide to yield 28.2 g of (E)-2(R)-[1(S)-[(tetrahydro-2 (RS)-pyranyloxy)carbamoyl]-4-phenyl-3-butenyl]-2'-isobutyl-4-methylvalerohydrazide in the form of a white solid.

MS: 460 (M+H)$^+$. HPLC: Gradient elution using solvent A containing 5% solvent B increasing to 95% solvent B over 15 minutes; flow rate 1 ml/minute. Retention time: 12.46 minutes. Solvent A: H$_2$O/0.1% TFA; solvent B: CH$_3$CN/ 0.085% TFA. Column type: HYPERPEP 300A.

(viii) A solution of 0.459 g of (E)-2(R)-[1(S)-[(tetrahydro-2(RS)-pyranyloxy)carbamoyl]-4-phenyl-3-butenyl]-2'-isobutyl-4-methylvalerohydrazide in 8 ml of dichloromethane was treated under nitrogen at room temperature with 0.25 ml of pyridine and a solution of 0.427 g of N-tert.-butoxycarbonyl-D-proline acid fluoride in 4 ml of dichloromethane. The mixture was stirred at room temperatue for 16 hours and evaporated. The residue was partitioned between ethyl acetate and 5% aqueous sodium hydrogen carbonate solution. The ethyl acetate layer was washed in succession with water, 5% citric acid solution and water and was then dried over anhydrous magnesium sulphate. The solvent was evaporated to give 0.696 g of (E)-2(R)-[1 (S)-[(tetrahydro-2(RS)-pyranyloxy)carbamoyl]-4-phenyl-3-butenyl)-2'-isobutyl-2'-(N-tert.-butoxycarbonyl-D-prolyl)-4-methylvalerohydrazide in the form of a white foam.

MS: 657 (M+H)$^+$.

EXAMPLE 2

(E)-2(R)-[1(S)-(Hydroxycarbamoyl)-4-phenyl-3-butenyl]-2'-isobutyl-2'-(L-prolyl)-4-methylvalerohydrazide hydrochloride A solution of 0.656 g of (E)-2(R)-[1(S)-[(tetrahydro-2'-(RS)-pyranyloxy)carbamoyl]-4-phenyl-3-butenyl]-2'-isobutyl-2 (N-tert.-butoxycarbonyl-L-prolyl)-4-methylvalerohydrazide in 8 ml of dioxan was treated with 4 ml of 4M hydrogen chloride in dioxan. The mixture was stirred for 2 hours at room temperature and diluted with diethyl ether. The solid was filtered off, washed with diethyl ether and dried to give 0.337 g of (E)-2(R)-[1(S)-(hydroxycarbamoyl)-4-phenyl-3-butenyl]-2'-isobutyl-2'-(L-prolyl)-4-methylvalerohydrazide hydrochloride in the form of a white solid.

MS: 473 (M+H)$^+$. HPLC: Gradient elution using solvent A containing 20% solvent B for 5 minutes increasing to 60% solvent B from 5 minutes to 20 minutes; flow rate 1 ml per minute. Retention time: 15.44 minutes. Solvent A: H$_2$O/ 0.1% TFA; solvent B: CH$_3$CN/0.085% TFA. Column type: HYPERPEP 300A.

The (E)-2(R)-[1(S)-[(tetrahydro-2(RS)-pyranyloxy) carbamoyl]-4-phenyl-3-butenyl]-2'-isobutyl-2'-(N-tert.-butoxycarbonyl-L-prolyl)-4-methylvalerohy drazide used as the starting material was prepared as follows:

In an analogous manner to that described in Example 1, part (vii), starting from (E)-2(R)-[1(S)-[(tetrahydro-2(RS)-pyranyloxy)carbamoyl]-4-phenyl-3-butenyl]-2'-isobutyl-4-methylvalerohydrazide and N-tert.-butoxycarbonyl-L-proline acid fluoride there was obtained (E)-2(R)-[1(S)-[(tetrahydro-2(RS)-pyranyloxy)carbamoyl]-4-phenyl-3-butenyl]-2'-isobutyl-2'-tert.-butoxycarbonyl-L-prolyl)-4-methylvalerohydrazide in the form of a white solid.

MS: 657 (M+H)$^+$.

EXAMPLE 3

(E)-2(R)-[1(S)-(Hydroxycarbamoyl)-4-phenyl-3-butenyl]-2'-isobutyl-2'-(D-lysyl)-4-methylvalerohydrazide hydrochloride In an analogous manner to that described in Example 1, starting from (E)-2(R)-[1(S)-[(tetrahydro-2(RS)-pyranyloxy)carbamoyl]-4-phenyl-3-butenyl]-2'-isobutyl-2'-(N$^{48}$, N$^{48}$-di-tert.-butoxycarbonyl-D-lysyl)-4-methylvalerohydrazide there was obtained (E)-2(R)-[1(S)-(hydroxycarbamoyl)-4-phenyl-3-butenyl]-2'-isobutyl-2'-(D-lysyl)-4-methylvalerohydrazide hydrochloride in the form of a white solid.

MS: 504 (M+H)$^+$. HPLC: Gradient elution using solvent A containing 5% solvent B increasing to 95% solvent B over 15 minutes; flow rate 1 ml/minute. Retention time: 9.955 minutes. Solvent A: H$_2$O/0.1% TFA; solvent B: CH$_3$CN/ 0.085% TFA. Column type: HYPERPEP 300A.

The (E)-2(R)-[1(S)-[(tetrahydro-2(RS)-pyranyloxy) carbamoyl]-4-phenyl-3-butenyl]-2'-isobutyl-2'-(N$^\square$,N$^\square$-di-tert.-butoxycarbonyl-D-lysyl)-4-methylvalerohydrazide used as the starting material was prepared as follows:

In an analogous manner to that described in Example 1, part (vii), starting from (E)-2(R)-[1(S)-[(tetrahydro-2(RS)-pyranyloxy)carbamoyl]-4-phenyl-3-butenyl]-2'-isobutyl-4-methylvalerohydrazide and N$^\alpha$,N$^\epsilon$-di-tert.-butoxycarbonyl-D-lysine acid fluoride there was obtained (E)-2(R)-[1(S)-[(tetrahydro-2(RS)-pyranyloxy)carbamoyl]-4-phenyl-3-butenyl]-2'-isobutyl-2'L(N$^\alpha$,N$^\epsilon$-di-tert.-butoxycarbonyl-D-lysyl)-4-methylvalerohydrazide in the form of a white solid.

MS: 788 (M+H)$^+$.

EXAMPLE 4

(E)-2(R)-[1(S)-(Hydroxycarbamoyl)-4-phenyl-3-butenyl]-2'-isobutyl-2'-(L-lysyl)-4-methylvalerohydrazide hydrochloride In an analogous manner to that described in Example 1, starting from (E)-2(R)-[1(S)-[(tetrahydro-2(RS)-pyranyloxy)carbamoyl]-4-phenyl-3-butenyl]-2'-isobutyl-2'-(N$^\alpha$,N$^\epsilon$-di-tert.-butoxycarbonyl-L-lysyl)-4-methylvalerohydrazide there was obtained (E)-2(R)-[1(S)-(hydroxycarbamoyl)-4-phenyl-3-butenyl]-2'-isobutyl-2'-(L-lysyl)-4-methylvalerohydrazide hydrochloride in the form of a white solid.

MS: 504 (M+H)$^+$. HPLC: Gradient elution using solvent A containing 5% solvent B increasing to 95% solvent B over 15 minutes; flow rate 1 ml/minute. Retention time: 9.70 minutes. Solvent A: H$_2$O/0.1% TFA; solvent B: CH$_3$CN/ 0.085% TFA. Column type: HYPERPEP 300A.

The (E)-2(R)-[1(S)-[(tetrahydro-2(RS)-pyranyloxy) carbamoyl]-4-phenyl-3-butenyl]-2'-isobutyl-2'-(N$^\alpha$,N$^\epsilon$-di-tert.-butoxycarbonyl-L-lysyl)-4-methylvalerohydrazide used as the starting material was prepared as follows:

In an analogous manner to that described in Example 1, part (vii), starting from (E)-2(R)-[1(S)-[(tetrahydro-2(RS)-pyranyloxy)carbamoyl]-4-phenyl-3-butenyl]-2'-isobutyl-4-methylvalerohydrazide and N$^\alpha$,N$^\epsilon$-di-tert.-butoxycarbonyl-L-lysine acid fluoride there was obtained (E)-2(R)-[1(S)-[(tetrahydro-2(RS)-pyranyloxy)carbamoyl]-4-phenyl-3- butenyl]-2'-isobutyl-2'-(N$^\alpha$,N$^\epsilon$-di-tert.-butoxycarbonyl-L-lysyl)-4-methylvalerohydrazide in the form of a white solid.

MS: 788 (M+H)$^+$.

EXAMPLE 5

(E)-2(R)-[1(S)-(Hydroxycarbamoyl)-4-phenyl-3-butenyl]-2'-isobutyl-2'-(O-tert.butyl-D-seryl)-4-methylvalerohydrazide p-toluenesulphonate A solution of 0.38 g of (E)-2(R)-[1(S)-[(tetrahydro-2(RS)-pyranyloxy)carbamoyl]-4-phenyl-3-butenyl]-2'-isobutyl-2'-(O-tert.butyl-D-seryl)-4-methylvalerohydrazide in 5 ml of methanol was treated with 0.144 g of p-toluenesulphonic acid. The mixture was stirred for 3.5 hours at room temperature and evaporated to give a solid. This was triturated with diethyl ether, filtered off and dried to give 0.38 g of (E)-2(R)-[1(S)-(hydroxycarbamoyl)-4-phenyl-3-butenyl]-2'-isobutyl-2'-(O-tert.butyl-D-seryl)-4-methylvalerohydrazide p-toluenesulphonate in the form of a white solid.

MS: 519 (M+H)$^+$. HPLC: Gradient elution using solvent A containing 5% solvent B increasing to 95% solvent B over 15 minutes; flow rate 1 ml/minute. Retention time: 11.97 minutes. Solvent A: H$_2$O/0.1% TFA; solvent B: CH$_3$CN/0.085% TFA. Column type: HYPERPEP 300A.

The (E)-2(R)-[1(S)-[(tetrahydro-2(RS)-pyranyloxy) carbamoyl]-4-phenyl-3-butenyl]-2'-isobutyl-2'-(O-tert.butyl-D-seryl)-4-methylvalerohydrazide used as the starting material was prepared as follows:

(i) A solution of 0.459 g of (E)-2(R)-[1(S)-[(tetrahydro-2 (RS)-pyranyloxy)carbamoyl]-4-phenyl-3-butenyl]-2'-isobutyl-4-methylvalerohydrazide in 4 ml of dichloromethane was treated under nitrogen at room temperature with 0.119 g of pyridine and a solution of 0.578 g of N-(9-fluorenylmethyloxycarbonyl)-O-tert.butyl-D-serine acid fluoride in 3 ml of dichloromethane. The mixture was stirred at room temperature for 16 hours and diluted with ethyl acetate. The solution was washed with 5% aqueous sodium hydrogen carbonate solution, water and saturated sodium chloride solution and then dried over anhydrous magnesium sulphate. The solvent was evaporated to give 0.88 g of (E)-2(R)-[1(S)-[(tetrahydro-2(RS)-pyranyloxy) carbamoyl]-4-phenyl-3-butenyl]-2'-isobutyl-2'-[N-(9-fluorenylmethyloxycarbonyl)-O-tert.butyl-D-seryl]-4-methylvalerohydrazide in the form of a white foam.

MS: 825 (M+H)$^+$.

(ii) A solution of 0.86 g of (E)-2(R)-[1(S)-[(tetrahydro-2 (RS)-pyranyloxy)carbamoyl]-4-phenyl-3-butenyl]-2'-isobutyl-2'-[N-(9-fluorenylmethyloxycarbonyl)-O-tert.butyl-D-seryl]-4-methylvalerohydrazide in a mixture of 8 ml of dichloromethane and 2 ml of piperidine was stirred at room temperature for 3 hours. The solution was evaporated and the residue was treated with diethyl ether. The ethereal solution was filtered and evaporated. Chromatography on silica gel using methanol/dichloromethane (1:19) for the elution followed by evaporation gave 0.39 g of (E)-2(R)-[1(S)-[(tetrahydro-2(RS)-pyranyloxy)carbamoyl]-4-phenyl- 3-butenyl]-2'-isobutyl-2'-(O-tert.butyl-D-seryl)-4-methylvalerohydrazide in the form of a gum.

MS: 603 (M+H)$^+$.

EXAMPLE 6

(E)-2'-[(1-Amino-1-cyclopentyl)carbonyl]-2(R)-[1 (S)-(hydroxycarbamoyl)-4-phenyl-3-butenyl]-2'-isobutyl-4-methylvalerohydrazide p-toluenesulphonate A solution of 0.35 g of (E)-2'-[(1-amino-1-cyclopentyl) carbonyl]-2(R)-[1(S)-[(tetrahydro-2(RS)-pyranyloxy) carbamoyl]4-phenyl-3-butenyl]-2'-isobutyl-4-methylvalerohydrazide in 3 ml of methanol was treated with 0.14 g of p-toluenesulphonic acid. The mixture was stirred for 1.7 hours at room temperature and evaporated to give a foam. This foam was triturated with diethyl ether, filtered off and dried to give 0.32 g of (E)-2'-[(1-amino-1-cyclopentyl) carbonyl]-2(R)-[1(S)-(hydroxycarbamoyl)-4-phenyl-3-butenyl]-2'-isobutyl-4-methylvalerohydrazide p-toluenesulphonate in the form of a white solid.

MS: 487 (M+H)$^+$. HPLC: Gradient elution using solvent A containing 5% solvent B increasing to 95% solvent B over 15 minutes; flow rate 1 ml/minute. Retention time: 10.93 minutes. Solvent A: H$_2$O/0.1% TFA; solvent B: CH$_3$CN/0.085% TFA. Column type: HYPERPEP 300A.

The (E)-2'-[(1-amino-1-cyclopentyl)carbonyl]-2(R)-[1 (S)-[(tetrahydro-2(RS)-pyranyloxy)carbamoyl]-4-phenyl-3-butenyl]-2'-isobutyl-4-methylvalerohydrazide used as the starting material was prepared as follows:

(i) A solution of 0.459 g of (E)-2(R)-[1(S)-[(tetrahydro-2 (RS)-pyranyloxy)carbamoyl]-4-phenyl-3-butenyl]-2'-isobutyl-4-methylvalerohydrazide in 3 ml of dichloromethane was treated under nitrogen at room temperature with 0.119 g of pyridine and a solution of the acid chloride prepared from 0.42 g of N-(9-fluorenylmethyloxycarbonyl)-cycloleucine in 3 ml of dichloromethane. The mixture was stirred at room temperature for 16 hours and diluted with ethyl acetate. The solution was washed with 5% aqueous sodium hydrogen carbonate solution, water and saturated sodium chloride solution and then dried over anhydrous magnesium sulphate. The solvent was evaporated to give a foam, which was crystallized from diethyl ether/hexane to give 0.71 g of (E)-2'-[(1-(9-fluorenylmethyloxycarbonylamino)-1-cyclopentyl)carbonyl]-2(R)-[1(S)-[(tetrahydro-2(RS)-pyranyloxy)carbamoy]-4-phenyl-3-butenyl]-2'-isobutyl-4-methylvalerohydrazide as a white solid.

MS: 793 (M+H)$^+$.

(ii) A solution of 0.69 g of (E)-2'-[(1-(9-fluorenylmethyloxycarbonylamino)-1-cyclopentyl) carbonyl]-2(R)-[1(S)-[(tetrahydro-2(RS)-pyranyloxy) carbamoyl]-4-phenyl-3-butenyl]-2'-isobutyl-4-methylvalerohydrazide in a mixture of 6.4 ml of dichloromethane and 1.6 ml of piperidine was stirred at room temperature for 1 hour. The solution was evaporated and the residue was treated with diethyl ether. The ethereal solution was filtered and evaporated. Chromatography on silica gel using methanol/dichloromethane (1:33) for the elution followed by evaporation gave 0.36 g of (E)-2'-[(1-amino-1-cyclopentyl)carbonyl]-2(R)-[1(S)-[(tetrahydro-2 (RS)-pyranyloxy)carbamoyl]-4-phenyl-3-butenyl]-2'-isobutyl-4-methylvalerohydrazide in the form of a white foam.

MS: 571 (M+H)$^+$.

EXAMPLE 7

(E)-2'-[(1-Amino-1-cyclopropyl)carbonyl]-2(R)-[1 (S)-(hydroxycarbamoyl)-4-phenyl-3-butenyl]-2'-isobutyl-14-methylvalerohydrazide p-toluenesulphonate In a manner analogous to that described in Example 6, but using 1-[N-(9-fluorenylmethyloxycarbonyl)amino]-cyclopropanecarboxylic acid in place of N-(9-fluorenylmethyloxycarbonyl)-cycloleucine, there was obtained (E)-2'-[(1-amino-1-cyclopropyl)carbonyl]-2(R)-[1 (S)-(hydroxycarbamoyl)-4-phenyl-3-butenyl]-2'-isobutyl-4-methylvalerohydrazide p-toluenesulphonate as a white solid.

MS: 459 (M+H)+. HPLC: Gradient elution using solvent A containing 5% solvent B increasing to 95% solvent B over 15 minutes; flow rate 1 ml/minute. Retention time: 11.41 minutes. Solvent A: $H_2O$/0.1% TFA; solvent B: $CH_3CN$/0.085% TFA. Column type: HYPERPEP 300A.

EXAMPLE 8

(E)-2'-(β-Alanyl)-2(R)-[1(S)-(hydroxycarbamoyl)-4-phenyl-3-butenyl]-2'-isobutyl-4-methylvalerohydrazide hydrochloride A solution of 0.47 g of (E)-2'-(N-tert.-butoxycarbonyl-β-alanyl)-2(R)-[1(S)-[(tetrahydro-2(RS)-pyranyloxy)-carbamoyl]-4-phenyl-3-butenyl]-2'-isobutyl-4-methylvalerohydrazide in 5 ml of 4M hydrogen chloride in dioxan was stirred for 2 hours at room temperature and diluted with diethyl ether. The solid was filtered off, washed with diethyl ether and dried to give 0.29 g of (E)-2'-(β-alanyl)-2(R)-[1(S)-(hydroxycarbamoyl)-4-phenyl-3-butenyl]-2'-isobutyl-4-methylvalerohydrazide hydrochloride in the form of a white solid.

MS: 447 (M+H)+. HPLC: Gradient elution using solvent A containing 5% solvent B increasing to 95% solvent B over 15 minutes; flow rate 1 ml/minute. Retention time: 10.54 minutes. Solvent A: $H_2O$/0.1% TFA; solvent B: $CH_3CN$/0.085% TFA. Column type: HYPERPEP 300A.

The (E)-2'-(N-tert.-butoxycarbonyl-β-alanyl)-2(R)-[1(S)-[(tetrahydro-2(RS)-pyranyloxy)-carbamoyl]-4-phenyl-3-butenyl]-2'-isobutyl-4-methylvalerohydrazide used as the starting material was prepared as follows:

A solution of 0.459 g of (E)-2(R)-[1(S)-[(tetrahydro-2(RS)-pyranyloxy)-carbamoyl]-4-phenyl-3-butenyl]-2'-isobutyl-4-methylvalerohydrazide in 5 ml of dimethylformamide was cooled to 0° C. and treated with 0.378 g of N-tert.-butoxycarbonyl-β-alanine and 0.383 g of 1-ethyl-3-(3-dimethylaminopropyl)carbodiimide hydrochloride. The mixture was stirred at room temperature for 16 hours and diluted with ethyl acetate. The solution was washed in succession with water, 5% citric acid solution and water, dried over anhydrous magnesium sulphate and evaporated. Chromatography on silica gel using ethyl acetate/hexane (1:1) for the elution followed by evaporation gave 0.48 g of (E)-2'-(N-tert.-butoxycarbonyl-β-alanyl)-2(R)-[1(S)-[(tetrahydro-2(RS)-pyranyloxy)-carbamoyl]-4-phenyl-3-butenyl]-2'-isobutyl-4-methylvalerohydrazide in the form of a white foam.

MS: 631 (M+H)+.

EXAMPLE 9

(E)-2(R)-[1(S)-(Hydroxycarbamoyl)-4-phenyl-3-butenyl]-2'-isobutyl-4-methyl-2'-[(2(R)-piperidinyl)carbonyl]valerohydrazide hydrochloride In a manner analogous to that described in Example 8, but using N-tert.-butoxycarbonyl-R-pipecolinic acid in place of N-tert.-butoxycarbonyl-β-alanine, there was obtained (E)-2(R)-[1(S)-(hydroxycarbamoyl)-4-phenyl-3-butenyl]-2'-isobutyl-4-methyl-2'-[(2(R)-piperidinyl)carbonyl]valerohydrazide hydrochloride in the form of a white solid.

MS: 487 (M+H)+. HPLC: Gradient elution using solvent A containing 5% solvent B increasing to 95% solvent B over 15 minutes; flow rate 1 mni/minute. Retention time: 11.02 minutes. Solvent A: $H_2O$/0.1% TFA; solvent B: $CH_3CN$/0.085% TFA. Column type: HYPERPEP 300A.

EXAMPLE 10

(E)-2(R)-[1(S)-(Hydroxycarbamoyl)-4-phenyl-3-butenyl]-2'-isobutyl-4-methyl-2'-[(2(S)-piperidinyl)carbonyl]valerohydrazide hydrochloride In a manner analogous to that described in Example 8, but using N-tert.-butoxycarbonyl-S-pipecolinic acid in place of N-tert.-butoxycarbonyl-β-alanine, there was obtained (E)-2(R)-[1(S)-(hydroxycarbamoyl)-4-phenyl-3-butenyl]-2'-isobutyl-4-methyl-2'-[(2(S)-piperidinyl)carbonyl]valerohydrazide hydrochloride in the form of a white solid.

MS: 487 (M+H)+. HPLC: Gradient elution using solvent A containing 5% solvent B increasing to 95% solvent B over 15 minutes; flow rate 1 ml/minute. Retention time: 10.825 minutes. Solvent A: $H_2O$/0.1% TFA; solvent B: $CH_3CN$/0.085% TFA. Column type: HYPERPEP 300A.

EXAMPLE 11

(E)-2'-(2-Acetamidoacetyl)-2(R)-[1(S)-(hydroxycarbamoyl)-4-phenyl-3-butenyl]-2'-isobutyl-4-methylvalerohydrazide A solution of 0.436 g of (E)-2'-(2-acetamidoacetyl)-2(R)-[1(S)-[(tetrahydro-2(RS)-pyranyloxy)carbamoyl]-4-phenyl-3-butenyl]-2'-isobutyl-4-methylvalerohydrazide in 10 ml of methanol was treated with 0.044 g of p-toluenesulphonic acid. The mixture was stirred for 1.5 hours at room temperature and evaporated. The residue was triturated with diethyl ether, filtered off and dried to give 0.333 g of (E)-2'-(2-acetamidoacetyl)-2(R)-[1(S)-(hydroxycarbamoyl)-4-phenyl-3-butenyl]-2-isobutyl-4-methylvalerohydrazide in the form of a white solid.

MS: 475 (M+H)+. HPLC: Gradient elution using solvent A containing 5% solvent B increasing to 95% solvent B over 15 minutes; flow rate 1 ml/minute. Retention time: 10.63 minutes. Solvent A: $H_2O$/0.1% TFA; solvent B: $CH_3CN$/0.085% TFA. Column type: HYPERPEP 300A.

The (E)-2'-(2-acetamidoacetyl)-2(R)-[1(S)-[(tetrahydro-2(RS)-pyranyloxy)-carbamoyl]-4-phenyl-3-butenyl]-2'-isobutyl-4-methylvalerohydrazide used as the starting material was prepared as follows:

A solution of 0.459 g of (E)-2(R)-[1(S)-[(tetrahydro-2(RS)-pyranyloxy)carbamoyl]-4-phenyl-3-butenyl]-2'-isobutyl-4-methylvalerohydrazide in 4 ml of dimethylformamide was cooled to 0° C. and treated with 0.351 g of N-acetyl-glycine and 690 mg of 1-ethyl-3-(3-dimethylaminopropyl)carbodiimide hydrochloride. The mixture was stirred at room temperature for 16 hours and evaporated. The residue in ethyl acetate was washed with 5% sodium hydrogen carbonate solution and water, dried over anhydrous magnesium sulphate and evaporated. The resulting solid was triturated with diethyl ether and filtered off to give 0.436 g of (E)-2'-(2-acetamidoacetyl)-2(R)-[1(S)-[(tetrahydro-2(RS)-pyranyloxy)carbamoyl]-4-phenyl-3-butenyl]-2'-isobutyl-4-methylvalerohydrazide in the form of a white solid.

MS: 559 (M+H)+.

EXAMPLE 12

(E)-2(R)-[1(S)-(Hydroxycarbanoyl)-4-phenyl-3-butenyl]-2'-isobutyl-4-methyl-2'-(2-ureidoacetyl)valerohydrazide A solution of 0.51 g of (E)-2(R)-[1(S)-[(tetrahydro-2(RS)-pyranyloxy)carbamoyl]-4-phenyl-3-butenyl]-2'-isobutyl-4-methyl-2'-(2-ureidoacetyl)valerohydrazide dissolved in 5 ml of 4M hydrogen chloride in dioxan was stirred for 2 hours at room temperature and diluted with diethyl ether. The solid was filtered off, washed with diethyl ether and dried to give 0.36 g of (E)-2(R)-[1(S)-(hydroxycarbamoyl)-4-phenyl-3-butenyl]-2'-isobutyl-4-methyl-2'-(2-ureidoacetyl)valerohydrazide in the form of a white solid.

MS: 476 (M+H)+. HPLC: Gradient elution using solvent A containing 5% solvent B increasing to 95% solvent B over 15 minutes; flow rate 1 ml/minute. Retention time: 10.30 minutes. Solvent A: $H_2O/0.1\%$ TFA; solvent B: $CH_3CN/0.085\%$ TFA. Column type: HYPERPEP 300A.

The (E)-2(R)-[1(S)-[(tetrahydro-2(RS)-pyranyloxy) carbamoyl]-4-phenyl-3-butenyl]-2'-isobutyl-4-methyl-2'-(2-ureidoacetyl)valerohydrazide used as the starting material was prepared in a manner analogous to Example 11 using hydantoic acid in place of N-acetyl-glycine.

EXAMPLE 13

(E)-2'-(2-Hydroxyacetyl)-2(R)-[1(S)-(hydroxycarbamoyl)-4-phenyl-3-butenyl]-2'-isobutyl-4-methylvalerohydrazide In a manner analogous to that described in Example 11, but using hydroxyacetic acid in place of N-acetyl-glycine, there was obtained (E)-2'-(2-hydroxyacetyl)-2(R)-[1(S)-(hydroxycarbamoyl)-4-phenyl-3-butenyl]-2'-isobutyl-4-methylvalerohydrazide in the form of a white solid.

MS: 434 $(M+H)^+$. HPLC: Gradient elution using solvent A containing 5% solvent B increasing to 95% solvent B over 15 minutes; flow rate 1 ml/minute. Retention time: 10.69 minutes. Solvent A: $H_2O/0.1\%$ TFA; solvent B: $CH_3CN/0.085\%$ TFA. Column type: HYPERPEP 300A.

EXAMPLE 14

(E)-2(R)-[1(S)-(Hydroxycarbamoyl)-4-phenyl-3-butenyl]-2'-isobutyl-4-methyl-2'-[(4-pyridyl)carbonyl]valerohydrazide p-toluenesulphonate In a manner analogous to that described in Example 11, but using 4-pyridinecarboxylic acid in place of N-acetyl-glycine, there was obtained (E)-2(R)-[1(S)-(hydroxycarbamoyl)-4-phenyl-3-butenyl]-2'-isobutyl-4-methyl-2'-[(4-pyridyl)-carbonyl]-valerohydrazide p-toluenesulphonate in the form of an off-white solid.

MS: 481 $(M+H)^+$. HPLC: Gradient elution using solvent A containing 5% solvent B increasing to 95% solvent B over 15 minutes; flow rate 1 ml/minute. Retention time: 10.915 minutes. Solvent A: $H_2O/0.1\%$ TFA; solvent B: $CH_3CN/0.085\%$ TFA. Column type: HYPERPEP 300A.

EXAMPLE 15

(E)-2(R)-[1(S)-(Hydroxycarbamoyl)-4-phenyl-3-butenyl]-2'-isobutyl-4-methyl-2'-[(3-pyridyl)carbonyl]valerohydrazide p-toluenesulphonate In a manner analogous to that described in Example 11, but using 3-pyridinecarboxylic acid in place of N-acetyl-glycine, there was obtained (E)-2(R)-[1(S)-(hydroxycarbamoyl)-4-phenyl-3-butenyl]-2'-isobutyl-4-methyl-2'-[(3-pyridyl)carbonyl]valerohydrazide p-toluenesulphonate in the form of a white solid.

MS: 481 $(M+H)^+$. HPLC: Gradient elution using solvent A containing 5% solvent B increasing to 95% solvent B over 15 minutes; flow rate 1 ml/minute. Retention time: 11.00 minutes. Solvent A: $H_2O/0.1\%$ TFA; solvent B: $CH_3CN/0.085\%$ TFA. Column type: HYPERPEP 300A.

EXAMPLE 16

(E)-2(R)-[1(S)-(Hydroxycarbamoyl)-4-phenyl-3-butenyl]-2'-isobutyl-4-methyl-2'-[(2-pyrrolyl)carbonyl]valerohydrazide p-toluenesulphonate A solution of 0.225 g (E)-2(R)-[1(S)-[(tetrahydro-2(RS)-pyranyloxy)carbamoyl]-4-phenyl-3-butenyl]-2'-isobutyl-4-methyl-2'-[(2-pyrrolyl)carbonyl]-valerohydrazide in 5 ml of methanol was treated with 0.095 g of p-toluenesulphonic acid. The mixture was stirred for 2 hours at room temperature and evaporated. The residue was triturated with hexane, filtered off and dried to give 0.220 g of (E)-2(R)-[1(S)-(hydroxycarbamoyl)-4-phenyl-3-butenyl]-2'-isobutyl-4-methyl-2'-[(2-pyrrolyl)carbonyl]valerohydrazide p-toluenesulphonate in the form of a white solid.

MS: 469 $(M+H)^+$. HPLC: Gradient elution using solvent A containing 5% solvent B increasing to 95% solvent B over 15 minutes; flow rate 1 ml/minute. Retention time: 11.93 minutes. Solvent A: $H_2O/0.1\%$ TFA; solvent B: $CH_3CN/0.085\%$ TFA. Column type: HYPERPEP 300A.

The (E)-2(R)-[1(S)-[(tetrahydro-2(RS)-pyranyloxy)carbamoyl]-4-phenyl-3-butenyl]-2'-isobutyl-4-methyl-2'-[(2-pyrrolyl)carbonyl]valerohydrazide used as the starting material was prepared as follows:

A solution of 0.459 g of (E)-2(R)-[1(S)-[(tetrahydro-2(RS)-pyranyloxy)carbamoyl]-4-phenyl-3-butenyl]-2'-isobutyl-4-methylvalerohydrazide in 5 ml of dichloromethane was treated under nitrogen at 0° C. with 0.28 ml of triethylamine and a solution of the acid chloride prepared from 0.166 g of 2-pyrrolecarboxylic acid in 3 ml of dichloromethane. The mixture was stirred at 0° C. for 2 hours and evaporated. The residue was dissolved in ethyl acetate. The solution was washed with 5% aqueous sodium hydrogen carbonate solution, water, 5% citric acid solution and saturated sodium chloride solution, dried over anhydrous magnesium sulphate and was evaporated to give a solid. Chromatography of this solid on silica gel using dichloromethane/methanol (50:1) for the elution followed by evaporation and trituration with diethyl ether gave 0.225 g of (E)-2(R)-[1(S)-[(tetrahydro-2(RS)-pyranyloxy)carbamoyl]-4-phenyl-3-butenyl]-2'-isobutyl-4-methyl-2'-[(2-pyrrolyl)carbonyl]valerohydrazide in the form of a white solid.

MS: 553 $(M+H)^+$.

EXAMPLE 17

(E)-2(R)-[1(S)-(Hydroxycarbamoyl)-4-phenyl-3-butenyl]-2'-(2(RS)-hydroxypropionyl)-2'-isobutyl-4-methylvalerohydrazide A solution of 0.71 g of (E)-2(R)-[1(S)-[(tetrahydro-2(RS)-pyranyloxy)carbamoyl]-4-phenyl-3-butenyl]-2'-(2(RS)-hydroxypropionyl)-2'-isobutyl-4-methylvalerohydrazide in 8 ml of methanol was treated with 0.071 g of p-toluenesulphonic acid. The mixture was stirred for 1 hour at room temperature and evaporated to give a foam. This foam was triturated with diethyl ether, filtered off and dried to give 0.425 g of (E)-2(R)-[1(S)-(hydroxycarbamoyl)-4-phenyl-3-butenyl]-2'-(2(RS)-hydroxypropionyl)-2'-isobutyl-4-methylvalerohydrazide in the form of a white solid.

MS: 448 $(M+H)^+$. HPLC: Gradient elution using solvent A containing 20% solvent B for 5 minutes increasing to 50% solvent B from 5 minutes to 35 minutes; flow rate 1 ml per minute. Retention time: 18.34 and 18.64 minutes. Solvent A: $H_2O/0.1\%$ TFA; solvent B: $CH_3CN/0.085\%$ TFA. Column type: HYPERPEP 300A. HPLC: Elution using 22.5% $CH_3CN$ in water; flow rate 1 ml per minute. Retention time: 27.2 and 29.5 minutes. Column type: Symmetry $C_{18}$ 5$\mu$.

The (E)-2(R)-[1(S)-[(tetrahydro-2(RS)-pyranyloxy)carbamoyl]-4-phenyl-3-butenyl]-2'-(2(RS)-hydroxypropionyl)-2'-isobutyl-4-methylvalerohydrazide used as the starting material was prepared as follows:

(i) A solution of 0.918 g of (E)-2(R)-[1(S)-[(tetrahydro-2(RS)-pyranyloxy)carbamoyl]-4-phenyl-3-butenyl]-2'-isobutyl-4-methylvalerohydrazide in 16 ml of dichloromethane was treated under nitrogen at 0° C. with 0.557 ml of triethylamine and a solution of the acid chloride prepared from 0.396 g of acetyl-RS-lactic acid in 5 ml of dichloromethane. The mixture was stirred at room temperature for 2 hours and diluted with dichloromethane. The solution was washed with 5% aqueous sodium hydrogen carbonate solution, water, 5% citric acid solution and saturated sodium chloride solution, dried over anhydrous magnesium sulphate and evaporated to give a foam. Trituration of this foam with hexane gave 1.113 g of (E)-2(R)-[1(S)-[(tetrahydro-2(RS)-pyranyloxy)carbamoyl]-4-phenyl- 3-butenyl]-2'-(2(RS)-acetoxypropionyl)-2'-isobutyl-4-methylvalerohydrazide in the form of a white solid.

MS: 574 (M+H)$^+$.

(ii) A solution of 1.11 g of (E)-2(R)-[1(S)-[(tetrahydro-2(RS)-pyranyloxy)carbamoyl]-4-phenyl-3-butenyl]-2'-(2(RS)-acetoxypropionyl)-2'-isobutyl-4-methylvalerohydrazide in a mixture of 8 ml of methanol and 4 ml of water was treated with 0.524 g of potassium carbonate. The mixture was stirred at room temperature for 2 hours, diluted with water and extracted with ethyl acetate. The ethyl acetate solution was washed with water, dried over anhydrous magnesium sulphate and was evaporated to give a foam. Trituration of this foam with diethyl ether gave 0.71 g of (E)-2(R)-[1(S)-[(tetrahydro-2(RS)-pyranyloxy)carbamoyl]-4-phenyl-3-butenyl]-2'-(2(RS)-hydroxypropionyl)-2'-isobutyl-4-methylvalerohydrazide in the form of a white solid.

MS: 532 (M+H)$^+$.

EXAMPLE 18

(E)-2(R)-[1(S)-(Hydroxycarbamoyl)-4-phenyl-3-butenyl]-2'-isobutyl-4-methyl-2'-(D-seryl)valerohydrazide p-toluenesulphonate A solution of 0.175 g (E)-2(R)-[1(S)-[(tetrahydro-2(RS)-pyranyloxy)carbamoyl]-4-phenyl-3-butenyl]-2'-isobutyl-4-methyl-2'-(D-seryl)valerohydrazide in 2 ml of methanol was treated with 0.073 g of p-toluenesulphonic acid. The mixture was stirred for 3 hours at room temperature and evaporated. The residue was triturated with diethyl ether, filtered off and dried to give 0.160 g of (E)-2(R)-[1(S)-(hydroxycarbamoyl)-4-phenyl-3-butenyl]-2'-isobutyl-4-methyl-2'-(D-seryl)valerohydrazide p-toluenesulphonate in the form of a white solid.

MS: 463 (M+H)$^+$. HPLC: Gradient elution using solvent A containing 5% solvent B increasing to 95% solvent B over 15 minutes; flow rate 1 ml/minute. Retention time: 10.75 minutes. Solvent A: H$_2$O/0.1% TFA; solvent B: CH$_3$CN/0.085% TFA. Column type: HYPERPEP 300A.

The (E)-2(R)-[1(S)-[(tetrahydro-2(RS)-pyranyloxy)carbamoyl]-4-phenyl-3-butenyl]-2'-isobutyl-4-methyl-2'-(D-seryl)valerohydrazide used as the starting material was prepared as follows:

(i) A solution of 0.624 g of (E)-2(R)-[1(S)-(tert-butoxycarbonyl)-4-phenyl-3-butenyl]-2'-isobutyl-4-methylvalerohydrazide in 10 ml of dichloromethane was treated at room temperature under nitrogen with 0.158 g of pyridine and a solution of 0.78 g of N-(9-fluorenylmethyloxycarbonyl)-O-tert.butyl-D-serine acid fluoride in 5 ml of dichloromethane. The mixture was stirred at room temperature for 16 hours and diluted with ethyl acetate. The solution was washed with 2M hydrochloric acid, water, 5% aqueous sodium hydrogen carbonate solution and saturated sodium chloride solution and dried over anhydrous magnesium sulphate. The solvent was evaporated to give 1.07 g of (E)-2(R)-[1(S)-(tert-butoxycarbonyl)-4-phenyl-3-butenyl]-2'-isobutyl-2'[N-(9-fluorenylmethyloxycarbonyl)-O-tert.butyl-D-seryl]-4-methylvalerohydrazide in the form of a white foam.

MS: 782 (M+H)$^+$.

(ii) A solution of 1.05 g of (E)-2(R)-[1(S)-(tert-butoxycarbonyl)-4-phenyl-3-butenyl]-2'-isobutyl-2'-[N-(9-fluorenylmethyloxycarbonyl)-O-tert.butyl-D-seryl]-4-methylvalerohydrazide in 5 ml of dichloromethane was treated at room temperature under nitrogen with 5 ml of trifluoroacetic acid. The mixture was stirred at room temperature for 2.5 hours and evaporated. Final traces of trifluoroacetic acid were removed by the addition and evaporation of three 10 ml portions of toluene. The residue in diethyl ether was treated with hexane to yield 0.78 g of (E)-2(R)-[1(S)-(carboxy)-4-phenyl-3-butenyl]-2'-isobutyl-2'[N-(9-fluorenylmethyloxycarbonyl)-D-seryl]-4-methylvalerohydrazide as a white solid.

MS: 670 (M+H)$^+$.

(iii) The carboxylic acid prepared in the part (ii) was dissolved in 3 ml of dimethylformamide, cooled to 0° C. and treated in succession with 0.68 g of O-(tetrahydro-2H-pyran-2(RS)-yl)hydroxylamine and 0.25 g of 1-ethyl-3-(3-dimethylaminopropyl)carbodiimide hydrochloride. The mixture was left to come to room temperature and was stirred overnight and then diluted with ethyl acetate. The solution was washed with 5% aqueous sodium hydrogen carbonate solution, water, 5% citric acid solution and saturated sodium chloride solution, dried over anhydrous magnesium sulphate and evaporated to give a foam. The residue in dichloromethane was treated with hexane and yielded 0.49 g of (E)-2(R)-[1(S)-[(tetrahydro-2(RS)-pyranyloxy)carbamoyl]-4-phenyl-3-butenyl]-2'-isobutyl- 2'[N-(9-fluorenylmethyloxycarbonyl)-D-seryl]-4-methylvalerohydrazide in the form of a white solid.

MS: 769 (M+H)$^+$.

(iv) A solution of 0.48 g of (E)-2(R)-[1(S)-[(tetrahydro-2(RS)-pyranyloxy)carbamoyl]-4-phenyl-3-butenyl]-2'-isobutyl-2'-[N-(9-fluorenylmethyloxycarbonyl)-D-seryl]-4-methylvalerohydrazide in a mixture of 5 ml of dichloromethane and 1 ml of piperidine was stirred at room temperature for 1.75 hours. The solution was evaporated to give a solid. Chromatography on silica gel using methanol/dichloromethane (1:12) for the elution followed by evaporation gave 0.18 g of (E)-2(R)-[1(S)-[(tetrahydro-2(RS)-pyranyloy)carbamoyl]-4-phenyl-3-butenyl]-2'-isobutyl-4-methyl-2'-(D-seryl)valerohydrazide in the form of a white solid.

MS: 547 (M+H)$^+$.

EXAMPLE 19

(E)-2(R)-[1(S)-(Hydroxycarbamoyl)-4-phenyl-3-butenyl]-2'-isobutyl-4-methyl-2'-(L-seryl)valerohydrazide p-toluenesulphonate In a manner analogous to that described in Example 18, but using N-(9-fluorenylmethyloxycarbonyl)-O-tert.butyl-L-serine acid fluoride in place of N-(9-fluorenylmethyloxycarbonyl)-O-tert.butyl-D-serine acid fluoride, there was obtained (E)-2(R)-[1(S)-(hydroxycarbamoyl)-4-phenyl-3-butenyl]-2'-isobutyl-4-methyl-2'-seryl)valerohydrazide p-toluenesulphonate in the form of a white solid.

MS: 463 (M+H)$^+$. HPLC: Gradient elution using solvent A containing 5% solvent B increasing to 95% solvent B over

EXAMPLE 20

(E)-2(R)-[1(S)-(Hydroxycarbamoyl)-4-phenyl-3-butenyl]-2'-(2(R)-hydroxypropionyl)-2'-isobutyl-4-methylvalerohydrazide A solution of 2.12 g of (E)-2(R)-[1(S)-[(tetrahydro-2(RS)-pyranyloxy)carbamoyl]-4-phenyl-3-butenyl]-2'-(2(R)-hydroxypropionyl)-2'-isobutyl-4-methylvalerohydrazide in 20 ml of methanol was treated with 0.212 g of p-toluenesulphonic acid. The mixture was stirred for 0.5 hour at room temperature and evaporated to give a foam. This foam in ethyl acetate was washed with 5% sodium hydrogen carbonate solution and water, dried over anhydrous magnesium sulphate and evaporated to low volume. The solid which separated was washed with cold ethyl acetate and dried to give 1.584 g of (E)-2(R)-[1(S)-(hydroxycarbamoyl)-4-phenyl-3-butenyl]-2'-(2(R)-hydroxypropionyl)-2'-isobutyl-4-methylvalerohydrazide in the form of a white solid.

MS: 448 (M+H)$^+$. HPLC: Elution using 22.5% CH$_3$CN in water; flow rate 1 ml per minute. Retention time: 27.1 minutes. Column type: Symmetry C$_{18}$ 5$\mu$.

The (E)-2(R)-[1(S)-[(tetrahydro-2(RS)-pyranyloxy) carbamoyl]-4-phenyl-3-butenyl]-2'-(2(R)-hydroxypropionyl)-2'-isobutyl-4-methylvalerohydrazide used as the starting material was prepared as follows:

(i) A solution of 2.318 g of (E)-2(R)-[1(S)-[(tetrahydro-2 (RS)-pyranyloxy)carbamoyl]-4-phenyl-3-butenyl]-2'-isobutyl-4-methylvalerohydrazide in 12 ml of dimethylformamide was treated under nitrogen at 0° C. with 1.47 g of acetyl-R-lactic acid and 2.32 g of 1-ethyl-3-(3-dimethylaminopropyl)carbodiimide hydrochloride. The mixture was stirred at room temperature for 3 hours and evaporated. The residue in ethyl acetate was washed with 5% aqueous sodium hydrogen carbonate solution, water, 5% citric acid solution, 5% aqueous sodium hydrogen carbonate solution and saturated sodium chloride solution, dried over anhydrous magnesium sulphate and evaporated to give a foam. This foam in diethyl ether was treated with hexane to give 2.78 g of (E)-2(R)-[1(S)-[(tetrahydro-2(RS)-pyranyloxy)carbamoyl]-4-phenyl-3-butenyl]-2'-(2(R)-acetoxypropionyl)-2'-isobutyl-4-methylvalerohydrazide in the form of a white solid.

MS: 574 (M+H)$^+$.

(ii) A solution of 2.77 g of (E)-2(R)-[1(S)-[(tetrahydro-2 (RS)-pyranyloxy)carbamoyl]-4-phenyl-3-butenyl]-2'-(2(R)-acetoxypropionyl)-2'-isobutyl-4-methylvalerohydrazide in a mixture of 20 ml of methanol and 10 ml of water was treated with 1.35 g of potassium carbonate. The mixture was stirred at room temperature for 2 hours, diluted with water and extracted with ethyl acetate. The ethyl acetate phase was washed with water, dried over anhydrous magnesium sulphate and evaporated to give a foam. Trituration of this foam with diethyl ether gave 2.12 g of (E)-2(R)-[1(S)-[(tetrahydro-2(RS)-pyranyloxy)carbamoyl]-4-phenyl-3-butenyl]-2'-(2(R)-hydroxypropionyl)-2'-isobutyl-4-methylvalerohydrazide in the form of a white solid.

MS: 532 (M+H)$^+$.

EXAMPLE 21

(E)-2(R)-[1(S)-(Hydroxycarbamoyl)-4-phenyl-3-butenyl]-2'-isobutyl-4-methyl-2'-(3-azetidinyl) carbonyl]valerohydrazide hydrochloride In a manner analogous to that described in Example 8, but using N-tert.-butyloxycarbonyl-azetidine-3-carboxylic acid in place of N-tert.-butoxycarbonyl-β-alanine, there was obtained (E)-2(R)-[1(S)-(hydroxycarbamoyl)-4-phenyl-3-butenyl]-2'-isobutyl-4-methyl-2'-[(3-azetidinyl)carbonyl] valerohydrazide hydrochloride in the form of a white solid.

MS: 459 (M+H)$^+$. HPLC: Gradient elution using solvent A containing 5% solvent B increasing to 95% solvent B over 15 minutes; flow rate 1 ml/minute. Retention time: 11.043 minutes. Solvent A: H$_2$O/0.1% TFA; solvent B: CH$_3$CN/ 0.085% TFA. Column type: HYPERPEP 300A.

EXAMPLE 22

(E)-2'-(L-Alanyl)-2(R)-[1(S)-(hydroxycarbamoyl)-4-phenyl-3-butenyl]-2'-isobutyl-4-methylvalerohydrazide hydrochloride In a manner analogous to that described in Example 8, but using N-tert.-butoxycarbonyl-L-alanine in place of N-tert.-butoxycarbonyl-β-alanine, there was obtained (E)-2'-(L-alanyl)-2(R)-[1(S)-(hydroxycarbamoyl)-4-phenyl-3-butenyl]-2'-isobutyl-4-methylvalerohydrazide hydrochloride as a white solid.

MS: 447 (M+H)$^+$. HPLC: Gradient elution using solvent A containing 5% solvent B increasing to 95% solvent B over 15 minutes; flow rate 1 ml/minute. Retention time: 10.35 minutes. Solvent A: H$_2$O/0.1% TFA; solvent B: CH$_3$CN/ 0.085% TFA. Column type: HYPERPEP 300A.

EXAMPLE 23

(E)-2'-(D-Alanyl)-2(R)-[1(S)-(hydroxycarbamoyl)-4-phenyl-3-butenyl]-2'-isobutyl-4-methylvalerohydrazide p-toluenesulphonate A solution of 0.750 g of (E)-2'-(D-alanyl)-2(R)-[1(S)-(tetrahydro-2(RS)-pyranyloxy)carbamoyl]-4-phenyl-3-butenyl]-2'-isobutyl-4-methylvalerohydrazide in 20 ml of methanol was treated with 0.300 g of p-toluenesulphonic acid monohydrate. The mixture was stirred for 3 hours at room temperature and evaporated. The residue was triturated with diethyl ether, filtered off and dried to give 0.858 g of (E)-2'-(D-alanyl)-2(R)-[1(S)-(hydroxycarbamoyl)-4-phenyl-3-butenyl]-2'-isobutyl-4-methylvalerohydrazide p-toluenesulphonate in the form of a white solid.

MS: 447 (M+H)$^+$. HPLC: Gradient elution using solvent A containing 5% solvent B increasing to 95% solvent B over 15 minutes; flow rate 1 ml per minute. Retention time: 10.65 minutes. Solvent A: H$_2$O/0.1% TFA; solvent B: CH$_3$CN/ 0.085% TFA. Column type: HYPERPEP 300A.

The (E)-2'-(D-alanyl)-2(R)-[1(S)-(tetrahydro-2(RS)-pyranyloxy)carbamoyl]-4-phenyl-3-butenyl]-2'-isobutyl-4-methylvalerohydrazide used as the starting material was prepared as follows:

(i) In a manner analogous to that described in Example 1, parts (iv) and (v), but using N-(9-fluorenylmethoxycarbonyl)-D-alanine acid chloride in place of trifluoroacetic anhydride, there was obtained (E)-2(R)-[1 (S)-(carboxy)-4-phenyl-3-butenyl]-2'-isobutyl-2'-[N-(9-fluorenylmethoxycarbonyl)-D-alanyl]-4-methylvalerohydrazide in the form of a white foam.

(ii) A solution of 1.85 g of (E)-2(R)-[1(S)-(carboxy)-4-phenyl-3-butenyl]-2'-isobutyl-2'-[N-(9-fluorenylmethoxycarbonyl)-D-alanyl]-4-methylvalerohydrazide in 3 ml of dimethylformamide was treated with 0.60 g of O-(tetrahydro-2H-pyran-2(RS)-yl)hydroxylamine and 0.54 g of 1-ethyl-3-(3-dimethylaminopropyl)carbodiimide hydrochloride. The mixture was stirred overnight at room temperature and then diluted with ethyl acetate and washed with 5% aqueous citric acid, 5% aqueous sodium hydrogen carbonate and brine. The ethyl acetate layer was then dried over magnesium sulphate and evaporated. The residue was triturated with hexane/diethyl ether (2:1) to give 1.67 g of (E)-2(R)-[1(S)-(tetrahydro-2(RS)-pyranyloxy)carbamoyl]-4-phenyl-3-butenyl]-2'-isobutyl-2'-[N-(9-fluorenylmethoxycarbonyl)-D-alanyl]-4-methylvalerohydrazide in the form of a white solid.

MS: 753 (M+H)$^+$.

(iii) A solution of 1.67 g of (E)-2(R)-[1(S)-(tetrahydro-2(RS)-pyranyloxy)carbamoyl]-4-phenyl-3-butenyl]-2'-isobutyl-2'-[N-(9-fluorenylmethoxycarbonyl)-D-alanyl]-4-methylvalerohydrazide in a mixture of 20 ml of dichloromethane and 5 ml of piperidine was stirred at room temperature for 2 hours. The solution was evaporated and the residue was triturated with hexane/diethyl ether (2:1). The residue was purified by flash column chromatography on silica gel using methanol/dichloromethane (5:95) for the elution to give 0.75 g of (E)-2'-(D-alanyl)-2(R)-[1(S)-(tetrahydro-2(RS)-pyranyloxy)carbamoyl]-4-phenyl-3-butenyl]-2'-isobutyl-4-methylvalerohydrazide in the form of a white foam.

MS: 531 (M+H)$^+$.

EXAMPLE 24

(E)-2'-(2-Aminoacetyl)-2(R)-[1(S)-(hydroxycarbamoyl)-4-phenyl-3-butenyl]-2'-isobutyl-4-methylvalerohydrazide p-toluenesulphonate A solution of 0.355 g of (E)-2'-(2-aminoacetyl)-2(R)-[1(S)-(tetrahydro-2(RS)-pyranyloxy)carbamoyl]-4-phenyl-3-butenyl]-2'-isobutyl-4-methylvalerohydrazide in 10 ml of methanol was treated with 0.144 g of p-toluenesulphonic acid monohydrate. The mixture was stirred for 3 hours at room temperature and evaporated. The residue was triturated with diethyl ether, filtered off and dried to give 0.350 g of (E)-2'-(2-aminoacetyl)-2(R)-[1(S)-(hydroxycarbamoyl)-4-phenyl-3-butenyl]-2'-isobutyl-4-methylvalerohydrazide p-toluenesulphonate in the form of a white solid.

MS: 433 (M+H)$^+$. HPLC: Gradient elution using solvent A containing 5% solvent B increasing to 95% solvent B over 15 minutes; flow rate 1 ml per minute. Retention time: 10.38 minutes. Solvent A: H$_2$O/0.1% TFA; solvent B: CH$_3$CN/0.085% TFA. Column type: HYPERPEP 300A.

The (E)-2'-(2-aminoacetyl)-2(R)-[1(S)-(tetrahydro-2(RS)-pyranyloxy)carbamoyl]-4-phenyl-3-butenyl]-2'-isobutyl-4-methylvalerohydrazide used as the starting material was prepared as follows:

(i) In a manner analogous to that described in Example 23, parts (i) and (ii), but using (N-phthaloyl)-glycine acid chloride in place of N-(9-fluorenylmethoxycarbonyl)-D-alanine acid chloride, there was obtained (E)-2(R)-[1(S)-(tetrahydro-2(RS)-pyranyloxy)carbamoyl]-4-phenyl-3-butenyl]-2'-isobutyl-2'-[(N-phthaloyl)-2-aminoacetyl]-4-methylvalerohydrazide in the form of a white foam.

MS: 647 (M+H)$^+$.

(ii) A solution of 0.534 g of (E)-2(R)-[1(S)-(tetrahydro-2(RS)-pyranyloxy)carbamoyl]-2'-isobutyl-2'-[(N-phthaloyl)-2-aminoacetyl]-4-methylvalerohydrazide in a mixture of 8 ml of ethanol and 4 ml of tetrahydrofuran was treated with 5.5 ml of hydrazine hydrate. The mixture was stirred for 2 hours at room temperature and then evaporated. The residue was taken up in ethyl acetate and washed with water and brine. The ethyl acetate phase was then dried over magnesium sulphate and evaporated. The residue was triturated with hexane to give 0.355 g of (E)-2'-(2-aminoacetyl)-2(R)-[1(S)-(tetrahydro-2(RS)-pyranyloxy)carbamoyl]-4-phenyl-3-butenyl]-2'-isobutyl-4-methylvalerohydrazide in the form of a white solid.

EXAMPLE 25

(E)-2(R)-[1(S)-(Hydroxycarbamoyl)-4-phenyl-3-butenyl]-2'-isobutyl-2'-(L-leucyl)-4-methylvalerohydrazide hydrochloride 0.288 g of (E)-2(R)-[1(S)-(tetrahydro-2(RS)-pyranyloxy)carbamoyl]-4-phenyl-3-butenyl]-2'-isobutyl-2'-(N-tert.-butoxycarbonyl-L-leucyl)-4-methylvalerohydrazide was treated with 3 ml of 4M hydrogen chloride in dioxan. The mixture was stirred for 2 hours at room temperature and evaporated. The residue was triturated with diethyl ether and then filtered off and dried to give 0.159 g of (E)-2(R)-[1(S)-(hydroxycarbamoyl)-4-phenyl-3-butenyl]-2'-isobutyl-2'-(L-leucyl)-4-methylvalerohydrazide hydrochloride in the form of a white solid.

MS: 489 (M+H)$^+$. HPLC: Gradient elution using solvent A containing 5% solvent B increasing to 95% solvent B over 15 minutes; flow rate 1 ml per minute. Retention time: 11.50 minutes. Solvent A: H$_2$O/0.1% TFA; solvent B: CH$_3$CN/0.085% TFA. Column type: HYPERPEP 300A.

The (E)-2(R)-[1(S)-(tetrahydro-2(RS)-pyranyloxy)carbamoyl]-4-phenyl-3-butenyl]-2'-isobutyl-2'-(N-tert.-butoxycarbonyl-L-leucyl)-4-methylvalerohydrazide used as the starting material was prepared as follows:

In an analogous manner to that described in Example 1, part (viii), starting from (E)-2(R)-[1(S)-[(tetrahydro-2(RS)-pyranyloxy)carbamoyl]-4-phenyl-3-butenyl]-2'-isobutyl-4-methylvalerohydrazide and N-tert.-butoxycarbonyl-L-leucine acid fluoride there was obtained (E)-2(R)-[1(S)-(tetrahydro-2(RS)-pyranyloxy)carbamoyl]-4-phenyl-3-butenyl]-2'-isobutyl-2'-(N-tert.-butoxycarbonyl-L-leucyl)-4-methylvalerohydrazide in the form of a white solid.

MS: 673 (M+H)$^+$.

EXAMPLE 26

(E)-2(R)-[1(S)-(Hydroxycarbamoyl)-4-phenyl-3-butenyl]-2'-isobutyl-2'-(D-leucyl)-4-methylvalerohydrazide hydrochloride In a manner analogous to that described in Example 25, but using N-tert.-butoxycarbonyl-D-leucine acid fluoride in place of N-tert.-butoxycarbonyl-L-leucine acid fluoride there was obtained (E)-2(R)-[1(S)-(hydroxycarbamoyl)-4-phenyl-3-butenyl]-2'-isobutyl-2'-(D-leucyl)-4-methylvalerohydrazide hydrochloride in the form of a white solid.

MS: 489 (M+H)$^+$. HPLC: Gradient elution using solvent A containing 20% solvent B increasing to 99% solvent B over 15 minutes; flow rate 1 ml per minute. Retention time: 11.47 minutes. Solvent A: H$_2$O/0.1% TFA; solvent B: CH$_3$CN/0.085% TFA. Column type: HYPERPEP 300A.

EXAMPLE 27

(E)-2(R)-[1(S)-(Hydroxycarbamoyl)-4-phenyl-3-butenyl]-2'-isobutyl-4-methyl-2'-(N-methyl-L-alanyl)valerohydrazide hydrochloride A solution of 0.600 g of (E)-2(R)-[1(S)-(tetrahydro-2(RS)-pyranyloxy)carbamoyl]-4-phenyl-3-butenyl]-2'- isobutyl-4-methyl-2'-(N-methyl-N-tert.-butoxycarbonyl-L-alanyl)valerohydrazide in 3 ml of dioxan was treated with 1 ml of 4M hydrogen chloride in dioxan. The mixture was stirred for 2.5 hours at room temperature and then diluted with 50 ml of diethyl ether. Filtration gave 0.215 g of (E)-2(R)-[1(S)-(hydroxycarbamoyl)-4-phenyl-3-butenyl]-2'-isobutyl-4-methyl-2'-(N-methyl-L-alanyl) valerohydrazide hydrochloride in the form of a white solid.

MS: 461 (M+H)$^+$. HPLC: Gradient elution using solvent A containing 5% solvent B increasing to 95% solvent B over 15 minutes; flow rate 1 ml per minute. Retention time: 10.78 minutes. Solvent A: $H_2O$/0.1% TFA; solvent B: $CH_3CN$/0.085% TFA. Column type: HYPERPEP 300A.

The (E)-2(R)-[1(S)-(tetrahydro-2(RS)-pyranyloxy) carbamoyl]-4-phenyl-3-butenyl]-2'-isobutyl-4-methyl-2'-methyl-N-tert.-butoxycarbonyl-L-alanyl)valerohydrazide used as the starting material was prepared as follows:

A solution of 0.233 g of N-methyl-N-tert.-butoxycarbonyl-L-alanine in 10 ml of tetrahydrofuran was cooled to −10° C. and treated with 0.140 ml of N-ethylmorpholine and 0.143 ml of isobutyl chloroformate. The mixture was stirred for a further 10 minutes at −10° C. and then treated with 0.459 g of (E)-2(R)-[1(S)-[(tetrahydro-2(RS)-pyranyloxy)-carbamoyl]-4-phenyl-3-butenyl]-2'-isobutyl-4-methylvalerohydrazide. The mixture was allowed to warm to 0° C. and stirring was continued for 45 minutes. The mixture was then diluted with ethyl acetate and washed in sequence with 5% aqueous citric acid, 5% aqueous sodium hydrogen carbonate and brine. Drying over magnesium sulphate and evaporation gave 0.608 g of (E)-2(R)-[1(S)-(tetrahydro-2(RS)-pyranyloxy)carbamoyl]-4-phenyl-3-butenyl]-2'-isobutyl-4-methyl-2'-(N-methyl-N-tert.-butoxycarbonyl-L-alanyl)valerohydrazide in the form of a white solid.

MS: 645 (M+H)$^+$.

EXAMPLE 28

(E)-2(R)-[1(S)-(Hydroxycarbamoyl)-4-phenyl-3-butenyl]-2'-isobutyl-4-methyl-2'-(N-methyl-D-alanyl)valerohydrazide hydrochloride In a manner analogous to that described in Example 27, but using N-methyl-N-tert.-butoxycarbonyl-D-alanine in place of N-methyl-N-tert.-butoxycarbonyl-L-alanine, there was obtained (E)-2(R)-[1(S)-(hydroxycarbamoyl)-4-phenyl-3-butenyl]-2'-isobutyl-4-methyl-2'-(N-methyl-D-alanyl) valerohydrazide hydrochloride in the form of a white solid.

MS: 461 (M+H)$^+$. HPLC: Gradient elution using solvent A containing 5% solvent B increasing to 95% solvent B over 15 minutes; flow rate 1 ml per minute. Retention time: 11.15 minutes. Solvent A: $H_2O$/0.1% TFA; solvent B: $CH_3CN$/0.085% TFA. Column type: HYPERPEP 300A.

EXAMPLE 29

(E)-2'-(N-Acetyl-L-alanyl)-2(R)-[1(S)-(hydroxycarbamoyl)-4-phenyl-3-butenyl]-2'-isobutyl-4-methylvalerohydrazide A solution of 0.600 g of (E)-2'-(N-acetyl-L-alanyl)-2(R)-[1(S)-(tetrahydro-2(RS)-pyranyloxy)carbamoyl]-4-phenyl-3-butenyl]-2'-isobutyl-4-methylvalerohydrazide in 10 ml of methanol was treated with 0.06 g of p-toluenesulphonic acid monohydrate. The mixture was stirred for 2 hours at room temperature and evaporated. The residue was triturated with diethyl ether, filtered off and dried to give 0.138 g of (E)-2'-(N-acetyl-L-alanyl)-2(R)-[1(S)-(hydroxycarbamoyl)-4-phenyl-3-butenyl]-2'-isobutyl-4-methylvalerohydrazide in the form of a white solid.

MS: 489 (M+H)$^+$. HPLC: Gradient elution using solvent A containing 5% solvent B increasing to 95% solvent B over 15 minutes; flow rate 1 ml per minute. Retention time: 10.82 minutes. Solvent A: $H_2O$/0.1% TFA; solvent B: $CH_3CN$/0.085% TFA. Column type: HYPERPEP 300A.

The (E)-2'-(N-acetyl-L-alanyl)-2(R)-[1(S)-(tetrahydro-2 (RS)-pyranyloxy)carbamoyl]-4-phenyl-3-butenyl]-2'-isobutyl-4-methylvalerohydrazide used as the starting material was prepared as follows:

A solution of 0.144 g of N-acetyl-L-alanine in 10 ml tetrahydrofuran was cooled to −10° C. and treated with 0.140 ml of N-ethylmorpholine and 0.143 ml of isobutyl chloroformate. The mixture was stirred for a further 10 minutes at 10° C. and then treated with 0.459 g of (E)-2 (R)-[1(S)-[(tetrahydro-2(RS)-pyranyloxy)carbamoyl]-4-phenyl-3-butenyl]-2'-isobutyl-4-methylvalerohydrazide. The mixture was allowed to warm to 0° C. and stirring was continued for 1.5 hours. The mixture was then diluted with ethyl acetate and washed in sequence with 5% aqueous citric acid, 5% aqueous sodium hydrogen carbonate and brine. Drying over magnesium sulphate and evaporation gave 0.601 g of (E)-2'-(N-acetyl-L-alanyl)-2(R)-[1(S)-(tetrahydro-2(RS)-pyranyloxy)carbamoyl]-4-phenyl-3-butenyl]-2'-isobutyl-4-methylvalerohydrazide in the form of a white solid.

MS: 573 (M+H)$^+$.

EXAMPLE 30

(E)-2'-(N-Acetyl-D-alanyl)-2(R)-[1(S)-(hydroxycarbamoyl)-4-phenyl-3-butenyl]-2'-isobutyl-4-methylvalerohydrazide In a manner analogous to that described in Example 29, but using N-acetyl-D-alanine in place of N-acetyl-L-alanine, there was obtained (E)-2'-(N-acetyl-D-alanyl)-(R)-[1(S)-(hydroxycarbamoyl)-4-phenyl-3-butenyl]-2'-isobutyl-4-methylvalerohydrazide in the form of a white solid.

MS: 489 (M+H)$^+$. HPLC: Gradient elution using solvent A containing 5% solvent B increasing to 95% solvent B over 15 minutes; flow rate 1 ml per minute. Retention time: 10.84 minutes. Solvent A: $H_2O$/0.1% TFA; solvent B: $CH_3CN$/0.085% TFA. Column type: HYPERPEP 300A.

EXAMPLE 31

(E)-2(R)-[1(S)-(Hydroxcarbamoyl)-4-phenyl-3-butenyl]-2'-isobutyl-4-methyl-2'-(2(RS)-ureidopropionyl)valerohydrazide A solution of 0.232 g of (E)-2(R)-[1(S)-(tetrahydro-2 (RS)-pyranyloxy)carbamoyl]-4-phenyl-3-butenyl]-2'-isobutyl-4-methyl-2'-(2(RS)-ureidopropionyl) valerohydrazide in 5 ml of methanol was treated with 0.03 g of p-toluenesulphonic acid monohydrate. The mixture was stirred for 2 hours at room temperature and evaporated. The residue was triturated with diethyl ether, filtered off and dried to give 0.168 g of (E)-2(R)-[1(S)-(hydroxycarbamoyl)-4-phenyl-3-butenyl]-2'-isobutyl-4-methyl-2'-(2(RS)-ureidopropionyl)valerohydrazide in the form of a white solid.

MS: 490 (M+H)$^+$. HPLC: Gradient elution using solvent A containing 5% solvent B increasing to 95% solvent B over 15 minutes; flow rate 1 ml per minute. Retention time: 10.69 minutes. Solvent A: $H_2O$/0.1% TFA; solvent B: $CH_3CN$/0.085% TFA. Column type: HYPERPEP 300A.

The (E)-2(R)-[1(S)-(tetrahydro-2(RS)-pyranyloxy)
carbamoyl]-4-phenyl-3-butenyl]-2'-isobutyl-4-methyl-2'-(2
(RS)-ureidopropionyl)valerohydrazide used as the starting
material was prepared as follows:

A solution of 0.145 g of N-carbamyl-DL-alanine in 5 ml
of dimethylformamide was treated with 0.140 ml of
N-ethylmorpholine and 0.459 g of (E)-2(R)-[1(S)-
[(tetrahydro-2(RS)-pyranyloxy)carbamoyl]-4-phenyl-3-
butenyl]-2'-isobutyl-4-methylvalerohydrazide. The mixture
was then treated with 0.15 g of 1-hydroxybenzotriazole and
0.211 g of 1-ethyl-3-(3-dimethylaminopropyl)carbodiimide
hydrochloride. Stirring was continued overnight at room
temperature and then the mixture was diluted with ethyl
acetate and washed in sequence with 5% aqueous citric acid,
5% aqueous sodium hydrogen carbonate and brine. Drying
over magnesium sulphate and evaporation gave 0.570 g of
a white foam which was purified by flash column chromatography on silica gel using ethyl acetate for the elution to
give 0.232 g of (E)-2(R)-[1(S)-(tetrahydro-2(RS)-
pyranyloxy)carbamoyl]-4-phenyl-3-butenyl]-2'-isobutyl-4-
methyl-2'-(2(RS)-ureidopropionyl)valerohydrazide in the
form of a white solid.

MS: 574 (M+H)$^+$.

EXAMPLE 32

(E)-2(R)-[1(S)-(Hydroxy-carbamoyl)-4-phenyl-3-
butenyl]-2'-isobutyl-4-methyl-2'-[2-(dimethylamino)
acetyl]valerohydrazide p-toluenesulphonate A solution of 0.590 g of (E)-2(R)-[1(S)-(tetrahydro-2
(RS)-pyranyloxy)carbamoyl]-4-phenyl-3-butenyl]-2'-
isobutyl-4-methyl-2'-[2-(dimethylamino)acetyl]
valerohydrazide in 10 ml of methanol was treated with 0.210
g of p-toluenesulphonic acid monohydrate. The mixture was
stirred for 2 hours at room temperature and evaporated. The
residue was triturated with diethyl ether, filtered off and
dried to give 0.478 g of (E)-2(R)-[1(S)-(hydroxy-
carbamoyl)-4-phenyl-3-butenyl]-2'-isobutyl-4-methyl-2'-[2-
(dimethylamino)acetyl]valerohydrazide
p-toluenesulphonate in the form of a white solid.

MS: 461 (M+H)$^+$. HPLC: Gradient elution using solvent
A containing 10% solvent B for 5 minutes increasing to 99%
solvent B from 5 minutes to 15 minutes; flow rate 1 ml per
minute. Retention time: 13.76 minutes. Solvent A: H$_2$O/
0.1% TFA; solvent B: CH$_3$CN/0.085% TFA. Column type:
HYPERPEP 300A.

The (E)-2(R)-[1(S)-(tetrahydro-2(RS)-pyranyloxy)
carbamoyl]-4-phenyl-3-butenyl]-2'-isobutyl-4-methyl-2'-[2-
(dimethylamino)acetyl]valerohydrazide used as the starting
material was prepared as follows:

A solution of 0.155 g of N,N-dimethylglycine in 10 ml of
dimethylformamide was treated in sequence with 0.167 ml
of N-ethylmorpholine, 0.216 g of 1-hydroxybenzotriazole
and 0.307 g of 1-ethyl-3-(3-dimethylaminopropyl)
carbodiimide hydrochloride. Stirring was continued for 1
hour at room temperature and then 0.459 g of (E)-2(R)-[1
(S)-[(tetrahydro-2(RS)-pyranyloxy)carbamoyl]-4-phenyl-3-
butenyl]-2'-isobutyl-4-methylvalerohydrazide was added.
Stirring was continued overnight and then the mixture was
diluted with ethyl acetate and washed in sequence with 5%
aqueous sodium hydrogen carbonate and brine. Drying over
magnesium sulphate and evaporation gave 0.591 g of (E)-
2(R)-[1(S)-(tetrahydro-2(RS)-pyranyloxy)carbamoyl]-4-
phenyl-3-butenyl]-2'-isobutyl-4-methyl-2'-[2-
(dimethylamino)acetyl]valerohydrazide in the form of a
white solid.

MS: 545 (M+H)$^+$.

EXAMPLE 33

2'-(D-Alanyl)-2(R)-[1(RS)-(hydroxycarbamoyl)-4-
phenylbutyl]-2'-isobutyl-4-methylvalerohydrazide A solution of 0.820 g of 2'-(N-benzyloxycarbonyl-D-
alanyl)-2(R)-[1(RS)-[(benzyloxy)carbamoyl]-4-
phenylbutyl]-2'-isobutyl-4-methylvalerohydrazide in 20 ml
methanol was hydrogenated in the presence of 0.240 g of 5%
palladium-on-carbon for 1.5 hours. The catalyst was
removed by filtration and the solvent was evaporated. The
residue was triturated with diethyl ether to give 0.480 g of
2'-(D-alanyl)-2(R)-[1(RS)-(hydroxycarbamoyl)-4-
phenylbutyl]-2'-isobutyl-4-methylvalerohydrazide in the
form of a colorless glass.

MS: 449 (M+H)$^+$. HPLC: Gradient elution using solvent
A containing 5% solvent B increasing to 95% solvent B over
15 minutes; flow rate 1 ml per minute. Retention time: 10.62
minutes. Solvent A: H$_2$O/0.1% TFA; solvent B: CH$_3$CN/
0.085% TFA. Column type: HYPERPEP 300A.

The 2'-(N-benzyloxycarbonyl-D-alanyl)-2(R)-[1(RS)-
[(benzyloxy)carbamoyl]-4-phenylbutyl]-2'-isobutyl-4-
methylvalerohydrazide used as the starting material was
prepared as follows:

(i) In an analogous manner to that described in Example 1,
part (iii), starting from 2(R)-[1(RS)-(tert.-butoxycarbonyl)-
4-phenylbutyl]-4-methylvaleric acid and isobutylhydrazine
ditosylate salt there was obtained 2(R)-[1(RS)-(tert.-
butoxycarbonyl)-4-phenylbutyl]-2'-isobutyl-4-
methylvalerohydrazide in the form of a clear oil.

(ii) A solution of 1.5 g of 2(R)-[1(RS)-(tert.-
butoxycarbonyl)-4-phenylbutyl]-2'-isobutyl-4-
methylvalerohydrazide in 25 ml dichloromethane was
treated with 0.454 g of 4-ethylmorpholine and 0.880 g of
N-benzyloxycarbonyl-D-alanine acid fluoride and the mixture was then stirred overnight at room temperature. The
mixture was washed in sequence with water, 2M aqueous
hydrochloric acid, water and brine and then dried over
anhydrous magnesium sulphate. Evaporation of the solvent
gave a residue which was purified by flash column chromatography on silica gel using ethyl acetate/hexane (1:3) for
the elution to give 1.29 g of 2'-(N-benzyloxycarbonyl-D-
alanyl)-2(R)-[1(RS)-(tert.-butoxycarbonyl)-4-phenylbutyl]-
2'-isobutyl-4-methylvalerohydrazide in the form of a clear
oil.

MS: 624 (M+H)$^+$.

(iii) A solution of 1.26 g of 2'-(N-benzyloxycarbonyl-D-
alanyl)-2(R)-[1(RS)-(tert.-butoxycarbonyl)-4-phenylbutyl]-
2'-isobutyl-4-methylvalerohydrazide in 5 ml dichloromethane was treated with 5 ml of trifluoroacetic acid and
the mixture was stirred at room temperature for 2 hours. The
solvent was evaporated to give 1.30 g of 2'-(N-
benzyloxycarbonyl-D-alanyl)-2(R)-[1(RS)-(carboxy)-4-
phenylbutyl]-2'-isobutyl-4-methylvalerohydrazide in the
form of a pale yellow foam.

MS: 568 (M+H)$^+$.

(iv) A solution of 1.15 g of 2'-(N-benzyloxycarbonyl-D-
alanyl)-2(R)-[1(RS)-(carboxy)-4-phenylbutyl]-2'-isobutyl-
4-methylvalerohydrazide in 5 ml of dimethylformamide was
cooled to 0° C. under a nitrogen atmosphere. The mixture
was then treated with 1.25 g of O-benzylhydroxylamine and
0.467 g of 1-ethyl-3-(3-dimethylaminopropyl)carbodiimide
hydrochloride and left to warm to room temperature overnight. The mixture was diluted with water and extracted
twice with ethyl acetate. The ethyl acetate layer was then
washed with aqueous 2M hydrogen chloride, water and brine. Drying over anhydrous magnesium sulphate and evaporation of the solvent gave 0.820 g of 2'-(N-benzyloxycarbonyl-D-alanyl)-2(R)-[1(RS)-[(benzyloxy)carbamoyl)-4-phenylbutyl]-2'-isobutyl-4-methylvalerohydrazide in the form of a white foam.

EXAMPLE 34

2'-(D-Alanyl)-2(R)-[1(RS)-(hydroxycarbamoyl)butyl]-2'-isobutyl-4-methylvalerohydrazide hydrochloride A solution of 0.560 g of 2'-(N-benzyloxycarbonyl-D-alanyl)-2(R)-[1(RS)-[(benzyloxy)carbamoyl]-3-butenyl]-2'-isobutyl-4-methylvalerohydrazide in 25 ml of methanol was hydrogenated in the presence of 0.150 g of 5% palladium-on-carbon for 2 hours. The catalyst was removed by filtration and the solvent was evaporated. The residue was triturated with diethyl ether to give 0.480 g of 2'-(D-alanyl)-2(R)-[1(RS)-(hydroxycarbamoyl)butyl]-2'-isobutyl-4-methylvalerohydrazide in the form of a white solid. This solid was then dissolved in 2 ml of dioxan and the solution was treated with 0.5 ml of 4M hydrogen chloride in dioxan. The mixture was stirred at room temperature for 15 minutes and then diluted with diethyl ether. Filtration and drying gave 0.188 g of 2'-(D-alanyl)-2(R)-[1(RS)-(hydroxycarbamoyl)butyl]-2'-isobutyl-4-methylvalerohydrazide hydrochloride in the form of a white solid.

MS: 373 (M+H)$^+$. HPLC: Gradient elution using solvent A containing 5% solvent B increasing to 95% solvent B over 15 minutes; flow rate 1 ml per minute. Retention time: 10.54 minutes. Solvent A: H$_2$O/0.1% TFA; solvent B: CH$_3$CN/0.085% TFA. Column type: HYPERPEP 300A.

The 2'-(N-benzyloxycarbonyl-D-alanyl)-2(R)-[1(RS)-[(benzyloxy)carbamoyl]-3-butenyl]-2'-isobutyl-4-methylvalerohydrazide used as the starting material was prepared as follows:

In an analogous manner to that described in Example 33, parts (i)–(iv), but using 2(R)-[1(RS)-(tert-butoxycarbonyl)-3-butenyl]-4-methylvaleric acid in place of 2(R)-[1(RS)-(tert-butoxycarbonyl)-4-phenylbutyl]-4-methylvaleric acid, there was obtained 2'-(N-benzyloxycarbonyl-D-alanyl)-2(R)-[1(RS)-[(benzyloxy)carbamoyl]-3-butenyl]-2'-isobutyl-4-methylvalerohydrazide in the form of a colorless glass.

MS: 595 (M+H)$^+$.

EXAMPLE 35

2'-(D-Alanyl)-2(R)-[4-cyclohexyl-1(RS)-(hydroxycarbamoyl)butyl]-2-isobutyl-4-methylvalerohydrazide In a manner analogous to that described in Example 33, but using 2(R)-[4-cyclohexyl-1(RS)-(tert.-butoxycarbonyl)butyl]-2'-isobutyl-4-methylvalerohydrazide in place of 2(R)-[1(RS)-(tert.-butoxycarbonyl)-4-phenylbutyl]-2'-isobutyl-4-methylvalerohydrazide in part (ii), there was obtained 2'-(D-alanyl)-2(R-[4-cyclohexyl-1(RS)-(hydroxycarbamoyl)butyl]-2'-isobutyl-4-methylvalerohydrazide in the form of a white solid.

MS: 455 (M+H)$^+$. HPLC: Gradient elution using solvent A containing 5% solvent B increasing to 95% solvent B over 15 minutes; flow rate 1 ml per minute. Retention time: 11.87 minutes. Solvent A: H$_2$O/0.1% TFA; solvent B: CH$_3$CN/0.085% TFA. Column type: HYPERPEP 300A.

The 2(R)-[4-cyclohexyl-1(RS)-(tert.-butoxycarbonyl)butyl]-2'-isobutyl-4-methylvalerohydrazide used as the starting material was prepared as follows:

A solution of 0.900 g of 2(R)-[1((RS)-(tert-butoxycarbonyl)-4-phenylbutyl]-2'-isobutyl-4-methylvalerohydrazide [prepared as described in Example 33, part (i)] in 30 ml of acetic acid was hydrogenated in the presence of 0.300 g of platinum (IV) oxide for 2 hours. The catalyst was removed by filtration and the solvent was evaporated. The residue was purified by flash column chromatography on silica gel using ethyl acetate/hexane (1:5) for the elution to give 0.370 g of 2(R)-[4-cyclohexyl-1(RS)-(tert.-butoxycarbonyl)butyl]-2'-isobutyl-4-methylvalerohydrazide in the form of a colorless oil.

MS: 425 (M+H)$^+$.

EXAMPLE 36

(E)-2(R)-[1(S)-(Hydroxycarbamoyl)-4-phenyl-3-butenyl]-2'-isobutyl-4-methyl-2'-(D-phenylalanyl)valerohydrazide p-toluenesulphonate A solution of 0.288 g of (E)-2(R)-[1(S)-(tetrahydro-2(RS)-pyranyloxy)-carbamoyl]-4-phenyl-3-butenyl]-2'-isobutyl-4-methyl-2'-(D-phenylalanyl)valerohydrazide in 3 ml of methanol was treated with 0.099 g of p-toluenesulphonic acid monohydrate. The mixture was stirred for 3 hours at room temperature and evaporated. The residue was triturated with diethyl ether and then with hexane, filtered off and dried to give 0.232 g of (E)-2(R)-[1(S)-(hydroxycarbamoyl)-4-phenyl-3-butenyl]-2'-isobutyl-4-methyl-2'-(D-phenylalanyl)valerohydrazide p-toluenesulphonate in the form of a pale yellow solid.

MS: 523 (M+H)$^+$. HPLC: Gradient elution using solvent A containing 10% solvent B for 5 minutes increasing to 99% solvent B from 5 minutes to 15 minutes; flow rate 1 ml per minute. Retention time: 12.01 minutes. Solvent A: H$_2$O/0.1% TFA; solvent B: CH$_3$CN/0.085% TFA. Column type: HYPERPEP 300A.

The (E)-2(R)-[1(S)-(tetrahydro-2(RS)-pyranyloxy)carbamoyl]-4-phenyl-3-butenyl]-2'-isobutyl-4-methyl-2'-(D-phenylalanyl)valerohydrazide used as the starting material was prepared as follows:

(i) A solution of 1.01 g of (E)-2(R)-[1(S)-(tert-butoxycarbonyl)-4-phenyl-3-butenyl]-2'-isobutyl-4-methylvalerohydrazide in 10 ml of dichloromethane was treated with 0.22 ml of pyridine and 1.04 g of N-(9-fluorenylmethyloxycarbonyl)-D-phenylalanyl acid fluoride. The mixture was stirred overnight at room temperature and then evaporated and the residue was taken up in ethyl acetate. The ethyl acetate phase was washed with 2M aqueous hydrogen chloride, 5% aqueous sodium hydrogen carbonate and brine and then dried over anhydrous magnesium sulphate. The solvent was evaporated to give 1.95 g of (E)-2(R)-[1(S)-(tert-butoxycarbonyl)-4-phenyl-3-butenyl]-2'-isobutyl-2'-[N-(9-fluorenylmethyloxycarbonyl)-(D-phenylalanyl)]- 4-methylvalerohydrazide in the form of a pale yellow oil.

MS: 786 (M+H)$^+$.

(ii) In an analogous manner to that described in Example 1, part (v)–(vi), starting from (E)-2(R)-[1(S)-(tert-butoxycarbonyl)-4-phenyl-3-butenyl]-2'-isobutyl-2'-[N-(9-fluorenylmethyloxycarbonyl)-(D-phenylalanyl)]-4-methylvalerohydrazide there was obtained (E)-2(R)-[1(S)-[(tetrahydro-2(RS)-pyranyloxy)carbamoyl]-4-phenyl-3-butenyl]-2'-isobutyl-2'-[N-(9-fluorenylmethyloxycarbonyl)-(D-phenylalanyl)]-4-methylvalerohydrazide in the form of a white solid.

MS: 745 (M-THP+H)$^+$.

(iii) In an analogous manner to that described in Example 23, part (iii), starting from (E)-2(R)-[1(S)-[(tetrahydro-2

(RS)-pyranyloxy)carbamoyl]-4-phenyl-3-butenyl]-2'-isobutyl-2'-[N-(9-fluorenylmethyloxycarbonyl)-(D-phenylalanyl)]-4-methylvalerohydrazide there was obtained (E)-2(R)-[1(S)-(tetrahydro-2(RS)-pyranyloxy)carbamoyl]-4-phenyl-3-butenyl]-2'-isobutyl-4-methyl-2'-(D-phenylalanyl)valerohydrazide in the form of a pale pink solid.

MS: 607 (M+H)$^+$.

EXAMPLE 37

(E)-2(R)-[1(S)-(Hydroxycarbamoyl)-4-phenyl-3-butenyl]-2'-isobutyl-4-methyl-2'-[2-(1-pyrrolidinyl)acetyl]valerohydrazide p-toluenesulphonate A solution of 0.363 g of (E)-2(R)-([1(S)-[(tetrahydro-2 (RS)-pyranyloxy)carbamoyl]-4-phenyl-3-butenyl]-2'-isobutyl-4-methyl-2'-[2-(1-pyrrolidinyl)acetyl] valerohydrazide in 5 ml of methanol was treated with 0.133 g of p-toluenesulphonic acid monohydrate. The mixture was stirred for 4 hours at room temperature and evaporated. The residue was triturated with diethyl ether, filtered off and dried to give 0.317 g of (E)-2(R)-[1(S)-(hydroxycarbamoyl)-4-phenyl-3-butenyl]-2'-isobutyl-4-methyl-2'-[2-(1-pyrrolidinyl)acetyl]valerohydrazide p-toluenesulphonate in the form of a white solid.

MS: 487 (M+H)$^+$. HPLC: Gradient elution using solvent A containing 10% solvent B for 5 minutes increasing to 99% solvent B from 5 minutes to 15 minutes; flow rate 1 ml per minute. Retention time: 11.24 minutes. Solvent A: H$_2$O/ 0.1% TFA; solvent B: CH$_3$CN/0.085% TFA. Column type: HYPERPEP 300A.

The (E)-2(R)-[1(S)-[(tetrahydro-2(RS)-pyranyloxy) carbamoyl]-4-phenyl-3-butenyl]-2'-isobutyl-4-methyl-2'-[2-(1-pyrrolidinyl)acetyl]valerohydrazide used as the starting material was prepared as follows:

A solution of 0.309 g of 2-(1-pyrrolidinyl)acetic acid hydrogen bromide in 20 ml of dimethylformamide was treated in sequence with 0.324 ml of N-ethylmorpholine, 0.212 g of 1-hydroxybenzotriazole and 0.301 g of 1-ethyl-3-(3-dimethylaminopropyl)carbodiimide hydrochloride. Stirring was continued at room temperature and for 1 hour then 0.450 g of (E)-2(R)-[1(S)-[(tetrahydro-2(RS)-pyranyloxy)carbamoyl]-4-phenyl-3-butenyl]-2'-isobutyl-4-methylvalerohydrazide was added. Stirring was continued overnight at room temperature and then the solvent was evaporated and replaced by ethyl acetate. The ethyl acetate phase was washed with 5% aqueous sodium hydrogen carbonate and brine and then dried over anhydrous magnesium sulphate. Evaporation and trituration of the residue with diethyl ether gave 0.363 g of (E)-2(R)-[1(S)-[(tetrahydro-2(RS)-pyranyloxy)carbamoyl]-4-phenyl-3-butenyl]-2'-isobutyl-4-methyl-2-[2-(1-pyrrolidinyl)acetyl] valerohydrazide in the form of a white solid.

MS: 571 (M+H)$^+$.

EXAMPLE 38

(E)-2(R)-[1(S)-(Hydroxycarbamoyl)-4-phenyl-3-butenyl]-2'-isobutyl-4-methyl-2'-[2-morpholinoacetyl]valerohydrazide p-toluenesulphonate In a manner analogous to that described in Example 37, but using 2-morpholinoacetic acid hydrogen bromide in place of 2-(1-pyrrolidinyl)acetic acid hydrogen bromide, there was obtained (E)-2(R)-[1(S)-(hydroxycarbamoyl)-4-phenyl-3-butenyl]-2'-isobutyl-4-methyl-2'-[2-morpholinoacetyl]valerohydrazide p-toluenesulphonate in the form of a white solid.

MS: 503 (M+H)$^+$. HPLC: Gradient elution using solvent A containing 10% solvent B for 5 minutes increasing to 99% solvent B from 5 minutes to 15 minutes; flow rate 1 ml per minute. Retention time: 11.10 minutes. Solvent A: H$_2$O/ 0.1% TFA; solvent B: CH$_3$CN/0.085% TFA. Column type: HYPERPEP 300A.

EXAMPLE 39

(E)-2(R)-[1(S)-(Hydroxycarbamoyl)-4-phenyl-3-butenyl]-2'-isobutyl-2'-(2-methoxyacetyl)-4-methylvalerohydrazide A solution of 0.543 g (E)-2(R)-[1(S)-(tetrahydro-2(RS)-pyranyloxy)carbamoyl]-4-phenyl-3-butenyl]-2'-isobutyl-2'-(2-methoxyacetyl)-4-methylvalerohydrazide in 2 ml of dioxan was treated with 1 ml of 4M hydrogen chloride in dioxan. The mixture was stirred for 1.5 hours at room temperature and then diluted with 80 ml of diethyl ether. Filtration gave 0.245 g of (E)-2(R)-[1(S)-(hydroxycarbamoyl)-4-phenyl-3-butenyl]-2'-isobutyl-(2-methoxyacetyl)-4-methylvalerohydrazide in the form of a white solid.

MS: 448 (M+H)$^+$. HPLC: Gradient elution using solvent A containing 5% solvent B increasing to 95% solvent B over 15 minutes; flow rate 1 ml per minute. Retention time: 11.13 minutes. Solvent A: H$_2$O/0.1% TFA; solvent B: CH$_3$CN/ 0.085% TFA. Column type: HYPERPEP 300A.

The (E)-2(R)-[1(S)-(tetrahydro-2(RS)-pyranyloxy) carbamoyl]-4-phenyl-3-butenyl]-2'-isobutyl-2'-(2-methoxyacetyl)-4-methylvalerohydrazide used as the starting material was prepared as follows:

A solution of 0.180 g of methoxyacetic acid in 10 ml of dimethylformamide was treated in sequence with 0.254 ml of N-ethylmorpholine, 0.270 g of 1-hydroxybenzotriazole and 0.384 g of 1-ethyl-3-(3-dimethylaminopropyl)-carbodiimide hydrochloride. Stirring was continued at room temperature for 1 hour and then 0.459 g of (E)-2(R)-[1(S)-[(tetrahydro-2(RS)-pyranyloxy)carbamoyl]-4-phenyl-3-butenyl]-2'-isobutyl-4-methylvalerohydrazide was added. Stirring was continued at room temperature overnight and then the solvent was evaporated and replaced by ethyl acetate. The ethyl acetate layer was washed with 5% aqueous citric acid, 5% aqueous sodium hydrogen carbonate and brine and then dried over anhydrous magnesium sulphate. Evaporation and trituration with diethyl ether gave 0.543 g of (E)-2(R)-[1(S)-(tetrahydro-2(RS)-pyranyloxy) carbamoyl]-4-phenyl-3-butenyl]-2'-isobutyl-2'-(2-methoxyacetyl)-4-methylvalerohydrazide in the form of a white solid.

MS: 532 (M+H)$^+$.

EXAMPLE 40

(E)-2(R)-[1(S)-(Hydroxycarbamoyl)-4-phenyl-3-butenyl]-2'-isobutyl-4-methyl-2'-[2-(methylamino)acetyl]valerohydrazide hydrochloride In a manner analogous to that described in Example 39, but using N-tert.-butoxycarbonyl-N-methylglycine in place of methoxyacetic acid there was obtained (E)-2(R)-[1(S)-(hydroxycarbamoyl)-4-phenyl-3-butenyl]-2'-isobutyl-4-methyl-2'-[2-(methylamino)acetyl]valerohydrazide hydrochloride in the form of a white solid.

MS: 447 (M+H)$^+$. HPLC: Gradient elution using solvent A containing 5% solvent B increasing to 95% solvent B over 15 minutes; flow rate 1 mml per minute. Retention time: 10.54 minutes. Solvent A: $H_2O/0.1\%$ TFA; solvent B: $CH_3CN/0.085\%$ TFA. Column type: HYPERPEP 300A.

EXAMPLE 41

(E)-2(R)-[1(S)-(Hydroxycarbamoyl)-4-phenyl-3-butenyl]-2'-isobutyl-4-methyl-2'-[(2-pyridyl)carbonyl]valerohydrazide hydrochloride In a manner analogous to that described in Example 8, but using picolinic acid in place of N-tert.-butoxycarbonyl-β-alanine, there was obtained (E)-2(R)-[1(S)-(hydroxycarbamoyl)-4-phenyl-3-butenyl]-2'-isobutyl-4-methyl-2'-[(2-pyridyl)carbonyl]valerohydrazide hydrochloride in the form of a white solid.

MS: 481 $(M+H)^+$. HPLC: Gradient elution using solvent A containing 5% solvent B increasing to 95% solvent B over 15 minutes; flow rate 1 ml per minute. Retention time: 11.38 minutes. Solvent A: $H_2O/0.1\%$ TFA; solvent B: $CH_3CN/0.085\%$ TFA. Column type: HYPERPEP 300A.

EXAMPLE 42

(E)-2(R)-[1(S)-(Hydroxycarbamoyl)-4-phenyl-3-butenyl]-2'-isobutyl-4-methyl-2'-[(3(RS)-piperidinyl)carbonyl]valerohydrazide hydrochloride In a manner analogous to that described in Example 8, but using racemic N-tert.-butoxycarbonylnipecotic acid in place of N-tert.-butoxycarbonyl-β-alanine, there was obtained (E)-2(R)-[1(S)-(hydroxycarbamoyl)-4-phenyl-3-butenyl]-2'-isobutyl-4-methyl-2'-[(3(RS)-piperidinyl)carbonyl]valerohydrazide hydrochloride in the form of a white solid.

MS: 487 $(M+H)^+$. HPLC: Gradient elution using solvent A containing 5% solvent B increasing to 95% solvent B over 15 minutes; flow rate 1 ml per minute. Retention time: 10.89 and 11.01 minutes. Solvent A: $H_2O/0.1\%$ TFA; solvent B: $CH_3CN/0.085\%$ TEA. Column type: HYPERPEP 300A.

EXAMPLE 43

(E)-2'-(Tetrahydro-2(RS)-furoyl)-2(R)-[1(S)-(hydroxycarbamoyl)-4-phenyl-3-butenyl]-2'-isobutyl-4-methylvalerohydrazide In a manner analogous to that described in Example 8, but using tetrahydro-2(RS)-furancarboxylic acid in place of N-tert.-butoxycarbonyl-β-alanine, there was obtained (E)-2'-(tetrahydro-2(RS)-furoyl)-2(R)-[1(S)-(hydroxycarbamoyl)-4-phenyl-3-butenyl]-2'-isobutyl-4-methylvalerohydrazide in the form of a white solid.

MS: 474 $(M+H)^+$. HPLC: Gradient elution using solvent A containing 5% solvent B increasing to 95% solvent B over 15 minutes; flow rate 1 ml per minute. Retention time: 11.39 minutes. Solvent A: $H_2O/0.1\%$ TFA; solvent B: $CH_3CN/0.085\%$ TFA. Column type: HYPERPEP 300A.

EXAMPLE 44

(E)-2(R)-[1(S)-(Hydroxycarbamoyl)-4-phenyl-3-butenyl]-2'-isobutyl-4-methyl-2'-[(4-piperidinyl)carbonyl]valerohydrazide hydrochloride In a manner analogous to that described in Example 8, but using N-tert.-butoxycarbonyl isonipecotic acid in place of N-tert.-butoxycarbonyl-β-alanine, there was obtained (E)-2(R)-[1(S)-(hydroxycarbamoyl)-4-phenyl-3-butenyl-2'-isobutyl-4-methyl-2'-[(4-piperidinyl)carbonyl]valerohydrazide hydrochloride in the form of a white solid.

MS: 487 $(M+H)^+$. HPLC: Gradient elution using solvent A containing 5% solvent B increasing to 95% solvent B over 15 minutes; flow rate 1 ml per minute. Retention time: 10.55 minutes. Solvent A: $H_2O/0.1\%$ TFA; solvent B: $CH_3CN/0.085\%$ TFA. Column type: HYPERPEP 300A.

EXAMPLE 45

(E)-2(R)-[1(S)-(Hydroxycarbamoyl)-4-phenyl-3-butenyl]-2'-isobutyl-4-methyl-2'-(L-valyl)valerohydrazide hydrochloride In a manner analogous to that described in Example 8, but using N-tert.-butoxycarbonyl-L-valine in the place of N-tert.-butoxycarbonyl-β-alanine, there was obtained (E)-2(R)-[1(S)-(hydroxycarbamoyl)-4-phenyl-3-butenyl]-2'-isobutyl-4-methyl-2'-(L-valyl)valerohydrazide hydrochloride in the form of a white solid.

MS: 475 $(M+H)^+$. HPLC: Gradient elution using solvent A containing 5% solvent B increasing to 95% solvent B over 15 minutes; flow rate 1 ml per minute. Retention time: 11.09 minutes. Solvent A: $H_2O/0.1\%$ TFA; solvent B: $CH_3CN/0.085\%$ TFA. Column type: HYPERPEP 300A.

EXAMPLE 46

(E)-2'-(D-α-Aminobutyryl)-2(R)-[1(S)-(hydroxycarbamoyl)-4-phenyl-3-butenyl]-2'-isobutyl-4-methylvalerohydrazide hydrochloride In a manner analogous to that described in Example 8, but using N-tert.-butoxycarbonyl-D-α-aminobutyric acid in place of N-tert.-butoxycarbonyl-β-alanine, there was obtained (E)-2'-(D-α-aminobutyryl)-2(R)-[1(S)-(hydroxycarbamoyl)-4-phenyl-3-butenyl]-2'-isobutyl-4-methylvalerohydrazide hydrochloride in the form of a white solid.

MS: 461 $(M+H)^+$. HPLC: Gradient elution using solvent A containing 5% solvent B increasing to 95% solvent B over 15 minutes; flow rate 1 ml per minute. Retention time: 10.89 minutes. Solvent A: $H_2O/0.1\%$ TFA; solvent B: $CH_3CN/0.085\%$ TFA. Column type: HYPERPEP 300A.

EXAMPLE 47

(E)-2(R)-[1(S)-(Hydroxycarbamoyl)-4-phenyl-3-butenyl]-2'-isobutyl-4-meythyl-2'-[(5-oxo-2(S)-pyrrolidinyl)carbonyl]valerohydrazide In a manner analogous to that described in Example 8, but using L-pyroglutamic acid in place of N-tert.-butoxycarbonyl-β-alanine, there was obtained (E)-2(R)-[1(S)-(hydroxycarbanoyl)-4-phenyl-3-butenyl]-2'-isobutyl-4-methyl-2'-[(5-oxo-2(S)-pyrrolidinyl)carbonyl]valerohydrazide in the form of a white solid.

MS: 487 $(M+H)^+$. HPLC: Gradient elution using solvent A containing 5% solvent B increasing to 95% solvent B over 15 minutes; flow rate 1 ml per minute. Retention time: 10.56 minutes. Solvent A: $H_2O/0.1\%$ TFA; solvent B: $CH_3CN/0.085\%$ TFA. Column type: HYPERPEP 300A.

EXAMPLE 48

(E)-2(R)-[1(S)-(Hydroxycarbamoyl)-4-phenyl-3-butenyl]-2'-isobutyl-4-methyl-2'-[(5-oxo-2(R)-pyrrolidinyl)carbonyl]valerohydrazide In a manner analogous to that described in Example 8, but using D-pyroglutamic acid in place of N-tert.- butoxycarbonyl-β-alanine, there was obtained (E)-2(R)-[1 (S)-(hydroxycarbamoyl)-4-phenyl-3-butenyl]-2'-isobutyl-4-methyl-2'-[(5-oxo-2(R)-pyrrolidinyl)carbonyl] valerohydrazide in the form of a white solid.

MS: 487 (M+H)⁺. HPLC: Gradient elution using solvent A containing 5% solvent B increasing to 95% solvent B over 15 minutes; flow rate 1 ml per minute. Retention time: 10.54 minutes. Solvent A: $H_2O$/0.1% TFA; solvent B: $CH_3CN$/0.085% TFA. Column type: HYPERPEP 300A.

EXAMPLE 49

(E)-2'-(DL-β-Aminobutyryl)-2(R)-[1(S)-(hydroxycarbamoyl)-4-phenyl-3-butenyl]-2'-isobutyl-4-methylvalerohydrazide hydrochloride In a manner analogous to that described in Example 8, but using racemic N-tert.-butoxycarbonyl-β-aminobutyric acid in place of N-tert.-butoxycarbonyl-β-alanine, there was obtained (E)-2'-(DL-β-aminobutyryl)-2(R)-[1(S)-(hydroxycarbamoyl)-4-phenyl-3-butenyl]-2'-isobutyl-4-methylvalerohydrazide hydrochloride in the form of a white solid.

MS: 461 (M+H)⁺. HPLC: Gradient elution using solvent A containing 5% solvent B increasing to 95% solvent B over 15 minutes; flow rate 1 ml per minute. Retention time: 10.54 minutes. Solvent A: $H_2O$/0.1% TFA; solvent B: $CH_3CN$/0.085% TFA. Column type: HYPERPEP 300A.

EXAMPLE 50

(E)-2(R)-[1(S)-(Hydroxycarbamoyl)-4-phenyl-3-butenyl]-2'-isobutyl-4-methyl-2'-(2-piperidinoacetyl) valerohydrazide p-toluenesulphonate In a manner analogous to that described in Example 37, but using 2-piperidinoacetic acid hydrogen bromide in place of 2-(1-pyrrolidinyl)acetic acid hydrogen bromide, there was obtained (E)-2(R)-[1(S)-(hydroxycarbamoyl)-4-phenyl-3-butenyl-2'-isobutyl-4-methyl-2'-(2-piperidinoacetyl) valerohydrazide p-toluenesulphonate in the form of a white solid.

MS: 501 (M+H)⁺. HPLC: Gradient elution using solvent A containing 10% solvent B for 5 minutes increasing to 99% solvent B from 5 minutes to 15 minutes; flow rate 1 ml per minute. Retention time: 11.62 minutes. Solvent A: $H_2O$/0.1% TFA; solvent B: $CH_3CN$/0.085% TFA. Column type: HYPERPEP 300A.

EXAMPLE 51

(E)-2(R)-[1(S)-(Hydroxycarbamoyl)-4-phenyl-3-butenyl]-2'-isobutyl-4-methyl-2'-(D-norvalyl) valerohydrazide hydrochloride In a manner analogous to that described in Example 8, but using N-tert.-butoxycarbonyl-D-norvaline in the place of N-tert.-butoxycarbonyl-β-alanine, there was obtained (E)-2 (R)-[1(S)-(hydroxycarbamoyl)-4-phenyl-3-butenyl]-2'-isobutyl-4-methyl-2'-(D-norvalyl)valerohydrazide hydrochloride in the form of a white solid.

MS: 475 (M+H)⁺. HPLC: Gradient elution using solvent A containing 5% solvent B increasing to 95% solvent B over 15 minutes; flow rate 1 ml per minute. Retention time: 11.30 minutes. Solvent A: $H_2O$/0.1% TFA; solvent B: $CH_3CN$/0.085% TFA. Column type: HYPERPEP 300A.

EXAMPLE 52

(E)-2(R)-[1(S)-(Hydroxycarbamoyl)-4-phenyl-3-butenyl]-2'-isobutyl-4-methyl-2'-(D-valyl) valerohydrazide p-toluenesulphonate In a manner analogous to that described in Example 5, but using N-(9-fluorenylmethyloxycarbonyl)-D-valine acid fluoride in the place of N-(9-fluorenylmethyloxycarbonyl)-O-tert.butyl-D-serine acid fluoride, there was obtained (E)-2(R)-[1(S)-(hydroxycarbamoyl)-4-phenyl-3-butenyl-2'-isobutyl-4-methyl-2'-(D-valyl)valerohydrazide p-toluenesulphonate in the form of a white solid.

MS: 475 (M+H)⁺. HPLC: Gradient elution using solvent A containing 5% solvent B increasing to 95% solvent B over 15 minutes; flow rate 1 ml per minute. Retention time: 11.11 minutes. Solvent A: $H_2O$/0.1% TFA; solvent B: $CH_3CN$/0.085% TFA. Column type: HYPERPEP 300A.

EXAMPLE 53

(E)-2'-(3-Amino-2(RS)-methylpropionyl)-2(R)-[1 (S)-(hydroxycarbamoyl)-4-phenyl-3-butenyl]-2'-isobutyl-4-methylvalerohydrazide hydrochloride In a manner analogous to that described in Example 8, but using N-tert.-butoxycarbonyl-3-amino-2(RS)-methylpropionic acid in place of N-tert.-butoxycarbonyl-β-alanine, there was obtained (E)-2'-(3-amino-2(RS)-methylpropionyl)-2(R)-[1(S)-(hydroxycarbamoyl)-4-phenyl-3-butenyl]-2'-isobutyl-4-methylvalerohydrazide hydrochloride in the form of a white solid.

MS: 461 (M+H)⁺. HPLC: Gradient elution using solvent A containing 5% solvent B increasing to 95% solvent B over 15 minutes; flow rate 1 ml per minute. Retention time: 10.75 and 10.87 minutes. Solvent A: $H_2O$/0.1% TFA; solvent B: $CH_3CN$/0.085% TFA. Column type: HYPERPEP 300A.

EXAMPLE 54

(E)-2'-[2-(Diethylamino)acetyl]-2(R)-[1(S)-(hydroxycarbamoyl)-4-phenyl-3-butenyl]-2'-isobutyl-4-methylvalerohydrazide p-toluenesulphonate In a manner analogous to that described in Example 37, but using 2-(diethylamino)acetic acid hydrogen bromide in place of 2-(1-pyrrolidinyl)acetic acid hydrogen bromide, there was obtained (E)-2'-[2-(diethylamino)acetyl]-2(R)-[1 (S)-(hydroxycarbamoyl)-4-phenyl-3-butenyl]-2'-isobutyl-4-methylvalerohydrazide p-toluenesulphonate in the form of a white solid.

MS: 489 (M+H)⁺. HPLC: Gradient elution using solvent A containing 10% solvent B for 5 minutes increasing to 99% solvent B from 5 minutes to 15 minutes; flow rate 1 ml per minute. Retention time: 11.65 minutes. Solvent A: $H_2O$/0.1% TFA; solvent B: $CH_3CN$/0.085% TFA. Column type: HYPERPEP 300A.

EXAMPLE 55

(E)-2(R)-[1(S)-(Hydroxycarbamoyl)-4-phenyl-3-butenyl]-2'-isobutyl-4-methyl-2'-[2-(methylthio) acetyl]valerohydrazide hydrochloride In a manner analogous to that described in Example 8, but using (methylthio)acetic acid in place of N-tert.-butoxycarbonyl-β-alanine, there was obtained (E)-2(R)-[1 (S)-(hydroxycarbamoyl)-4-phenyl-3-butenyl]-2'-isobutyl-4-methyl-2'-[2-(methylthio)acetyl]valerohydrazide hydrochloride in the form of a white solid.

MS: 464 (M+H)⁺. HPLC: Gradient elution using solvent A containing 5% solvent B increasing to 95% solvent B over 15 minutes; flow rate 1 ml per minute. Retention time: 12.09 minutes. Solvent A: $H_2O$/0.1% TFA; solvent B: $CH_3CN$/0.085% TFA. Column type: HYPERPEP 300A.

EXAMPLE 56

(E)-2(R)-[1(S)-(Hydroxycarbamoyl)-4-phenyl-3-butenyl]-2'-[2-(1-imidazolyl)acetyl]-2'-isobutyl-4-methylvalerohydrazide p-toluenesulphonate In a manner analogous to that described in Example 11, but using 2-(1-imidazoyl)acetic acid in place of N-acetyl-glycine, there was obtained (E)-2(R)-[1(S)-(hydroxycarbamoyl)-4-phenyl-3-butenyl]-2'-[2-(1-imidazolyl)acetyl]-2'-isobutyl-4-methylvalerohydrazide p-toluenesulphonate in the form of a white solid.

MS: 484 (M+H)$^+$. HPLC: Gradient elution using solvent A containing 5% solvent B increasing to 95% solvent B over 15 minutes; flow rate 1 ml per minute. Retention time: 10.99 minutes. Solvent A: H$_2$O/0.1% TFA; solvent B: CH$_3$CN/0.085% TFA. Column type: HYPERPEP 300A.

EXAMPLE 57

(E)-2(R)-[1(S)-(Hydroxycarbamoyl)-4-phenyl-3-butenyl]-2'-isobutyl-4-methyl-2'-[2-(1-piperazinyl)acetyl]valerohydrazide hydrochloride In a manner analogous to that described in Example 8, but using 2-(1-piperazinyl)acetic acid in place of N-tert.-butoxycarbonyl-β-alanine, there was obtained (E)-2(R)-[1(S)-(hydroxycarbamoyl)-4-phenyl-3-butenyl]-2'-isobutyl-4-methyl-2'-[2-(1-piperazinyl)acetyl]valerohydrazide hydrochloride in the form of a white solid.

MS: 502 (M+H)$^+$. HPLC: Gradient elution using solvent A containing 5% solvent B increasing to 95% solvent B over 15 minutes; flow rate 1 ml per minute. Retention time: 10.48 minutes. Solvent A: H$_2$O/0.1% TFA; solvent B: CH$_3$CN/0.085% TFA. Column type: HYPERPEP 300A.

EXAMPLE 58

(E)-2'-(Tetrahydro-1,4-thiazin-4-yl)-2(R)-[1(S)-(hydroxycarbamoyl)-4-phenyl-3-butenyl]-2'-isobutyl-4-methylvalerohydrazide p-toluenesulphonate In a manner analogous to that described in Example 11, but using 2-(tetrahydro-1,4-thiazin-4-yl)acetic acid in the place of N-acetyl-glycine, there was obtained (E)-2'-(tetrahydro-1,4-thiazin-4-yl)-2(R)-[1(S)-(hydroxycarbamoyl)-4-phenyl-3-butenyl]-2'-isobutyl-4-methylvalerohydrazide p-toluenesulphonate in the form of a white solid.

MS: 551 (M+H)$^+$. HPLC: Gradient elution using solvent A containing 5% solvent B increasing to 95% solvent B over 15 minutes; flow rate 1 ml per minute. Retention time: 11.36 minutes. Solvent A: H$_2$O 0.1% TFA; solvent B: CH$_3$CN/0.085% TFA. Column type: HYPERPEP 300A.

EXAMPLE 59

(E)-2'-(D-Alanyl)-2'-(cyclopropylmethyl)-2(R)-[1(S)-(hydroxycarbamoyl)-4-phenyl-3-butenyl]-4-methylvalerohydrazide p-toluenesulphonate In a manner analogous to that described in the first paragraph of Example 5, starting from 0.083 g of (E)-2'-(D-alanyl)-2'-(cyclopropylmethyl)-2(R)-[1(S)-[(tetrahydro-2 (RS)-pyranyloxy)carbamoyl]-4-phenyl-3-butenyl]-4-methylvalerohydrazide there was obtained 0.064 g of (E)-2'-(D-alanyl)-2'-(cyclopropylmethyl)-2(R)-[1(S)-(hydroxycarbamoyl)-4-phenyl-3-butenyl]-4-methyl-valerohydrazide p-toluenesulphonate in the form of a pale pink solid.

MS: 445 (M+H)$^+$. HPLC: Gradient elution using solvent A containing 5% solvent B increasing to 95% solvent B over 15 minutes; flow rate 1 ml/minute. Retention time: 10.392 minutes. Solvent A: H$_2$O/0.1% TFA; solvent B: CH$_3$CN/0.085% TFA. Column type: HYPERPEP 300A.

The (E)-2'-(D-alanyl)-2'-(cyclopropylmethyl)-2(R)-[1(S)-[(tetrahydro-2(RS)-pyranyloxy)carbamoyl]-4-phenyl-3-butenyl]-4-methylvalerohydrazide used as the starting material was prepared as follows:

(i) A mixture of 11 g of pentafluorophenol and 4.12 g of 1,3-dicyclohexylcarbodiimide in 50 ml of hexane was stirred at room temperature for 5 minutes. The resulting solid was filtered off, washed with hexane, dried and then added to a solution of 5.0 g of (E)-2(R)-[1(S)-(tert.-butoxycarbonyl)-4-phenyl-3-butenyl]-4-methylvaleric acid in 50 ml of dimethoxyethane. The mixture was left to stand at 4° C. overnight and then filtered to remove dicyclohexylurea. The filtrate was evaporated, the residue was dissolved in 50 ml of dichloromethane and 3 ml of hydrazine hydrate were added to the solution obtained. The mixture was stirred for 6 hours and then washed in sequence with 5% citric acid solution, saturated sodium hydrogen carbonate solution, water and saturated sodium chloride solution, dried over anhydrous magnesium sulphate and evaporated. The residue was triturated with hexane/ethyl acetate (4:1) and the resulting solid was filtered off. There were obtained 4.68 g of (E)-2(R)-[1(S)-(tert.-butoxycarbonyl)-4-phenyl-3-butenyl]-4-methylvalerohydrazide in the form of an off-white solid.

MS: 361 (M+H)$^+$.

(ii) A solution of 0.5 g of (E)-2(R)-[1(S)-(tert.-butoxycarbonyl)-4-phenyl-3-butenyl]-4-methyl-valerohydrazide, 0.097 g of cyclopropane carboxaldehyde and a crystal of 4-toluenesulphonic acid in 5 ml of dichloromethane was stirred for 0.2 hour over 4 Å moleculer sieves. The mixture was filtered and the solvent was evaporated with 5 ml of methanol. A few crystals of bromocresol green were added to give a yellow solution. To this was added 0.092 g of sodium cyanoborohydride in small batches. The yellow color of the solution was maintained by the periodic addition of a 4M solution of hydrogen chloride in dioxan. The methanol was evaporated and the residue was partitioned between ethyl acetate and 5% aqueous sodium hydrogen carbonate solution. The ethyl acetate phase was washed twice with 5% aqueous sodium hydrogen carbonate and then with saturated sodium chloride solution, dried over anhydrous magnesium sulphate and the solvent evaporated. The residue was purified by flash chromatography on silica gel using hexane/ethyl acetate (4:1) for the elution. There was obtained 0.258 g of (E)-2'-(cyclopropylmethyl)-2(R)-[1(S)-(tert.-butoxycarbonyl)-4-phenyl-3-butenyl]-4-methylvalerohydrozide in the form of a white solid.

MS: 415 (M+H)$^+$.

(iii) In an analogous manner to that described in Example 18, parts (i)–(iv), starting from (E)-2'-(cyclopropylmethyl)-2(R)-[1(S)-(tert.-butoxycarbonyl)-4-phenyl-3-butenyl]-4-methylvalerohydrazide and N-(9-fluorenylmethyloxycarbonyl)-D-alanine acid fluoride there was obtained (E)-2'-(D-alanyl)-2'-(cyclopropylmethyl)-2(R)-[1(S)-[(tetrahydro-2(RS)-pyranyloxy)carbamoyl]-4-phenyl-3-butenyl]-4-methylvalerohydrazide in the form of a gum.

MS: 529 (M+H)$^+$.

EXAMPLE 60

(E)-2'-(D-Alanyl)-2'-benzyl-2(R)-[1(S)-(hydroxycarbamoyl)-4-phenyl-3-butenyl]-4-methylvalerohydrazide p-toluenesulphonate In a manner analogous to that described in the first paragraph of Example 5, from 0.09 g of (E)-2'-(D-alanyl)-

2'-benzyl-2(R)-[1(S)-[(tetrahydro-2(RS)-pyranyloxy) carbamoyl-4-phenyl-3-butenyl]-4-methylvalerohydrazide there was obtained 0.096 g of (E)-2'-(D-alanyl)-2'-benzyl-2 (R)-[1(S)-(hydroxycarbamoyl)-4-phenyl-3-butenyl]-4-methylvalerohydrazide p-toluenesulphonate in the form of a pale pink solid.

MS: 481 (M+H)$^+$. HPLC: Gradient elution using solvent A containing 5% solvent B increasing to 95% solvent B over 15 minutes; flow rate 1 ml/minute. Retention time: 11.190 minutes. Solvent A: $H_2O$/0.1% TFA. solvent B: $CH_3CN$/ 0.085% TFA. Column type: HYPERPEP 300A.

The (E)-2'-(D-alanyl)-2'-benzyl-2(R)-[1(S)-[(tetrahydro-2(RS)-pyranyloxy)carbamoyl-4-phenyl-3-butenyl]-4-methylvalerohydrazide used as the starting material was prepared as follows:

(i) A mixture of 3.46 g of (E)-2(R)-[1(S)-(tert.-butoxycarbonyl)-4-phenyl-3-butenyl]-4-methylvaleric acid, 4.0 g of N-methyl morpholine, 2.95 g of benzylhydrazine dihydrochloride and 1.7 g of 1-hydroxybenzotriazole hydrate in 25 ml of dimethylformamide was cooled to 0° C. while stirring under nitrogen and 2.4 g of 1-ethyl-3-(3-dimethylaminopropyl)carbodiimide were added. The mixture was gradually allowed to come to room temperature and was then stirred overnight. The dimethylformamide was evaporated and the residue was partitioned between ethyl acetate and saturated sodium hydrogen carbonate solution. The ethyl acetate phase was washed in sequence with water, 5% citric acid solution, water and saturated sodium chloride solution. After drying over anhydrous magnesium sulphate the ethyl acetate was evaporated to give a yellow gum. Crystallization from hexane gave 1.87 g of (E)-2'-benzyl-2 (R)-[1(S)-(tert.-butoxycarbonyl)-4-phenyl-3-butenyl]-4-methylvalerohydrazide as a white solid.

MS: 451 (M+H)$^+$.

(ii) In an analogous manner to that described in Example 18, parts (i)–(iv), starting from (E)-2'-benzyl-2(R)-[1(S)-(tert.-butoxycarbonyl)-4-phenyl-3-butenyl]-4-methyl- valerohydrazide and N-(9-fluorenylmethyloxycarbonyl)-D-alanine acid fluoride there was obtained (E)-2'-(D-alanyl)-2'-benzyl-2(R)-[1(S)-[(tetrahydro-2(RS)-pyranyloxy)carbamoyl-4-phenyl-3-butenyl]-4-methylvalerohydrazide in the form of a white foam.

MS: 565 (M+H)$^+$.

EXAMPLE 61

(E)-2'-(D-Alanyl)-2(R)-[1(S)-(hydroxycarbamoyl)-4-phenyl-3-butenyl]-4-methyl-2'-(3-methyl-2-butenyl) valerohydrazide p-toluenesulphonate In a manner analogous to that described in the first paragraph of Example 5, starting from 0.072 mg of (E)-2'-(D-alanyl)-2(R)-[1(S)-[(tetrahydro-2(RS)-pyranyloxy) carbamoyl]-4-phenyl-3-butenyl]-4-methyl-2'-(3-methyl-2-butenyl)valerohydrazide there was obtained 0.052 g of (E)-2'-(D-alanyl)-2(R)-[1(S)-(hydroxycarbamoyl)-4-phenyl-3-butenyl]-4-methyl-2'-(3-methyl-2-butenyl)valerohydrazide p-toluenesulphonate in the form of an off-white solid.

MS: 459 (M+H)$^+$. HPLC: Gradient elution using solvent A containing 5% solvent B increasing to 95% solvent B over 15 minutes; flow rate 1 ml/minute. Retention time: 11.052 minutes. Solvent A: $H_2O$/1% TFA; solvent B: $CH_3CN$/ 0.085% TFA. Column type: HYPERPEP 300A.

The (E)-2'-(D-alanyl)-2(R)-[1(S)-[(tetrahydro-2(RS)-pyranyloxy)carbamoyl]-4-phenyl-3-butenyl]-4-methyl-2'-(3-methyl-2-butenyl)valerohydrazide used as the starting material was prepared as follows:

In a manner analogous to that described in Example 59, parts (ii) and (iii), starting from (E)-2(R)-[1(S)-(tert.-butoxycarbonyl)-4-phenyl-3-butenyl]-4-methylvalerohydrazide and 3-methylcrotonaldehyde there was obtained (E)-2'-(D-alanyl)-2(R)-[1(S)-[(tetrahydro-2(RS)-pyranyloxy)carbamoyl]-4-phenyl-3-butenyl]-4-methyl-2'-(3-methyl-2-butenyl)valerohydrazide in the form of a gum.

MS: 543 (M+H)$^+$.

EXAMPLE 62

(E)-2'-(D-Alanyl)-2(R)-[1(S)-(hydroxycarbamoyl)-4-phenyl-3-butenyl]-4-methyl-2'-octylvalerohydrazide p-toluenesulphonate In a manner analogous to that described in the first paragraph of Example 5, starting from 0.156 g of (E)-2'-(D-alanyl)-2(R)-[1(S)-[(tetrahydro-2(RS)-pyranyloxy) carbamoyl]-4-phenyl-3-butenyl]-4-methyl-2'-octylvalerohydrazide there was obtained 0.131 g of (E)-2'-(D-alanyl)-2(R)-[1(S)-(hydroxycarbamoyl)-4-phenyl-3-butenyl]-4-methyl-2'-octylvalerohydrazide p-toluenesulphonate in the form of a pale yellow solid.

MS: 503 (M+H)$^+$. HPLC: Gradient elution using solvent A containing 5% solvent B increasing to 95% solvent B over 15 minutes; flow rate 1 ml/minute. Retention time: 13.283 minutes. Solvent A: $H_2O$/0.1% TFA; solvent B: $CH_3CN$/ 0.085% TFA. Column type: HYPERPEP 300A.

The (E)-2'-(D-alanyl)-2(R)-[1(S)-[(tetrahydro-2(RS)-pyranyloxy)carbamoyl]-4-phenyl-3-butenyl]-4-methyl-2'-octylvalerohydrazide used as the starting material was prepared as follows:

In a manner analogous to that described in Example 59, parts (ii) and (iii), starting from (E)-2(R)-[(S)-(tert.-butoxycarbonyl)-4-phenyl-3-butenyl]-4-methylvalerohydrazide and octyl aldehyde there was obtained (E)-2'-(D-alanyl)-2(R)-[1(S)-[(tetrahydro-2(RS)-pyranyloxy) carbamoyl]-4-phenyl-3-butenyl]-4-methyl-2'-octylvalerohydrazide in the form of a gum.

MS: 587 (M+H)$^+$.

EXAMPLE 63

(E)-2'-(D-Alanyl)-2'-[(cyclohexyl)methyl]-2(R)-[1 (S)-(hydroxycarbamoyl)-4-phenyl-3-butenyl]-4-methylvalerohydrazide p-toluenesulphonate In a manner analogous to that described in the first paragraph of Example 5, starting from 0.180 g of (E)-2'-[(D-alanyl)-2'-[(cyclohexyl)methyl]-2(R)-[1(S)-[(tetrahydro-2(RS)-pyranyloxy)carbamoyl]-4-phenyl-3-butenyl]-4-methylvalerohydrazide there was obtained 0.196 g of (E)-2'-(D-alanyl)-2'-[(cyclohexyl)methyl]-2(R)-[1(S)-(hydroxycarbamoyl)-4-phenyl-3-butenyl]-4-methylvalerohydrazide p-toluenesulphonate in the form of a pale yellow solid.

MS: 487 (M+H)$^+$. HPLC: Gradient solution using solvent A containing 5% solvent B increasing to 95% solvent B over 15 minutes; flow rate 1 ml/minute. Retention time: 11.987 minutes. Solvent A: $H_2O$/0.1% TFA; solvent B: $CH_3CN$/ 0.085% TFA. Column type: HYPERPEP 300A.

The (E)-2'-(D-alanyl)-2'-[(cyclohexyl)methyl]-2(R)-[1 (S)-[(tetrahydro-2(RS)-pyranyloxy)carbamoyl]-4-phenyl-3-butenyl]-4-methylvalerohydrazide used as the starting material was prepared as follows:

In a manner analogous to that described in Example 59, parts (ii) and (iii), starting from (E)-2(R)-[1(S)-(tert.- butoxycarbonyl)-4-phenyl-3-butenyl]-4-methylvalerohydrazide and cyclohexanecarboxaldehyde there was obtained (E)-2'-(D-alanyl)-2'-[(cyclohexyl)methyl]-2(R)-[1(S)-[(tetrahydro-2(RS)-pyranyloxy)carbamoyl]-4-phenyl-3-butenyl]-4-methylvalerohydrazide in the form of a gum.

MS: 571 (M+H)⁺.

EXAMPLE 64

(E)-2'-(D-Alanyl)-2(R)-[1(S)-(hydroxycarbamol)-4-phenyl-3-butenyl]-4-methyl-2'-neopentylvalerohydrazide p-toluenesulphonate In a manner analogous to that described in the first paragraph of Example 5, starting from 0.062 g of (E)-2'-(D-alanyl)-2(R)-[1(S)-[(tetrahydro-2(RS)-pyranyloxy)carbamoyl]-4-phenyl-3-butenyl]-4-methyl-2'-neopentylvalerohydrazide there was obtained 0.065 g of (E)-2'-(D-alanyl)-2(R)-[1(S)-(hydroxycarbamoyl)-4-phenyl-3-butenyl]-4-methyl-2'-neopentylvalerohydrazide p-toluenesulphonate in the form of a pale yellow solid.

MS: 461 (M+H⁺. HPLC; Gradient elution using solvent A containing 5% solvent B increasing to 95% solvent B over 15 minutes; flow rate 1 ml/minute. Retention time: 11.45 minutes. Solvent A: H₂O/0.1% TFA; solvent B: CH₃CN/0.085% TFA. Column type: HYPERPEP 300A.

The (E)-2'-(D-alanyl)-2(R)-[1(S)-[(tetrahydro-2(RS)-pyranyloxy)carbamoyl]-4-phenyl-3-butenyl]-4-methyl-2'-neopentylvalerohydrazide used as the starting material was prepared as follows:

In a manner analogous to that described in Example 59, parts (ii) and (iii), starting from (E)-2(R)-[1(S)-(tert.-butoxycarbonyl)-4-phenyl-3-butenyl]-4-methylvalerohydrazide and trimethylacetaldehyde there was obtained (E)-2'-(D-alanyl)-2(R)-[1(S)-[(tetrahydro-2(RS)-pyranyloxy)carbamoyl]-4-phenyl-3-butenyl]-4-methyl-2'-neopentylvalerohydrazide in the form of a gum.

MS: 545 (M+H)⁺.

EXAMPLE 65

(E)-2'-(D-Alanyl)-2(R)-[1(S)-(hydroxycarbamoyl)-4-phenyl-3-butenyl]-4-methyl-2'-(3,3-dimethylbutyl)valerohydrazide p-toluenesulphonate In a manner analogous to that described in the first paragraph of Example 5, starting from 0.148 g of (E)-2'-(D-alanyl)-2(R)-[1(S)-[(tetrahydro-2(RS)-pyranyloxy)carbamoyl]-4-phenyl-3-butenyl]-4-methyl-2'-(3,3-dimethylbutyl)valerohydrazide there was obtained 0.163 g of (E)-2'-(D-alanyl)-2(R)-[1(S)-(hydroxycarbamoyl)-4-phenyl-3-butenyl]-4-methyl-2'-(3,3-dimethylbutyl)valerohydrazide p-toluenesulphonate in the form of a pale pink solid.

MS: 475 (M+H)⁺. HPLC: Gradient elution using solvent A containing 5% solvent B increasing to 95% solvent B over 15 minutres; flow rate 1 ml/minute. Retention time: 11.652 minutes. Solvent A: H₂O/0.1% TFA; solvent B: CH₃CN/0.085% TFA. Column type: HYPERPEP 300A.

The (E)-2'-(D-alanyl)-2(R)-[1(S)-[(tetrahydro-2(RS)-pyranyloxy)carbamoyl]-4-phenyl-3-butenyl]-4-methyl-2'-(3,3-dimethylbutyl)valerohydrazide used as the starting material was prepared as follows:

In a manner ananlogous to that described in Example 59, parts (ii) and (iii), starting from (E)-2(R)-[1(S)-(tert.-butoxycarbonyl)-4-phenyl-3-butenyl]-4-methylvalerohydrazide and 3,3-dimethyl butyraldehyde there was obtained (E)-2'-(D-alanyl)-2(R)-[1(S)-[(tetrahydro-2(RS)-pyranyloxy)carbamoyl]-4-phenyl-3-butenyl]-4-methyl-2'-(3,3-dimethylbutyl)valerohydrazide in the form of a gum.

MS: 559 (M+H)⁺.

EXAMPLE 66

(E)-2'-(D-Alanyl)-2'-(2-ethylbutyl)-2(R)-[1(S)-(hydroxycarbamoyl)-4-phenyl-3-butenyl]-4-methylvalerohydrazide p-toluenesulphonate In a manner analogous to that described in the first paragraph of Example 5, starting from 0.224 g of (E)-2'-(D-alanyl)-2'-(2-ethylbutyl)-2(R)-[1(S)-[(tetrahydro-2(RS)-pyranyloxy)carbamoyl]-4-phenyl-3-butenyl]-4-methylvalerohydrazide there was obtained 0.188 g of (E)-2'-(D-alanyl)-2'-(2-ethylbutyl)-2(R)-[1(S)-(hydroxycarbamoyl)-4-phenyl-3-butenyl]-4-methylvalerohydrazide p-toluenesulphonate in the form of a pale pink solid.

MS: 475 (M+H)⁺. HPLC: Gradient elution using solvent A containing 5% solvent B increasing to 95% solvent B over 15 minutes; flow rate 1 ml/minute. Retention time: 11.735 minutes. Solvent A: H₂O/0.1% TFA; solvent B: CH₃CN/0.085% TFA. Column type: HYPERPEP 300A.

The (E)-2'-(D-alanyl)-2'-(2-ethylbutyl)-2(R)-[1(S)-[(tetrahydro-2(RS)-pyranyloxy)carbamoyl]-4-phenyl-3-butenyl]-4-methylvalerohydrazide used as the starting material was prepared as follows:

In a manner analogous to that described in Example 59, parts (ii) and (iii), starting from (E)-2(R)-[1(S)-(tert.-butoxycarbonyl)-4-phenyl-3-butenyl]-4-methylvalerohydrazide and 2-ethylbutyraldehyde there was obtained (E)-2'-(D-alanyl)-2'-(2-ethylbutyl)-2(R)-[1(S)-[(tetrahydro-2(RS)-pyranyloxy)carbamoyl]-4-phenyl-3-butenyl]-4-methylvalerohydrazide in the form of a gum.

MS: 559 (M+H)⁺.

EXAMPLE 67

(E)-2'-(D-Alanyl)-2'-(2,2-dichloroethyl)-2(R)-[1(S)-(hydroxycarbamoyl)-4-phenyl-3-butenyl]-4-methylvalerohydrazide p-toluenesulphonate In a manner analogous to that described in the first paragraph of Example 5, starting from 0.074 g of (E)-2'-(D-alanyl)-2'-(2,2-dichloroethyl)-2(R)-[1(S)-[(tetrahydro-2(RS)-pyranyloxy)carbamoyl]-4-phenyl-3-butenyl]-4-methylvalerohydrazide there was obtained 0.057 g of (E)-2'-(D-alanyl)-2'-(2,2-dichloroethyl)-2(R)-[1(S)-(hydroxycarbamoyl)-4-phenyl-3-butenyl]-4-methylvalerohydrazide p-toluenesulphonate in the form of a pale pink solid.

MS: 487 (M+H)⁺. HPLC: Gradient elution using solvent A containing 5% solvent B increasing to 95% solvent B over 15 minutes; flow rate 1 ml/minute. Retention time: 11.127 minutes. Solvent A: H₂O/0/1% TFA; solvent B: CH₃CN/0.085% TFA. Column type: HYPERPEP 300A.

The (E)-2'-(D-alanyl)-2'-(2,2-dichloroethyl)-2(R)-[1(S)-[(tetrahydro-2(RS)-pyranyloxy)carbamoyl]-4-phenyl-3-butenyl]-4-methylvalerohydrazide used as the starting material was prepared as follows:

In a manner analogous to that described in Example 59, parts (ii) and (iii), starting from (E)-2(R)-[1(S)-(tert.-butoxycarbonyl)-4-phenyl-3-butenyl]-4-methylvalerohydrazide and dichloroacetaldehyde there was obtained (E)-2'-(D-alanyl)-2'-(2,2-dichloroethyl)-2(R)-[1(S)-[(tetrahydro-2(RS)-pyranyloxy)carbamoyl]-4-phenyl-3-butenyl]-4-methylvalerohydrazide as a gum.

MS: 571 (M+H)$^+$.

EXAMPLE 68

(E)-2'-(D-Alanyl)-2(R)-[1(S)-(hydroxycarbamoyl)-4-phenyl-3-butenyl]-2'-isopropyl-4-methylvalerohydrazide p-toluenesulphonate In a manner analogous to that described in the first paragraph of Example 5, starting from 0.082 g of (E)-2'-(D-alanyl)-2(R)-[1(S)-[(tetrahydro-2(RS)-pyranyloxy)carbamoyl]-4-phenyl-3-butenyl]-2'-isopropyl-4-methylvalerohydrazide there was obtained 0.072 g of (E)-2'-(D-alanyl)-2(R)-[1(S)-(hydroxycarbamoyl)-4-phenyl-3-butenyl]-2'-isopropyl-4-methylvalerohydrazide p-toluenesulphonate in the form of a pale pink solid.

MS: 433 (M+H)$^+$. HLPC: Gradient elution using solvent A containing 5% solvent B increasing to 95% solvent B over 15 minutes; flow rate 1 ml/minute. Retention time: 10.337 minutes. Solvent A: H$_2$O/0.1% TFA; Solvent B: CH$_3$CN/0.085% TFA. Column type: HYPERPEP 300A.

The (E)-2'-(D-alanyl)-2(R)-[1(S)-[(tetrahydro-2(RS)-pyranyloxy)carbamoyl]-4-phenyl-3-butenyl]-2'-isopropyl-4-methylvalerohydrazide used as the starting material was prepared as follows:

In a manner analogous to that described in Example 59, parts (ii) and (iii), starting from (E)-2(R)-[1(S)-(tert.-butoxycarbonyl)-4-phenyl-3-butenyl]-4-methylvalerohydrazide and acetone there was obtained (E)-2'-(D-alanyl)-2(R)-[1(S)-[(tetrahydro-2(RS)-pyranyloxy)carbamoyl]-4-phenyl-3-butenyl]-2'-isopropyl-4-methylvalerohydrazide in the form of a gum.

MS: 517 (M+H)$^+$.

EXAMPLE 69

(E)-2'-(D-Alanyl)-2(R)-[1(S)-(hydroxycarbamoyl)-4-phenyl-3-butenyl]-4-methyl-2'-(2(S)-methylbutyl)valerohydrazide p-toluenesulphonate In a manner analogous to that described in the first paragraph of Example 5, starting from 0.132 g of (E)-2'-(D-alanyl)-2(R)-[1(S)-[(tetrahydro-2(RS)-pyranyloxy)carbamoyl]-4-phenyl-3-butenyl]-4-methyl-2'-(2(S)-methylbutyl)valerohydride there was obtained 0.121 g of (E)-2'-(D-alanyl)-2(R)-[1(S)-(hydroxycarbamoyl)-4-phenyl-3-butenyl]-4-methyl-2'-(2(S)-methylbutyl)valerohydrazide p-toluenesulphonate in the form of an off-white solid.

MS: 461 (M+H)$^+$. HLPC: Gradient elution using solvent A containing 5% solvent B increasing to 95% solvent B over 15 minutes; flow rate 1 ml/minute. Retention time: 11.237 minutes. Solvent A: H$_2$O/0.1% TFA; solvent B: CH$_3$CN/0.085% TFA. Column type HYPERPEP 300A.

The of (E)-2'-(D-alanyl)-2(R)-[1(S)-[(tetrahydro-2(RS)-pyranyloxy)carbamoyl]-4-phenyl-3-butenyl]-4-methyl-2'-(2(S)-methylbutyl)valerohydride used as the starting material was prepared as follows:

(i) A mixture of 0.5 g of (E)-2(R)-[1(S)-(tert.-butoxycarbonyl)-4-phenyl-3-butenyl]-4-methylvalerohydrazide and 0.288 g of p-toluenesulphonyl chloride in 6 ml of dry pyridine was stirred at room temperature for 2 hours. The pyridine was evaporated and the residue partitioned between ethyl acetate and water. The ethyl acetate layer was washed successively with water, 1M hydrochloric acid, saturated sodium chloride solution, dried over anhydrous magnesium sulphate and evaporated. The residue was crystallized from ether/hexane and there was obtained 0.373 g of (E)- 2(R)-[1(S)-(tert.-butoxycarbonyl)-4-phenyl-3-butenyl]-4-methyl-2'-(p-toluenesulphonyl)valerohydride in the form of a white solid.

MS: 515 (M+H)$^+$.

(ii) A mixture of 0.323 g of (E)-2(R)-[1(S)-(tert.-butoxycarbonyl)-4-phenyl-3-butenyl]-4-methyl-2'-(p-toluenesulphonyl)valerohydrazide, 0.111 g of S(+)-1-bromo-2-methylbutane and 0.053 g of anhydrous potassium carbonate in 5 ml of dry dimethylformamide was stirred at room temperature overnight. The solvent was evaporated and the residue was partitioned between ethyl acetate and water. The ethyl acetate layer was washed with saturated sodium chloride solution, dried over anhydrous magnesium sulphate and evaporated. The residue was purified by flash chromatography on silica gel using hexane/ethyl acetate (5:1) for the elution. There was obtained 0.187 g of (E)-2(R)-[1(S)-(tert.-butoxycarbonyl)-4-phenyl-3-butenyl]-4-methyl-2'-(2(S)-methylbutyl)-2'-(p-toluenesulphonyl)valerohydrazide in the form of a gum. MS: 585 (M+H)$^+$. Continued elution of the column gave 0.21 g of the hydrazide used in the reaction.

(iii) A mixture of 0.325 g of (E)-2(R)-[1(S)-(tert.-butoxycarbonyl)-4-phenyl-3-butenyl]-4-methyl-2'-(2(S)-methylbutyl)-2'-(p-toluenesulphonyl)valerohydrazide and 0.135 g of magnesium powder was placed in a sonic bath for 1.5 hours. The methanol was evaporated and the residue was partitioned between diethyl ether and potassium hydrogen sulphate solution. The ethereal layer was washed in sequence with potassium hydrogen sulphate solution, 5% sodium hydrogen carbonate solution, water and saturated sodium chloride solution, dried over anhydrous magnesium sulphate and evaporated. The residue was purified by flash chromatography on silica gel using hexane/ethyl acetate (5:1) for the elution. There was obtained 0.146 g of (E)-2(R)-[1(S)-(tert.-butoxycarbonyl)-4-phenyl-3-butenyl]-4-methyl-2'-(2(S)-methylbutyl)valerohydrazide in the form of a white solid.

MS: 431 (M+H)$^+$.

(iv) In an analogous manner to that described in Example 18, parts (i)–(iv), starting from (E)-2(R)-[1(S)-(tert.-butoxycarbonyl)-4-phenyl-3-butenyl]-4-methyl-2'-(2(S)-methylbutyl)valerohydrazide and N-(9-fluorenylmethyloxycarbonyl)-D-alanine fluoride there was obtained (E)-2'-(D-alanyl)-2(R)-[1(S)-[(tetrahydro-2(RS)-pyranyloxy)carbamoyl]-4-phenyl-3-butenyl)-4-methyl-2'-(2(S)-methylbutyl)valerohydrazide in the form of a gum.

MS: 544 (M+H)$^+$.

EXAMPLE 70

(E)-2'-(D-Alanyl)-2(R)-[1(S)-(hydroxycarbamoyl)-4-phenyl-3-butenyl]-4-methyl-2'-phenylvalerohydrazide p-toluenesulphonate In a manner analogous to that described in the first paragraph of Example 5, starting from 0.189 g of (E)-2'-(D-alanyl)-2(R)-[1(S)-[(tetrahydro-2(RS)-pyranyloxy)carbamnoyl]-4-phenyl-3-butenyl]-4-methyl-2-phenylvalerohydrazide there was obtained 0.191 g of (E)-2'-(D-alanyl)-2(R)-[1(S)-(hydroxycarbamoyl)-4-phenyl-3-butenyl]-4-methyl-2'-phenylvalerohydrazide in the form of a pale pink solid.

MS: 467 (M+H)$^+$. HPLC: Gradient elution using solvent A containing 5% solvent B increasing to 95% solvent B over 15 minutes; flow rate 1 ml/minute. Retention time: 10.328 minutes. Solvent A: H$_2$O/0.1% TFA; solvent B: CH$_3$CN/ 0.085% TFA. Column type: HYPERPEP 300A.

The (E)-2'-(D-alanyl)-2(R)-[1(S)-[(tetrahydro-2(RS)-pyranyloxy)carbamoyl]-4-phenyl-3-butenyl]-3-4-methyl-2'-phenylvalerohydrazide used as the starting material was prepared as follows:

(i) A solution of 1.75 g of (E)-2(R)-[1(S)-(tert.-butoxycarbonyl)-4-phenyl-3-butenyl]-4-methylvaleric acid in 15 ml of dimethylformamide was cooled to 0° C. and treated in succession with 0.5 ml of N-methylmorpholine, 0.8 g of 1-hydroxybenzotriazole, 0.6 g of phenylhydrazine and 1.1 g of 1-ethyl-3-(3-dimethylaminopropyl) carbodiimide hydrochloride. The solution was left to warm to room temperature and was stirred overnight. The solvent was evaporated and the residue was partitioned between ethyl acetate and 5% aqueous sodium hydrogen carbonate solution. The ethyl acetate phase was washed in sequence with water, 5% citric acid solution, water and saturated sodium chloride solution, dried over anhydrous magnesium sulphate and evaporated. The residue was purified by flash chromatography on silica gel using hexane/ethyl acetate (6:1) for the elution. There was obtained a yellow oil which, after crystallization from hexane, gave 1.5 g of (E)-2(R)-[1(S)-(tert.-butoxycarbonyl)-4-phenyl-3-butenyl]-4-methyl-2'-phenylhydrazide in the form of a white solid.

MS: 437 (M+H)$^+$.

(ii) A solution of 0.35 g of (E)-2(R)-[1(S)-(tert.-butoxycarbonyl)-4-phenyl-3-butenyl]-4-methyl-2'-phenylhydrazine in 4 ml of dichloromethane was cooled to 0° C. and 0.9 g of pyridine was added. A solution of 0.24 g of N-phthaloyl-Dalanine acid chloride in 4 ml of dichloromethane was added dropwise and the mixture was stirred at 0° C. for 2.5 hours. The dichloromethane was evaporated and the residue was dissolved in ethyl acetate and washed in sequence with 5% citric acid solution, water, two portions of 5% sodium hydrogen carbonate solution and saturated sodium chloride solution, dried over anhydrous magnesium sulphate and evaporated. The residue was purified by flash chromatography on silica gel using hexane/ethyl acetate (3:1) for the elution to give 0.316 g of product containing 13% of the 2(S)-phthalimidopropyl isomer resulting from partial racemization. Recrystallization of this product from a mixture of 4 ml of dichloromethane and 20 ml of hexane gave 0.215 g of (E)-2(R)-[1(S)-(tert.-butoxycarbonyl)-4-phenyl-3-butenyl]-4-methyl-2'-phenyl-2'-(2(R)-phthalimidopropyl)valerohydrazide containing 3% of the 2-(S)-phthalimidopropyl isomer.

MS: 638 (M+H)$^+$.

(iii) In a manner analogous to that described in Example 18, parts (ii) and (iii), from 0.638 g of (E)-2(R)-[1(S)-(tert.-butoxycarbonyl)-4-phenyl-3-butenyl]-4-methyl-2'-phenyl-2'-(2(R)-phthalimidopropyl)valerobydrazide there was obtained 0.363 g of (E)-2(R)-[1(S)-[(tetrahydro-2(RS)-pyranyloxy)carbamoyl]-4-phenyl-3-butenyl]-4-methyl-2'-phenyl-2'-(2(R)-phthalimidopropyl)valerohydrazide in the form of a colorless glass.

MS: 681 (M+H)$^+$.

(iv) A solution of 0.22 g of (E)-2(R)-[1(S)-[(tetrahydro-2 (RS)-pyranyloxy)carbamoyl]-4-phenyl-3-butenyl]-4-methyl-2'-phenyl-2'-(2(R)-phthalimidopropyl) valerohydrazide in 4 ml of methanol was treated with 0.04 g of hydrazine hydrate. The mixture was stirred for 5.5 hours and then the solvent was evaporated. The residue was suspended in 2 ml of dichloromethane and stirred at 4° C. overnight. The suspended solid was filtered off, the filtrate was evaporated and the residue was purified by flash chromatography on silica gel using dichloromethane/methanol (20:1) for the elution. There was obtained 0.189 of (E)-2'-(D-alanyl)-2(R)-[1(S)-[(tetrahydro-2(RS)-pyranyloxy) carbamoyl]-4-phenyl-3-butenyl]-4-methyl-2'-phenylvalerohydrazide in the form of a colorless foam.

MS: 551 (M+H)$^+$.

EXAMPLE 71

(E)-2'-(L-Alanyl)-2(R)-[1(S)-(hydroxycarbamoyl)-4-phenyl-3-butenyl]-4-methyl-2'-phenylvalerohydrazide p-toluenesulphonate In a manner analogous to that described in the first paragraph of Example 5, starting from 0.103 g of (E)-2'-(L-alanyl)-2(R)-[1(S)-[(tetrahydro-2(RS)-pyranyloxy) carbamoyl]-4-phenyl-3-butenyl]-4-methyl-2'-phenylvalerohydrazide there was obtained 0.068 g of (E)-2'-(L-alanyl)-2(R)-[1(S)-(hydroxycarbamoyl)-4-phenyl-3-butenyl]-4-methyl-2'-phenylvalerohydrazide p-toluenesulpbonate in the form of a pink solid.

MS: 467 (M+H)$^+$. PLC: Gradient elution using solvent A containing 5% solvent B increasing to 95% solvent B over 15 minutes; flow rate 1 ml/minute. Retention time: 10.337 minutes. Solvent A: H$_2$O/0.1% TFA; solvent B; CH$_3$CN/ 0.085% TFA. Column type: HYPERPEP 300A.

The (E)-2'-(L-alanyl)-2(R)-[1(S)-[(tetrahydro-2(RS)-pyranyloxy)carbamoyl]-4-phenyl-3-butenyl]-4-methyl-2'-phenylvalerohydrazide used as the starting material was prepared as follows:

In a manner analogous to that described in Example 70, parts (ii)-(iv), starting from (E)-2(R)-[1(S)-(tert.-butoxycarbonyl)-4-phenyl-3-butenyl]-4-methyl-2'-phenylydrazide and N-phthaloyl-L-alanine acid chloride there was obtained (E)-2'-(L-alanyl)-(R)-[1(S)-[(tetrahydro-2(RS)-pyranyloxy)carbamoyl]-4-phenyl-3-butenyl]-4-methyl-2'-phenylvalerohydrazide in the form of a colorless foam.

MS: 551 (M+H)$^+$.

EXAMPLE 72

(E)-2'-(D,L-Alanyl)-2(R)-[1(S)-(hydroxycarbamoyl)-4-phenyl-3-butenyl]-4-methyl-2'-(1-naphthyl)valerohydrazide p-toluenesulphonate In a manner analogous to that described in the first paragraph of Example 5, starting from 0.131 g of (E)-2'-(D, L-alanyl)-2(R)-[1(S)-[(tetrahydro-2(RS)-pyranyloxy) carbamoyl]-4-phenyl-3-butenyl]-4-methyl-2'-(1-naphthyl) valerohydrazide there was obtained 0.165 g of (E)-2'-(D,L-alanyl)-2(R)-[1(S)-(hydroxycarbamoyl)-4-phenyl-3-butenyl]-4-methyl-2'-(1-naphthyl)valerohydrazide p-toluenesulphonate in the form of a pale pink solid.

MS: 517 (M+H)$^+$. HPLC: Gradient elution using solvent A containing 5% solvent B increasing to 95% solvent B over 15 minutes; flow rate 1 ml/minute. Retention time: 11.122 minutes. Solvent A: H$_2$O/0.1% TFA; solvent B: CH$_3$CN/ 0.085% TFA. Column type: HYPERPEP 300A.

The (E)-2'-(D,L-alanyl)-2(R)-[(S)-[(tetrahydro-(2(RS)-pyranyloxy)carbamoyl]-4-phenyl-3-butenyl]-4-methyl-2'-(1-naphthyl)valerohydrazide used as the starting material was prepared as follows:

(i) In a manner analogous to that described in Example 70, part (i), from (E)-2(R)-[1(S)-(tert.-butoxycarbonyl)-4-phenyl-3-butenyl]-4-methylvaleric acid and 1-naphthylhydrazine there was obtained (E)-2(R)-[1(S)-

(tert.-butoxycarbonyl)-4-phenyl-3-butenyl]-4-methyl-2'-(1-naphthyl)valerohydrazide in the form of a white solid.

MS: 487 (M+H)$^+$.

(ii) In a manner analogous to that described in Example 70, parts (ii)–(iv) except that the reaction in part (ii) was allowed to proceed to three days at 4° C., from (E)-2(R)-[1(S)-(tert.-butoxycarbonyl)-4-phenyl-3-butenyl]-4-methyl-2'-(1-naphthyl)valerohydrazide and N-phthaloyl-D-alanine acid chloride there was obtained (E)-2'-(D,L-alanyl)-2(R)-[1(S)-[(tetrahydro-(2(RS)-pyranyloxy)carbamoyl]-4-phenyl-3-butenyl]-4-methyl-2'-(1-naphthyl)valerohydrazide in the form of a pale cream foam. Racemnization of the alanyl group occurred during part (ii).

EXAMPLE 73

Mixture of (E)-2'-(D-alanyl)-2'-(tetrahydro4-thiopyranyl)-2(R)-[1(S)-(hydroxycarbamoyl)-4-phenyl-3-butenyl]-4-methylvalerohydrazide p-toluenesulphonate and (E)-2'-(D-alanyl)-2'-(tetrahydro-4-thiopyranyl)-2(S)-[1(R)-(hydroxycarbamoyl)-4-phenyl-3-butenyl]-4-methylvalerohydrazide p-toluenesulphonate In a manner analogous to that described in the first paragraph of Example 5, starting from 0.1 g of a 1:1 mixture of (E)-2'-(D-alanyl)-2'-(tetrahydro-4-thiopyranyl)-2(R)-[1 (S)-[(tetrahydro-2(RS)-pyranyloxy)carbamoyl]- 4-phenyl-3-butenyl]-4-methylvalerohydrazide and (E)-2'-(D-alanyl)-2'-(tetrahydro-4-thiopyranyl)-2(S)-[1(R)-[(tetrahydro-2 (RS)-pyranyloxy)carbamoyl]-4-phenyl-3-butenyl]-4-methylvalerohydrazide there was obtained 0.09 g of a 1:1 mixture of (E)-2'-(D-alanyl)-2'-(tetrahydro-4-thiopyranyl)-2 (R)-[1(S)-(hydroxycarbamoyl)-4-phenyl-3-butenyl]-4-methylvalerohydrazide p-toluenesulphonate and (E)-2'-(D-alanyl)-2'-(tetrahydro-4-thiopyranyl)-2(S)-[1(R)-(hydroxycarbamoyl)-4-phenyl-3-butenyl]-4-methylvalerohydrazide p-toluenesulphonate in the form of a pink solid.

MS: 491 (M+H)$^+$. HPLC: Gradient elution using solvent A containing 25% solvent B increasing to 55% solvent B over 15 minutes; flow rate 1 ml/minute. Retention time: 8.535 minutes, isomer 1 and 9.252 minutes, isomer 2. Solvent A: H$_2$O/0.1% TFA; solvent B: CH$_3$CN/0.085% TFA. Column type: HYPERPEP 300A.

The mixture of (E)-2'-(D-alanyl)-2'-(tetrahydro-4-thiopyranyl)-2(R)-[1(S)-[(tetrahydro-2(RS)-pyranyloxy) carbamoyl]-4-phenyl-3-butenyl]-4-methylvalerohydrazide and (E)-2'-(D-alanyl)-2'-(tetrahydro-4-thiopyranyl)-2(S)-[1 (R)-[(tetrahydro-2(RS)-pyranyloxy)carbamoyl]-4-phenyl-3-butenyl]-4-methylvalerohydrazide used as the stating material was prepared as follows:

(i) In a manner analogous to that described in Example 1, parts (i)–(ii), and Example 59, part (i), starting from 4-tert-butyl hydrogen 2(RS)-isobutylsuccinate and cinnamyl bromide there was obtained a 1:1 mixture of (E)-2(R)-[1(S)-(tert.-butoxycarbonyl)-4-phenyl-3-butenyl]-4-methylvalerohydrazide and (E)-2(S)-[1(R)-(tert.-butoxycarbonyl)-4-phenyl-3-butenyl]-4-methylvalerohydrazide in the form of a white solid.

MS: 361 (M+H)$^+$.

(ii) In a manner analogous to that described in Example 59, parts (ii)–(iii), starting from a 1:1 mixture of (E)-2(R)-[1 (S)-(tert.-butoxycarbonyl)-4-phenyl-3-butenyl]-4-methylvalerohydrazide and (E)-2(S)-[1(R)-(tert.-butoxycarbonyl)-4-phenyl-3-butenyl]-4-methylvalerohydrazide and tetrahydrothiopyran-4-one there was obtained a 1:1 mixture of (E)-2'-(D-alanyl)-2'-(tetrahydro-4-thiopyranyl)-2(R)-[1(S)-[(tetrahydro-2(RS)-pyranyloxy) carbamoyl]-4-phenyl-3-butenyl]-4-methylvalerohydrazide and (E)-2'-(D-alanyl)-2'-(tetrahydro-4-thiopyranyl)-2(S)-[1 (R)-[(tetrahydro-2(RS)-pyranyloxy) carbamoyl]-4-phenyl-3-butenyl]-4-methylvalerohydrazide in the form of a white MS: 575 (M+H)$^+$.

EXAMPLE 74

(E)-2'-(D-Alanyl)-3-cyclobutyl-2(R)-[1(S)-(hydroxycarbamoyl)-4-phenyl-3-butenyl]-2'-isobutylpropionohydrazide p-toluenesulphonate In a manner analogous to that described in the first paragraph of Example 5, starting from 0.076 g of (E)-2'-(D-alanyl)-3-cyclobutyl-2(R)-[1(S)-[(tetrahydro-2(RS)-pyranyloxy)carbamoyl]-4-phenyl-3-butenyl]-2'-isobutylpropionohydrazide there was obtained 0.071 g of (E)-2'-(D-alanyl)-3-cyclobutyl-2(R)-[1(S)-(hydroxycarbamoyl)-4-phenyl-3-butenyl]-2'-isobutylpropionohydrazide p-toluenesulphonate in the form of a pale pink solid.

MS: 459 (M+H)$^+$. HPLC: Gradient elution using solvent A containing 5% solvent B increasing to 95% solvent B over 15 minutes; flow rate 1 ml/minute. Retention time: 10.987 minutes. Solvent A: H$_2$O/0.1% TFA; solvent B: CH$_3$CN/0.085% TFA. Column type: HYPERPEP 300A.

The (E)-2'-(D-alanyl)-3-cyclobutyl-2(R)-[1(S)-[(tetrahydro-2(RS)-pyranyloxy)carbamoyl]-4-phenyl-3-butenyl]-2'-isobutylpropionohydrazide used as the starting material was prepared as follows:

(i) In a manner analogous to that described in Example 1, parts (i)–(iii), starting from 4-tert.-butyl hydrogen 2(R)-(cyclobutylmethyl)succinate and cinnamyl bromide there was obtained (E)-2(R)-[1(S)-(tert.-butoxycarbonyl)-4-phenyl-3-butenyl]-3-cyclobutyl-2'-isobutylpropionohydrazide in the form of a white solid.

MS: 428 (M+H)$^+$.

(ii) In a manner analogous to that described in Example 18, parts (i)–(iv), starting from (E)-2(R)-[1(S)-(tert.-butoxycarbonyl)-4-phenyl-3-butenyl]-3-cyclobutyl-2'-isobutylpropionohydrazide and N-(9-fluorenylmethyl-oxycarbonyl)-D-alanine acid fluoride there was obtained (E)-2'-(D-alanyl)-3-cyclobutyl-2(R)-[1(S)-[(tetrahydro-2 (RS)-pyranyloxy)carbamoyl]-4-phenyl-3-butenyl]-2'-isobutylpropionohydrazide in the form of a colorless gum.

MS: 543 (M+H)$^+$.

EXAMPLE 75

(E)-2'-(D-Alanyl)-3-cyclopentyl-2(R)-[1(S)-(hydroxycarbamoyl)-4-phenyl-3-butenyl]-2'-isobutylpropionohydrazide p-toluenesulphonate In a manner analogous to that described in the first paragraph of Example 5, starting from 0.205 g of (E)-2'-(D-alanyl)-3-cyclopentyl-2(R)-[1(S)-[(tetrahydro-2(RS)-pyranyloxy)carbamoyl]-4-phenyl-3-butenyl]-2'-isobutylpropionohydrazide there was obtained 0.222 g of (E)-2'-(D-alanyl)-3-cyclopentyl-2(R)-[1(S)-(hydroxycarbamoyl)-4-phenyl-3-butenyl]-2'-isobutylpropionohydrazide in the form of a pale pink solid.

MS: 473 (M+H)$^+$. HPLC: Gradient elution using solvent A containing 5% solvent B increasing to 95% solvent B over 15 minutes; flow rate 1 ml/minute. Retention time: 11.417 minutes. Solvent A: H$_2$O/0.1% TFA; solvent B: CH$_3$CN/0.085% TEA. Column type: HYPERPEP 300A.

The (E)-2'-(D-alanyl)-3-cyclopentyl-2(R)-[1(S)-[(tetrahydro-2(RS)-pyranyloxy)carbamoyl]-4-phenyl-3-butenyl]-2'-isobutylpropionohydrazide used as the starting material was prepared as follows:

(i) In a manner analogous to that described in Example 1, parts (i)–(iii), starting from 4-tert.-butyl hydrogen 2(R)-(cyclopentylmethyl)succinate and cinnamyl bromide there was obtained (E)-2(R)-[1(S)-(tert-butoxycarbonyl)-4-phenyl-3-butenyl]-3-cyclopentyl-2'-isobutylpropionohydrazide in the form of a white solid.

MS: 443 (M+H)$^+$.

(ii) In a manner analogous to that described in Example 18, parts (i)–(iv), starting from (E)-2(R)-[1(S)-(tert.-butoxycarbonyl)-4-phenyl-3-butenyl]-3-cyclopentyl-2'-isobutylpropionohydrazide and N-(9-fluorenylmethyloxycarbonyl)-D-alanine acid fluoride there was obtained (E)-2'-(D-alanyl)-3-cyclopentyl-2(R)-[1(S)-[(tetrahydro-2(RS)-pyranyloxy)carbamoyl]-4-phenyl-3-butenyl]-2'-isobutylpropionohydrazide in the form of a colorless gum.

MS: 557 (M+H)$^+$.

EXAMPLE 76

(E)-2'-(D-Alanyl)-2(R)-[1(S)-(hydroxycarbamoyl)-4-(3-pyridyl)-3-butenyl]-2'-isobutyl-4-methylvalerohydrazide p-toluenesulphonate A solution of 0.035 g of (E)-2'-(D-alanyl)-2(R)-[1(S)-(tetrahydro-2(RS)-pyranyloxy)carbamoyl]-4-(3-pyridyl)-3-butenyl]-2'-isobutyl-4-methylvalerohydrazide in 3 ml of methanol was treated with 0.014 g of p-toluenesulphonic acid monohydrate. The mixture was stirred for 2 hours at room temperature and evaporated. The residue was triturated with diethyl ether, filtered off and dried to give 0.030 g of (E)-2'-(D-alanyl)-2(R)-[1(S)-(hydroxycarbamoyl)-4-(3-pyridyl)-3-butenyl]-2'-isobutyl-4-methylvalerohydrazide p-toluenesulphonate in the form of a white solid.

MS: 448 (M+H)$^+$. HPLC: Gradient elution using solvent A containing 5% solvent B increasing to 95% solvent B over 15 minutes; flow rate 1 ml per minute. Retention time: 8.46 minutes. Solvent A; H$_2$O/0.1% TFA; solvent B: CH$_3$CN/0.085% TFA. Column type: HYPERPEP 300A.

The (E)-2'-(D-alanyl)-2(R)-[1(S)-(tetrahydro-2(RS)-pyranyloxy)carbamoyl]-4-(3-pyridyl)-3-butenyl]-2'-isobutyl-4-methylvalerohydrazide used as the starting material was prepared as follows:

(i) In an analogous manner to that described in Example 1, part (i), but using 2(R)-[1(RS)-(tert-butoxycarbonyl)-3-butenyl]-4-methylvaleric acid in place of (E)-2(R)-[1(S)-(tert-butoxycarbonyl)-4-phenyl-3-butenyl]-4-methylvaleric acid there was obtained 2(R)-[1(RS)-(tert-butoxycarbonyl)-3-butenyl]-2'-isobutyl-4-methylvalerohydrazide as a yellow oil.

MS: 341 (M+H)$^+$.

(ii) A solution of 0.500 g of 2(R)-[1(RS)-(tert-butoxycarbonyl)-3-butenyl]-2'-isobutyl-4-methylvalerohydrazide in 10 ml of dimethylformamide was treated with 0.465 g of 3-bromopyridine, 0.297 g of triethylamine, 0.017 g of palladium(II) acetate and 0.045 g of tri-(o-tolyl)phosphine. The mixture was heated at 100° C. for 24 hours. After cooling to room temperature the mixture was diluted with water and extracted three times with ethyl acetate. The combined ethyl acetate extracts were washed with water and brine and then dried over anhydrous magnesium sulphate. Evaporation of the solvents and flash column chromatography of the residue on silica gel using ethyl acetate/hexane gave 0.090 g of (E)-2(R)-[1(S)-(tert-butoxycarbonyl)-4-(3-pyridyl)-3-butenyl]-2'-isobutyl-4-methylvalerohydrazide in the form of a yellow oil.

MS: 418 (M+H)$^+$.

(iii) In a manner analogous to that described in Example 33, parts (ii)–(iii), starting from (E)-2(R)-[1(S)-(tert-butoxycarbonyl)-4-(3-pyridyl)-3-butenyl]-2'-isobutyl-4-methylvalerohydrazide and N-(9-fluorenylmethoxycarbonyl)-D-alanyl acid fluoride there was obtained (E)-2(R)-[1(S)-(carboxy)-4-(3-pyridyl)-3-butenyl]-2'-isobutyl-2'-[N-(9-fluorenylmethoxycarbonyl)-D-alanyl]-4-methylvalerohydrazide trifluoroacetate in the form of a white solid.

MS: 655 (M+H)$^+$.

(iv) In a manner analogous to that described in Example 23, parts (ii)–(iii), starting from (E)-2(R)-[1(S)-(carboxy)-4-(3-pyridyl)-3-butenyl]-2'-isobutyl-2'-[N-(9-fluorenylmethoxycarbonyl)-D-alanyl]-4-methylvalerohydrazide trifluoroacetate there was obtained (E)-2'-(D-alanyl)-2(R)-[1(S)-(tetrahydro-2(RS)-pyranyloxy)carbamoyl]-4-(3-pyridyl)-3-butenyl]-2'-isobutyl-4-methylvalerohydrazide in the form of a white solid.

MS: 532 (M+H)$^+$.

EXAMPLE 77

(E)-2(R)-[1(S)-(Hydroxycarbamoyl)-4-phenyl-3-butenyl]-2'-isobutyl-4-methyl-2'-[2-(1H-tetrazol-5-yl)acetyl]valerohydrazide hydrochloride In a manner analogous to that described in Example 8 but using 2-(1H-tetrazol-5-yl)acetic acid in place of N-tert.butyloxycarbonyl-β-alanine there was obtained (E)-2(R)-[1(S)-(hydroxycarbamoyl)-4-phenyl-3-butenyl]-2'-isobutyl-4-methyl-2'-[2-(1H-tetrazol-5-yl)acetyl]valerohydrazide hydrochloride in the form of a white solid.

MS: 486 (M+H)$^+$. HPLC: Gradient elution using solvent A containing 5% solvent B increasing to 95% solvent B over 15 minutes; flow rate 1 ml per minute. Retention time: 9.79 minutes. Solvent A: H$_2$O/0.1% TFA; solvent B: CH$_3$CN/0.085% TFA. Column type: HYPERPEP 300A.

EXAMPLE 78

(E)-2(R)-[1(S)-(Hydroxycarbamyl)-4-phenyl-3-butenyl]-2'-isobutyl-4-methyl-2'-2-(4-methyl-1-piperazinyl)acetyl]valerohydrazide p-toluenesulphonate In a manner analogous to that described in Example 11, but using 2-(4-methylpiperazinyl)acetic acid in the place of N-acetyl-glycine, there was obtained (E)-2(R)-[1(S)-(hydroxycarbamoyl)-4-phenyl-3-butenyl]-2'-isobutyl-4-methyl-2'-[2-(4-methyl-1-piperazinyl)acetyl]valerohydrazide p-toluenesulphonate in the form of a white solid.

MS: 516 (M+H)$^+$. HPLC: Gradient elution using solvent A containing 5% solvent B increasing to 95% solvent B over 15 minutes; flow rate 1 ml per minute. Retention time: 10.47 minutes. Solvent A: H$_2$O/0.1% TFA; solvent B: CH$_3$CN/0.085% TFA. Column type: HYPERPEP 300A.

EXAMPLE 79

2'-Benzyl-2(R)-[4-cyclohexyl-1(S)-(hydroxycarbamoyl)butyl]-4-methyl-2'-[2-(1,2,4-triazol-1-yl)acetyl]valerohydrazide p-toluenesulphonate In a manner analogous to that described in the first paragraph of Example 5, starting from 0.612 g of 2'-benzyl- 2(R)-[4-cyclohexyl-1(S)-[(tetrahydro-2(RS)-pyranyloxy) carbamoyl]butyl]-4-methyl-2'-[2-(1,2,4-triazol-1-yl)acetyl] valero-hydrazide there was obtained 0.61 g of 2'-benzyl-2 (R)-[4-cyclohexyl-1(S)-(hydroxycarbamoyl)butyl]-methyl-2'-[2-(1,2,4-triazol-1-yl)acetyl]valerohydrazide p-toluenesulphonate in the form of a white solid.

MS: 527 (M+H)$^+$. HPLC: Gradient elution using solvent A containing 10% solvent B for 5 minutes increasing to 90% solvent B from 5 minutes to 15 minutes flow rate 1 ml/minute. Retention time: 11.82 minutes. Solvent A: H$_2$O/ 0.1% TFA, solvent B: 90% CH$_3$CN/10% H$_2$O/0.085% TFA. Column type: WMC, C18, 50×4.6 mm.

The 2'-benzyl-2(R)-[4-cyclohexyl-1(S)-[(tetrahydro-2 (RS)-pyranyloxy)carbamoyl]butyl]-4-methyl-2'-[2-(1,2,4-triazol-1-yl)acetyl]valerohydrazide used as the starting material was prepared as follows:

(i) In a manner analogous to that described in Example 35, from (E)-2(R)-[1(S)-(tert.butoxycarbonyl)-4-phenyl-3-butenyl]-4-methylvaleric acid there was obtained 2(R)-[1 (S)-(tert.butoxycarbonyl)-4-cyclohexylbutyl]-4-methylvaleric acid in the form of yellow gum.

(ii) In a manner to that described in Example 1, parts (iii)–(vii) and Example 8, from 2(R)-[1(S)-(tert.butoxycarbonyl)-4-cyclohexylbutyl]-4-methylvaleric acid and benzylhydrazine and using 1,2,4-triazole-1-acetic acid in place of N-tert.butoxycarbonyl-β-alanine in Example 8, there was obtained 2'-benzyl-2(R)-[4-cyclohexyl-1(S)-[(tetrahydro-2-(RS)-pyranyloxy)carbamoyl]butyl]-4-methyl-2'-[2-(1,2,4-triazol-1-yl)acetyl]valerohydrazide in the form of a white solid.

MS: 611 (M+H)$^+$.

EXAMPLE 80

2'-Benzyl-2(R)-[4-cyclohexyl-(S)-(hydroxycarbamoyl)butyl-2'-[2-(1-imidazolyl) acetyl]-4-methylvalerohydrazide p-toluenesulphonate In a manner analogous to that described in the first paragraph of Example 5, starting from 0.579 g of 2'-benzyl-2(R)-[4-cyclohexyl-1(S)-[(tetrahydro-2(RS)-pyranyloxy) carbamoyl]butyl]-2'-[2-(1-imidazolyl)acetyl]-4-methylvalerohydrazide there was obtained 0.554 g of 2'-benzyl-2(R)-[4-cyclohexyl-1(S)-(hydroxy-carbamoyl) butyl]-2'-[2-(1-imidazolyl)acetyl)-4-methylvalerohydrazide p-toluenesulphonate in the form of a white solid.

MS: 526 (M+H)$^+$. HPLC: Gradient elution using Solvent A containing 10% solvent B for 5 minutes increasing to 90% solvent B from 5 minutes to 15 minutes; flow rate 1 ml/minute. Retention time: 11.17 minutes. Solvent A: H$_2$O/ 0.1% TFA; solvent B: 90% CH$_3$CN/10% H$_2$O/0.085% TFA. Column type: WMC, C18, 50×4.6 mm.

The 2'-benzyl-2(R)-[4-cyclohexyl-1(S)-[(tetrahydro-2-(RS)-pyranyloxy)carbamoyl]butyl]-2'-(1-imidazolyl) acetyl]-4-methyl-valerohydrazide used as the starting material was prepared as follows:

In a manner analogous to that described to that described in Example 1, parts (iii)–(vii) and Example 8, from 2(R)-[1(S)-(tert-butoxycarbonyl)-4-cyclohexyl-butyl]-4-methylvaleric acid and benzylhydrazine and using imidazole-1-acetic acid in place of N-(tert-butoxycarbonyl)-β-alanine in Example 8 there was obtained 2'-benzyl-2(R)-[4-cyclohexyl-1(S)-[(tetrahydro-2(RS)-pyranyloxy) carbamoyl]butyl]-2'-[2-(1-imidazolyl)acetyl]-4-methylvalerohydrazide in the form of a white solid.

MS: 610(M+H)$^+$.

EXAMPLE 81

2'-Benzyl-2(R)-[4-cyclohexyl-1(S)-(hydroxycarbamoyl)butyl]-4-methyl-2'[-2-(1,2,3-triazol-1-yl)acetyl]valerohydrazide p-toluenesulphonate In a manner analogous to that described in the first paragraph of Example 5, starting from 0.61 g of 2'-benzyl-2(R)-[4-cyclohexy]-1(S)-[(tetrahydro-2(RS)-pyranyloxy) carbamoyl)butyl]-2'-[2-(1,2,3-triazol-1-yl)acetyl] valerohydrazide there was obtained 0.545 g of 2'-benzyl-2 (R)-[4-cyclohexyl-1(S)-(hydroxycarbamoyl)butyl]-4-methyl-2'-[2-(1,2,3-triazol-1-yl)acetyl]valerobydrazide p-toluenesulphonate in the form of a white solid.

MS: 527 (M+H)$^+$. HPLC: Gradient elution using solvent A containing 10% solvent B for 5 minutes increasing to 90% solvent B from 5 minutes to 15 minutes; flow rate 1 ml/minute. Retention time: 12.12 minutes. Solvent A: H$_2$O/ 0.1% TFA; solvent B: 90% CH$_3$CN/10% H$_2$O/0.085% TFA. Column type: WMC, C18, 50×4.6 mm.

The 2'-benzyl-2(R)-[4-cyclohexyl-1(S)-[(tetrahydro-2 (RS)-pyranyloxy)carbamoyl]butyl]-2'-[2-(1,2,3-triazol-1-yl)acetyl]valerohydrazide used as the starting material was prepared as follows:

In a manner analogous to that described in Example 1, parts (iii)–(vii) and Example 8, from 2(R)-[1(S)-(tert-butoxycarbonyl)-4-cyclohexylbutyl]-4-methylvaleric acid and benzylhydrazine and using 1,2,3-triazole-1-acetic acid in place of N-tert.butoxycarbonyl-β-alanine in Example 8, there was obtained 2'-benzyl-2(R)-[4-cyclohexyl-1(S)-[(tetrahydro-2(RS)-pyranyloxy)carbonyl]butyl]-2'-[2-(1,2, 3-triazol-1-yl)acetyl]valerohydrazide in the form of a white solid.

MS: 611 (M+H)$^+$.

EXAMPLE 82

(E)-2'-(D-Alanyl)-2(R)-[1(S)-(hydroxycarbamoyl)-4-phenyl-3-butenyl]-2'-(2-hydroxyethyl)-4-methylvalerohydrazide p-toluenesulphonate In a manner analogous to that described in the first paragraph of Example 5, starting from 0.034 g of (E)-2'-(D-alanyl)-2(R)-[1(S)-[(tetrahydro-2(RS)-pyranyloxy) carbamoyl]-4-phenyl-3-butenyl]-2'-[2-(tetrahydro-2(RS)-pyranyloxy)ethyl]-4-methylvalerohydrazide there was obtained 0.009 g of (E)-2'-(D-alanyl)-2(R)-[1(S)-(hydroxycarbamoyl)-4-phenyl-3-butenyl]-2'-(2-hydroxyethyl)-4-methydvalero-hydrazide p-toluenesulphonate in the form of an off-white solid.

MS: 435 (M+H)$^+$ HPLC: Gradient elution using solvent A containing 10% solvent B for 5 minutes increasing to 90% solvent B from 5 minutes to 15 minutes; flow rate 1 ml/minute. Retention time: 8.80 minutes, solvent A: H$_2$O/ 0.1% TFA; solvent B: 90% CH$_3$CN/10% H$_2$O/0.085% TFA. Column type: WMC, C18, 50×4.6 mm.

The (E)-2'-(D-alanyl)-2(R)-[1(S)-[(tetrahydro-2(RS)-pyranyloxy)carba-moyl]-4-phenyl-3-butenyl]-2'-[2-(tetrahydro-2(RS)-pyranyloxy)ethyl]-4-methyl-valerohydrazide used as the starting material was prepared as follows:

(i) In a manner analogous to that described in Example 1, part (iii), from (E)-2(R)-[1(S)-(tert.-butoxycarbonyl)-4-phenyl-3-butenyl]-4-methylvaleric acid and 2-hydroxyethylhydrazine there was obtained (E)-2(R)-[1 (S)-(tert.-butoxycarbonyl)-4-phenyl-3-butenyl]-2'-(2-hydroxyethyl)-4-methylvalerohydrazide in the form of a yellow gum.

MS: 405 (M+H)$^+$.

(ii) A solution of 1.4 g of (E)-2(R)-[1(S)-(tert.-butoxycarbonyl)-4-phenyl-3-butenyl]-2'-(2-hydroxyethyl)-4-methylhydrazide, 1.08 ml of tert.-butylchlorodiphenylsilane and 0.596 g of imidazole in 30 ml of dry dimethylformamide was stirred under nitrogen at room temperature for 3.5 hours. The solvent was evaporated and the residue was partitioned between ethyl acetate and 0.5 M aqueous hydrochloric acid. The ethyl acetate layer was washed in succession with 0.5 M aqueous hydrochloric acid, water and saturated sodium chloride solution and dried over anhydrous magnesium sulphate. After evaporation of the ethyl acetate there were obtained 2.35 g of (E)-2'-(2-tert-butyldiphenylsilyloxyethyl)-2(R)-[1(S)-(tert.-butoxycarbonyl)-4-phenyl-3-butenyl]-4-methylvalerohydrazide in the form of a pale yellow gum.

MS: 643 (M+H)$^+$.

(iii) In a manner analogous to that described in Example 18, parts (i)–(iii), starting from (E)-2'-(2-tert.-butyidiphenylsilyloxy)-2(R)-[1(S)-(tert.-butoxycarbonyl)-4-phenyl-3-butenyl]-4-methylvalerohydrazide and N-(9-fluorenylmethoxycarbonyl)-D-alanine acid fluoride there was obtained (E)-2(R)-[1(S)-[(tetrahydro-2(RS)-pyranyloxy)carbamoyl]-4-phenyl-3-butenyl]-2'-[N-(9-fluorenylmethoxycarbonyl)-D-alanyl]-2'-(2-hydroxyethyl)-4-methylvalerohydrazide in the form of a white foam after purification by flash chromatography on silica gel using ethyl acetate/hexane (1:1) for the elution.

(iv) A solution of 0.131 g of (E)-2(R)-[1(S)-[(tetrahydro-2(RS) pyranyloxy)carbaroyl]-4-phenyl-3-butenyl]-2'-N-(9-fluorenylmethoxycarbonyl)-D-alanyl]-2'-(2-hydroxyethyl)-4-methylvalerohydrazide, 0.05 g of 2,3-dihydro-4H-pyran and a crystal of p-toluenesulphonic acid in 3 ml of tetrahydrofuran were stirred at room temperature for 2 days under a nitrogen atmosphere. The solvent was evaporated and the residue was dissolved in ethyl acetate and washed in succession with two portions of aqueous 5% sodium hydrogen carbonate solution, water and aqueous saturated sodium chloride solution. After drying over anhydrous magnesium sulphate the ethyl acetate was evaporated and the residue was purified by flash chromatography on silica gel using ethyl acetate/hexane (2:1) for the elution. There was obtained 0.104 g of (E)-2(R)-[1(S)-[(tetrahydro-2(RS)-pyranyloxy)carbamoyl]-4-phenyl-3-butenyl]-2'-[N-(9-fluorenylmethoxycarbonyl)-D-alanyl]-2'-[2-(tetrahydro-2(RS)-pyranyloxy)ethyl]-4-methylvalerohydrazide in the form of a gum.

MS: 847 (M+Na)$^+$.

(v) In a manner analogous to that described in Example 18, part (iv), from 0.1 g of (E)-2(R)-[1(S)-[(tetrahydro-2(RS)-pyranyloxy)carbamoyl]-4-phenyl-3-butenyl]-2'-[N-(9-fluorenylmethoxycarbonyl)-D-alanyl]-2'-[2-(tetrahydro-2(RS)-pyranyl-oxy)ethyl]-4-methylvalerohydrazide there was obtained 0.034 g of (E)-2'-(D-alanyl)-2(R)-[1(S)-[(tetrahydro-2(RS)-pyranyloxy)carbamoyl]-4-phenyl-3-butenyl]-2'-[2-(tetrahydro-2(RS)pyranyloxy)ethyl]-4-methylvalerohydrazide in the form of a gum.

MS: 603 (M+H)$^+$.

EXAMPLE 83

2'-(D-Alanyl)-2(R)-[1(RS)-(hydroxycarbamoyl)-4-phenylbutyl]-2'-isobutyl-3-methylbutyrohydrazide p-toluenesulphonate In a manner analogous to that described in the first paragraph of Example 5, starting from 0.689 g of 2'-(D-alanyl)-2(R)-[1(RS)-[(tetrahydro-2(RS)-pyranyloxy)carbamoyl]-4-phenylbutyl]-2'-isobutyl-3-methylbutyrohydrazide there was obtained 0.768 mg of 2'-(D-alanyl)-2(R)-[1(RS)-(hydroxycarbamoyl)-4-phenyl-butyl]-2'-isobutyl-3-methylbutyrohydrazide p-toluenesulphonate in the form of a white solid.

MS: 435 (M+H)$^+$. HPLC: Gradient elution using solvent A containing 5% solvent B increasing to 95% solvent B over 15 minutes; flow rate 1 ml/minute. Retention time: 10.495 minutes. Solvent A: H$_2$O/0.1% TFA; solvent B: CH$_3$CN/0.085% TEA. Column type: HYPERPEP 300A.

The 2'-(D-alanyl)-2(R)-[(RS)-[(tetrahydro-2(RS)-pyranyloxycarbamoyl]-4-phenylbutyl]-2'-isobutyl-3-methylbutyrohydrazide used as the starting material was prepared as follows:

(i) A solution of (E)-2(R)-[1-(RS)-(tert-butoxycarbonyl)-4-phenyl-3-butenyl]-3-methylbutyric acid in ethanol was shaken in a hydrogen atmosphere in the presence of 10% palladium on charcoal catalyst until the uptake of hydrogen had stopped. The catalyst was filtered off and the solvent was evaporated to give 2(R)-[1(RS)-(tert.-butoxycarbonyl)-4-phenylbutyl]-3-methylbutyric acid in the form of a pale yellow oil.

MS: 335 (M+H)$^+$.

(ii) In a manner analogous to that described in Example 18, parts (i)–(iv), starting from 2(R)-[1(RS)-tert.-butoxycarbonyl)-4-phenylbutyl]-3-methylbutyric acid and N-(9-fluorenylmethoxycarbonyl)-D-alanine acid fluoride that was obtained 2'-(D-alanyl)-2(R)-[1(RS)-[tetrahydro-2(RS)-pyranyloxy)carbamoyl]-4-phenylbutyl]-2'-isobutyl-3-methylbutyrohydrazide in the form of a gum.

MS: 519 (M+H)$^+$.

EXAMPLE 84

(E)-2'-(D-Alanyl)-2(R)-[1(S)-(hydroxycarbamoyl)-4-phenyl-3-butenyl]-2'-isobutyl-3-methylbutyrohydrazide p-toluenesulphonate In a manner analogous to that described in the first paragraph of Example 5, starting from 0.088 g of (E)-2'-(D-alanyl)-2(R)-[1(S)-[(tetrahydro-2(RS)-pyranyloxy)carbamoyl]-4-phenyl-3-butenyl]-2'-isobutyl-3-methylbutyrohydrazide there was obtained 0.090 g of (E)-2'-(D-alanyl)-2(R)-[1(S)-(hydroxycarbamoyl)-4-phenyl-3-butenyl]-2'-isobutyl-3-methylbutyrohydrazide p-toluenesulphonate in the form of a white solid.

MS: 433 (M+H)$^+$. HPLC: Gradient elution using solvent A containing 5% solvent B increasing to 95% solvent B over 15 minutes, flow rate 1 ml/minute. Retention time: 10.467. Solvent A: H$_2$O/0.1% TFA; solvent B: CH$_3$CN/0.085% TFA. Column type: HYPERPEP 300A.

The (E)-2'-(D-alanyl)-2(R)-[1(S)-[tetrahydro-2(RS)-pyranyloxy)carbamoyl]-4-phenyl-3-butenyl]-2'-isobutyl-3-methylbutyrohydrazide used as the starting material was prepared as follows:

(i) In a manner analogous to that described in Example 1, parts (i)–(iii), starting from 4-tert-butyl hydrogen 2(R)-isopropylsuccinate and cinnamyl bromide there was obtained (E)-2(R)-[1(S)-(tert.-butoxycarbonyl)-4-phenyl-3-butenyl]-2'-isobutyl-3-methylbutyrohydrazide in the form of a creamy white solid.

MS: 403 (M+H)$^+$.

(ii) In a manner analogous to that described in Example 18, parts (i)–(iv), starting from (E)-2(R)-[1(S)-(tert.-butoxycarbonyl)-4-phenyl-3-butenyl]-2'-isobutyl-3-methylbutyrohydrazide and N-(9-fluorenylmethoxycarbonyl)-D-alanine acid fluoride there was obtained (E)-

2'-(D-alanyl)-2(R)-[1(S)-[(tetrahydro-2(RS)-pyranyloxy) carbamoyl]-4-phenyl-3-butenyl]-2'-isobutyl-3-methylbutyrohydrazide in the form of a gum.

MS: 517 (M+H)+.

EXAMPLE 85

(E)-2'-(D-Alanyl)-2'-(tetrahydro-2H-pyran-4-yl)-2 (R)-[1(S)-(hydroxycarbamoyl)-4-phenyl-3-butenyl]-4-methylvalerohydrazide p-toluenesulphonate In a manner analogous to that described in the first paragraph of Example 5, starting from 0.093 g of (E)-2'-(D-alanyl)-2'-(tetrahydro-2H-pyran-4-yl)-2(R)-[1(S)-[(tetrahydro-2(RS)-pyranyloxy)carbamnoyl]-4-phenyl-3-butenyl]-4-methylvalerohydrazide there was obtained 0.11 g of (E)-2'-(D-alanyl)-2'-tetrahydro-2H-pyran-4-yl)-2(R)-1(S)-(hydroxycarbamoyl)-4-phenyl-3-butenyl]-4-methylvalerohydrazide in form of an off-white solid.

MS: 475 (M+H)+. HPLC: Gradient elution using solvent A containing 5% solvent B for 5 minutes increasing to 70% solvent B over 15 minutes; flow rate 1 ml/minute. Retention time: 13.907 minutes. Solvent A: $H_2O$/0.1% TFA; solvent B: $CH_3CN$/0.085% TFA, column type: HYPERPEP 300A.

The (E)-2'-(D-alanyl)-2'-(tetrahydro-2H-pyran-4-yl)-2(R)-[1(S)-[(tetrahydro-2(RS)-pyranyloxy)carbamoyl]-4-phenyl-3-butenyl]-4-methylvalerohydrazide used as the starting material was prepared as follows:

In a manner analogous to that described in Example 59, parts (ii) and (iii), starting from (E)-2(R)-[1(S)-(tert.-butoxycarbonyl)-4-phenyl-3-butenyl]-4-methylvalerohydrazide and tetrahydro-4H-pyran-4-one there was obtained (E)-2'-(D-alanyl)- 2'-(tetrahydro-2H-pyran-4-yl)-2(R)-[1(S)-[(tetrahydro-2(RS)-pyranyloxy)carbamoyl]-4-phenyl-3-butenyl]-4-methylvalerohydrazide in the form of a pale yellow gum.

MS: 559 (M+H)+.

EXAMPLE 86

(E)-2'-(D-Alanyl)-2'-(2,2,2-trifluoroethyl)-2(R)-[1(S)-(hydroxycarbamoyl)-4-phenyl-3-butenyl]-4-methylvalerohydrazide p-toluenesulphonate In a manner analogous to that described in the first paragraph of Example 5, starting from 0.110 mg of (E)-2'-(D-alanyl)-2'-(2,2,2-trifluoroethyl)-2(R)-[1(S)-[(tetrahydro-2(RS)-pyranyloxy)carbamoyl]-4-phenyl-3-butenyl]-4-methylvalerohydrazide there was obtained 0.115 mg of (E)-2'-(2,2,2-trifluoroethyl)-2(R)-[1(S)-(hydroxycarbamoyl)-4-phenyl-3-butenyl]-4-methylvalerohydrazide p-toluene in the form of a buff-colored solid.

MS: 473(M+H+. HPLC: Gradient elution using solvent A containing 5% solvent B increasing to 95% solvent B over 15 minutes, flow rate 1 ml/minute. Retention time: 10.785 minutes. Solvent A: $H_2O$/0.1% TFA; solvent B: $CH_3CN$/0.085% TFA. Column type: HYPERPEP 300A.

The (E)-2'-(D-alanyl)-2'-(2,2,2-trifluoroethyl)-2(R)-[1(S)-[(tetrahydro-2(RS)-pyranyloxy)carbamoyl]-4-phenyl-3-butenyl]-4-methylvalerohydrazide used as the starting material was prepared as follows:

(i) In a manner analogous to that described in Example 70, part (i), starting from (E)-2(R)-[1(S)-(tert.-butoxycarbonyl)-4-phenyl-3-butenyl]-4-methylvaleric acid and 2,2,2-trifluoroethylhydrazine there was obtained (E)-2(R)-[1(S)-(tert-butoxycarbonyl)-4-phenyl-3-butenyl]-2'-(2,2,2-trifluoroethyl)-4-methylvalerohydrazide in the form of a pale yellow solid.

MS: 443 (M+H)+.

(ii) In a manner analogous to that described in Example 18, parts (i)–(iv), starting from (E)-2(R)-[1(S)-(tert.-butoxycarbonyl)-4-phenyl-3-butenyl]-2'-(2,2,2-trifluoroethyl)-4-methylvalerohydrazide and N-(9-fluorenylmethoxycarbonyl)-D-alanine acid fluoride there was obtained (E)-2'-(D-alanyl)-2'-(2,2,2-trifluoroethyl)-2(R)-[1(S)-[(tetrahydro-2(RS)-pyranyloxy)carbamoyl]-4-phenyl-3-butenyl]-4-methylvalero-hydrazide in the form of a gum.

MS: 557 (M+H)+.

EXAMPLE 87

(E)-2'-(D-Alanyl)-2'-(2-cyanoethyl)-2(R)-[1(S)-(hydroxycarbamoyl)-4-phenyl-3-butenyl]-4-methylvalerohydrazide p-toluenesulphonate In a manner analogous to that described in the first paragraph of Example 5, starting from 0.038 mg of (E)-2'-(D-alanyl)-2'-(2-cyanoethyl)-2(R)-[1(S)-[(tetrahydro-2(RS)-pyranyloxy)carbamoyl]-4-phenyl-3-butenyl]-4-methylvalerohydrazide there was obtained 0.034 g of (E)-2'-(D-alanyl)-2'-(2-cyanoethyl)-2(R)-[1(S)-(hydroxycarbamoyl)-4-phenyl-3-butenyl]-4-methylvalerohydrazide p-toluene-sulphonate in the form of an off-white solid.

MS: 444 (M+H)+. HPLC: Gradient elution using solvent A containing 5% solvent B increasing to 95% solvent B over 15 minutes; flow rate 1 ml/minute. Retention time: 9.957 minutes. Solvent A: $H_2O$/0.1% TFA; solvent B: $CH_3CN$/0.085% TFA. Column type: HYPERPEP 300A.

The (E)-2'-(D-alanyl)-2'-(2-cyanoethyl)-2(R)-[1(S)-[(tetrahydro-2(RS)-pyranyloxy)carbamoyl]-4-phenyl-3-butenyl]-4-methylvalerohydrazide used as the starting material was prepared as follows:

(i) In a manner analogous to that described in Example 70, part (i), starting from (E)-2(R)-2(R)-[1(S)-(tert.-butoxycarbonyl)-4-phenyl-3-butenyl]-4-methylvaleric acid and 2-cyanoethylhydrazine there was obtained (E)-2(R)-[1(S)-(tert.-butoxycarbonyl)-4-phenyl-3-butenyl]-2'-(2-cyanoethyl)-4-methylvalerohydrazide in the form of a white solid.

MS: 414 (M+H)+.

(ii) In a manner analogous to that described in Example 18, parts (i)–(iv), starting from (E)-2(R)-[1(S)-(tert.-butoxycarbonyl)-4-phenyl-3-butenyl]-2'-(2-cyanoethyl)-4-methylvalerohydrazide and N-(9-fluorenylmethoxycarbonyl)-D-alanine acid fluoride there was obtained (E)-2'-(D-alanyl)-2'-(2-cyanoethyl)-2(R)-[1(S)-[(tetra-hydro-2(RS)-pyranyloxy)carbamoyl]-4-phenyl-3-butenyl]-4-methylvalerohydrazide in the form of a gum.

MS: 528 (M+H)+.

EXAMPLE 88

(E)-2'-(D-Alanyl)-2'-cyclohexyl-2(R)-[1(S)-(hydroxycarbamoyl)-4-phenyl-3-butenyl]-4-methylvalerohydrazide p-toluenesulphonate In a manner analogous to that described in the first paragraph of Example 5, starting from 0.17 g of (E)-2'-(D-alanyl)-2'-cyclohexyl-2(R)-[1(S)-[(tetrahydro-2(RS)-pyranyloxy)carbamoyl]-4-phenyl-3-butenyl]-4-methylvalerohydrazide there was obtained 0.186 g of (E)-2'-(D-alanyl)-2'-cyclohexyl-2(R)-[1(S)-(hydroxycarbamoyl)4-phenyl-3-butenyl]-4-methylvalerohydrazide p-toluenesulphonate in the form of an off-white solid.

MS: 473 (M+H)$^+$. HPLC: Gradient elution using solvent A containing 5% solvent B increasing to 95% solvent B over 15 minutes; flow rate 1 ml/minute. Retention time: 11.257 minutes. Solvent A: H$_2$O/0.1% TFA; solvent B: CH$_3$CN/ 0.085% TFA, column type: HYPERPEP 300A.

The (E)-2'-(D-alanyl)-2'-cyclohexyl-2(R)-[1(S)-[(tetrahydro-2(RS)-pyranyloxy)carbamoyl]-4-phenyl-3-butenyl]-4-methylvalerohydrazide used as the starting material was prepared as follows:
(i) In a manner analogous to that described in Example 70, part (1), starting from (E)-2(R)-[1(S)-(tert.-butoxycarbonyl)-4-phenyl-3-butenyl]-4-methylvaleric acid and cyclohexylhydrazine there was obtained (E)-2(R)-[1(S)-(tert.-butoxycarbonyl)-4-phenyl-3-butenyl]-2'-cyclohexyl-4-methylvalerohydrazide in the form of an off-white solid.
(ii) In a manner analogous to that described in Example 18, parts (i)–(iv), starting from (E)-2(R)-[1(S)-tert.-butoxycarbonyl)-4-phenyl-3-butenyl]-2'-cyclohexyl-4-methylvalerohydrazide and N-(9-fluorenylmethoxycarbonyl)-D-alanine acid fluoride there was obtained (E)-2'-(D-alanyl)-2'-cyclohexyl-2(R)-[1(S)-[(tetrahydro-2(RS)-pyranyloxy)carbamoyl]-4-phenyl-3-butenyl]-4-methylvalerohydrazide in the form of a gum.

MS: 557 (M+H)$^+$.

EXAMPLE 89

(E)-2'-(D-Alanyl)-2(R)-[1(S)-(hydroxycarbamol)-4-phenyl-3-butenyl]-4-methyl-2'-(2-phenylethyl) valerohydrazide p-toluenesulphonate In a manner analogous to that described in the first paragraph of Example 5, starting from 0.14 g of (E)-2'-(D-alanyl)-2(R)-[1(S)-[(tetrahydro-2(RS)-pyranyloxy)carbamoyl]-4-phenyl-3-butenyl]-4-methyl-2'-(2-phenylethyl)valerohydrazide there was obtained 0.148 g of (E)-2'-(D-alanyl)-2(R)-[1(S)-(hydroxycarbamoyl)-4-phenyl-3-butenyl]-4-methyl-2'-(2-phenylethyl) valerohydrazide p-toluenesulphonate in the form of a cream solid.

MS: 495 (M+H)$^+$. HPLC: Gradient elution using solvent A containing 5% solvent B increasing to 95% solvent B over 15 minutes; flow rate 1 ml/minute. Retention time: 11.355 minutes. Solvent A: H$_2$O/0.1% TEA; solvent B: CH$_3$CN/ 0.085% TFA. Column type HYPERPEP 300A.

The (E)-2'-(D-alanyl)-2(R)-[1(S)-[(tetrahydro-2(RS)-pyranyloxy)carbamoyl-4-phenyl-3-butenyl]-4-methyl-2'-(2-phenylethyl)valerohydrazide used as the starting material was prepared as follows:
(i) In a manner analogous to that described in Example 70, part (i), starting from (E)-2(R)-[1(S)-(tert.-butoxycarboxycarbonyl)-4-phenyl-3-butenyl]-4-methylvaleric acid and phenelzine sulphate there was obtained (E)-2(R)-[1(S)-(tert-butoxy-carbonyl)-4-phenyl-3-butenyl]-4-methyl-2'-(2-phenylethyl)valerohydrazide in the form of a cream solid.

MS: 465 (M+H)$^+$.
(ii) In a manner analogous to that described in Example 18, parts (i)–(iv), starting from (E)-2(R)-[1(S)-(tert.-butoxycarbonyl)-4-phenyl-3-butenyl]-4-methyl-2'-(2-phenylethyl)valerohydrazide and N-(9-fluorenyl-methoxycarbonyl)-D-alanine acid fluoride there was obtained (E)-2'-(D-alanyl)-2(R)-[1(S)-[(tetrahydro-2(RS)-pyranyloxy)carbamoyl]-4-phenyl-3-butenyl]-4-methyl-2'-(2-phenylethyl)valero-hydrazide in the form of a gum.

MS: 579 (M+H)$^+$.

EXAMPLE 90

Mixture of (E)-2'-(D-alanyl)-2'-cyclopentyl-2(R)-[1(S)-(hydroxycarbamoyl)-4-phenyl-3-butenyl]-4-methylvalerohydrazide p-toluenesulphonate and (E)-2'-(D-alanyl)-2'-cyclopentyl-2(S)-[1(R)-(hydroxycarbamoyl)-4-phenyl-3-butenyl]-4-methylvalerohydrazide p-toluenesulphonate.

In a manner analogous to that described in the first paragraph of Example 5, starting from 0.058 g of a mixture of (E)-2'-(D-alanyl)-2'-cyclopentyl-2(R)-[1(S)-[tetrahydro-2(RS)-pyranyloxy)carbamoyl]-4-phenyl-3-butenyl]-4-methylvalero-hydrazide and (E)-2'-(D-alanyl)-2'-cyclopentyl-2(S)-[1(R)-[(tetrahydro-2(RS)-pyranyloxy)carbamoyl]-4-phenyl-3-butenyl]-4-methylvalerohydrazide there was obtained 0.048 mg of a mixture of (E)-2'-(D-alanyl)-2'-cyclopentyl-2(R)-[1(S)-(hydroxycarbamoyl)-4-phenyl-3-butenyl]-4-methylvalerohydrazide p-toluene-sulphonate and (E)-2'-(D-alanyl)-2'-cyclopentyl-2(S)-[1(R)-(hydroxycarbonyl)-4-phenyl-3-butenyl]-methylvalerohydrazide p-toluenesulphonate in the form of a pale pink solid.

MS: 459 (M+H)$^+$. HPLC: Gradient elution using solvent A containing 20% solvent B increasing to 40% solvent B over 20 minutes; flow rate 1 ml/minute. Retention time: 6.607 minutes for isomer 1 and 7.390 minutes for isomer 2; Solvent A: H$_2$O/0.1% TFA; solvent B: CH$_3$CN/0.085% TFA. Column type: HYPERPEP 300A.

The mixture of (E)-2'-(D-alanyl)-2'-cyclopentyl-2(R)-[1(S)-[(tetrahydro-2(RS)-pyranyloxy)carbamoyl]-4-phenyl-3-butenyl]-4-methylvalerohydrazide and (E)-2'-(D-alanyl)-2'cyclopentyl-2(S)-[1(R)-[(tetrahydro-2(RS)-pyranyloxy)-carbamoyl]-4-phenyl-3-butenyl]-4-methylvalerohydrazide used as the starting material was prepared as follows:

In a manner analogous to that described in Example 73, part (ii), starting from a mixture of(E)-2(R)-[1(S)-(tert.-butoxycarbonyl)-4-phenyl-3-butenyl]-4-methylvalero-hydrazide and (E)-2(S)-[1(R)-(tert.-butoxycarbonyl)-4-phenyl-3-butenyl]-4-methlvalerohydrazide and cyclopentanone there was obtained a mixture of (E)-2'-(D-alanyl)-2'-cyclopentyl-2(R)-[1(S)-[(tetrahydro-2(RS)-pyranyloxy) carbamoyl]-4-phenyl-3-butenyl]-4-methylvalerohydrazide and (E)-2'-D-alanyl)-2'-cyclopentyl-2(S)-[1(R)-[(tetrahydro-2(RS)-pyranyloxy)carbamoyl]-4-phenyl-3-butenyl]-4-methylvalerohydrazide in the form of a colorless gum.

MS: 543 (M+H)$^+$.

EXAMPLE 91

(E)-2'-(D-Alanyl)-2(R)-[1(S)-(hydroxycarbamoyl)-4-phenyl-3-butenyl]-4-methyl-2'-propylvalerohydrazide p-toluenesulphonate.

In a manner analogous to that described in the first paragraph of Example 5, starting from 0.148 g of (E)-2'-(D-alanyl)-2(R)-[1(S)-[(tetrahydro-2(RS)-pyranyloxy) carbamoyl]-4-phenyl-3-butenyl]-4-methyl-2'-propylvalerohydrazide p-toluenesulphonate there was obtained 0.146 g of (E)-2'-(D-alanyl)-2(R)-[1(S)-(hydroxycarbamoyl)-4-phenyl-3-butenyl]-4-methyl-2'-propylvalerohydrazide p-toluene-sulphonate in the form of a white solid.

MS: 433 (M+H)$^+$ HPLC: Gradient elution using solvent A containing 5% solvent B increasing to 95% solvent B over 15 minutes; flow rate 1 ml/minute. Retention time 10.218 minutes. Solvent A: $H_2O/0.1\%$. TFA; solvent □: $CH_3CN/0.085\%$ TFA. Column type: HYPERPEP 300A.

The (E)-2'-(D-alanyl)-2(R)-[1(S)-[(tetrahydro-2(RS)-pyranyloxy)carba-moyl]-4-phenyl-3-buetnyl]-4-methyl-2'-propylvalerohydrazide used as the starting material was prepared as follows:

In a manner analogous to that described in Example 59, parts (i) and (iii), starting from (E)-2(R)-[1(S)-(tert.-butoxycarbonyl)-4-phenyl-3-butenyl]-4-methylvalerohydrazide and propionaldehyde there was obtained (E)-2'-(D-alanyl)-2(R)-[1(S)-[(tetrahydro-2(RS)-pyranyloxy)carbamoyl]-4-phenyl-3-butenyl]-4-methyl-2'-propylvalerohydrazide in the form of a gum.

MS: 517 (M+H)$^+$.

EXAMPLE 92

(E)-2'-(D-Alanyl)-2(R)-[1(S)-(hydroxycarbamoyl)-4-pheny-3-butenyl]-2'-(5-hydroxypentyl)-4-methylvalerohydrazide p-toluenesulphonate In a manner analogous to that described in the first paragraph of Example 5, starting from 0.042 g of (E)-2'-(D-alanyl)-2(R)-[1(S)-[(tetrahydro-2(RS)-pyranyloxy)carbamoyl]-4-phenyl-3-butenyl]-2'-(5-hydroxypentyl)-4-methylvalerohydrazide there was obtained 0.05 g of (E)-2'-(D-alanyl)-2(R)-[1(S)-(hydroxycarbamoyl)-4-phenyl-3-butenyl]-2'-(5-hydroxypentyl)-4-methylvalerohydrazide p-toluene-sulphonate in the form of an orange foam.

MS: 477 (M+H)$^+$. HPLC: Gradient elution using solvent A containing 5% solvent B increasing to 95% solvent B over 15 minutes; flow rate 1 ml/minute. Retention time: 9.317 minutes.

Solvent A: $H_2O/0.1\%$ TFA; solvent B: $CH_3CN/0.085\%$ TFA. Column type: HYPERPEP 300A.

The (E)-2'-(D-alanyl)-2(R)-[1(S)-[(tetrahydro-2(RS)-pyranyloxy)-carbamoyl]-4-phenyl-3-butenyl]-2'-(5-hydroxypentyl)-4-methylvalerohydrazide used as the starting material was prepared as follows:

(i) In a manner analogous to that described in Example 59, part (ii), starting from (E)-2(R)-[1(S)-(tert.-butoxycarbonyl)-4-phenyl-3-butenyl]-4-methylvalerohydrazide and 5-hydroxypentanal there was obtained (E)-2(R)-[1(S)-(tert.-butoxycarbonyl)-4-phenyl-3-butenyl]-2'-(5-hydroxypentyl)-4-methylvalerohydrazide in the form of a gum.

MS: 447 (M+H)$^+$.

(ii) A solution of 0.439 g of (E)-2(R)-[1(S)-(tert.-butoxycarbonyl)-4-phenyl-3-butenyl]-2'-(5-hydroxypentyl)-4-methylvalerohydrazide in 5 ml of dry dimethylformamide was treated with 0.31 ml of tert.-butylchlorodiphenylsilane and 0.169 g of imidazole. The mixture was stirred at room temperature for 3 hours and the solvent was evaporated. The residue was partitioned between ethyl acetate and 1M hydrochloric acid and the ethyl acetate layer was washed with saturated sodium chloride solution, dried over anhydrous magnesium sulphate and evaporated to give 0.629 g of (E)-2'-(tert.-butyldiphenylsilyloxypentyl)-2(R)-[1(S)-(tert.-butoxycarbonyl)-4-phenyl-3-butenyl]-4-methylvalerohydrazide in the form of a gum.

MS: 685 (M+H)$^+$.

(iii) In an analogous manner to that described in Example 18, parts (i)–(iv), starting from (E)-2'-(tert.-butyldiphenylsilylpentyl)-2(R)-[1(S)-(tert.-butoxycarbonyl)-4-phenyl-3-butenyl]-4-methylvalerohydrazide and N-(9-fluorenylmethoxy-carbonyl)-D-alanine acid fluoride there was obtained (E)-2'-(D-alanyl)-2(R)-[1(S)-[(tetrahydro-2(RS)-pyranyloxy)carbamoyl]-4-phenyl-3-butenyl]-2'-(5-hydroxy-pentyl)-4-methylvalerohydrazide in the form of a gum.

MS: 561 (M+H)$^+$.

EXAMPLE 93

(E)-2'-(D-Alanyl)-2(R)-[1(S)-(hydroxycarbamoyl)-4-phenyl-3-butenyl]-2'-(3-hydroxy-2,2-dimethylpropyl)-4-methylvalerohydrazide p-toluenesulphonate.

In a manner analogous to that described in the first paragraph of Example 5, starting from 0.04 g of (E)-2'-(D-alanyl)-2(R)-[1(S)-[(tetrahydro-2(RS)-pyranyloxy)carbamoyl]-4-phenyl-3-butenyl]-2'-(3-hydroxy-2,2-dimethylpropyl)-4-methylvalerohydrazide there was obtained 0.041 g of (E)-2'-(D-alanyl)-2(R)-[1(1S)-(hydroxycarbamoyl)-4-phenyl-4-butenyl]-2'-(3-hydroxy-2,2-dimethylpropyl)-4-methylvalerohydrazide in the form of a pale orange solid.

MS: 477 (M+H)$^+$. HPLC: Gradient elution using solvent A containing 5% solvent B increasing to 95% Solvent B over 15 minutes; flow rate 1 ml/minute. Retention time: 8.21 minutes. Solvent A: $H_2O/0.1\%$ TFA; solvent B: 95% $CH_3CN/5\%$ $H_2O/0.085\%$ TFA. Column type: HYPERPEP 300A.

The (E)-2'-(D-alanyl)-2(R)-[1(S)-[(tetrahydro-2(RS)-pyranyloxy)carbamoyl]-4-phenyl-3-butenyl]-2'-(3-hydroxy-2,2-dimethylpropyl)-4-methylvalero-hydrazide used as the starting material was prepared as follows:

In a manner analogous to that described in Example 92, parts (i)–(iii), starting from (E)-2(R)-[1(S)-(tert.-butoxycarbonyl)-4-phenyl]-4-methylvalerohydrazide and 2,2-dimethyl-3-hydroxypropionaldehyde there was obtained (E)-2'-(D-alanyl)-2(R)-[1(S)-[(tetrahydro-2(RS)-pyranyloxy)carbamoyl]-4-phenyl-3-butenyl]-2'-(3-hydroxy-2,2-dimethylpropyl)-4-methylvalerohydrazine in the form of a gum.

MS: 561 (M+H)$^+$.

EXAMPLE 94

2'-Benzyl-2(R)-[4-cyclohexyl-1(S)-(hydroxycarbamoyl)butyl]-4-methyl-2'-[2-(3-pyridyl)acetyl]valerohydrazide p-toluenesulphonate In a manner analogous to that described in the first paragraph of Example 5, starting from 0.311 g of 2'-benzyl-2(R)-[4-cyclohexyl-1(S)-[(tetrahydro-2(RS)-pyranyloxy)carbamoyl]butyl-4-methyl-2-[2-(3-pyridylacetyl] valerohydrazide there was obtained 0.33 g of 2'-benzyl-2(R)-[4-cyclobexyl-1(S)-(hydroxycarbamoyl)butyl]-4-methyl-2'-[2-(3-pyridyl)acetyl]valerohydrazide p-toluenesulphonate in the form of an off-white solid.

MS: 537 (M+H)$^+$. HPLC: Gradient elution using solvent A containing 5% solvent B increasing to 95% solvent B over 15 minutes; flow rate 1 ml/minute. Retention time 11.885 minutes. Solvent A: $H_2O/0.1\%$ TFA; Solvent B: $CH_3CN/0.085\%$. TFA. Column type: HYPERPEP 300A.

The 2'-benzyl-2(R)-[4-cyclohexyl-1(S)-[(tetrahydro-2(RS)-pyranyloxy)carbamoyl]butyl]-4-methyl-2'-[2-(3-pyridyl)acetyl]valerohydrazide used as the starting material was prepared as follows:

In a manner analogous to that described in Example 1, parts (iii)–(vii) and Example 8, from 2(R)-[1(S)-(tert-butoxycarbonyl)-4-cyclohexylbutyl]-4-methylvaleric acid and benzylhydrazine and using 3-pyridylacetic acid in place of N-tert-butoxycarbony-β-alanine in Example 8 there was obtained 2'-benzyl-2(R)-[4-cyclohexyl-1(S)-[(tetrahydro-2 (RS)-pyranyloxy)carbamoyl]butyl]-4-methyl-2'-[2-(3-pyridyl)acetyl]valerohydrazide in the form of a white foam.

MS: 621 (M+H)+.

EXAMPLE 95

2(R)-[4-Cyclohexyl-1(S)-(hydroxycarbamoyl)butyl]-4-methyl-2'-(2-phenylethyl)-2'-[2-(1H-1,2,4-triazol-1-yl)acetyl]valerohydrazide p-toluenesulphonate In a manner analogous to that described in the first paragraph of Example 5, starting from 0.286 g of 2(R)-[4-cyclohexyl-1(S)-[(tetrahydro-2(RS)-pyranyloxy) carbamoyl]butyl]-4-methyl-2'-(2-phenylethyl)-2'-[2-(1H-1,2,4-triazol-1-yl)acetyl]valerohydrazide there was obtained 0.24 g of 2(R)-[4-cyclohexyl-1(S)-(hydroxcarbamoyl) butyl]-4-methyl-2'-(2-phenylethyl)-2'-[2-(1H-1,2,4-triazol-1-yl)acetyl]valerohydrazide in the form of an off-white solid.

MS: 541 (M+H)+ HPLC: Gradient elution using solvent A containing 5% solvent B increasing to 95% solvent B over 15 minutres; flow rate 1 ml/minute. Retention time: 12.972 minutes. Solvent A: H$_2$O/0.1% TFA; Solvent B: CH$_3$CN/ 0.085%. TFA. Column type: HYPERPEP 300A.

The 2(R)-[4-cyclohexyl-1(S)-[(tetrahydro-2(RS)-pyranyloxy)carbamoyl]butyl]-4-methyl-2'-(2-phenylethyl)-2'-[2-(1H-1,2,4-triazole-1-yl)acetyl]valerohydrazide used as the starting material was prepared as follows:

In a manner analogous to that described in Example 1, parts (iii)–(vii) and Example 8, from 2(R)-[1(S)-tert-butoxycarbonyl)-4-cyclohexylbutyl]-4-methylvaleric acid and 2-phenylethylhydrazine and using 1,2,4-triazole-1-acetic acid in place of N-tertbutoxycarbonyl-β-alanine in Example 8 there was obtained 2(R)-[4-cyclohexyl-1(S)-[(tetrahydro-2(RS)-pyranyloxycarbonyl]butyl]-4-methyl-2'-(2-phenylethyl)-2'-[2-(1H-1,2,4-triazol-1-yl)acetyl] valerohydrazide in the form of a white solid.

MS: 625 (M+H)+.

EXAMPLE 96

(R)-[4-Cyclohexyl-1(S)-(hydroxycarbamoyl)butyl]-4-methyl-2'-(2-phenylethyl)-2'-[2-(3-pyridyl)acetyl) valerohydrazide p-toluenesulphonate In a manner analogous to that described in the first paragraph of Example 5, starting from 0.09 g of 2(R)-[4-cyclohexyl-1(S)-[(tetrahydro-2(RS)-pyranyloxy) carbamoyl]butyl]-4-methyl-2'-2-phenylethyl)-2'-[2-(3-pyridyl)acetyl]valerohydrazide there was obtained 0.103 g of 2(R)-[4-cyclohexyl-1(S)-(hydroxycarbamoyl)butyl]-4-methyl-2'-(2-phenylethyl)-2'-[2-(3-pyridyl)acetyl] valerohydrazide p-toluenesulphonate in the form of a white solid.

MS: 551 (M+H)+. HPLC: Gradient elution using solvent A containing 5% solvent B increasing to 95% solvent B over 15 minutes: flow rate 1 ml/minute. Retention time: 12.537 minutes. Solvent A: H$_2$O/0.1% TEA: Solvent B: CH$_3$CN/ 0.085%. TFA. Column type: HYPERPEP 300A.

The 2(R)-[4-cyclohexyl-1(S)-[(tetrahydro-2(RS)-pyranyloxy)carbamoyl]butyl]-4-methyl-2'-(2-phenylethyl)-2'-[2-(3-pyridyl)acetyl]valerohydrazide used as the starting material was prepared as follows In a manner analogous to that described in Example 1, parts (iii)–(vii) and Example 8, from 2(R)-[1(S)-(tert-butoxycarbonyl)-4-cyclohexylbutyl]-4-methylvaleric acid and 2-phenylethylhydrazine and using 3-pyridylacetic acid in place of N-tert-butoxycarbonyl-β-alanine in Example 8 there was obtained 2(R)-[4-cyclohexyl-1(S)-[(S)-[(tetrahydro-2(RS)-pyranyloxy)carbamoyl]butyl]-4-methyl-2'-(2-phenylethyl)-2'-[2-(3-pyridyl)acetyl]valerohydrazide in the form of a white solid

MS: 635 (M+H)+.

EXAMPLE 97

2(R)-[4-Cyclohexyl-1(S)-(hydroxycarbamoyl)butyl]-2'-[2-(1H-imidazol-1-yl)acetyl]-4-methyl-2'-(2-phenylethyl)valerohydrazide p-toluenesulphonate In a manner analogous to that described in the first paragraph of Example 5, starting from 0.28 g of 2(R)-[4-cyclohexyl-1(S)-[(tetrahydro-2(RS)-pyranyloxy) carbamoyl]butyl]-2'-[2-(1H-imidazol-1-yl)acetyl]-4-methyl-2'-(2-phenylethyl)valerohydrazide there was obtained 0.282 g of 2(R)-[4-cyclohexyl-1(S)-(hydroxycarbamoyl)butyl]-2'-[2-(1H-imidazol-1-yl)acetyl]-4-methyl-2'-(2-phenylethyl}valerohydrazide p-toluenesulphate in the form of a white solid.

MS: 540 (M+H)+. HPLC: Gradient elution using solvent A containing 5% solvent B increasing to 95% solvent B over 15 minutes; flow rate 1 ml/minute. Retention time: 12.970 minutes Solvent A: H$_2$O/0.1% TFA; Solvent B: CH$_3$CN/ 0.085%. Column type: HYPERPEP 300A.

The 2(R)-[4-cyclohexyl-1(S)-[(tetrahydro-2(RS)-pyranyloxy)carbamoyl]butyl]-2'-[2-(1H-imidazol-1-yl)acetyl]-4-methyl-2'-(2-phenylethyl)valerohydrazide used as the starting material was prepared as follows In a manner analogous to that described in Example 1, parts (iii)–(vii) and Example 8, from 2(R)-[1(S)-tert-butoxycarbonyl)-4-cyclohexylbutyl]-4-methylvaleric acid and 2-phenylethylbydrazine and using 1-imidazoleacetic acid in place of N-tert-butoxycarbonyl-β-alanine in Example 8 there was obtained 2(R)-[4-cyclohexyl-1(S)-[(tetrahydro-2(RS)-pyranyloxy)carbamoyl]butyl]-2'-[2-(1H-imidazol-1-yl)acetyl]-4-methyl-2'-(2-phenylethyl) valerohydrazide in the form of a white solid.

MS: 624 (M+H)+.

EXAMPLE 98

2(R)-[4-Cyclohexyl-1(S)-(hydroxycarbamoyl)butyl]-4-methyl-2'-(2-phenylethyl)-2'-[2-(1H-1,2,3-triazol-1-yl)acetyl]valerohydrazide p-toluenesulphonate In a manner analogous to that described in the first paragraph of Example 5, starting from 0.3 g of 2(R)-[4-cyclohexyl-1(S)-[(tetrahydro-2(RS)-pyranyloxy) carbamoyl]butyl]-4-methyl-2'-(2-phenylethyl)-2'-[-2-(1H)-1,2,3-triazol-1-yl)acetyl]valerohydrazide there was obtained 0.287 g of 2(R)-[4-cyclohexyl-1(S)-(hydroxycarbamoyl) butyl]-4-methyl-2'-(2-phenethyl)-2'-[2-(1H-1,2,3-triazol-1-yl)acetyl]valerohydrazide in the form of a white solid.

MS: 541 (M+H)+. HPLC: Gradient elution using solvent A containing 5% solvent B increasing to 95% solvent B over 15 minutes; flow rate 1 ml/minute. Retention time: 13.27 minutes. Solvent A: H$_2$O/0.1% TFA; Solvent B: CH$_3$CN/ 0.085% TFA. Column type: HYPERPEP 300A.

The 2(R)-[4-cyclohexyl-1(S)-[(tetrahydro-2(RS)-pyranyloxy)carbamoyl]buty]-4-methyl-2'-(2-phenylethyl)-

2'-[2-(1H-1,2,3-triazol-1-yl)acetyl)valerohydrazide used as the starting material was prepared as follows:

In a manner analogous to that described in Example 1, parts (iii)–(vii) and Example 8, from 2(R)-[1(S)-tert-butoxycarbonyl)-4-cyclohexylbutyl]-4-methylvaleric acid and 2-phenylethylhydrazine and using 1,2,3-triazole-1-acetic acid in place of N-tert-butoxycarbonyl-β-alanine in Example 8 there was obtained 2(R)-[4-cyclohexyl-1(S)-[(tetrahydro-2(RS)-pyranyloxy)carbamoyl]butyl]-4-methyl-2'-(2-phenylethyl)-2'-[2-(1H-1,2,3-triazol-1-yl)acetyl) valerohydrazide in the form of a white solid.

MS: 625 (M+H)+.

EXAMPLE 99

2'-Benzyl-2(R)-[1(S)-(hydroxycarbamoyl)-4-phenylbutyl]-4-methyl-2'-[2-(1H-1,2,3-triazol-1-yl) acetyl]valerohydrazide p-toluenesulphonate In a manner analogous to that described in the first paragraph of Example 5, starting from 0.305 g of 2'-benzyl-2(R)-[(S)-[(tetrahydro-2(RS)-pyranyloxy)carbamoyl]-4-phenylbutyl]-4-methyl-2'-[2-(1H-1,2,3-triazol-1-yl)acetyl] valerohydrazide there was obtained 0.234 g of 2'-benzyl-2 (R)-[1(S)-(hydroxycarbamoyl)-4-phenylbutyl]-4-methyl-2'-[2-(1H-1,2,3-triazol 1-yl)acetyl]valerohydrazide p-toluenesulphonate in the form of a white solid.

MS: 521 (M+H)+. HPLC: Gradient elution using solvent A containing 5% solvent B increasing to 95% solvent B over 15 minutes: flow rate 1 ml/minute. Retention time: 12.278 minutes. Solvent A: $H_2O$/0.1% TFA; Solvent B: $CH_3CN$/0.085% TFA. Column type: HYPBDDS, C18.

The 2'-benzyl-2(R)-[1(S)-[(tetrahydro-2(RS)-pyranyloxy)carbamoyl]-4-phenylbutyl]-4-methyl-2'-[2-(1H-1,2,3-triazol-1-yl)acetyl]valerohydrazide used as the starting material was prepared as follows:

In an analogous manner to that described in Example 1, parts (iii)–(vii) and Example 8, from 2(R)-[1(S)-(tert-butoxycarbonyl)-4-phenylbutyl]-4-methylvaleric acid and benzylhydrazine and using 1,2,3-triazol-1-acetic acid in place of N-tert-butoxycarbonyl-β-alanine in Example 8, there was obtained 2'-benzyl-2(R)-[1(S)-[(tetrahydro-2(RS)-pyranyloxy)carbamoyl]-4-phenylbutyl]-4-methyl-2'-[2-(1H-1,2,3-triazol-1-yl)acetyl]valerohydrazide in the form of a white foam.

MS: 605 (M+H)+.

EXAMPLE 100

2'-Benzyl-2(R)-[1(S)-(hydroxycarbamoyl)-4-phenylbutyl]-4-methyl-2'-[2-(1H-1,2,4-triazol-1-yl) acetyl]valerohydrazide p-toluenesulphonate In a manner analogous to that described in the first paragraph of Example 5, starting from 0.285 g of 2'-benzyl-2(R)-1(S)-[(tetrahydro-2(RS)-pyranyloxy)carbamoyl]-4-phenylbutyl]-4-methyl-2'-[2-(1H-1,2,4-triazol-1-yl)acetyl] valerohydrazide there was obtained 0.31 g of 2'-benzyl-2 (R)-[1(S)-(hydroxycarbamoyl)-4-phenylbutyl]-4-methyl-2'-[2-(1H-1,2,4-triazol-1-yl)acetyl]valerohydrazide p-toluenesulphonate in the form of an off-white solid.

MS: 521 (M+H)+. HPLC: Gradient elution using solvent A containing 5% solvent B increasing to 95% solvent B over 15 minutes; flow rate 1 ml/minute. Retention time 11.963 minutes. Solvent A: $H_2O$/0.1% TFA; Solvent B: $CH_3CN$/0.085% TFA. Column type: HYPBDS, C18.

The 2'-benzyl-2(R)-[1(S)-[(tetrabydro-2(RS)-pyranyloxy)carbamoyl]-4-phenylbutyl]-4-methyl-2'-[2-(1H-1,2,4-triazol-1-yl)acetyl]valerohydrazide used as the starting material was prepared as follows:

In a manner analogous to that described in Example 1, parts (iii)–(vii) and Example 8, from 2(R)-[1(S)-(tert-butoxycarbonyl)-4-phenylbutyl]-4-methylvaleric acid and benzylhydrazine and using 1,2,4-triazol-1-acetic acid in place of N-tert-butoxycarbonyl-β-alanine in Example 8, there was obtained 2'-benzyl-2(R)-[1(S)-[(tetrahydro-2(RS)-pyranyloxy)carbamoyl]-4-phenylbutyl]-4-methyl-2'-[2-(1H-1,2,4-triazol-1-yl)acetyl]valerohydrazide in the form of a white foam.

MS: 605 (M+H)+.

EXAMPLE 101

2'-Benzyl-2(R)-[1(S)-(hydroxycarbamol)-4-phenylbutul]-4-methy-2'-[2-(3-pyridyl)acetyl] valerohydrazide p-toluenesulphonate In a manner analogous to that described in the first paragraph of Example 5, starting from 0.317 g of 2'-benzyl-2(R)-[1(S)-[(tetrahydro-2(RS)-pyranyloxy)carbamoyl]-4-phenylbutyl]-4-methyl-2'-[2-(3-pyridyl)acetyl] valerohydrazide there was obtained 0.318 g of 2'-benzyl-2 (R)-[1(S)-(hydroxycarbamoyl)-4-phenylbutyl]-4-methy-2'-[2-(3-pyridyl)acetyl]valerohydrazide p-toluenesulphonate in the form of a cream colored solid.

MS: 531 (M+H)+. HPLC: Gradient elution using solvent A containing 5% solvent B increasing to 95% solvent B over 15 minutes. Solvent A: $H_2O$/0.1% TFA; Solvent B: $CH_3CN$/0.085% TFA. Column type: HYPBDS, C18.

The 2'-benzyl-2(R)-[1(S)-[(tetrahydro-2(RS)-pyranyloxy)carbamoyl]-4-phenylbutyl]-4-methyl-2'-[2-(3-pyridyl)acetyl]valerohydrazide used as the starting material was prepared as follows:

In a manner analogous to that described in Example 1, parts (iii)–(vii) and Example 8, from 2(R)-[1(S)-(tert-butoxycarbonyl)-4-phenylbutyl]-4-methylvaleric acid and benzylhydrazine and using 3-pyridylacetic acid in place of N-tert-butoxycarbonyl-β-alanine in Example 8, there was obtained 2-benzyl-2(R)-[1(S)-[(tetrahydro-2(RS)-pyranyloxy)carbamoyl]-4-phenylbutyl]-4-methyl-2'-[2-(3-pyridyl)acetyl]valerohydrazide in the form of a white foam.

MS: 615 (M+H)+.

EXAMPLE 102

2'-(4-Aminobutyryl)-2'-benzyl-2(R)-[4-cyclohexyl-1 (S)-(hydroxycarbamoyl)butyl]-4-methylvalerohydrazide p-toluenesulphonate In a manner analogous to that described in the first paragraph of Example 5, starting from 0.303 g of 2'-(4-aminobutyryl)-2'-benzyl-2(R)-[4-cyclohexyl-1(S)-(tetrahydro-2(RS)-pyranyloxy)carbamoyl]butyl]-4-methylvalerohyrazide there was obtained 0.191 g of 2'-(4-aminobutytyl)-2'-benzyl-2(R)-[4-cyclohexyl-1(S)-(hydroxycarbamoyl)butyl]-4-methylvalerohydrazide p-toluenesulphonate in the form of a white solid.

MS: 503 (M+H)+. HPLC: Gradient elution using solvent A containing 5% solvent B increasing to 95% solvent B over 15 minutes; flow rate 1 ml/minute. Retention time 12.36 minutes. Solvent A: $H_2O$/0.1% TFA; Solvent B: $CH_3CN$/0.085% TFA. Column type: HYPBDS, C18.

The 2'-(4-aminobutyryl)-2'-benzyl-2(R)-[4-cyclohexyl-1 (S)-[(tetrahydro-2(RS)-pyranyloxy)carbamoyl]butyl]-4-methylvalerohydrazide used as the starting material was prepared as follows:

(i) In a manner analogous to that described in Example 1, parts (iii)–(vii) and Example 8, from 2(R)-[1(S)-(tert-butoxycarbonyl)-4-cyclohexylbutyl]-4-methylvaleric acid and benzyl hydrazine and using 4-benzyloxycarbonylaminobutyric acid in place of N-tert-butoxycarbonyl-β-alanine in Example 8, there was obtained 2'-benzyl-2'-(4-benzyloxycarbonylaminobutyryl)-2(R)-[4-cyclohexyl-1(S)-[(tetrahydro-2(RS)-pyranyloxy)carbamoyl]butyl]-4-methylvalerohydrazide in the form of a white solid.

MS: 721 (M+H)+.

(ii) A solution of 2'-benzyl-2'-(4-benzyloxycarbonylaminobutyryl)-2(R)-[4-cyclohexyl-1(S)-[(tetrahydro-2(RS)-pyranyloxy)carbamoyl]butyl]-4-methylvalerohydrazide in methanol was shaken in an atmosphere of hydrogen in the presence of 10% palladium-on-charcoal catalyst for 3 hours. The catalyst was filtered off and the methanol evaporated to give 2'-(4-aminobutyryl)-2'-benzyl-2(R)-[4-cyclohexyl-1(S)-[(tetrahydro-2(RS)-pyranyloxy)carbamoyl]butyl]-4-methylvalerohydrazide in the form of a white solid.

MS: 587 (M+H)+.

EXAMPLE 103

2'-(4-Aminobutyryl)-2(R)-[1(S)-(hydroxycarbamoyl)-4-phenylbutyl]-4-methyl-2'-(2 (S)-methylbutyl)valerohydrazide A solution of 0.216 g of (E)-2(R)-[1(S)-(benzyloxycarbamoyl)-4-phenyl-3-butenyl]-2'-(4-benzyloxycarbonylaminobutyryl)-4-methyl-2'-(2(S)-methylbutyl)valerohydrazide in 5 ml of methanol was hydrogenated in the presence of 0.1 g of 10% palladium-on-carbon catalyst for 1 hour. The catalyst was removed by filtration and the methanol was evaporated. The residue was re-evaporated from diethyl ether and then triturated with a mixture of diethyl ether and hexane and there was obtained 0.104 g of 2'-(4-aminobutyryl)-2(R)-[1(S)-(hydroxycarbamoyl)-4-phenylbutyl]-4-methyl-2'-(2(S)-methylbutyl)valerohydrazide in the form of a white solid.

MS: 477 (M+H)+. HPLC: Gradient elution using solvent A containing 5% solvent B increasing to 95% solvent B over 15 minutes; flow rate 1 ml/minute. Retention time 11.198 minutes. Solvent A: H₂O/0.1% TFA; Solvent B: CH₃CN/ 0.085% TFA. Column type: HYPBDS, C18.

The (E)-2(R)-[1(S)-(benzyloxycarbamoyl)-4-phenyl-3-butenyl]-2'-(4-benzyloxycarbonylaminobutyryl)-4-methyl-2'-(2(S)-methylbutyl)valerohydrazide used as the starting material was prepared as follows:

(i) In a manner analogous to that described in Example 1, parts (iv)–(vii) using O-benzylhydroxyalanine in part (vi) there was obtained (E)-2(R)-[1(S)-(benzyloxycarbamoyl)-4-phenyl-3-butenyl[-4-methyl-2'-(2(S)-methylbutyl) valerohydrazide in the form of a pale yellow solid.

MS: 480 (M+H)+.

(ii) In a manner analogous to that described in Example 8 from (E)-2(R)-[1(S)-(benzyloxycarbamoyl)-4-phenyl-3-butenyl]-4-metbyl-2'-(2(S)-methylbutyl)valerohydrazide and using 4-benzyloxycarbonylaminobutyric acid in place of N-tert-butoxycarbonyl-β-alanine there was obtained (E)-(2(R)-[1(S)-(benzyloxycarbamoyl)-4-phenyl-3-butenyl]-2'-(4-benzyloxycarbonylaminobutyryl)-4-methyl-2'-(2(S)-methylbutyl)valerohydrazide in the form of a white solid.

MS: 699 (M+H)+.

EXAMPLE 104

2(R)-[1(S)-(hydroxycarbamoyl)-4-phenylbutyl]-4-methyl-2'-(2(S)-methylbutyl)-2'-2-(1H-1,2,4-triazol-1-yl)acetyl]valerohydrazide In a manner analogous to that described in Example 103 starting from 0.212 g of (E)-2(R)-[1(S)-benzyloxycarbamoyl)-4-phenyl-3-butenyl]-4-methyl-2'-(2 (S)-methylbutyl)-2'-[2-(1H-1,2,4-triazol-1-yl)acetyl] valerohydrazide there was obtained 0.13 g of 2(R)-[1(S)-(hydroxycarbamoyl)-4-phenylbutyl]-4-methyl-2'-(2(S)-methylbutyl)-2'-[2-(1H-1,2,4-triazol-1-yl)acetyl] valerohydrazide in the form of a white solid.

MS: 501 (M+H)+. HPLC: Gradient elution using solvent A containing 5% solvent B increasing to 95% solvent B over 15 minutes; flow rate 1 ml/minute. Retention time 11.39 minutes. Solvent A: H₂O/0.1% TFA; Solvent B: CH₃CN/ 0.085% TFA. Column type: HYPERPEP 300A The (E)-2(R)-[1(S)-(benzyloxycarbamoyl)-4-phenyl-3-butenyl]-4-methyl-2'-(2(S)-methylbutyl)-2'-[2-(1H-1,2,4-triazol-1-yl)acetyl]valerohydrazide used as the starting material was prepared as follows:

In a manner analogous to that described in Example 8 from (E)-2(R)-[1(S)-(benzyloxycarbamoyl)-4-phenyl-3-butenyl]-3-4-methyl-2'-(2(S)-methylbutyl)valerohydrazide and using 1,2,4-triazol-1-acetic acid in place of N-tert-butoxycarbonyl-β-alanine there was obtained (E)-2(R)-[1 (S)-(benzyloxycarbamoyl)-4-phenyl-3-butenyl]-4-methyl-2'-(2(S)-methylbutyl)-2'-[2-(1H-1,2,4-triazol-1-yl)acetyl]-valerohydrazide in the form of a gum.

EXAMPLE 105

2(R)-[1(S)-(hydroxycarbamoyl)-4-phenylbutyl]-2'-[2-(1H-imidazol-1-yl)acetyl]-4-methyl-2'-(2(S)-methylbutyl)valerohydrazide In a manner analogous to that described for Example 103 starting from 0.162 g of (E)-2(R)-[1(S)-(benzyloxycarbamoyl)-4-phenyl-3-butenyl]-2'-[2-(1H-imidazol-1-yl)acetyl]-4-methyl-2'-(2(S)-methylbutyl) valerohydrazide there was obtained 0.065 g of 2(R)-[1(S)-(hydroxycarbamoyl)-4-phenylbutyl]-2'-[2-(1H-imidazol-1-yl)acetyl]-4-methyl-2'-(2(S)-methylbutyl)valerohydrazide in the form of a white solid.

MS: 500 (M+H)+. HPLC: Gradient elution using solvent A containing 5% solvent B increasing to 95% solvent B over 15 minutes, flow rate 1 ml/minute. Retention time 11.273 minutes Solvent A: H₂O/0.1% TPA; solvent B: CH₃CN/ 0.085% TFA. Column type: HYPERPEP 300A.

The (E)-2(R)-[1(S)-(benzyloxycarbamoyl)-4-phenyl-3-butenyl]-2'-[2-(1H-imidazol-1-yl)acetyl]-4-methyl-2'-(2(S)-methylbutyl)valerohydrazide used as the starting material was prepared as follows:

In a manner analogous to that described in Example 8 from (E)-2(R)-[1(S)-(benzyloxycarbamoyl)-4-phenyl-3-butenyl]-4-methyl-2'-(2(S)-methylbutyl)valerohydrazide and using imidazole-1-acetic acid in place of N-tert-butoxycarbonyl-β-alanine in Example 8 there was obtained (E)-2(R)-[1(S)-(benzyloxycarbamoyl)-4-phenyl-3-butenyl]-2'-[2-(1H-imidazol-1-yl)acetyl]-4-methyl-2'-(2(S)-methylbutyl)valerohydrazide in the form of a gum.

MS: 588 (M+H)+.

EXAMPLE 106

2'-Benzyl-2(R)-[1(S)-(hydroxycarbamoyl)-4-phenylbutyl]-2'-[2-(1H-imidazol-1-yl)acetyl]-4-methylvalerohydrazide p-toluenesulphonate In a manner analogous to that described in the first paragraph of Example 5, starting from 0.25 g of 2'-benzyl-2(R)-[1(S)-[(tetrahydro-2(RS)-pyranyloxy)carbamoyl]-4-phenylbutyl]-2'-[2-(1-imidazolyl)acetyl]-4- methylvalerohydrazide there was obtained 0.246 g of 2'-benzyl-2(R)-[1(S)-(hydroxycarbamoyl)-4-phenylbutyl]-2'-[2-(1H-imidazol-1-yl)acetyl]-4-methylvalerohydrazide p-toluenesulphonate in the form of a cream solid.

MS: 520 (M+H)$^+$. HPLC: Gradient elution using solvent A containing 5% solvent B increasing to 95% solvnet B over 15 minutes; flow rate 1 ml/minute. Retention time: 11.107 minutes. Solvent A: $H_2O$/0.1% TFA; solvent B: $CH_3CN$/0.085% TFA. Column type: HYPERPEP 300A.

The 2'-benzyl-2(R)-[1(S)-[(tetrahydro-2(RS)-pyranyloxy)carbamoyl]-4-phenylbutyl]-2'-[2-(1-imidazolyl)acetyl]-4-methylvalerohydrazide used as the starting material was prepared as follows:

In a manner analogous to that described in Example 1, parts (iii)–(vii) and Example 8, from 2(R)-[1(S)-(tert-butoxycarbonyl)-4-[phenylbutyl[-4-methylvaleric acid and benzylhydrazine and using imidazole-1-acetic acid in place of N-tert-butoxycarbonyl-β-alanine in Example 8 there was obtained 2'-benzyl-2)-[(1(S)-[(tetrahydro-2(RS)-pyranyloxy)carbamoyl]-4-phenylbutyl]-2'-[2-(1-imidazolyl)acetyl]-4-methylvalerohydrazide.

EXAMPLE 107

2'-(4-Aminobutyryl)-2'-benzyl-2(R)-[1(S)-(hydroxycarbamoyl)-4-phenylbutyl]-4-methylvalerohydrazide p-toluene sulphonate In a manner analogous to that described in the first paragraph of Example 5, starting from 0.237 g of 2'-(4-aminobutyl)-2'-benzyl-2(R)-[1(S)-[(tetrahydro-2(RS)-pyranyloxy)carbamoyl]-4-phenylbutyl]-4-methylvalerohydrazide there was obtained 0.219 g of 2'-(4-aminobutyryl)-2'-benzyl-2(R)-[1(S)-(hydroxycarbamoyl)-4-phenylbutyl]-4-methylvalerohydrazide p-toluenesulphonate in the form of an off-white solid.

MS: 497 (M+H)$^+$. HPLC: Gradient elution using solvent A containing 5% solvent B increasing to 95% solvent B over 15 minutes; flow rate 1 ml/minute. Retention time 10.623 minutes. Solvent A: $H_2O$/0.1 TFA; solvent B: $CH_3CN$/0.085% TFA. Column type: HYPERPEP 300A.

The 2'-(4-aminobutyl)-2'-benzyl-2(R)-[1(S)-[(tetrahydro-2(RS)-pyranyloxy)carbamoyl]-4-phenylbutyl]-4-methylvalerohydrazide used as the starting material as prepared as follows:

(i) In a manner analogous to that described in Example 1, parts (iii)–(iv) and Example 8, from 2(R)-[1(S)-(tert-butoxycarbonyl)-4-phenylbutyl]-4-methylvaleric acid and benzylhydrazine and using 4-benzyloxycarbonylaminobutyric acid in place of N-tert-butoxycarbonyl-β-alanine in Example 8, there was obtained 2'-benzyl-2'-(4-benzyloxycarbonylaminobutyryl)-2(R)-[1(S)-[(tetrahydro-2(RS)-pyranyloxy)carbamoyl]-4-phenylbutyl]-4-methylvalerohydrazide in the form of a white solid.

MS: 715 (M+H)$^+$.

In a manner analogous to that described in Example 102 part (ii) from 2'-benzyl-2'-(4-benzyloxycarbonyl-aminobutyl)-2(R)-[1(S)-[(tetrahydro-2(RS)-pyranyloxy)carbamoyl]-4-phenylbutyl]-4-methylvalerohydrazide there was obtained 2'-(4-aminobutyl)-2'-benzyl-2(R)-[1(S)-[(tetrahydro-2(RS)-pyranyloxy)carbamoyl]-4-phenylbutyl]-4-methylvalerohydrazide in the form of a gum.

MS: 581 (M+H$^+$.

EXAMPLE 108

(E)-2(R)-[1(S)-(Hydroxycarbamoyl)-4-phenyl-3-butenyl]-2'-isobutyl-4-methyl-2'-(1-methyl-L-prolyl)valerohydrazide p-toluenesulphonate In a manner analogous to that described in Example 11 but using N-methyl-L-proline in the place of N-acetyl-glycine there was obtained (E)-2(R)-[1(S)-(hydroxycarbamoyl)-4-phenyl-3-butenyl]-2'-isobutyl-4-methyl-2'-(1-methyl-L-prolyl)valerohydrazide p-toluenesulphonate in the form of a white solid.

MS: 487 (M+H)$^+$. HPLC: Gradient elution using solvent A containing 5% solvent B increasing to 95% solvent B over 15 minutes; flow rate 1 ml per minute. Retention time: 10.93 minutes. Solvent A: $H_2O$/0.1% TFA; solvent B: $CH_3CN$/0.085% TFA. Column type: HYPERPEP 300A.

EXAMPLE 109

(E)-2(R)-[1(S)-(Hydroxycarbamoyl)-4-phenyl-3-butenyl]-2'-isobutyl-4-methyl-2'-[2-(2-thienyl)acetyl]valerohydrazide In a manner analogous to that described in Example 11 but using 2-(2-thienyl)acetic acid in the place of N-acetyl-glycine there was obtained (E)-2(R)-[1(S)-(hydroxycarbamoyl)-4-phenyl-3-butenyl]-2'-isobutyl-4-methyl-2'-[2-(2-thienyl)acetyl]valerohydrazide in the form of a white solid.

MS: 500 (M+H)$^+$. HPLC: Gradient elution using solvent A containing 5% solvent B increasing to 95% solvent B over 15 minutes; flow rate 1 ml per minute. Retention time: 13.00 minutes. Solvent A: $H_2O$/0.1% TFA; solvent B: $CH_3CN$/0.085% TFA. Column type: HYPERPEP 300A.

EXAMPLE 110

(E)-2(R)-[1(S)-(Hydroxycarbamoyl)-4-phenyl-3-butenyl]-2'-isobutyl-4-methyl-2'-[2-(3-thienyl)acetyl]valerohydrazide In a manner analogous to that described in Example 11 but using 2-(3-thienyl)acetic acid in the place of N-acetyl-glycine there was obtained (E)-2(R)-[1(S)-(hydroxycarbamoyl)-4-phenyl-3-butenyl]-2'-isobutyl-4-methyl-2'-[2-(3-thienyl)acetyl]valerohydrazide in the form of a white solid.

MS: 500 (M+H)$^+$. HPLC: Gradient elution using solvent A containing 5% solvent B increasing to 95% solvent B over 15 minutes; flow rate 1 ml per minute. Retention time: 12.91 minutes. Solvent A: $H_2O$/0.1% TFA; solvent B: $CH_3CN$/0.085% TFA. Column type: HYPERPEP 300A.

EXAMPLE 111

(E)-2'-(2-Furoyl)-2(R)-[(1(S)-(hydroxycarbamoyl)-4-phenyl-3-butenyl]-2'-isobutyl-4-methylvalerohydrazide In a manner analogous to that described in Example 11 but using 2-furanoic acid in the place of N-acetyl-glycine there was obtained (E)-2'-(2-furoyl)-2(R)-[1(S)-(hydroxycarbamoyl)-4-phenyl-3-butenyl]-2'-isobutyl-4-methylvalerohydrazide in the form of an off-white solid.

MS: 470 (M+H)$^+$. HPLC: Gradient elution using solvent A containing 5% solvent B increasing to 95% solvent B over 15 minutes; flow rate 1 ml per minute. Retention time: 12.11 minutes. Solvent A: $H_2O$/0.1% TFA; solvent B: $CH_3CN$/0.085% TFA. Column type: HYPERPEP 300A.

EXAMPLE 112

(E)-2'-(3-Furoyl)-2(R)-[1(S)-(hydroxycarbamoyl)-4-phenyl-3-butenyl]-2'-isobutyl-4-methylvalerohydrazide In a manner analogous to that described in Example 11 but using 3-furanoic acid in the place of N-acetyl-glycine there was obtained (E)-2'-(3-furoyl)-2(R)-[1(S)-(hydroxycarbamoyl)-4-phenyl-3-butenyl]-2'-sobutyl-4-methylvalerohydrazide in the form of a white solid.

MS: 470 (M+H)⁺. HPLC: Gradient elution using solvent A containing 5% solvent B increasing to 95% solvent B over 15 minutes; flow rate 1 ml per minute. Retention time: 12.10 minutes. Solvent A: $H_2O$/0.1% TFA; solvent B: $CH_3CN$/0.085% TFA. Column type: HYPERPEP 300A.

EXAMPLE 113

(E)-2(R)-[1(S)-(Hydroxycarbamoyl)-4-phenyl-3-butenyl]-2'-isobutyl-2'-[2-(methanesulphonyl)acetyl]-4-methylvalerohydrazide In a manner analogous to that described in Example 11 but using methanesulphonyl acetic acid in the place of N-acetyl-glycine there was obtained (E)-2(R)-[1(S)-(hydroxycarbamoyl)-4-phenyl-3-butenyl]-2'-isobutyl-2'-[2-(methanesulphonyl)acetyl]-4-methylvalerohydrazide in the form of a white solid.

MS: 496 (M+H)⁺. HPLC: Gradient elution using solvent A containing 5% solvent B increasing to 95% solvent B over 15 minutes; flow rate 1 ml per minute. Retention time: 11.84 minutes. Solvent A: $H_2O$/0.1% TFA; solvent B: $CH_3CN$/0.085% TFA. Column type: HYPERPEP 300A.

EXAMPLE 114

(E)-2(R)-[1(S)-(Hydroxycarbamoyl)-4-phenyl-3-butenyl]-2'-isobutyl-4-methyl-2'-[2-(1-pyrrolyl)acetyl]valerohydrazide In a manner analogous to that described in Example 11 but using 2-(1-pyrrole) acetic acid in the place of N-acetyl-glycine there was obtained (E)-2(R)-[1(S)-(hydroxycarbamoyl)-4-phenyl-3-butenyl]-2'-isobutyl-4-methyl-2'-[2-(1-pyrrolyl)acetyl]-valerohydrazide in the form of a white solid.

MS: 483 (M+H)⁺. HPLC: Gradient elution using solvent A containing 5% solvent B increasing to 95% solvent B over 15 minutes; flow rate 1 ml per minute. Retention time: 12.80 minutes. Solvent A: $H_2O$/0.1% TFA; solvent B: $CH_3CN$/0.085% TFA. Column type: HYPERPEP 300A.

EXAMPLE 115

(E)-2(R)-[1(S)-(Hydroxycarbamoyl)-4-phenyl-3-butenyl]-2'-isobuty-4-methyl-2'-(1-methyl-D-prolyl)valerohydrazide p-toluenesulphonate In a manner analogous to that described in Example 11 but using N-methyl-D-proline in the place of N-acetyl-glycine there was obtained (E)-2(R)-[1(S)-(hydroxycarbamoyl)-4-phenyl-3-butenyl]-2'-isobutyl-4-methyl-2'-(1-methyl-D-prolyl)valerohydrazide p-toluenesulphonate in the form of a white solid.

MS: 487 (M+H)⁺. HPLC: Gradient elution using solvent A containing 5% solvent B increasing to 95% solvent B over 15 minutes; flow rate 1 ml per minute. Retention time: 11.56 minutes. Solvent A: $H_2O$/0.1% TFA; solvent B: $CH_3CN$/0.085% TFA. Column type: HYPERPEP 300A.

EXAMPLE 116

(E)-2'-[2-(1,2,3,6-tetrahydro-2,6-dioxo-4-pyrimidinyl)acetyl]-2(R)-[1(S)-(hydroxycarbamoyl)-4-phenyl-3-butenyl]-2'-isobutyl-4-methylvalerohydrazide In a manner analogous to that described in Example 8 but using 4-uracil acetic acid in the place of N-tert.butyloxycarbonyl-β-alanine there was obtained (E)-2'-[2-(1,2,3,6-tetrahydro-2,6-dioxo-4-pyrimidinyl)acetyl]-2(R)-[1(S)-(hydroxycarbamoyl)-4-phenyl-3-butenyl]-2'-isobutyl-4-methylvalerohydrazide in the form of a white solid.

MS: 528 (M+H)⁺. HPLC: Gradient elution using solvent A containing 5% solvent B increasing to 95% solvent B over 15 minutes; flow rate 1 ml per minute. Retention time: 10.61 minutes. Solvent A: $H_2O$/0.1% TFA; solvent B: $CH_3CN$/0.085% TFA. Column type: HYPERPEP 300A.

EXAMPLE 117

(E)-2(R)-[1(S)-(Hydroxycarbamoyl)-4-phenyl-3-butenyl]-2'-isobutyl-4-methyl-2'-[2-(2-thioxo-4-oxo-5-thiazolidinyl)acetyl]valerohydrazide In a manner analogous to that described in Example 8 but using 3-rhodamine acetic acid in the place of N-tert.butyloxycarbonyl-β-alanine there was obtained (E)-2(R)-[1(S)-(hydroxycarbamoyl)-4-phenyl-3-butenyl]-2'-isobutyl-4-methyl-2'-[2-(2-thioxo-4-oxo-5-thiazolidinyl)acetyl]valerohydrazide in the form of a white solid.

MS: 549 (M+H)⁺. HPLC: Gradient elution using solvent A containing 5% solvent B increasing to 95% solvent B over 15 minutes; flow rate 1 ml per minute. Retention time: 12.92 minutes. Solvent A: $H_2O$/0.1% TFA; solvent B: $CH_3CN$/0.085% 1TFA. Column type: HYPERPEP 300A.

EXAMPLE 118

(E)-2(R)-[1(S)-(Hydroxycarbamoyl)-4-phenyl-3-butenyl]-1-2'-isobutyl-4-methyl-2'-(1-methyl-2-pylrolyl)carbonyl]valerobydrazide In a manner analogous to that described in Example 11 but using N-methylpyrrole-2-carboxylic acid in the place of N-acetyl-glycine there was obtained (E)-2(R)-[1(S)-(hydroxycarbamoyl)-4-phenyl-3-butenyl]-2'-isobutyl-4-methyl-2'-[(1-methyl-2-pyrrolyl)carbonyl]valerohydrazide in the form of a white solid.

MS: 483 (M+H)⁺. HPLC: Gradient elution using solvent A containing 5% solvent B increasing to 95% solvent B over 15 minutes; flow rate 1 ml per minute. Retention time: 12.58 minutes. Solvent A: $H_2O$/0.1% TFA; solvent B: $CH_3CN$/0.085% TFA. Column type: HYPERPEP 300A.

EXAMPLE 119

(E)-2(R)-[1(S)-(Hydroxycarbamoyl)-4-phenyl-3-butenyl]-2'-[2-(3-indolyl)acetyl]-2'-isobutyl-4-methylvalerohydrazide In a manner analogous to that described in Example 8 but using 3-indole acetic acid in the place of N-tert.butyloxycarbonyl-β-alanine there was obtained (E)-2(R)-[1(S)-(hydroxycarbamoyl)-4-phenyl-3-butenyl]-2'-[2-(3-indolyl)acetyl]-2'-isobutyl-4-methylvalerohydrazide in the form of a white solid.

MS: 533 (M+H)⁺. HPLC: Gradient elution using solvent A containing 5% solvent B increasing to 95% solvent B over 15 minutes; flow rate 1 ml per minute. Retention time: 12.86 minutes. Solvent A: $H_2O$/0.1% TFA; solvent B: $CH_3CN$/0.085% TFA. Column type: HYPERPEP 300A.

EXAMPLE 120

(E)-2(R)-[1(S)-(Hydroxycarbamoyl)-4-pheny -3-butenyl]-2'-[3-(4-imidazolyl)propionyl]-2'-isobutyl-4-methylvalerohydrazide hydrochloride In a manner analogous to that described in Example 25 but using deamino histadine acid chloride in the place of N-tert.butoxycarbonyl-L-leucine acid fluoride there was obtained (E)-2(R)-[1(S)-(hydroxycarbamoyl)-4-phenyl-3-butenyl]-2'-[3-(4-imidazolyl)propionyl]-2'-isobutyl-4-methylvalerohydrazide hydrochloride in the form of a white solid.

MS: 498 (M+H)+. HPLC: Gradient elution using solvent A containing 5% solvent B increasing to 95% solvent B over 15 minutes; flow rate 1 ml per minute. Retention time: 10.72 minutes. Solvent A: $H_2O$/0.1% TFA; solvent B: $CH_3CN$/0.085% TFA. Column type: HYPERPEP 300A.

EXAMPLE 121

(E)-2(R)-[1(S)-(Hydroxycarbamoyl)-4-phenyl-3-butenyl]-2'-isobutyl-4-methyl-2'-[2-(1-pyrazolyl)acetyl]valerohydrazide p-toluenesulphonate In a manner analogous to that described in Example 37 but using 2-(1-pyrazolyl)acetic acid hydrogen bromide in the place of 2-(1-pyrrolidinyl)acetic acid hydrogen bromide there was obtained (E)-2(R)-[1(S)-hydroxycarbamoyl)-4-phenyl-3-butenyl]-2'-isobutyl-4-methyl-2'-[2-(1-pyrazolyl)acetyl]valerohydrazide p-toluenesulphonate in the form of a white solid.

MS: 484 (M+H)+. HPLC: Gradient elution using solvent A containing 5% solvent B increasing to 95% solvent B over 15 minutes; flow rate 1 ml per minute. Retention time: 11.80 minutes. Solvent A: $H_2O$/0.1% TFA; solvent B: $CH_3CN$/0.085% TFA. Column type: HYPERPEP 300A.

EXAMPLE 122

(E)-2(R)-[1(S)-(Hydroxycarbamoyl)-4-phenyl-3-butenyl]-2'-isobutyl-4-methyl-2'-[2-(1H-1,2,3-triazol-1-yl)acetyl]valerohydrazide p-toluenesulphonate In a manner analogous to that described in Example 37 but using 2-(1H-1,2,3-triazol-1-yl)acetic acid hydrogen bromide in the place of 2-(1-pyrrolidinyl)acetic acid hydrogen bromide there was obtained (E)-2(R)-[1(S)-(hydroxycarbamoyl)-4-phenyl-3-butenyl]-2'-isobutyl-4-methyl-2'-[2-(1H-1,2,3-triazol-1-yl)acetyl]valerohydrazide p-toluenesulphonate in the form of an off-white solid.

MS: 485 (M+H)+. HPLC: Gradient elution using solvent A containing 5% solvent B increasing to 95% solvent B over 15 minutes; flow rate 1 ml per minute. Retention time: 11.42 minutes. Solvent A: $H_2O$/0.1% TFA; solvent B: $CH_3CN$/0.085% TFA. Column type: HYPERPEP 300A.

EXAMPLE 123

(E)-2(R)-[1(S)-(Hydroxycarbamoyl)-4-phenyl-3-butenyl]-2'-isobutyl-4-methyl-2'-[2-(1H-1,2,4-triazol-1-yl)acetyl]valerohydrazide p-toluenesulphonate In a manner analogous to that described in Example 37 but using 2-(1H-1,2,4-triazol-1-yl)acetic acid hydrogen bromide in the place of 2-(1-pyrrolidinyl)acetic acid hydrogen bromide there was obtained (E)-2(R)-[1(S)-(hydroxycarbamoyl)-4-phenyl-3-butenyl]-2'-isobutyl-4-methyl-2'-[2-(1H-1,2,4-triazol-1-yl)acetyl]valerohydrazide p-toluenesulphonate in the form of an off-white solid.

MS: 485 (M+H)+. HPLC: Gradient elution using solvent A containing 5% solvent B increasing to 95% solvent B over 15 minutes; flow rate 1 ml per minute. Retention time: 11.07 minutes. Solvent A: $H_2O$/0.1% TFA; solvent B: $CH_3CN$/0.085% TFA. Column type: HYPERPEP 300A.

EXAMPLE 124

(E)-2'-[2-(Tetrahydro-2H-pyran-4-yl)acetyl]-2(R)-[1 (S)-(hydroxycarbamoyl)-4-phenyl-3-butenyl]-2'-isobutyl-4-methylvalerohydrazide In a manner analogous to that described in Example 11 but using 2-(tetrahydro-2H-pyran-4-yl)acetic acid in the place of N-acetyl-glycine there was obtained (E)-2'-[2-(Tetrahydro-2H-pyran-4-yl)acetyl]-2(R)-[1(S)-(hydroxycarbamoyl)-4-phenyl-3-butenyl]-2'-isobutyl-4-methylvalerohydrazide in the form of a white solid.

MS: 502 (M+H)+. HPLC: Gradient elution using solvent A containing 5% solvent B increasing to 95% solvent B over 15 minutes; flow rate 1 ml per minute. Retention time: 11.62 minutes. Solvent A: $H_2O$/0.1% TFA; solvent B: $CH_3CN$/0.085% TFA. Column type: HYPERPEP 300A.

EXAMPLE 125

(E)-2'-[4-(Diethylamino)butyryl]-2(R)-[1(S)-(hydroxycarbamoyl)-4-phenyl-3-butenyl]-2'-isobutyl-4-methylvalerohydrazide p-toluenesulphonate In a manner analogous to that described in Example 11 but using 4-(diethylamino)butanoic acid in the place of N-acetyl-glycine there was obtained (E)-2'-[4-(diethylamino)butyryl]-2(R)-[1(S)-(hydroxycarbamoyl)-4-phenyl-3-butenyl]-2'-isobutyl-4-methylvalerohydrazide p-toluenesulphonate in the form of a white solid.

MS: 517 (M+H)+. HPLC: Gradient elution using solvent A containing 10% solvent B for 5 minutes and then increasing to 90% solvent B over 10 minutes; flow rate 1 ml per minute. Retention time: 11.18 minutes. Solvent A: $H_2O$/0.1% TFA; solvent B: $CH_3CN$/0.085% TFA. Column type: LUNA 3U C18(2) GRAD.

EXAMPLE 126

(E)-2(R)-[1(S)-(Hydroxycarbamoyl)-4-phenyl-3-butenyl]-2'-[2-(4-imidazolyl)acety]-2-isobutyl-4-methylvalerohydrazide hydrochloride In a manner analogous to that described in Example 25 but using 2-(4-imidazolyl)acetic acid chloride in the place of N-tert.butoxycarbonyl-L-leucine acid fluoride there was obtained (E)-2(R)-[1(S)-(hydroxycarbamoyl)-4-phenyl-3-butenyl]-2'-[2-(4-imidazolyl)acetyl]-2'-isobutyl-4-methylvalerohydrazide hydrochloride in the form of a white solid.

MS: 484 (M+H)+. HPLC: Gradient elution using solvent A containing 5% solvent B increasing to 90% solvent B over 15 minutes; flow rate 1 ml per minute. Retention time: 10.73 minutes. Solvent A: $H_2O$/0.1% TFA; solvent B: $CH_3CN$/0.085% TFA. Column type: HYPERPEP 300A.

EXAMPLE 127

(E)-2(R)-[1(S)-(Hydroxycarbamoyl)-4-phenyl-3-butenyl]-2'-isobutyl]-4-methyl-2'-[2-(1-methyl-4-piperidinyl)acetyl]valerohydrazide p-toluenesulphonate In a manner analogous to that described in Example 37 but using 2-(1-methyl-4-piperidine)acetic acid hydrogen chloride in the place of 2-(1-pyrrolidinyl)acetic acid hydrogen bromide there was obtained (E)-2(R)-[1(S)-(hydroxycarbamoyl)-4-phenyl-3-butenyl]-2'-isobutyl-4- methyl-2'-[2-(1-methyl-4-piperidinyl)acetyl]
valerohydrazide p-toluenesulphonate in the form of a white
solid.

MS: 515 (M+H)⁺. HPLC: Gradient elution using solvent
A containing 5% solvent B increasing to 95% solvent B over
15 minutes; flow rate 1 ml per minute. Retention time: 10.53
minutes. Solvent A: $H_2O/0.1\%$ TFA; solvent B: $CH_3CN/$
0.085% TFA. Column type: HYPERPEP 300A.

EXAMPLE 128

(E)-2(R)-[1(S)-(Hydroxycarbamoyl)-4-phenyl-3-
butenyl]-2'-isobutyl-4-methyl-2'-(3-
phthalimidopropionyl)valerohydrazide A solution of 0.050 g of (E)-2(R)-[1(S)-[(tetrahydro-2
(RS)-pyranyloxy)carbamoyl]-4-phenyl-3-butenyl]-2'-
isobutyl-4-methyl-2'-(3-phthalimidopropionyl)
valerohydrazide in 5 ml of methanol was treated with 0.005
g of p-toluenesulphonic acid monohydrate. The mixture was
stirred for 1 hr at room temperature and evaporated. The
residue was triturated with diethyl ether, filtered off and
dried to give 0.009 g of (E)-2(R)-[1(S)-
(hydroxycarbamoyl)-4-phenyl-3-butenyl]-2'-isobutyl-4-
methyl-2'-(3-phthalimidopropionyl)valerohydrazide in the
form of an off-white solid.

MS: 577 (M+H)⁺. HPLC: Gradient elution using solvent
A containing 5% solvent B increasing to 95% solvent B over
15 minutes; flow rate 1 ml per minute. Retention time: 13.16
minutes. Solvent A: $H_2O/0.1\%$ TFA; solvent B: $CH_3CN/$
0.085% TFA. Column type: HYPERPEP 300A.

The (E)-2(R)-[1(S)-[(tetrahydro-2(RS)-pyranyloxy)
carbamoyl]-4-phenyl-3-butenyl]-2'-isobutyl-4-methyl-2'-(3-
phthalimidopropionyl)valerohydrazide used as the starting
material was prepared in a manner analogous to that
described in Example 24, part (i) but using
2-isoindolinepropionic acid chloride in place of
(N-phthaloyl)-glycine acid chloride.

MS: 661 (M+H)⁺.

EXAMPLE 129

(E)-2(R)-[1(S)-(Hydroxycarbamoyl)-4-phenyl-3-
butenyl]-2'-isobutyl-4-methyl-2'-(2(S)-
phthalimidopropionyl)valerohydrazide In a manner analogous to that described in Example 128
but using 2(S)-phthalimidopropionic acid chloride in the
place of 2-isoindolinepropionic acid chloride there was
obtained (E)-2(R)-[1(S)-(hydroxycarbamoyl)-4-phenyl-3-
butenyl]-2'-isobutyl-4-methyl-2'-(2(S)-phthalimidopro-
pionyl)valerohydrazide in the form of a white solid.

MS: 577 (M+H)⁺. HPLC: Gradient elution using solvent
A containing 5% solvent B increasing to 95% solvent B over
15 minutes; flow rate 1 ml per minute. Retention time: 12.60
minutes. Solvent A: $H_2O0.1\%$ TFA; solvent B: $CH_3CN/$
0.085% TFA. Column type: HYPERPEP 300A.

EXAMPLE 130

(E)-2'-(2-Amino-2-methylpropionyl)-2(R)-[1(S)-
(hydroxycarbamoyl)-4-phenyl-3-butenyl]-2'-
isobutyl-4-methylvalerohydrazide p-
toluenesulphonate In a manner analogous to that described in Example 6 but
using 2-(9-fluorenylmethyloxycarbonyl)amino-isobutyric
acid in place of N-(9-fluorenylmethyloxycarbonyl)-
cycloleucine there was obtained (E)-2'-(2-amino-2-methyl-
propionyl)-2(R)-[1(S)-(hydroxycarbamoyl)-4-phenyl-3-
butenyl]-2'-isobutyl-4-methylvalerohydrazide
p-toluenesulphonate in the form of a white solid.

MS: 461 (M+H)⁺. HPLC: Gradient elution using solvent
A containing 5% solvent B increasing to 95% solvent B over
15 minutes; flow rate 1 ml per minute. Retention time: 10.49
minutes. Solvent A: $H_2O/0.1\%$ TFA; solvent B: $CH_3CN/$
0.085% TFA. Column type: HYPERPEP 300A.

EXAMPLE 131

(E)-2(S)-Amino-3-[[2-[2(R)-[1(S)-
(hydroxycarbamoyl)-4-phenyl-3-butenyl]-4-
methylvaleryl]-1-isobutylhydrazino]carbonyl]
propionic acid trifluoroacetate A solution of 0.050 g of (E)-2(S)-amino-3-[[2-[2(R)-[1
(S)-(hydroxycarbamoyl)-4-phenyl-3-butenyl]-4-
methylvaleryl]-1-isobutylhydrazino]carbonyl]
tert.butoxypropionate hydrogen chloride in 1 ml of
dichloromethane was treated with 0.400 mL of trifluoroace-
tic acid. The mixture was stirred for 4 hours at room
temperature and evaporated. The residue was triturated with
diethyl ether, filtered off and dried to give 0.022 g of
(E)-2(S)-amino-3-[[2-[2(R)-[1(S)-(hydroxycarbamoyl)-4-
phenyl-3-butenyl]-4-methylvaleryl]-1-isobutylhydrazino]
carbonyl]propionic acid trifluoroacetate in the form of a
white solid.

MS: 491 (M+H)⁺. HPLC: Gradient elution using solvent
A containing 5% solvent B increasing to 95% solvent B over
15 minutes; flow rate 1 ml per minute. Retention time: 10.23
minutes. Solvent A: $H_2O/0.1\%$ TFA; solvent B: $CH_3CN/$
0.085% TFA. Column type: HYPERPEP 300A.

The (E)-2(S)-Amino-3-[[2-[2(R)-[1(S)-
(hydroxycarbamoyl)-4-phenyl-3-butenyl]-4-methylvaleryl]-
1-isobutylhydrazino]carbonyl]tert.butoxypropionate hydro-
gen chloride used as the starting material was prepared in a
manner analogous to that described in example 8 but using
N-tert.-butoxycarbonyl-L-aspartic acid α-tert.butyl ester in
place of N-tert.-butoxycarbonyl-α-alanine.

MS: 547 (M+H)⁺.

EXAMPLE 132

(E)-2(R)-[1(S)-(Hydroxycarbamoyl)-4-phenyl-3-
butenyl]-2'-isobutyl-4-methyl-2'-[2-(2-pyridyl)
acetyl]valerohydrazide hydrochloride In a manner analogous to that described in Example 8 but
using 2-(2-pyridyl) acetic acid in the place of
N-tert.butyloxycarbonyl-β-alanine there was obtained (E)-
2(R)-[1(S)-(hydroxycarbamoyl)-4-phenyl-3-butenyl]-2'-
isobutyl-4-methyl-2'-[2-(2-pyridyl)acetyl]valerohydrazide
hydrochloride in the form of a pale yellow solid.

MS: 495 (M+H)⁺. HPLC: Gradient elution using solvent
A containing 5% solvent B increasing to 95% solvent B over
15 minutes; flow rate 1 ml per minute. Retention time: 10.95
minutes. Solvent A: $H_2O/0.1\%$ TFA; solvent B: $CH_3CN/$
0.085% TFA. Column type: HYPERPEP 300A.

EXAMPLE 133

(E)-2(R)-[1(S)-(Hydroxycarbamoyl)-4-phenyl-3-
butenyl]-2'-isobutyl-4-methyl-2'-[2-(3-pyridyl)
acetyl]valerohydrazide p-toluenesulphonate In a manner analogous to that described in Example 11
but using 2-(3-pyridyl) acetic acid in the place of N-acetylglycine there was obtained (E)-2(R)-[1(S)-(hydroxycarbamoyl)-4-phenyl-3-butenyl]-2'-isobutyl-4-methyl-2'-[2-(3-pyridyl)-acetyl]valerohydrazide p-toluenesulphonate in the form of a white solid.

MS: 495 (M+H)$^+$. HPLC: Gradient elution using solvent A containing 5% solvent B increasing to 95% solvent B over 15 minutes; flow rate 1 ml per minute. Retention time: 10.71 minutes. Solvent A: H$_2$O/0.1% TFA; solvent B: CH$_3$CN/0.085% TFA. Column type: HYPERPEP 300A.

EXAMPLE 134

(E)-2(R)-[1(S)-(Hydroxycarbamgyl)-4-phenyl-3-butenyl]-2'-isobutyl-4-methyl-2'-2-(4-pyridyl)acetyl] valerohydrazide p-toluenesulphonate In a manner analogous to that described in Example 11 but using 2-(4-pyridyl) acetic acid in the place of N-acetyl-glycine there was obtained (E)-2(R)-[1(S)-(hydroxycarbamoyl)-4-phenyl-3-butenyl]-2'-isobutyl-4-methyl-2'-[2-(4-pyridyl)-acetyl]valerohydrazide p-toluenesulphonate in the form of a white solid.

MS: 495 (M+H)$^+$. HPLC: Gradient elution using solvent A containing 5% solvent B increasing to 95% solvent B over 15 minutes; flow rate 1 ml per minute. Retention time: 10.62 minutes. Solvent A: H$_2$O/0.1% TFA; solvent B: CH$_3$CN/0.085% TFA. Column type: HYPERPEP 300A.

EXAMPLE 135

(E)-2(R)-[1(S)-(Hydroxycarbamoyl)-4-phenyl-3-butenyl]-2'-isobutyl-4-methyl-2'-[2-(1H-tetrazol-5-yl)acetyl]valerohydrazide A solution of 0.190 g of (E)-2(R)-[1(S)-[(tetrahydro-2(RS)-pyranyloxy)-carbamoyl]-4-phenyl-3-butenyl]-2'-isobutyl-4-methyl-2'-[2-(1H-tetrazol-5-yl)-acetyl] valerohydrazide in 5 mL of methanol was treated with 0.020 g of p-toluenesulphonic acid monohydrate. The mixture was stirred for 2 hours at room temperature and evaporated. The residue was triturated with diethyl ether, filtered off and dried to give 0.152 g of (E)-2(R)-[1(S)-(hydroxycarbamoyl)-4-phenyl-3-butenyl]-2'-isobutyl-4-methyl-2'-[2-(1H-tetrazol-5-yl)acetyl]valerohydrazide in the form of a white solid.

MS: 486 (M+H)$^+$. HPLC: Gradient elution using solvent A containing 5% solvent B increasing to 95% solvent B over 15 minutes; flow rate 1 ml per minute. Retention time: 11.09 minutes. Solvent A: H$_2$O/0.1% TFA; solvent B: CH$_3$CN/0.085% TFA. Column type: HYPERPEP 300A.

The (E)-2(R)-[1(S)-[(tetrahydro-2(RS)-pyranyloxy) carbamoyl]-4-phenyl-3-butenyl]-2'-isobutyl-4-methyl-2'-[2-(1H-tetrazol-5-yl)acetyl]valerohydrazide used as the starting material was prepared as follows:

(i) A solution of 0.416 g of (E)-2(R)-[1(S)-(tert-butoxycarbonyl)-4-phenyl-3-butenyl]-2'-isobutyl-4-methylvalerohydrazide and 0.282 g of 2-(1H-tetrazol-5-yl) acetic acid in 4 ml of dimethylformamide was treated at room temperature under nitrogen with 0.461 g of 1-ethyl-3-(3-dimethylaminopropyl)-carbodiimide hydrochloride. The mixture was stirred for 0.5 hours at room temperature and evaporated. The residue was dissolved in ethyl acetate and washed with 5% aqueous sodium hydrogen carbonate solution and saturated sodium chloride solution, dried over anhydrous magnesium sulphate and evaporated to give 0.630 g of (E)-2(R)-[1(S)-(tert-butoxycarbonyl)-4-phenyl-3-butenyl]-2'-isobutyl-4-methyl-2'-[2-(1H-tetrazol-5-yl) acetyl]valerohydrazide in the form of an off-white foam.

MS: 527 (M+H)$^+$.

(ii) In a manner analogous to that described in Example 18, parts (ii)–(iii), but using (E)-2(R)-[1(S)-(tert-butoxycarbonyl)-4-phenyl-3-butenyl]-2'-isobutyl-4-methyl-2-[2-(1H-tetrazol-5-yl)acetyl]valerohydrazide in the place of (E)-2(R)-[1(S)-(tert-butoxycarbonyl)-4-phenyl-3-butenyl]-2'-isobutyl-2'-[N-(9-fluorenylmethyloxycarbonyl)-O-tert.butyl-D-seryl]-4-methylvalerohydrazide there was obtained (E)-2(R)-[1(S)-[(tetrahydro-2(RS)-pyranyloxy) carbamoyl]-4-phenyl-3-butenyl]-2'-isobutyl-4-methyl-2'-[2-(1H-tetrazol-5-yl)acetyl]valerohydrazide in the form of a white solid.

MS: 570 (M+H)$^+$.

EXAMPLE 136

(E)-2(R)-[1(S)-(Hydroxycarbamoyl)-4-phenyl-3-butenyl]-2'-isobutyl-4-methyl-2'-[2-(4-piperidinyl) acetyl]valerohydrazide hydrochloride A solution of 0.300 g of (E)-2(R)-[1(S)-[(tetrahydro-2(RS)-pyranyloxy)carbamoyl]-4-phenyl-3-butenyl]-2'-isobutyl-4-methyl-2'-[2-(4-piperidinyl)acetyl] valerohydrazide in 3 ml of 4M hydrogen chloride in dioxan was stirred for 2.5 hours at room temperature and diluted with diethyl ether. The solid was filtered off, washed with diethyl ether and dried to give 0.256 g of (E)-2(R)-[1(S)-(hydroxycarbamoyl)-4-phenyl-3-butenyl]-2'-isobutyl-4-methyl-2'-[2-(4-piperidinyl)acetyl]valerohydrazide hydrochloride in the form of an off-white solid.

MS: 501 (M+H)$^+$. HPLC: Gradient elution using solvent A containing 5% solvent B increasing to 95% solvent B over 15 minutes; flow rate 1 ml per minute. Retention time: 10.56 minutes. Solvent A: H$_2$O/0.1% TFA; solvent B: CH$_3$CN/0.085% TFA. Column type: HYPERPEP 300A.

The (E)-2(R)-[1(S)-[(tetrahydro-2(RS)-pyranyloxy) carbamoyl]-4-phenyl-3-butenyl]-2'-isobutyl-4-methyl-2'-[2-(4-piperidinyl)acetyl]valerohydrazide used as the starting material was prepared as follows:

(i) A solution of 0.157 g of (E)-2(R)-[1(S)-[(tetrahydro-2(RS)-pyranyloxy)carbamoyl]-4-phenyl-3-butenyl]-2'-isobutyl-methylvalerohydrazide in 5 ml of dimethylformamide was treated at room temperature under nitrogen with 0.250 g of 2-[N-(9-fluorenylmethyloxycarbonyl)-4-piperidine]acetic acid and 0.132 g of 1-ethyl-3-(3-dimethylaminopropyl)-carbodiimide hydrochloride. The mixture was stirred overnight at room temperature and evaporated. The residue was dissolved in ethyl acetate and washed with 5% aqueous citric acid solution, 5% aqueous sodium hydrogen carbonate solution, saturated sodium chloride solution, and then dried over anhydrous magnesium sulphate and evaporated to give 0.500 g of (E)-2(R)-[1(S)-[(tetrahydro-2(RS)-pyranyloxy)carbamoyl]-4-phenyl-3-butenyl]-2'-isobutyl-2'-2-(N-(9-fluorenylmethyloxycarbonyl)-4-piperidyl)acetyl]-4-methylvalerohydrazide in the form of a clear oil.

MS: 807 (M+H)$^+$.

(i) A solution of 0.500 g of (E)-2(R)-[1(S)-[(tetrahydro-2(RS)-pyranyloxy)carbamoyl]-4-phenyl-3-butenyl]-2'-isobutyl-2'-[2-(N-(9-fluorenylmethyloxycarbomyl)-4-piperidyl)acetyl]-4-methylvalerohydrazide in a mixture of 1.6 ml of dichloromethane and 0.4 ml of piperidine was stirred at room temperature for 3 hours. The solution was evaporated and the residue was triturated with hexane. The resulting solid was filtered off and dried to give 0.304 g of (E)-2(R)-[1(S)-[(tetrahydro-2(RS)-pyranyloxy)carbamoyl]-4-phenyl-3-butenyl]-2'-isobutyl-4-methyl-2'-[2-(4-piperidinyl)acetyl]-valerohydrazide in the form of a white solid.

MS: 585 (M+H)$^+$.

EXAMPLE 137

(E)-2'-(4-Aminobutyryl)-2(R)-[1(S)-(hydroxycarbamoyl)-4-phenyl-3-butenyl]-2'-isobutyl-4-methylvalerohydrazide In a manner analogous to that described in Example 8 but using N-(tert.-butyloxycarbonyl)-4-aminobutyric acid in the place of N-tert.butyloxycarbonyl-β-alanine there was obtained (E)-2'-(4-Aminobutyryl)-2(R)-[1(S)-(hydroxycarbamoyl)-4-phenyl-3-butenyl]-2'-isobutyl-4-methylvalerohydrazide in the form of a white solid.

MS: 461 (M+H)$^+$. HPLC: Gradient elution using solvent A containing 5% solvent B increasing to 95% solvent B over 15 minutes; flow rate 1 ml per minute. Retention time: 10.36 minutes. Solvent A: H$_2$O/0.1% TFA; solvent B: CH$_3$CN/0.085% TFA. Column type: HYPERPEP 300A.

EXAMPLE 138

(E)-2'-(D-alpha-Glutamyl)-2(R)-[1(S)-(hydroxycarbamoyl)-4-phenyl-3-butenyl]-2'-isobutyl-4-methylvalerohydrazide trifluoroacetate A solution of 0.620 g of (E)-2'-((N-tert.butyloxycarbonyl)-D-alpha-(tert.butyloxy)glutamyl)-2(R)-[1(S)- [(tetrahydro-2(RS)-pyranyloxy)carbamoyl]-4-phenyl-3-butenyl]-2'-isobutyl-4-methylvalerohydrazide in 6 ml of dichloromethane was treated with 6 ml of trifluoroacetic acid. The mixture was stirred for 2.5 hours at room temperature under nitrogen and evaporated. The residue was triturated with diethyl ether, filtered off and further purified by flash column chromatography on silica gel using dichloromethane/methanol (80:20) for the elution. The solvent was then evaporated to give 0.280 g of (E)-2'-(D-alpha-glutamyl)-2(R)-[1(S)-(hydroxycarbamoyl)-4-phenyl-3-butenyl]-2'-isobutyl-4-methylvalerohydrazide trifluoroacetate in the form of a light brown solid.

MS: 505 (M+H)$^+$. HPLC: Gradient elution using solvent A containing 5% solvent B increasing to 95% solvent B over 15 minutes; flow rate 1 ml per minute. Retention time: 10.77 minutes. Solvent A: H$_2$O/0.1% TFA; solvent B: CH$_3$CN/0.085% TFA. Column type: HYPERPEP 300A.

The (E)-2'-((N-tert.butyloxycarbonyl)-D-alpha-(tert.butyloxy)-glutamyl)-2(R)-[1(S)-[(tetrahydro-2(RS)-pyranyloxy)carbamoyl]-4-phenyl-3-butenyl]-2'-isobutyl-4-methylvalerohydrazide used as the starting material was prepared as follows:

A solution of 0.459 g of (E)-2(R)-[1(S)-[(tetrahydro-2(RS)-pyranyloxy)carbamoyl]-4-phenyl-3-butenyl]-3-2'-isobutyl-4-methylvalerohydrazide in 7 ml of dichloromethane was treated at 0° C. under nitrogen with 0.606 g of N-[(1,1-dimethylethoxy)carbonyl]-5-(1,1-dimethylethyl) ester-D-glutamic acid and 0.383 g of 1-ethyl-3-(3-dimethylaminopropyl)-carbodiimide hydrochloride. The mixture was stirred for a further 1 hour at 0° C. and then overnight at room temperature. Evaporation of solvents gave a residue which was dissolved in ethyl acetate and washed with 5% aqueous citric acid solution, 5% aqueous sodium hydrogen carbonate solution, saturated sodium chloride solution, and then dried over anhydrous magnesium sulphate and evaporated. Purification of the residue by chromatography on silica gel using hexane/ethyl acetate (2:1) for the elution and evaporation gave 0.64 g of (E)-2'-((N-tert.butyloxycarbonyl)-D-alpha-(tert.butyloxy)-Glutamyl)-2(R)-[1(S)-[(tetrahydro-2(RS)-pyranyloxy)carbamoyl]-4-phenyl-3-butenyl]-2'-isobutyl-4-methylvalerohydrazide.

MS: 745 (M+H)$^+$.

EXAMPLE 139

(E)-2(R)-[1(S)-(Hydroxycarbamoyl)-4-phenyl-3-butenyl]-2'-isobutyl-4-methyl-2'-(2-thienoyl) valerohydrazide In a manner analogous to that described in Example 11 but using 2-thiophenecarboxylic acid in the place of N-acetyl-glycine there was obtained (E)-2(R)-[1(S)-(hydroxycarbamoyl)-4-phenyl-3-butenyl]-2'-isobutyl-4-methyl-2'-(2-thienoyl)valerohydrazide in the form of a white solid.

MS: 486 (M+H)$^+$. HPLC: Gradient elution using solvent A containing 5% solvent B increasing to 95% solvent B over 15 minutes; flow rate 1 ml per minute. Retention time: 12.58 minutes. Solvent A: H$_2$O/0.1% TFA; solvent B: CH$_3$CN/0.085% TFA. Column type: HYPERPEP 300A.

EXAMPLE 140

(E)-2(R)-[1(S)-(Hydroxycarbamoyl)-4-phenyl-3-butenyl]-2'-isobutyl-4-methyl-2'-(3-thienoyl) valerohydrazide In a manner analogous to that described in Example 11 but using 3-thiophenecarboxylic acid in the place of N-acetyl-glycine there was obtained (E)-2(R)-[1(S)-(hydroxycarbamoyl)-4-phenyl-3-butenyl]-2'-isobutyl-4-methyl-2'-(3-thienoyl)valerohydrazide in the form of a white solid.

MS: 486 (M+H)$^+$. HPLC: Gradient elution using solvent A containing 5% solvent B increasing to 95% solvent B over 15 minutes; flow rate 1 ml per minute. Retention time: 12.28 minutes. Solvent A: H$_2$O/0.1% TFA; solvent B: CH$_3$CN/0.085% TFA. Column type: HYPERPEP 300A.

EXAMPLE 141

(E)-2(R)-[1(S)-(Hydroxycarbamoyl)-4-phenyl-3-butenyl]-2'-isobutyl-4-methyl-2'-[(1,2,3-thiadiazol-4-yl)carbonyl]valerohydrazide In a manner analogous to that described in Example 11 but using 1,2,3-thiadiazole-4-carboxylic acid in the place of N-acetyl-glycine there was obtained (E)-2(R)-[1(S)-(hydroxycarbamoyl)-4-phenyl-3-butenyl]-2'-isobutyl-4-methyl-2'-[(1,2,3-thiadiazol-4-yl)carbonyl]valerohydrazide in the form of an off-white solid.

MS: 488 (M+H)$^+$. HPLC: Gradient elution using solvent A containing 5% solvent B increasing to 95% solvent B over 15 minutes; flow rate 1 ml per minute. Retention time: 11.96 minutes. Solvent A: H$_2$O/0.1% TFA; solvent B: CH$_3$CN/0.085% TFA. Column type: HYPERPEP 300A.

EXAMPLE 142

(E)-2(R)-[1(S)-(Hydroxycarbamoyl)-4-phenyl-3-butenyl]-2'-isobutyl-2'-[N-(methanesulphonyl)-D-alanyl]-4-methylvalerohydrazide A solution of 0.332 g of (E)-2(R)-[1(S)-[(tetrahydro-2(RS)-pyranyloxy)carbamoyl]-4-phenyl-3-butenyl]-2'-isobutyl-2'-[N-(methanesulphonyl)-D-alanyl]-4-methylvalerohydrazide in 10 ml of methanol was treated with 0.040 g of p-toluenesulphonic acid monohydrate. The mixture was stirred at room temperature for 2 hours and evaporated. The residue was triturated with diethyl ether, filtered off and dried to give 0.010 g of in the form of an off-white solid.

MS: 525 (M+H)⁺. HPLC: Gradient elution using solvent A containing 5% solvent B increasing to 95% solvent B over 15 minutes; flow rate 1 ml per minute. Retention time: 11.40 minutes. Solvent A: H₂O/0.1% TFA; solvent B: CH₃CN/0.085% TFA. Column type: HYPERPEP 300A.

The (E)-2(R)-[1(S)-[(tetrahydro-2(RS)-pyranyloxy)carbamoyl]-4-phenyl-3-butenyl]-2'-isobutyl-2'-[N-(methanesulphonyl)-D-alanyl]-4-methylvalerohydrazide used as the starting material was prepared as follows: A solution of 0.663 g of (E)-2'-(D-alanyl)-2(R)-[1(S)-(tetrahydro-2(RS)-pyranyloxy)carbamoyl]-4-phenyl-3-butenyl]-2'-isobutyl-4-methylvalerohydrazide (prepared as described in example 23, parts (i)–(iii)) in 10 ml of dichloromethane was treated with 0.115 ml of pyridine and 0.210 g of methane sulphonic anhydride and stirred overnight at room temperature. Evaporation gave a residue which was dissolved in ethyl acetate and washed with 5% aqueous citric acid solution, 5% aqueous sodium hydrogen carbonate solution, saturated sodium chloride solution, and then dried over anhydrous magnesium sulphate and evaporated to give 0.332 g of (E)-2(R)-[1(S)-[(tetrahydro-2(RS)-pyranyloxy)carbamoyl]-4-phenyl-3-butenyl]-2'-isobutyl-2'-[N-(methanesulfonyl)-D-alanyl]-4-methylvalerohydrazide in the form of a clear oil.

MS: 609 (M+H)⁺.

EXAMPLE 143

(E)-2'-(Tetrahydro-3(RS)-furoyl)-2(R)-[1(S)-(hydroxycarbamoyl)-4-phenyl-3-butenyl]-2'-isobutyl-4-methylvalerohydrazide In a manner analogous to that described in Example 11 but using tetrahydro-3(RS)-furoic acid in the place of N-acetyl-glycine there was obtained (E)-2'-(tetrahydro-3(RS)-furoyl)-2(R)-[1(S)-(hydroxycarbamoyl)-4-phenyl-3-butenyl]-2'-isobutyl-4-methylvalerohydrazide in the form of a white solid.

MS: 474 (M+H)⁺. HPLC: Gradient elution using solvent A containing 5% solvent B increasing to 95% solvent B over 15 minutes; flow rate 1 ml per minute. Retention time: 11.46 minutes. Solvent A: H₂O/0.1% TFA; solvent B: CH₃CN/0.085% TFA. Column type: HYPERPEP 300A.

EXAMPLE 144

(E)-2'-[(2(RS)-Azetidinyl)carbonyl]-2(R)-[1(S)-(hydroxycarbamoyl)-4-phenyl-3-butenyl]-2'-isobutyl-4-methylvalerohydrazide hydrochloride In a manner analogous to that described in Example 8 but using N-tert.butyloxycarbonyl-2(RS)-azetidinylcarboxylic acid in the place of N-tert.-butyloxycarbonyl-β-alanine there was obtained (E)-2'-[( 2(RS)-azetidinyl)carbonyl]-2(R)-[1(S)-(hydroxycarbamoyl)-4-phenyl-3-butenyl]-2'-isobutyl-4-methylvalerohydrazide hydrochloride in the form of a white solid.

MS: 459 (M+H)⁺. HPLC: Gradient elution using solvent A containing 5% solvent B increasing to 95% solvent B over 15 minutes; flow rate 1 ml per minute. Retention time: 10.89 and 11.04 minutes. Solvent A: H₂O/0.1% TFA; solvent B: CH₃CN/0.085% TFA. Column type: HYPERPEP 300A.

EXAMPLE 145

(E)-2'-(L-Asparaginyl)-2(R)-[1(S)-(hydroxycarbamoyl)-4-phenyl-3-butenyl]-2'-isobuty-4-methylvalerohydrazide hydrochloride In a manner analogous to that described in Example 8 but using (L)-N-tert.butyloxycarbonyl-asparagine in the place of N-tert.butyloxycarbonyl-β-alanine there was obtained (E)-2'-(L-asparaginyl)-2(R)-[1(S)-(hydroxycarbamoyl)-4-phenyl-3-butenyl]-2'-isobutyl-4-methylvalerohydrazide hydrochloride in the form of a white solid.

MS: 490 (M+H)⁺. HPLC: Gradient elution using solvent A containing 5% solvent B increasing to 95% solvent B over 15 minutes; flow rate 1 ml per minute. Retention time: 10.22 minutes. Solvent A: H₂O/0.1% TFA; solvent B: CH₃CN/0.085% TFA. Column type: HYPERPEP 300A.

EXAMPLE 146

(E)-2'-(D-alpha-Aspartyl)-2(R)-[1(S)-(hydroxycarbamoyl)-4-phenyl-3-butenyl]-2'-isobutyl-4-methylvalerohydrazide trifluoroacetate In a manner analogous to that described in example 131 but using N-tert.butyloxycarbonyl-L-aspartic acid β-tert.butyl ester in the place of N-tert.-butoxycarbonyl-L-aspartic acid α-tert.butyl ester there was obtained (E)-2'-(D-alpha-aspartyl)-2(R)-[1(S)-(hydroxycarbamoyl)-4-phenyl-3-butenyl]-2'-isobutyl-4-methylvalerohydrazide trifluoroacetate in the form of a white solid.

MS: 491 (M+H)⁺. HPLC: Gradient elution using solvent A containing 5% solvent B increasing to 95% solvent B over 15 minutes; flow rate 1 ml per minute. Retention time: 10.58 minutes. Solvent A: H₂O/0.1% TFA; solvent B: CH₃CN/0.085% TFA. Column type: HYPERPEP 300A.

EXAMPLE 147

(E)-2(R)-[1(S)-(Hydroxycarbamoyl)-4-phenyl-3-butenyl]-2'-(4(RS)-hydroxyvaleryl)-2'- isobutyl-4-methylvalerohydrazide A solution of 0.150 g of (E)-2(R)-[1(S)-[(tetrahydro-2(RS)-pyranyloxy)carbamoyl]-4-phenyl-3-butenyl]-2'-(4(RS)-hydroxyvaleryl)-2'-isobutyl-4-methylvalerohydrazide in 5 ml of methanol was treated with 0.015 g of p-toluenesulphonic acid monohydrate. The mixture was stirred at room temperature for 2 hours and evaporated. The residue was triturated with diethyl ether, filtered off and dried to give 0.027 g of (E)-2(R)-[1(S)-(hydroxycarbamoyl)-4-phenyl-3-butenyl]-2'-(4(RS)-hydroxyvaleryl)-2'-isobutyl-4-methylvalerohydrazide in the form of a white solid.

MS: 476 (M+H)⁺. HPLC: Gradient elution using solvent A containing 5% solvent B increasing to 95% solvent B over 15 minutes; flow rate 1 ml per minute. Retention time: 10.61 and 11.03 minutes. Solvent A: H₂O/0.1% TFA; solvent B: CH₃CN/0.085% TFA. Column type: HYPERPEP 300A.

The (E)-2(R)-[1(S)-[(tetrahydro-2(RS)-pyranyloxy)carbamoyl]-4-phenyl-3-butenyl]-2'-(4(RS)-hydroxyvaleryl)-2'-isobutyl-4-methylvalerohydrazide used as the starting material was prepared as follows:

(i) A solution of 0.459 g of (E)-2(R)-[1(S)-[(tetrahydro-2(RS)-pyranyloxy)carbamoyl]-4-phenyl-3-butenyl]-2'-isobutyl-4-methylvalerohydrazide in 5 ml of dimethylformamide was treated with 0.232 g of levulinic acid and 0.384 g of 1-ethyl-3-(3-dimethylaminopropyl)carbodiimide hydrochloride. The mixture was stirred overnight at room temperature and evaporated. The residue in ethyl acetate was washed with 5% aqueous citric acid solution, 5% aqueous sodium hydrogen carbonate solution, saturated sodium chloride solution, and then dried over anhydrous magnesium sulphate and evaporated to give 0.570 g of (E)-2(R)-[1(S)-[(tetrahydro-2(RS)-pyranyloxy)carbamoyl]-4-phenyl-3-butenyl]-2'-(4-oxovaleryl)-2'-isobutyl-4-methylvalerohydrazide in the form of a white foam.

MS: 558 (M+H)⁺.

(ii) A solution of 0.160 g of (E)-2(R)-[1(S)-[(tetrahydro-2 (RS)-pyranyloxy)carbamoyl]-4-phenyl-3-butenyl]-2'-(4-oxovaleryl)-2'-isobutyl-4-methylvalerohydrazide in 10 ml of ethanol was treated with 0.012 g of sodium borobydride. The mixture was stirred for 48 hours and then diluted with ethyl acetate and washed with water and saturated sodium chloride solution. Drying over anhydrous magnesium sulfate and evaporation gave 0.150 g of (E)-2(R)-[1(S)-[(tetrahydro-2(RS)-pyranyloxy)carbamoyl]-4-phenyl-3-butenyl]-2'-(4(RS)-hydroxyvaleryl)-2'-isobutyl-4-methylvalerohydrazide in the form of a white foam.

MS: 560 (M+H)$^+$.

EXAMPLE 148

(E)-2'-[(Tetrahydro-2H-pyran-2(RS)-yl)carbonyl]-2 (R)-[1(S)-(hydroxycarbamoyl)-4-phenyl-3-butenyl]-2'-isobutyl-4-methylvalerohydrazide In a manner analogous to that described in Example 11 but using tetrahydro-2H-pyran-2(RS)-yl carboxylic acid in the place of N-acetyl-glycine there was obtained (E)-2'-[(tetrahydro-2H-pyran-2(RS)-yl)carbonyl]-2(R)-[1(S)-(hydroxycarbamoyl)-4-phenyl-3-butenyl]-2'-isobutyl-4-methylvalerohydrazide in the form of a white solid.

MS: 488 (M+H)$^+$. HPLC: Gradient elution using solvent A containing 5% solvent B increasing to 95% solvent B over 15 minutes; flow rate 1 ml per minute. Retention time: 11.80 minutes. Solvent A: H$_2$O/0.1% TFA; solvent B: CH$_3$CN/0.085% TFA. Column type: HYPERPEP 300A.

EXAMPLE 149

(E)-2'-[(Tetrahydro-2H-pyran-4-yl)carbonyl]-2(R)-[1 (S)-(hydroxycarbamoyl)-4-phenyl-3-butenyl]-2'-isobutyl-4-methylvalerohydrazide In a manner analogous to that described in Example 11 but using tetrahydro-2H-pyran-4-yl carboxylic acid in the place of N-acetyl-glycine there was obtained (E)-2'-[(tetrahydro-2H-pyran-4-yl)carbonyl]-2(R)-[1(S)-(hydroxycarbamoyl)-4-phenyl-3-butenyl]-2'-isobutyl-4-methylvalerohydrazide in the form of a white solid.

MS: 488 (M+H)$^+$. HPLC: Gradient elution using solvent A containing 5% solvent B increasing to 95% solvent B over 15 minutes; flow rate 1 ml per minute. Retention time: 11.59 minutes. Solvent A: H$_2$O/0.1% TFA; solvent B: CH$_3$CN/0.085% TFA. Column type: HYPERPEP 300A.

EXAMPLE 150

(E)-2(R)-[1(S)-(Hydroxycarbamoyl)-4-phenyl-3-butenyl]-2'-[2-(2-imino-1-imidazolidinyl)acetyl]-2'-isobutyl-4-methylvalerohydrazide hydrochloride In a manner analogous to that described in Example 25 but using 2-(2-imino-1-imidazolidine)acetic acid chloride in the place of N-tert.butoxycarbonyl-L-leucine acid fluoride there was obtained (E)-2(R)-[1(S)-(hydroxycarbamoyl)-4-phenyl-3-butenyl]-2'-[2-(2-imino-1-imidazolidinyl)acetyl]-2'-isobutyl-4-methylvalerohydrazide hydrochloride in the form of a white solid.

MS: 501 (M+H)$^+$. HPLC: Gradient elution using solvent A containing 5% solvent B increasing to 90% solvent B over 15 minutes; flow rate 1 ml per minute. Retention time: 11.02 minutes. Solvent A: H$_2$O/0.1% TFA; solvent B: CH$_3$CN/0.085% TFA. Column type: HYPERPEP 300A.

EXAMPLE 151

(E)-2(R)-[1(S)-(Hydroxycarbamoyl)-4-phenyl-3-butenyl]-2'-isobutyl-4-methyl-2'-[(1-pyrazolidinyl) carbonyl]valerohydrazide hydrochloride A solution of 0.267 g of (E)-2(R)-[1(S)-[(tetrahydro-2 (RS)-pyranyloxy)carbamoyl]-4-phenyl-3-butenyl]-2'-isobutyl-4-methyl-2'-[(2-tert.butyloxycarbonyl-1-pyrazolidinyl)carbonyl]valerohydrazide was treated with 2 ml of 4M hydrogen chloride in dioxan and stirred for 2 hours at room temperature. The mixture was diluted with diethyl ether and the resulting solid was filtered off, washed with diethyl ether and dried to give 0.142 g of (E)-2(R)-[1(S)-(hydroxycarbamoyl)-4-phenyl-3-butenyl]-2'-isobutyl-4-methyl-2'-[(1-pyrazolidinyl)carbonyl]valerohydrazide hydrochloride in the form of a pale yellow solid.

MS: 474 (M+H)$^+$. HPLC: Gradient elution using solvent A containing 5% solvent B increasing to 95% solvent B over 15 minutes; flow rate 1 ml per minute. Retention time: 10.56 minutes. Solvent A: H$_2$O/0.1% TFA; solvent B: CH$_3$CN/0.085% TFA. Column type: HYPERPEP 300A.

The (E)-2(R)-[1(S)-[(tetrahydro-2(RS)-pyranyloxy) carbamoyl]-4-phenyl-3-butenyl]-2'-isobutyl-4-methyl-2'-[(2-tert.butyloxycarbonyl-1-pyrazolidinyl)carbonyl] valerohydrazide used as the starting material was prepared as follows:

A solution of 0.241 g of 2-tert.butyloxycarbonyl-pyrazolidine in 5 ml of toluene as added slowly, at 0° C. under nitrogen, to a solution of 0.725 ml of phosgene in 5 ml of toluene. The mixture was allowed to warm to room temperature over 2 hours and then a solution of 0.459 g of (E)-2(R)-[1(S)-[(tetrahydro-2(RS)-pyranyloxy)carbamoyl]-4-phenyl-3-butenyl]-2'-isobutyl-4-methylvalerohydrazide in 5ml toluene/dichloromethane (1:1) was added dropwise. The mixture was stirred for 48 hours at room temperature and evaporated. The residue was dissolved in ethyl acetate and washed with 2N aqueous hydrogen chloride and water and then dried over anhydrous magnesium sulphate and evaporated. The residue was triturated with ether to give 0.267 g of (E)-2(R)-[1(S)-[(tetrahydro-2(RS)-pyranyloxy) carbamoyl)-4-phenyl-3-butenyl]-2'-isobutyl-4-methyl-2'-[(2-tert.butyloxycarbonyl-1-pyrazolidinyl)carbonyl] valerohydrazide in the form of a pale yellow solid.

MS: 658 (M+H)$^+$.

EXAMPLE 152

(E)-2'-[2(R)-(Benzyloxy)propionyl]-2(R)-[1(S)-(hydroxycarbamoyl)-4-phenyl-3-butenyl]-2'-isobutyl-4-methylvalerohydrazide In a manner analogous to that described in Example 11 but using 2(R)-(benzyloxy)propionic acid in the place of N-acetyl-glycine there was obtained (E)-2'-[2(R)-(Benzyloxy)propionyl]-2(R)-[1(S)-(hydroxycarbamoyl)-4-phenyl-3-butenyl]-2'-isobutyl-4-methylvalerohydrazide in the form of a pale yellow foam.

MS: 538 (M+H)$^+$. HPLC: Gradient elution using solvent A containing 5% solvent B increasing to 95% solvent B over 15 minutes; flow rate 1 ml per minute. Retention time: 13.23 minutes. Solvent A: H$_2$O/0.1% TFA; solvent B: CH$_3$CN/0.085% TFA. Column type: HYPERPEP 300A.

EXAMPLE 153

(E)-2(R)-[1(S)-(Hydroxycarbamoyl)-4-phenyl-3-butenyl]-2'-isobutyl-2'-(2(R)-methoxypropionyl)-4-methylvalerohydrazide In a manner analogous to that described in Example 11 but using 2(R)-(methoxy)propionic acid in the place of N-acetyl-glycine there was obtained (E)-2(R)-[1(S)-(hydroxycarbamoyl)-4-phenyl-3-butenyl]-2'-isobutyl-2'-(2 (R)-methoxypropionyl)-4-methylvalerohydrazide in the form of a white solid.

MS: 462 (M+H)⁺. HPLC: Gradient elution using solvent A containing 5% solvent B increasing to 95% solvent B over 15 minutes; flow rate 1 ml per minute. Retention time: 11.29 minutes. Solvent A: $H_2O$/0.1% TFA; solvent B: $CH_3CN$/0.085% TFA. Column type: HYPERPEP 300A.

EXAMPLE 154

(E)-2(R)-[1(S)-(Hydroxycarbamoyl)-4-phenyl-3-butenyl]-2'-isobutyl-4-methyl-2'-[3-(3-pyridyl)propionyl]valerohydrazide p-toluenesulphonate In a manner analogous to that described in Example 11 but using 3-(3-pyridine)propionic acid in the place of N-acetyl-glycine there was obtained (E)-2(R)-[1((S)-(hydroxycarbamoyl)-4-phenyl-3-butenyl]-2'-isobutyl-4-methyl-2'-[3-(3-pyridyl)propionyl]valerohydrazide p-toluenesulphonate in the form of a white solid.

MS: 509 (M+H)⁺. HPLC: Gradient elution using solvent A containing 5% solvent B increasing to 95% solvent B over 15 minutes; flow rate 1 ml per minute. Retention time: 10.66 minutes. Solvent A: $H_2O$/0.1% TFA; solvent B: $CH_3CN$/0.085% TFA. Column type: HYPERPEP 300A.

EXAMPLE 155

(E)-2'-(5-Aminovaleryl)-2(R)-[1(S)-(hydroxycarbamoyl)-4-phenyl-3-butenyl]-2'-isobutyl-4-methylvalerohydrazide hydrochloride In a manner analogous to that described in Example 8 but using N-tert.-butyloxycarbonyl-5-aminovaleric acid in the place of N-tert.butyloxycarbonyl-□-alanine there was obtained (E)-2'-(5-aminovaleryl)-2(R)-[1(S)-(hydroxycarbamoyl)-4-phenyl-3-butenyl]-2'-isobutyl-4-methylvalerohydrazide hydrochloride in the form of a white solid.

MS: 475 (M+H)⁺. HPLC: Gradient elution using solvent A containing 5% solvent B increasing to 95% solvent B over 15 minutes; flow rate 1 ml per minute. Retention time: 10.34 minutes. Solvent A: $H_2O$/0.1% TFA; solvent B: $CH_3CN$/0.085% TFA. Column type: HYPERPEP 300A.

EXAMPLE 156

(E)-2(R)-[1(S)-(Hydroxycarbamoyl)-4-phenyl-3-butenyl]-2'-isobutyl-4-methyl-2'-[4-(dimethylamino)butyryl]valerohydrazide p-toluenesulphonate In a manner analogous to that described in Example 11 but using 4-(dimethylamino)butyric acid in the place of N-acetyl-glycine there was obtained (E)-2(R)-[1(S)-(hydroxycarbamoyl)-4-phenyl-3-butenyl]-2'-isobutyl-4-methyl-2'-[4-(dimethylamino)butyryl]valerohydrazide p-toluenesulphonate in the form of an off-white solid.

MS: 489 (M+H)⁺. HPLC: Gradient elution using solvent A containing 5% solvent B increasing to 95% solvent B over 15 minutes; flow rate 1 ml per minute. Retention time: 10.64 minutes. Solvent A: $H_2O$/0.1% TFA; solvent B: $CH_3CN$/0.085% TFA. Column type: HYPERPEP 300A.

EXAMPLE 157

(E/Z)-2'-[(4-Aminocyclohexyl)carbonyl]-2(R)-[1(S)-hydroxycarbamoyl)-4-phenyl-3-butenyl]-2'-isobutyl-4-methylvalerohydrazide hydrochloride In a manner analogous to that described in Example 8 but using N-tert.-butyloxycarbonyl-4-aminocyclo-hexanecarboxylic acid in the place of N-tert.butyloxycarbonyl-□-alanine there was obtained (E/Z)-2'-[(4-aminocyclohexyl)carbonyl]-2(R)-[1(S)-(hydroxycarbanoyl)-4-phenyl-3-butenyl]-2'-isobutyl-4-methylvalerohydrazide hydrochloride in the form of an off-white solid.

MS: 501 (M+H)⁺. HPLC: Gradient elution using solvent A containing 5% solvent B increasing to 95% solvent B over 15 minutes; flow rate 1 ml per minute. Retention time: 10.54 and 10.96 minutes. Solvent A: $H_2O$/0.1% TFA; solvent B: $CH_3CN$/0.085% TFA. Column type: HYPERPEP 300A.

EXAMPLE 158

(E)-2(S)-Amino-3-[[2-[2(R)-[1(S)-(hydroxycarbamoyl)-4-phenyl-3-butenyl]-4-methylvaleryl]-1-isobutylhydrazino]carbonyl]tert.butoxypropionate hydrogen chloride In a manner analogous to that described in example 8 but using N-tert.-butoxycarbonyl-L-aspartic acid α-tert.butyl ester in place of N-tert.-butoxycarbonyl-□-alanine there was obtained (E)-2(S)-amino-3-[[2-[2(R)-[1(S)-(hydroxycarbamoyl)-4-phenyl-3-butenyl]-4-methylvaleryl]-1-isobutylhydrazino]carbonyl]tert.butoxypropionate hydrogen chloride in the form of a white solid.

MS: 547 (M+H)⁺. HPLC: Gradient elution using solvent A containing 5% solvent B increasing to 95% solvent B over 15 minutes; flow rate 1 ml per minute. Retention time: 10.27 minutes. Solvent A: $H_2O$/0.1% TFA; solvent B: $CH_3CN$/0.085% TFA. Column type: HYPERPEP 300A.

EXAMPLE 159

2'-(D-Alanyl)-2(R)-[2-benzamido-1(R)-(hydroxycarbamoyl)ethyl]-2'-isobutyl-4-methylvalerylhydrazide A solution of 0.123 g of 2'-(N-benzyloxycarbonyl-D-alanyl)-2(R)-[2-benzamido-1(R)-(benzyloxycarbamoyl)ethyl]-2'-isobutyl-4-methylvalerylhydrazide in 5 ml of methanol was hydrogenated in the presence of 0.037 g of 5% palladium-on-carbon for 12 hours. The catalyst was removed by filtration and the solvent was evaporated. The residue was triturated with diethyl ether to give 0.068 g of 2'-(D-alanyl)-2(R)-[2-benzamido-1(R)-(hydroxycarbamoyl)ethyl]-2'-isobutyl-4-methylvalerylhydrazide in the form of a white solid.

MS: 464 (M+H)⁺. HPLC: Gradient elution using solvent A containing 5% solvent B increasing to 95% solvent B over 15 minutes; flow rate 1 ml per minute. Retention time: 10.05 minutes. Solvent A: $H_2O$/0.1% TFA; solvent B: $CH_3CN$/0.085% TFA. Column type: HYPERPEP 300A.

The 2'-(N-benzyloxycarbonyl-D-Alanyl)-2(R)-[2-benzamido-1(R)-(benzyloxycarbamoyl)ethyl]-2'-isobutyl-4-methylvalerylhydrazide used as the starting material was prepared as follows:

(i) A solution of 3.16 g of 2(R)-[2-benzamido-1(R)-(tert.butoxycarbonyl)ethyl]-4-methylvaleric acid in 50 ml of dichloromethane was cooled to 0° C. and treated in succession with 2.22 ml of N-ethyl morpholine, 1.84 g of 1-hydroxybenzotriazole, 2.08 g of 1-ethyl-3-(3-dimethylaminopropyl)carbodiimide hydrochloride and 1.76 g of benzyloxycarbonyl hydrazine. The mixture was allowed to warm to room temperature and stirred overnight. The solvent was evaporated and the residue was dissolved in ethyl acetate and washed with 5% aqueous sodium hydrogen carbonate solution and saturated aqueous sodium chloride solution. Drying over anhydrous magnesium sulfate and evaporation gave a residue which was purified by flash chromatography on silica gel using methanol/dichloromethane (2:98) for the elution. There was obtained 1.55 g of 2(R)-[2-benzamido-1(R)-(tert.butoxycarbonyl)ethyl]-2'-benzyloxycarbonyl-4-methylvalerylhydrazide in the form of a white foam.

MS: 512 (M+H)$^+$.

(ii) A solution of 0.500 g of 2(R)-[2-benzamido-1(R)-(tert.butoxycarbonyl)ethyl]-2'-benzyloxycarbonyl-4-methylvalerylhydrazide in 6 ml of dimethylformamide was treated, at room temperature under nitrogen, with 0.405 g of potassium carbonate and 0.135 g of bromo-2-methyl-prop-2-ene. The mixture was stirred overnight at room temperature and evaporated. The residue was dissolved in ethyl acetate and washed with water until neutral and then dried over anhydrous magnesium sulphate, filtered and evaporated to give 0.320 g of 2(R)-[2-benzamido-1(R)-(tert.butoxycarbonyl)ethyl]-2'-isobut-2-ene-4-methylvalerylhydrazide in the form of a white foam.

(iii) A solution of 0.300 g of 2(R)-[2-benzamido-1(R)-(tert.butoxycarbonyl)ethyl]-2'-isobut-2-ene-4-methylvalerylhydrazide in 6 ml of methanol was hydrogenated in the presence of 5% palladium-on-carbon for 3 hours. The catalyst was removed by filtration and the solvent was evaporated to give 0.230 g of 2(R)-[2-benzamido-1(R)-(tert.butoxycarbonyl)ethyl]-2'-isobutyl-4-methylvalerylhydrazide in the form of a white foam.

(iv) In an analogous manner to that described in Example 33, parts (ii)–(iv), starting from 2(R)-[2-benzamido-1(R)-(tert.butoxycarbonyl)ethyl]-2'-isobutyl-4-methylvalerylhydrazide there was obtained 2'-(N-benzyloxycarbonyl-D-Alanyl)-2(R)-[2-benzanido-1(R)-(benzyloxycarbamoyl)ethyl]-2'-isobutyl-4-methylvalerylhydrazide in the form of a white solid.

MS: 688 (M+H)$^+$.

EXAMPLE 160

2(R)-[1(S)-(Hydroxycarbamoyl)-4-phenylbutyl]-2'-[2-(1-imidazoyl)acetyl]-2'-isobutyl-4-methylvalerohydrazide p-toluenesulphonate A solution of 0.390 g of 2(R)-[1(S)-[(tetrahydro-2(RS)-pyranyloxy)carbamoyl]-4-phenylbutyl]-2'-[2-(1-imidazoyl)acetyl]-2'-isobutyl-4-methylvalerohydrazide in 5 ml of methanol was treated with 0.143 g of p-toluenesulphonic acid monohydrate. The mixture was stirred at room temperature for 1 hour and evaporated. The residue was triturated with diethyl ether, filtered and dried to give 0.320 g of 2(R)-[1(S)-(hydroxycarbamoyl)-4-phenylbutyl]-2'-[2-(1-imidazoyl)acetyl]-2'-isobutyl-4-methylvalerohydrazide p-toluenesulphonate in the form of a pale pink solid.

MS: 486 (M+H)$^+$. HPLC: Gradient elution using solvent A containing 5% solvent B increasing to 95% solvent B over 15 minutes; flow rate 1 ml per minute. Retention time: 10.79 minutes. Solvent A: H$_2$O/0.1% TFA; solvent B: CH$_3$CN/0.085% TFA. Column type: HYPERPEP 300A.

The 2(R)-[1(S)-[(tetrahydro-2(RS)-pyranyloxy)carbamoyl]-4-phenylbutyl]-2'-[2-(1-imidazoyl)acetyl]-2'-isobutyl-4-methylvalerohydrazide used as the starting material was prepared as follows:

(i) A solution of 1.0 g of (E)-2(R)-[1(S)-[(tetrahydro-2(RS)-pyranyloxy)carbamoyl]-4-phenyl-3-butenyl]-2'-isobutyl-4-methylvalerohydrazide in 20 ml of methanol was hydrogenated in the presence of 0.100 g of 5% palladium-on-carbon for 0.5 hours. The catalyst was removed by filtration and the solvent was evaporated to give 0.93 g of 2(R)-[1(S)-[(tetrahydro-2(RS)-pyranyloxy)carbamoyl]-4-phenylbutyl]-2'-isobutyl-4-methylvalerohydrazide in the form of a white solid.

MS: 462 (M+H)$^+$.

(ii) A solution of 0.415 g of 2-(1-imidazoyl)acetic acid hydrogen bromide and 0.461 g of 2(R)-[1(S)-[(tetrahydro-2(RS)-pyranyloxy)carbamoyl]-4-phenylbutyl]-2'-isobutyl-4-methylvalerohydrazide in 5 ml of dimethylformamide was treated with 0.230 g of N-ethylmorpholine and 0.422 g of 1-ethyl-3-(3-dimethylaminopropyl)carbodiimide hydrochloride and the mixture stirred overnight at room temperature. Evaporation gave a residue which was dissolved in ethyl acetate and washed with water and saturated aqueous sodium chloride solution. Drying over anhydrous magnesium sulphate, evaporation and trituration with diethyl ether followed by filtration and evaporation gave 0.340 g of 2(R)-[1(S)-[(tetrahydro-2(RS)-pyranyloxy)carbamoyl]-4-phenylbutyl]-2'-[2-(1-imidazoyl)acetyl]-2'-isobutyl-4-methylvalerohydrazide in the form of a white solid.

MS: 567 (M+H)$^+$.

EXAMPLE 161

2(R)-[4-Cyclohexyl-1(S)-(hydroxycarbamoyl)butyl]-2'-isobutyl-4-methyl-2'-[2-(1-imidazoyl)acetyl] valerohydrazide p-toluenesulphonate A solution of 0.205 g of 2(R)-(4-Cyclohexyl-1(S)-[(tetrahydro-2(RS)-pyranyloxy)carbamoyl]butyl]-2'-isobutyl-4-methyl-2'-[2-(1-imidazoyl)acetyl] valerohydrazide in 5 ml of methanol was treated with 0.075 g of p-toluenesulphonic acid monohydrate. The mixture was stirred at room temperature for 6 hours and evaporated. The residue was purified by flash column chromatography on silica gel using methanol/dichloromethane (5:95) as the eluant to give 0.080 g of 2(R)-[4-cyclohexyl-1(S)-(hydroxycarbamoyl)butyl]-2'-isobutyl-4-methyl-2'-(2-(1-imidazoyl)acetyl]valerohydrazide p-toluenesulphonate in the form of a white solid.

MS: 492 (M+H)$^+$. HPLC: Gradient elution using solvent A containing 5% solvent B increasing to 95% solvent B over 15 minutes; flow rate 1 ml per minute. Retention time: 12.19 minutes. Solvent A: H$_2$O/0.1% TFA; solvent B: CH$_3$CN/0.085% TFA. Column type: HYPERPEP 300A.

The 2(R)-[4-cyclohexyl-1(S)-[(tetrahydro-2(RS)-pyranyloxy)carbamoyl]butyl]-2'-isobutyl-4-methyl-2'-[2-(1-imidazoyl)acetyl]valerohydrazide used as the starting material was prepared as follows:

(i) A solution of 1.0 g of (E)-2(R)-[1(S)-[(tetrahydro-2(RS)-pyranyloxy)carbarnoyl]-4-phenyl-3-butenyl]-2'-isobutyl-4-methylvalerohydrazide in 30 ml of glacial acetic acid was hydrogenated in the presence of 0.300 g of platinum(II) oxide for 2 hours. The catalyst was removed by filtration and the solvent was evaporated and trituration with hexane gave 0.94 g of 2(R)-[4-cyclohexyl-1(S)-[(tetrahydro-2(RS)-pyranyloxy)carbamoyl]butyl]-2'-isobutyl-4-methylvalerohydrazide in the form of a white solid.

MS: 468 (M+H)$^+$.

(ii) A solution of 0.429 g of 2-(1-imidazoyl)acetic acid hydrogen bromide and 0.467 g of 2(R)-[4-Cyclohexyl-1(S)-[(tetrahydro-2(RS)-pyranyloxy)carbamoyl]butyl]-2'-isobutyl-4-methylvalerohydrazide in 5 ml of dimethylformamide was treated with 0.230 g of N-ethylmorpholine and 0.422 g of 1-ethyl-3-(3-dimethylaminopropyl)carbodiimide hydrochloride and the mixture stirred overnight at room temperature. Evaporation gave a residue which was dissolved in ethyl acetate and washed with water and saturated aqueous sodium chloride solution then dried over anhydrous magnesium sulfate and evaporated. Purification by flash column chromatography on silica gel using methanol/dichloromethane (5:95) as the eluant gave 0.213 g of 2(R)-[4-cyclohexyl-1(S)-[(tetrahydro-2(RS)-pyranyloxy)carbamoyl]butyl]-2'-isobutyl-4-methyl-2'-[2-(1-imidazoyl)acetyl]valerohydrazide in the form of a white foam.

MS: 576 (M+H)$^+$.

EXAMPLE 162

2(R)-[4-Cyclohexyl-1(S)-(hydroxycarbamoyl)butyl]-2'-isobutyl-4-methyl-2'-[2-(3-pyridyl)acetyl]valerohydrazide p-toluenesulphonate In a manner analogous to that described in Example 161 but using pyridine-3-acetic acid in the place of 2-(1-imidazoyl)acetic acid hydrogen bromide there was obtained 2(R)-[4-cyclohexyl-1(S)-(hydroxycarbamoyl)butyl]-2'-isobutyl-4-methyl-2'-[2-(3-pyridyl)acetyl]valerohydrazide p-toluenesulphonate in the form of a white solid.

MS: 503 (M+H)$^+$. HPLC: Gradient elution using solvent A containing 5% solvent B increasing to 95% solvent B over 15 minutes; flow rate 1 ml per minute. Retention time: 11.90 minutes. Solvent A: H$_2$O/0.1% TFA; solvent B: CH$_3$CN/0.085% TFA. Column type: HYPERPEP 300A.

EXAMPLE 163

2'-(4-Aminobutyryl)-[2(R)-[4-cyclohexyl-1(RS)-(hydroxycarbamoyl)butyl]-2'-isobutyl-4-methylvalerohydrazide hydrochloride A solution of 0.450 g of 2'-(N-benzyloxycarbonyl-4-aminobutyryl)-[2(R)-[4-cyclohexyl-1(RS)-(hydroxycarbamoyl)butyl]-2'-isobutyl-4-methylvalerohydrazide in 10 ml of methanol was hydrogenated in the presence of 0.040 g of 5% palladium-on-carbon for 1 hour. Filtration and evaporation gave a residue which was triturated with a 1M solution of hydrogen chloride in diethyl ether. Filtration gave 0.142 g of 2'-(4-aminobutyryl)-[2(R)-14-cyclohexyl-1(RS)-(hydroxycarbamoyl)butyl]-2'-isobutyl-4-methylvalerohydrazide hydrochloride in the form of pale pink solid.

MS: 469 (M+H)$^+$. HPLC: Gradient elution using solvent A containing 5% solvent B increasing to 95% solvent B over 15 minutes; flow rate 1 ml per minute. Retention time: 12.94 minutes. Solvent A: H$_2$O/0.1% TFA; solvent B: CH$_3$CN/0.085% TFA. Column type: HYPERPEP 300A.

The 2'-(N-benzyloxycarbonyl-4-aminobutyryl)-[2(R)-[4-cyclohexyl-1(RS)-(hydroxycarbamoyl)butyl]-2'-isobutyl-4-methylvalerohydrazide used as the starting material was prepared as follows:

(i) In a manner analogous to that described in Example 161, part (ii), but using (N-benzyloxycarbonyl)-4-aminobutyric acid in the place of 2-(1-imidazoyl)acetic acid hydrogen bromide there was obtained 2'-[(N-benzyloxycarbonyl)-4-amninobutyryl]-2(R)-[4-cyclohexyl-1(S)-[(tetrahydro-2(RS)-pyranyloxy)carbamoyl]butyl]-2'-isobutyl-4-methylvalerohydrazide in the form of a clear glass.

MS: 687 (M+H)$^+$.

(ii) A solution of 0.400 g of 2'-[(N-benzyloxycarbonyl)-4-aminobutyryl]-2(R)-[4-cyclohexyl-1(S)-[(tetrahydro-2(RS)-pyranyloxy)carbamoyl]butyl]-2'-isobutyl-4-methylvalerohydrazide in 10 ml of methanol was treated with 0.123 g of p-toluenesulphonic acid monohydrate for 1.5 hours. Evaporation gave 0.450 g of 2'-(N-benzyloxycarbonyl-4-aminobutyryl)-[2(R)-[4-cyclohexyl-1(RS)-(hydroxycarbamoyl)butyl]-2'-isobutyl-4-methylvalerohydrazide in the form of a white foam.

EXAMPLE 164

2(R)-[4-Cyclohexyl-1(RS)-(hydroxycarbamoyl)butyl]-2'-isobutyl-4-methyl-2'-[2-(1-methyl-4-piperidinyl)acetyl]valerohydrazide p-toluenesulphonate In a manner analogous to that described in Example 161 but using 2-(1-methyl-4-piperidinyl)acetic acid in the place of 2-(1-imidazoyl)acetic acid hydrogen bromide there was obtained 2(R)-[4-cyclohexyl-1(RS)-(hydroxycarbamoyl)butyl]-2'-isobutyl-4-methyl-2'-[2-(1-methyl-4-piperidinyl)acetyl]valerohydrazide p-toluenesulphonate in the form of a white solid.

MS: 523 (M+H)$^+$.

EXAMPLE 165

2'-(D-Alanyl)-2(R)-[5-cyclohexyl-1(RS)-(hydroxycarbamoyl)pentyl]-2'-isobutl]-4-methylvalerohydrazide p-toluenesulphonate A solution of 0.210 g of 2'-(D-alanyl)-2(R)-[5-cyclohexyl-1(RS)-[(tetrahydro-2(RS)-pyranyloxy)carbamoyl]pentyl]-2'-isobutyl-4-methylvalerohydrazide in 5 ml of methanol was treated with 0.080 g of p-toluenesulphonic acid monohydrate. The mixture was stirred at room temperature for 6 hours and evaporated. The residue was triturated with diethyl ether to give 0.151 g of 2'-D-alanyl)-2(R)-[5-cyclohexyl-1(RS)-(hydroxycarbamoyl)pentyl]-2'-isobutyl-4-methylvalerohydrazide p-toluenesulphonate in the form of a white solid.

MS: 469 (M+H)$^+$.

The 2'-(D-alanyl)-2(R)-[5-cyclohexyl-1(RS)-[(tetrahydro-2(RS)-pyranyloxy)arbamoyl]pentyl]-2'-isobutyl-4-methylvalerohydrazide used as the starting material was prepared as follows:

(i) A solution of 7.54 g of (E)-4-cyclohexyl-2-butenol in 200 ml of diethyl ether was treated with 9.99 g of acetic anhydride and 7.42 g of triethylamine and stirred overnight at room temperature. The mixture was then treated with 0.005 g of 4-dimethylaminopyridine and stirred for a further 0.5 hours. The mixture was washed with 5% aqueous sodium hydrogen carbonate, water and brine, then dried over anhydrous magnesium sulphate and evaporated. The residue was dried under vacuum to give 9.50 g of (E)-4-cyclohexyl-2-butenol acetate in the form of a pale yellow oil.

(ii) A solution of 22.2 g of 1,2-dibenzyl 1-tert-butyl-4-methyl-1(RS),1,2(R)-pentanetricarboxylate in 200 ml of dry tetrahydrofuran was treated with 2.35 g of 60% sodium hydride at room temperature under a nitrogen atmosphere. The mixture was stirred until the evolution of hydrogen had ceased and then treated with a solution of 9.50 g of (E)-4-cyclohexyl-2-butenol acetate and 2.8 g of tetrakis(triphenylphosphine)palladium(0) in 50 ml of dry tetrahydrofuran. The mixture was stirred overnight at room temperature and evaporated. The residue was partitioned between ethyl acetate and water and the ethyl acetate layer was washed further with water and a saturated aqueous sodium chloride solution. Drying over anhydrous magnesium sulphate and evaporation gave a residue which was purified by column chromatography on silica gel using ethyl acetate/hexane (1:9) for the elution to give 14.27 g of (E)-1,2-dibenzyl 1-tert-butyl-1-(4-cyclohexyl-2-butenyl)-4-methyl-1(RS),1,2(R)-pentanetricarboxylate in the form of a clear oil.

MS: 535 (M-t.Bu+H)$^+$.

(iii) A solution of 14.27 g of (E)-1,2-dibenzyl 1-tert-butyl-1-(4-cyclohexyl-2-butenyl)-4-methyl-1(RS),1,2(R)-pentanetricarboxylate in 200 ml of iso-propyl alcohol was hydrogenated in the presence of 1.4 g of 10% palladium-on-carbon for 1.5 hours. The catalyst was removed by filtration and the solvent was evaporated. The residue was dissolved in 200 ml of toluene and heated at reflux for 3 hours in the presence of 2.44 g of triethylamine. After allowing the mixture to cool to room temperature overnight it was washed with 2M aqueous hydrogen chloride, water and saturated aqueous sodium chloride. Drying over anhydrous magnesium sulphate and evaporation gave 8.18 g of 2(R)-isobutyl-4-tert-butyl-3-[(RS)-(4-cyclohexylbutyl)] succinate in the form of a clear oil.

(iv) A solution of 3.0 g of 2(R)-isobutyl-4-tert-butyl-3-[(RS)-(4-cyclohexylbutyl)]succinate in 50 ml of dichloromethane was cooled to 0° C. and treated in succession with 3.85 g of N-ethyl morpholine, 1.49 g of 1-hydroxbenzotriazole, 4.89 g of isobutylhydrazine ditosylate and 1.88 g of 1-ethyl-3-(3-dimethylaminopropylcarbodiimide hydrochloride. The solution was left to warm to room temperature and was stirred overnight. The solvent was evaporated and the residue was partitioned between ethyl acetate and 5% aqueous sodium hydrogen carbonate solution. The ethyl acetate layer was washed in succession with water, 5% citric acid solution, water and saturated sodium chloride solution, dried over anhydrous magnesium sulfate and evaporated. The residue was purified by flash column chromatography on silica gel using hexane/ethyl acetate (5:1) for the elution. There was obtained 1.0 g of 2(R)-[5-cyclohexyl-1(RS)-(tert.butoxycarbonyl)pentyl]-2'-isobutyl-4-methylvalerohydrazide in the form of a clear oil.

MS: 439 (M+H)$^+$.

(v) In an analogous manner to that described in Example 33, parts (ii)–(iii), but using 2(R)-[5-cyclohexyl-1(RS)-(tert.butoxycarbonyl)pentyl]-2'-isobutyl-4-methylvalerohydrazide in the place of 2(R)-[1(RS)-(tert.butoxycarbonyl)-4-phenylbutyl]-2'-isobutyl-4-methylvalerohydrazide there was obtained 2'-(N-benzyloxycarbonyl-D-alanyl)-2(R)-[5-cyclohexyl-1(RS)-(carboxy)pentyl]-2'-isobutyl-4-methylvalerohydrazide in the form of a clear glass.

MS: 676 (M+H)$^+$.

(vi) In an analogous manner to that described in Example 1, part (vi), and Example 6, part (ii), starting from 2'-(N-benzyloxycarbonyl-D-alanyl)-2(R)-[5-cyclohexyl-1(RS)-(carboxy)pentyl]-2'-isobutyl-4-methylvalerohydrazide there was obtained 2'-(D-Alanyl)-2(R)-[5-cyclohexyl-1(RS)-[(tetrahydro-2(RS)-pyranyloxy)carbamoyl]pentyl]-2'-isobutyl-4-methylvalerohydrazide in the form of a white solid.

MS: 553 (M+H)$^+$.

EXAMPLE 166

2'-(D-Alanyl)-2(R)-[1(RS)-(hydroxycarbamoyl)-5-phenylpentyl]-2'-isobutyl-4-methylvalerohydrazide p-toluenesulphonate In a manner analogous to that described in Example 165 but using (E)-4-phenyl-2-butenol in the place of (E)-4-cyclohexyl-2-butenol there was obtained 2'-(D-alanyl)-2(R)-[1(RS)-(hydroxycarbamoyl)-5-phenylpentyl]-2'-isobutyl-4-methylvalerohydrazide p-toluenesulphonate in the form of a white solid.

MS: 463 (M+H)$^+$. HPLC: Gradient elution using solvent A containing 5% solvent B increasing to 95% solvent B over 15 minutes; flow rate 1 ml per minute. Retention time: 11.09 minutes. Solvent A: H$_2$O/0.1% TFA; solvent B: CH$_3$CN/0.085% TFA. Column type: HYPERPEP 300A.

EXAMPLE 167

2(R)-[4-cyclopentyl-1(S)-(hydroxycarbamoyl)butyl]-2'-isobutyl-2'-[2-(imidazoyl)acetyl]-4-methylvalerohydrazide A solution of 0.130 g of 2(R)-[1(S)-(N-benzyloxycarbamoyl)-4-cyclopentylbutyl]-2'-isobutyl-2'-[2-(imidazoyl)acetyl]-4-methylvalerohydrazide in 3 ml of methanol was hydrogenated in the presence of 0.040 g of 5% palladium-on-carbon for 4 hours. Filtration and evaporation gave a residue which was triturated with diethyl ether. Filtration gave 0.083 g of 2(R)-[4-cyclopentyl-1(S)-(hydroxycarbamoyl)butyl]-2'-isobutyl-2'-[2-(imidazoyl)acetyl]-4-methylvalerohydrazide in the form of a white solid.

MS: 478 (M+H)$^+$. HPLC: Gradient elution using solvent A containing 5% solvent B increasing to 95% solvent B over 15 minutes; flow rate 1 ml per minute. Retention time: 11.64 minutes. Solvent A: H$_2$O/0.1% TFA; solvent B: CH$_3$CN/0.085% TFA. Column type: HYPERPEP 300A.

The 2(R)-[1(S)-(N-benzyloxycarbamoyl)-4-cyclopentylbutyl]-2'-isobutyl-2'-[2-(imidazoyl)acetyl]-4-methylvalerohydrazide used as the starting material was prepared as follows:

(i) A solution of 30 g of (E)-2(R)-[1(S)-(tert-butoxycarbonyl)-4-phenyl-3-butenyl]-4-methylvaleric acid in 400 ml of ethyl acetate was treated with 9.63 g of triethylamine and 16.31 g of benzyl bromide and then heated at reflux for 4 hours. On cooling the mixture to room temperature filtration and evaporation of the filtrate gave a residue which was purified by column chromatography on silica gel, using ethyl acetate/hexane (1:9) for the elution, to give 15.8 g of (E)-benzyl-2(R)-[1(S)-(tert-butoxycarbonyl)-4-phenyl-3-butenyl]-4-methylvalerate in the form of a clear oil.

MS: 381 (M-tBu+H)$^+$.

(ii) A solution of 15.8 g of (E)-benzyl-2(R)-[1(S)-(tert-butoxycarbonyl)-4-phenyl-3-butenyl]-4-methylvalerate in 150 ml of dichloromethane was cooled to −78° C. and ozone was bubbled into the mixture until a blue color persisted. The mixture was treated with 20 ml of dimethyl sulfide and stirred overnight at room temperature. Evaporation gave a residue which was purified by column chromatography on silica gel, using ethyl acetate/hexane (1:9 to 1:4) for the elution, to give 8.8 g of (E)-benzyl-2(R)-[1(S)-(tert-butoxycarbonyl)-propan-3-al]-4-methylvalerate in the form of a yellow oil.

MS: 307 (M-tBu+H)$^+$.

(iii) A suspension of 5.65 g of cyclopentylmethyl triphenylphosphonium iodide in 200 ml of toluene was treated with 1.34 g of potassium t-butoxide and the mixture was stirred at room temperature for 4 hours. A solution of 2.9 g of (E)-benzyl-2(R)-[1(S)-(tert-butoxycarbonyl)-propan-3-al]-4-methylvalerate in 10 ml of toluene was then added dropwise to the mixture over 5 minutes. The mixture was stirred for a further 48 hours at room temperature and evaporated. The residue was stirred in 100 ml of hexane for 20 minutes and then filtered and evaporated. The residue was purified by column chromatography on silica gel, using hexane/ethyl acetate (6:1) for the elution, to give 0.800 g of (E),(Z)-benzyl-2(R)-[4-cyclopentyl-1(S)-(tert-butoxycarbonyl)-3-butenyl]-4-methylvalerate in the form of a colorless oil.

MS: 429 (M +H)$^+$.

(iv) A solution of 0.800 g of (E),(Z)-benzyl-2(R)-[4-cyclopentyl-1(S)-(tert-butoxycarbonyl)-3-butenyl]-4-methylvalerate in 25 ml of isopropyl alcohol was hydrogenated in the presence of 0.100 g of 10% palladium-on-carbon. The mixture was filtered and evaporated to give 0.570 g of 2(R)-[4-cyclopentyl-1(S)-(tert-butoxycarbonyl)butyl]-4-methylvaleric acid in the form of a clear oil.

(v) In a manner analogous to that described in Example 165, part (iv), but using 2(R)-[4-cyclopentyl-1(S)-(tert-butoxycarbonyl)-butyl]-4-methylvaleric acid in the place of 2(R)-isobutyl-4-tert-butyl-3-[(RS)-(4-cyclohexylbutyl)]succinate there was obtained 2(R)-[4-cyclopentyl-1(S)-(tert-butoxycarbonyl)-butyl]-2'-isobutyl-4-methylvalerohydrazide in the form of a pale yellow oil.

(vi) A solution of 0.510 g of 2(R)-[4-cyclopentyl-1(S)-(tert-butoxycarbonyl)-butyl]-2'-isobutyl-4-methylvalerohydrazide in 10 ml of dimethylformamide was treated in sequence with 0.308 g of 2-(1-imidazoyl)acetic acid hydrogen bromide, 0.172 g of N-ethylmorpholine and 0.286 g of 1-ethyl-3-(3-dimethylaminopropyl)-carbodiimide hydrochloride and then stirred overnight at room temperature. The mixture was diluted with diethyl ether and washed with water and saturated aqueous sodium chloride solution. Drying over anhydrous magnesium sulphate and evaporation gave a residue which was purified by column chromatography on silica gel, using ethyl acetate/hexane (1:3) and then dichloromethane/methanol (3:1) for the elution, to give 0.255 g of 2(R)-[4-cyclopentyl-1(S)-(tert-butoxycarbonyl)-butyl]-2'-isobutyl-2'-[2-(1-imidazoyl)acetyl]-4-methylvalerohydrazide in the form of a yellow oil.

(vii) In a manner analogous to that described in Example 33, parts (iii)–(iv), but using 2(R)-[4-cyclopentyl-1(S)-(tert-butoxycarbonyl)-butyl]-2'-isobutyl-2'-[2-(1-imidazoyl)acetyl]-4-methylvalerohydrazide in the place of 2'-(N-benzyloxycarbonyl-D-alanyl)-2(R)-[1(RS)-(tert.butoxycarbonyl)-4-phenylbutyl]-2'-isobutyl-4-methylvalerohydrazide there was obtained 2(R)-[1(S)-(N-benzyloxycarbamoyl)-4-cyclopentyl-butyl]-2'-isobutyl-2'-[2-(imidazoyl)acetyl]-4-methylvalerohydrazide in the form of a clear glass.
MS: 568 (M +H)$^+$.

EXAMPLE 168

2(R)-[1(S)-(hydroxycarbamoyl)-5-methyl-hexyl]-2'-isobutyl-2'-[2-(imidazoyl)acetyl]-4-methylvalerohydrazide In a manner analogous to that described in Example 167 but using isobutylmethyl triphenyiphosphonium bromide in the place of cyclopentylmethyl triphenylphosphonium iodide there was obtained 2(R)-[1(S)-(hydroxycarbamoyl)-5-methyl-hexyl]-2'-isobutyl-2'-[2-(imidazoyl)acetyl]-4-methylvalerohydrazide in the form of a white solid.
MS: 452 (M+H)$^+$. HPLC: Gradient elution using solvent A containing 5% solvent B increasing to 95% solvent B over 15 minutes; flow rate 1 ml per minute. Retention time: 10.41 minutes. Solvent A: H$_2$O/0.1% TFA; solvent B: CH$_3$CN/0.085% TFA. Column type: HYPERPEP 300A.

EXAMPLE 169

(E)-2(R)-[1(S)-(Hydroxycarbamoyl)-4-phenyl-3-butenyl]-2'-isobutyl-4-methyl-2'-[2-(1-hexamethyleneimino)acetyl]valerohydrazide p-toluenesulphonate In a manner analogous to that described in Example 37 but using 2-(1-hexamethyleneimino)acetic acid hydrogen bromide in the place of 2-(1-pyrrolidinyl)acetic acid hydrogen bromide there was obtained (E)-2(R)-[1(S)-(Hydroxycarbamoyl)-4-phenyl-3-butenyl]-2'-isobutyl-4-methyl-2'-[2-(1-hexamethyleneimino)acetyl]valerohydrazide p-toluenesulphonate in the form of a white solid.
MS: 515 (M+H)$^+$. HPLC: Gradient elution using solvent A containing 5% solvent B increasing to 95% solvent B over 15 minutes; flow rate 1 ml per minute. Retention time: 12.47 minutes. Solvent A: H$_2$O/0.1% TFA; solvent B: CH$_3$CN/0.085% TFA. Column type: HYPBDSC 18.

EXAMPLE 170

(E)-2'-(D-alanyl)-2(R)-[1(RS)-(Hydroxycarbamoyl)-4-(2-thienyl)-3-butenyl]-2'-isobutyl-4-methylvalerohydrazide A solution of 0.180 g of (E)-2'-(D-alanyl)-2(R)-[1(RS)-[(tetrahydro-2(RS)-pyranyloxy)carbamoyl]-4-(2-thienyl)-3-butenyl]-2'-isobutyl-4-methylvalerohydrazide in 5 ml of methanol was treated with 0.077 g of p-toluenesulphonic acid monohydrate. The mixture was stirred at room temperature for 2 hours and evaporated. The residue was purified by column chromatography on silica gel, using dichloromethane/methanol (95:5) for the elution, to give 0.056 g of (E)-2'-(D-alanyl)-2(R)-[1(RS)-(hydroxycarbamoyl)-4-(2-thienyl)-3-butenyl]-2'-isobutyl-4-methylvalerohydrazide in the form of an off-white solid.
MS: 453 (M+H)$^+$. HPLC: Gradient elution using solvent A containing 5% solvent B increasing to 95% solvent B over 15 minutes; flow rate 1 ml per minute. Retention time: 10.32 minutes. Solvent A: H$_2$O/0.1% TFA; solvent B: CH$_3$CN/0.085% TFA. Column type: HYPERPEP 300A.

The (E)-2'-(D-alanyl)-2(R)-[1(RS)-[(tetrahydro-2(RS)-pyranyloxy)carbamoyl]-4-(2-thienyl)-3-butenyl]-2'-isobutyl-4-methylvalerohydrazide used as the starting material was prepared as follows:

(i) In a manner analogous to that described in Example 165, parts (i)–(ii), but using (E)-3-(2-thienyl)-2-propenol in the place of (E)-4-cyclohexyl-2-butenol there was obtained (E)-1,2-dibenzyl 1-tert-butyl-1-(3-(2-thienyl)-2-propenyl)-4-methyl-1(RS),1,2(R)-pentanetricarboxylate in the form of a pale yellow oil.
MS: 521 (M-tBu+H)$^+$.

(ii) A solution of 7.22 g of (E)-1,2-dibenzyl-1-tert-butyl-1-(3-(2-thienyl)-2-propenyl)-4-methyl-1(RS),1,2(R)-pentanetricarboxylate in 35 ml of ethanol was treated with 32 ml of 4M aqueous sodium hydroxide and heated at reflux overnight. On cooling to room temperature the ethanol was evaporated and the residue was diluted with water and acidified with 4M aqueous hydrogen chloride. This was washed with ether and the combined organic layers were then washed with water and saturated aqueous sodium chloride. Drying over anhydrous magnesium sulfate and evaporation gave a residue which was dissolved in 50 ml toluene and treated with 1.26 g of triethylamine. The mixture was heated at reflux for 3 hours and then cooled to room temperature and washed with 2M aqueous hydrogen chloride, water, and saturated aqueous sodium chloride. Drying over anyhdrous magnesium sulfate and evaporation gave a residue which was purified by column chromatography on silica gel, using ethyl acetate/hexane (1:5) for the elution, to give 2.15 g of 2(R)-isobutyl-4-tert-butyl-3-[(RS)-(3-(2-thienyl)-2-propenyl)]succinate in the form of a yellow oil.

(iii) In an analogous manner to that described in Example 165, part (iv), but using 2(R)-isobutyl-4-tert-butyl-3-[(RS)-

(3-(2-thienyl)-2-propenyl)]succinate in the place of 2(R)-isobutyl-4-tert-butyl-3-[(RS)-(4-cyclohexylbutyl)]succinate there was obtained (E)-2(R)-[1(RS)-[(tert.butyloxy)carbonyl]-4-(2-thienyl)-3-butenyl]-2'-isobutyl-4-methylvalerohydrazide in the form of a pale yellow oil.

MS: 423 (M+H)⁺.

(iv) In an analogous manner to that described in Example 18, part (i), but using N-(9-fluorenylmethyloxycarbonyl)-D-alanine acid fluoride in the place of using N-(9-fluorenylmethyloxycarbonyl)-O-tert.butyl-D-serine acid fluoride there was obtained (E)-2(R)-[1(RS)-[(tert.butyloxy)carbonyl]-4-(2-thienyl)-3-butenyl]-2'-isobutyl-2'[N-(9-fluorenylmethyloxycarbonyl)-D-alanyl]-4-methylvalerohydrazide in the form of a white foam.

MS: 716 (M+H)⁺.

(v) A solution of 1.04 g of (E)-2(R)-[1(RS)-[(tert.butyloxy)carbonyl]-4-(2-thienyl)-3-butenyl]-2'-isobutyl-2'-[N-(9-fluorenylmethyloxycarbonyl)-D-alanyl]-4-methylvalerohydrazide in 50 ml of dichloromethane was treated with 1.0 ml of a 33% solution of hydrogen bromide in acetic acid at −15° C. The mixture was stirred at this temperature for 1.5 hours and then washed with water and dried over anhydrous magnesium sulfate. Evaporation was followed by addition of hexane and filtration of the resulting precipitate. The precipitate was dried to give 0.665 g of (E)-2(R)-[1(RS)-(carboxy)]-4-(2-thienyl)-3-butenyl]-2'-isobutyl-2'-[N-(9-fluorenylmethyloxycarbonyl)-D-alanyl]-4-methylvalerohydrazide in the form of a light brown solid.

MS: 660 (M+H)⁺.

(vi) In an analogous manner to that described in Example 18, parts (iii)–(iv), but using (E)-2(R)-[1(RS)-(carboxy)]-4-(2-thienyl)-3-butenyl]-2'-isobutyl-2'-[N-(9-fluorenylmethyloxycarbonyl)-D-alanyl]-4-methylvalerohydrazide in the place of (E)-2(R)-[1(S)-(carboxy)]-4-phenyl-3-butenyl]-2'-isobutyl-2'-[N-(9-fluorenylmethyloxycarbonyl)-D-seryl]-4-methylvalerohydrazide there was obtained (E)-2'-(D-alanyl)-2(R)-[1(RS)-[(tetrahydro-2(RS)-pyranyloxy)carbamoyl]-4-(2-thienyl)-3-butenyl]-2'-isobutyl-4-methylvalerohydrazide in the form of a yellow oil.

MS: 537 (M+H)⁺.

EXAMPLE 171

2'-(2-Ethylbutyl)-2(R)-[1(S)-(hydroxycarbamoyl)-4-phenylbutl]-4-methyl-2-[2-(1H-1,2,3-triazol-1-yl)acetyl]valerohydrazide In a manner analogous to that described in Example 103 starting from 0.315 g of (E)-2(R)-[1(S)-(benzyloxycarbamoyl)-4-phenyl-3-butenyl]-2'-(2-ethylbutyl)-4-methyl-2'-[2-(1H-1,2,3-triazol-1-yl)acetyl]valerohydrazide there was obtained 0.198 g of 2'-(2-ethylbutyl)-2(R)-[1(S)-(hydroxycarbamoyl)-4-phenylbutyl]-4-methyl-2'-[2-(1H-1,2,3-triazol-1-yl)acetyl]valerohydrazide in the form of a white solid.

MS: 515 (M+H)⁺. HPLC: Gradient elution using solvent A containing 5% solvent B increasing to 95% solvent B over 15 minutes; flow rate 1 ml/minute. Retention time: 12.358 minutes. Solvent A: H₂O/0.1% TFA; Solvent B: CH₃CN/ 0.085%. Column type: HYPERPEP 300A.

The (E)-2(R)-[1(S)-(benzyloxycarbamoyl)-4-phenyl-3-butenyl-2'-(2-ethylbutyl)-4-methyl-2'-[2-(1H-1,2,3-triazol-1-yl)acetyl]valerohydrazide used as the starting material was prepared as follows:

(i) In a manner analogous to that described in Example 1, parts (iv)–(vii) starting from (E)-2(R)-[1(S)-(tert-butoxycarbonyl)-4-phenyl-3-butenyl]-2'-(2-ethylbutyl)-4-methylvalerohydrazide and using O-benzylhydroxylamine in part (vi) there was obtained (E)-2(R)-[1(S)-(benzyloxycarbamoyl)-4-phenyl-3-butenyl]-2'-(2-ethylbutyl)-4-methylvalerohydrazide in the form of a white solid.

MS: 494 (M+H)⁺.

(ii) In a manner analogous to that described in Example 8 from (E)-2(R)-[1(S)-(benzyloxycarbamoyl)-4-phenyl-3-butenyl]-2'-(2-ethylbutyl)-4-methylvalerohydrazide and using 1,2,3-triazole-1-acetic acid in place of N-tert-butoxycarbonyl-β-alanine there was obtained (E)-2(R)-[1(S)-(benzyloxycarbamoyl)-4-phenyl-3-butenyl]-2'-(2-ethylbutyl)-4-methyl-2'-[2-(1H-1,2,3-triazol-1-yl)acetyl]valerohydrazide in the form of a gum.

EXAMPLE 172

2'-(2-Ethylbutyl)-2(R)-[1(S)-(hydroxycarbamoyl)-4-phenylbutyl]-4-methyl-2'-[2-(1H-1,2,4-triazol-1-yl)acetyl]valerohydrazide In a manner analogous to that described in Example 103 starting from 0.205 g of (E)-2(R)-[1(S)-(benzyloxycarbamoyl)-4-phenyl-3-butenyl]-2'-(2-ethylbutyl)-4-methyl-2'-[2-(1H-1,2,4-triazol-1-yl)acetyl]valerohydrazide there was obtained 0.10 g of 2'-(2-ethylbutyl)-2(R)-[1(S)-(hydroxycarbamoyl)-4-phenylbutyl]-4-methyl-2'-[2-(1H-1,2,4-triazol-1-yl)acetyl]valerohydrazide in the form of a white solid.

MS: 515 (M+H)⁺. HLPC: Gradient elution using solvent A containing 5% solvent B increasing to 95% solvent B over 15 minutes; flow rate 1 ml/minute. Retention time: 11.918 minutes. Solvent A: H₂O/0.1% TFA; Solvent B: CH₃CN/ 0.085% TFA. Column type: HYPERPEP 300A.

The (E)-2(R)-[1(S)-(enzyloxycarbamoyl)-4-phenyl-3-butenyl]-2'-(2-ethylbutyl)-4-methyl-2'-[2-(1H-1,2,4-triazol-1-yl)acetyl]valerohydrazide used as the starting material was prepared as follows:

In a manner analogous to that described in Example 8 from (E)-2(R)-[1(S)-(benzyloxycarbamoyl)-4-phenyl-3-butenyl]-2'-(2-ethylbutyl)-4-methylvalerohydrazide and using 1,2,4-triazole-1-acetic acid in place of N-tert-butoxycarbonyl-β-alanine there was obtained (E)-2(R)-[1(S)-(benzyloxycarbamoyl)-4-phenyl-3-butenyl]-2'-(2-ethylbutyl)-4-methyl-2'-[2-(1H-1,2,4-triazol-1-yl)acetyl]valerohydrazide.

EXAMPLE 173

2'-(2-Ethylbutyl)-2(R)-[1(S)-(hydroxycarbamoyl)-4-phenylbutyl]-2'-[2-(1H-imidazol-1-yl)acetyl]-4-methylvalerohydrazide In a manner analogous to that described in Example 103 starting from 0.293 g of (E)-2(R)-[1(S)-(benzyloxycarbamoyl)-4-phenyl-3-butenyl]-2'-(2-ethylbutyl)-2'-[2-(1H-imidazol-1-yl)acetyl]-4-methylvalerohydrazide there was obtained 0.187 g of 2'-(2-ethylbutyl)-2(R)-[1(S)-(hydroxycarbamoyl)-4-phenylbutyl]-2'-[2-(1H-imidazol-1-yl)acetyl]-4-methylvalerohydrazide in the form of a white solid.

MS: 514 (M+H)⁺. HPLC: Gradient elution using solvent A containing 5% solvent B increasing to 95% solvent B over 15 minutes; flow rate 1 ml/minute. Retention time: 11.838 minutes. Solvent A: H₂O/0.1% TFA; Solvent B: CH₃CN/ 0.085% TFA. Column type: HYPERPEP 300A.

The (E)-2(R)-[1(S)-(benzyloxycarbamoyl)-4-phenyl-3-butenyl]-2'-(2-ethylbutyl)-2'-[2-(1H-imidazol-1-yl)acetyl]-

4-methylvalerohydrazide used as the starting material was prepared as follows:

In a manner analogous to that described in Example 8 from (E)-2(R)-[1(S)-(benzyloxycarbamoyl)-4-phenyl-3-butenyl]-2'-(2-ethylbutyl)-4-methylvalerohydrazide and using imidazole-1-acetic acid in place of N-tert-butoxycarbonyl-β-alanine there was obtained (E)-2(R)-[1(S)-(benzyloxycarbamoyl)-4-phenyl-3-butenyl]-2'-(2-ethylbutyl)-2'-[2-(1H-imidazol-1-yl)acetyl]-4-methylvalerohydrazide in the form of a gum.

EXAMPLE 174

2'-(4-Aminobutyryl-2'-(2-ethylbutyl-2(R)-[1(S)-hydroxycarbamoyl)-4-phenylbutyl-4-methylvalerohydrazide In a manner analogous to that described in Example 103 starting from 0.27 g of (E)-2(R)-[1(S)-(benzyloxycarbamoyl)-4-phenyl-3-butenyl]-2'-(4-benzyloxycarbonylaminobutyryl)-2'-(2-ethylbutyl)-4-methylvalerohydrazide there was obtained 0.101 g of 2'-(4-aminobutyryl-2'-(2-ethylbutyl-2(R)-[1(S)-hydroxycarbamoyl)-4-phenylbutyl-4-methylvalerohydrazide in the form of a white solid.

MS: 491 (M+H)$^+$. HPLC: Gradient elution using solvent A containing 5% solvent B increasing to 95% solvent B over 15 minutes; flow rate 1 ml/minute. Retention time: 11.002 minutes. Solvent A: H$_2$O/0.1% TFA; Solvent B: CH$_3$CN/0.085% TFA. Column type: HYPERPEP 300A.

The (E)-2(R)-[1(S)-(benzyloxycarbamoyl)-4-phenyl-3-butenyl]-2'-(4-benzyloxycarbonylaminobutyryl)-2'-(2-ethylbutyl)-4-methylvalerohydrazide used as the starting material was prepared as follows:

In a manner analogous to that described in Example 8 from (E)-2(R)-[1(S)-(benzyloxycarbamoyl)-4-phenyl-3-butenyl]-2-(2-ethylbutyl)-4-methylvalerohydrazide and using 4-benzyloxycarbonylaminobutyric acid in place of N-tert-butoxycarbonyl-□-alanine there was obtained (E)-2(R)-[1(S)-(benzyloxycarbamoyl)-4-phenyl-3-butenyl]-2'-(4-benzyloxycarbonylaminobutyryl)-2'-(2-ethylbutyl)-4-methylvalerohydrazide in the form of a gum.

EXAMPLE 175

2(R)-[1(S)-(hydroxycarbamoy)-4-phenylbutyl]-4-methyl-2'-(2(S)-methylbutyl)-2'-2-(1H-1,2,3-triazol-1-yl)-acetyl]valerohydrazide In a manner analogous to that described in Example 103 starting from 0.24 g of (E)-2(R)-[1(S)-(benzyloxycarbamoyl)-4-phenyl-3-butenyl]-4-methyl-2'-(2(S)-methylbutyl)-2'-[2-(1H-1,2,3-triazol-1-yl)acetyl] valerohydrazide there was obtained 0.121 g of 2(R)-[1(S)-(hydroxycarbamoyl)-phenylbutyl]-4-methyl-2'-(2(S)-methylbutyl)-2'-[2-(1H-1,2,3-triazol-1-yl)acetyl] valerohydrazide in the form of a white solid.

MS: 501 (M+H)$^+$. HPLC: Gradient elution using solvent A containing 5% solvent B increasing to 95% solvent B over 15 minutes, flow rate 1 ml/minute. Retention time: 11.75 minutes. Solvent A: H$_2$O/0.1% TFA; Solvent B: CH$_3$CN/0.085% TFA. Column type: HYPERPEP 300A:

The (E)-2(R)-[1(S)-(benzyloxycarbamoyl)-4-phenyl-3-butenyl]-4-methyl-2'-(2(S)-methylbutyl)-2'-[2-(1H-1,2,3-triazol-1-yl)acetyl]valerohydrazide used as the starting material was prepared as follows:

In a manner analogous to that described in Example 8 from (E)-2(R)-[1(S)-(benzyloxycarbamoyl)-4-phenyl-3-butenyl]-4-methyl-2'-(2(S)-methylbutyl)valerohydrazide and using 1,2,3-triazole-1-acetic acid in place of N-tert-butoxycarbonyl-β-alanine there was obtained (E)-2(R)-[1(S)-(benzyloxycarbamoyl)-4-phenyl-3-butenyl]-4-methyl-2'-(2(S)-methylbutyl)-2'-[2-(1H-1,2,3-triazol-1-yl)acetyl]valerohydrazide in the form of a gum.

MS: 589 (M+H)$^+$.

EXAMPLE 176

2(R)-[3-benzamido-1(S)-(hydroxycarbamoyl)propyl]-2'-[(2-(1H-imidazol-1-yl)acetyl]-2'-isobutyl-4-methylvalerohydrazide A solution of 0.420 g of 2(R)-[3-benzamido-1(S)-(benzyloxycarbamoyl)propyl]-2'-[2-(1H-imidazol-1-yl)acetyl]-2'-isobutyl-4-methylvalerohydrazide in 5 ml of methanol was hydrogenated in the presence of 0.126 g of 5% palladium-on-carbon for 12 hours. The catalyst was removed by filtration and the solvent was evaporated. The residue was triturated with diethyl ether to give 0.304 g of 2(R)-[3-benzamido-1(S)-(hydroxycarbamoyl)propyl]-2'-[2-(1H-imidazol-1-yl)acetyl]-2'-isobutyl-4-methylvalerohydrazide in the form of a white solid.

MS: 515 (M+H)$^+$. HPLC: Gradient elution using solvent A containing 5% solvent B increasing to 95% solvent B over 15 minutes; flow rate 1 ml per minute. Retention time: 10.12 minutes. Solvent A: H$_2$O/0.1% TFA; solvent B: CH$_3$CN/0.085% TFA. Column type: HYPBDSC18.

The 2(R)-[3-benzamido-1(S)-(benzyloxycarbamoyl)propyll-2'-[2-(1H-imidazol-1-yl)acetyl]-2'-isobutyl-4-methylvalerohydrazide used as the starting material was prepared as follows:

(i) A solution of 1.0 g of (E)-2(R)-[1(S)-(tert-butoxycarbonyl)-4-phenyl-3-butenyl]-4-methylvaleric acid in 10 ml of dimethylformamide was treated in succession with 2.0 g of potassium carbonate and 0.45 ml of benzyl bromide. The mixture was stirred at room temperature for 1 hour and then the solvent was evaporated and the residue was dissolved in ethyl acetate and washed with water until the water washings were neutral (pH=7). Drying over anhydrous magnesium sulfate and evaporation gave 1.28 g of (E)-benzyl-2(R)-[1(S)-(tert-butoxycarbonyl)-4-phenyl-3-butenyl]-4-methylvalerate in the form of an orange oil.

(ii) A solution of 32.12 g of (E)-benzyl-2(R)-[1(S)-(tert-butoxycarbonyl)-4-phenyl-3-butenyl]-4-methylvalerate in 300 ml of dichloromethane was cooled to −78° C. and ozone was then bubbled through the mixture for 2.5 hours. 35 ml of dimethyl sulfide was then addded to the mixture and stirring continued overnight at room temperature. The solvent was evaporated to give an orange oil. This was dissolved in 300 ml of methanol, cooled to 0° C. under nitrogen and then treated portionwise with 5.6 g of sodium borohydride. The mixture was then quenched with glacial acetic acid and evaporated. The residue was dissolved in ethyl acetate and washed sequentially with 2M aqueous hydrogen chloride, water, 5% aqueous sodium hydrogen carbonate and brine and then dried over anhydrous magnesium sulfate. Filtration and evaporation gave a residue which was purified by flash column chromatography on silica gel, using ethyl acetate/hexane (2:8 increasing to 4:6) for the elution, to give 15.3 g of benzyl-2(R)-[1(S)-(tert-butoxycarbonyl)-3-hydroxypropyl]-4-methylvalerate in the form of a pale yellow oil.

(iii) A solution of 1.5 g of benzyl-2(R)-[1(S)-(tert-butoxycarbonyl)-3-hydroxypropyl]-4-methylvalerate in 30 ml of dichloromethane was cooled to 0° C. under nitrogen and then treated with 3.3 ml of pyridine and 3.5 g of methanesulfonic anhydride. The mixture was stirred for 1 hour and then the solvent was evaporated. The residue was dissolved in ethyl acetate and washed sequentially with 2M aqueous hydrogen chloride, 5% aqueous sodium hydrogen carbonate and brine, and then dried over anhydrous magnesium sulfate. Filtration and evaporation gave a yellow oil which was purified by flash column chromatography, using ethyl acetate/hexane (2:8) for the elution, to give 1.07 g of benzyl-2(R)-[1(S)-(tert-butoxycarbonyl)-3-methanesulfonyloxypropyl]-4-methylvalerate in the form of a colorless oil.

MS: 465 (M+Na)$^+$.

(iv) A solution of 1.0 g of benzyl-2(R)-[1(S)-(tert-butoxycarbonyl)-3-methanesulfonyloxypropyl]-4-methylvalerate in 10 ml of dry dimethylformamide was treated with 0.735 g of sodium azide and 0.034 g of sodium iodide and then heated under nitrogen at 50° C. for 12 hours. The solvent was evaporated and the residue was dissolved in ethyl acetate and washed with water (2x). Drying over anhydrous magnesium sulfate, filtration and evaporation gave 0.88 g of benzyl-2(R)-[3-azido-1(S)-(tert-butoxycarbonyl)propyl]methylvalerate in the form of a yellow oil.

(v) A solution of 0.880 g of benzyl-2(R)-[3-azido-1(S)-(tert-butoxycarbonyl)propyl]-4-methylvalerate in 10 ml of ethanol was hydrogenated in the presence of 0.090 g of 5% palladium-on-carbon for 12 hours. The catalyst was removed by filtration and the solvent was evaporated to give 0.600 g of 2(R)-[3-amino-1(S)-(tert-butoxycarbonyl) propyl]-4-methylvaleric acid in the form of a white solid.

MS: 274 (M+H)$^+$.

(vi) A solution of 1.0 g of 2(R)-[3-amino-1(S)-(tert-butoxycarbonyl)propyl]-4-methylvaleric acid in 20 ml of dichloromethane was cooled to 5° C. under nitrogen and treated with 1.3 ml of triethylamine and a solution of 0.54 g of benzoyl chloride in 10 ml of dichloromethane. The mixture was stirred overnight at room temperature and then the solvent was evaporated. The residue was dissolved in ethyl acetate and washed with 2M aqueous hydrogen chloride and water. Drying over anhydrous magnesium sulfate, filtration and evaporation of the solvent gave a pale yellow oil which was purified by flash column chromatography on silica gel, using ethyl acetate/hexane (3:1), to give 0.78 g of 2(R)-[3-benzamido-1(S)-(tert-butoxycarbonyl)propyl]-4-methylvaleric acid in the form of a colorless oil.

(vii) A solution of 0.78 g of 2(R)-[3-benzamido-1(S)-(tert-butoxycarbonyl)propyl]-4-methylvaleric acid in 10 ml of dichloromethane was cooled to 0° C. under nitrogen and treated sequentially with 0.80 ml of N-ethylmorpholine, 0.437 g of hydroxybenzotriazole hydrate, and 0.50 g of 1-ethyl-3-(3-dimethylaminopropyl)carbodiimide hydrochloride. The mixture was stirred for 5 minutes at 0° C. and then 1.1 g of isobutyl hydrazine was added. Stirring was continued overnight at room temperature and then the solvent was evaporated. The residue was dissolved in ethyl acetate and washed with 5% aqueous sodium hydrogen carbonate, water, 2M aqueous hydrogen chloride, and saturated aqueous sodium chloride. Drying over anhydrous magnesium sulfate, filtration and evaporation of the solvent gave 0.763 g of 2(R)-[3-benzamido-1(S)-(tert-butoxycarbonyl)propyl]-2'-isobutyl-4-methylvalerohydrazide in the form of an off-white foam.

MS: 448 (M+H)$^+$.

(viii) A solution of 0.763 g of 2(R)-[3-benzamido-1(S)-(tert-butoxycarbonyl)propyl]-2'-isobutyl-4-methylvalerohydrazide and 0.780 g of 2-(1H-imidazol-1-yl)acetic acid hydrogen bromide in 8 ml of dimethylformamide was cooled to 0° C. under nitrogen and treated with 0.45 ml of N-ethylmorpholine and 0.720 g of 1-ethyl-3-(3-dimethylaminopropyl)carbodiimide hydrochloride. The mixture was allowed to warm to room temperature and stirred overnight. Evaporation of the solvent gave a residue which was dissolved in ethyl acetate and washed with water and saturated aqueous sodium chloride. Drying over anhydrous magnesium sulfate, filtration, and evaporation gave 0.914 g of 2(R)-[3-benzamido-1(S)-(tert-butoxycarbonyl) propyl]-2'-[2-(1H-imidazol-1-yl)acetyl]-2'-isobutyl-4-methylvalerohydrazide in the form of an off-white foam.

MS: 556 (M+H)$^+$.

(ix) A solution of 0.907 g of 2(R)-[3-benzamido-1(S)-(tert-butoxycarbonyl)propyl]-2'-[2-(1H-imidazol-1-yl)acetyl]-2'-isobutyl-4-methylvalerohydrazide in 8 ml of dichloromethane was treated with 6 ml of trifluoroacetic acid. The mixture was stirred at room temperature for 2 hours and then the solvent was evaporated. The residue was dried in vacuo to give 2(R)-[3-benzamido-1(S)-(carboxy)propyl]-2'-[2-(1H-imidazol-1-yl)acetyl]-2'-isobutyl-4-methylvalerohydrazide in the form of a pale orange oil.

MS: 500 (M+H)$^+$.

(x) A solution of 0.81 g of 2(R)-[3-benzamido-](S)-(carboxy)propyl]-2'-[2-(1H-imidazol-1-yl)acetyl]-2'-isobutyl-4-methylvalerohydrazide and 1.2 g of O-benzyl hydroxylamine in 4 ml of dimethylformamide was cooled to 0° C. under nitrogen and then treated with 0.23 ml of N-ethylmorpholine and 0.350 g of 1-ethyl-3-(3-dimethylaminopropyl)carbodiimide hydrochloride. The mixture was allowed to warm to room temperature and then stirred overnight. The solvent was evaporated and the residue was dissolved in ethyl acetate. The ethyl acetate layer was washed with water and saturated aqueous sodium chloride and then dried over anhydrous magnesium sulfate. Filtration and evaporation gave a yellow oil which was purified by flash column chromatography on silica gel, using methanol/dichloromethane (2:98 increasing to 10:90) for the elution. Trituration of the purified material with diethyl ether gave 0.420 g of 2(R)-[3-benzamido-1(S)-(benzyloxycarbamoyl)propyl]-2'-[2-(1H-imidazol-1-yl) acetyl]-2'-isobutyl-4-methylvalerohydrazide in the form of a white solid.

MS: 605 (M+H)$^+$.

EXAMPLE 177

2(R)-[3-(Benzenesulfonamido)-1(S)-(hydroxycarbamoyl)propyl]-2'-[(2-(1H-imidazol-1-yl)acetyl]-2'-isobutyl-4-methylvalerohydrazide In a manner analogous to that described in Example 176, but using benzene sulfonyl chloride in the place of benzoyl chloride in step (vi), there was obtained 0.546 g of 2(R)-[3-(Benzenesulfonamido)-1(S)-(hydroxycarbamoyl) propyl]-2'-[2-(1H-imidazol-1-yl)acetyl]-2'-isobutyl-4-methylvalerohydrazide in the form of a white solid.

MS: 551 (M+H)$^+$. HPLC: Gradient elution using solvent A containing 5% solvent B increasing to 95% solvent B over 15 minutes; flow rate 1 ml per minute. Retention time: 10.40 minutes. Solvent A: H$_2$O/0.1% TFA; solvent B: CH$_3$CN/0.085% TFA. Column type: HYPBDSC 18.

BIBLIOGRAPHY

1. Soluble TNF Receptor (p75) fusion protein (Enbrel) as a therapy for rheumatoid arthritis. Moreland, L. W. Rheum. Dis. Clin. North Am. (1998) 24, p579–591.

2. The future role of anti-tumour necrosis factor alpha products in the treatment of Crohn's disease. Van Hogezand, R. A. and Verspaget, H. W. Drugs (1998) 56, p299–305.

(Note: numbers 3 and 4 not used.)

5. TNFalpha convertase enzyme from human arthritis-affected cartilage: Isolation of cDNA by differential display, expression of the active enzyme, and regulation of TNFalpha. J.Immunol (1998)160, p4570–4579. Patel, I. R., Attur, M. G., Patel, R. N., Stuchin, S. A., Abagyan, R. A., Abramson, S. B. and Amin, A. R.

6. Chondrocyte tumour necrosis factor receptors and focal loss of cartilage in osteoarthritis. Osteoarthritis Cartilage (1997) 5, p427–437. Webb, G. R., Westacott, C. J. and Elson, C. J.

7. Tumour necrosis factor alpha gene polymorphisms in chronic bronchitis. Am.J. Respiratory and Critical Care Medicine (1997),156, p1436–1439. Huang-Song-Lih, Su-Chern-Huey and Chang-Shi-Chuan.

8. Pathology of Asthma and COPD: A Synopsis. Eur. Resp. Rev. (1997) 7, p111–118. Jeffery, P. K.

9. Tumour necrosis factor alpha (TNFalpha)-induced ICAM-1 surface expression in airway epithelial cells in vitro: possible signal transduction mechanisms. Ann. N.Y. Acad. Sci (1996) 796, p30–37.

10. Investigational New Drugs, 1997, vol. 15, no. 1, p. 49–59 Journal of Molecular Medicine (Berlin), 1995, vol. 73, no. 7, p. 333–346

11. Association between tumour necrosis factor in serum and cachexia in patients with prostate cancer. Clin Cancer Res. (1998), 4, pp 1743–1748. Nakashima, J., Tachibara, M., Ueno, M., Miyajima, A., Baba,S. and Murai, M.

12. Effect of FR 143430, a Novel Cytokine Suppressive Agent, on Adenocarcinoma Colon 26- Induced Cachexia in Mice. Anticancer Res. (1998) 18, pp 139–144. Yamoto, N., Kawamura, I., Nishigaki, F., Tsujimoto, S., Naoe, Y., Inami, M., Elizabeth, L., Manda, T. and Shimomura, K.

13. Tumour necrosis factor in congestive heart failure: a mechanism of disease for the new millenium. Ceconi, C., Curello, S., Bachetti, T., Corti, A. and Ferrari, R. Prog. Cardiovascul. Dis. (1998) 48, pp25–30

14. Cardiac failure in transgenic mice with myocardial expression of tumour necrosis factor-alpha. Circulation (1998) 97, pp1375–1381. Bryant, D., Becker, L., Richardson, J., Shelton, J., Franco.F., Peshock, R., Thompson, M. and Giroir, B.

15. Journal of the American Academy of Dermatology, 1996, vol. 35, no. 6, p. 969–979

16. Peripheral blood monocytes in psoriatic patients over-produce cytokines. J. Derm. Sci. (1998),17, p223–232. Okubo, Y and Koga, M.

17. Mast cells of psoriatic and atopic dermatitis skin are positive for TNFalpha and their degranulation is associated with expression of ICAM-1 in the epidermis. Archives of Dermatological Research (1998),290, p353–359. Ackermann, L. and Harvima, I. T.

18. Cytokine-induced fever in obese(fa/fa) and lean(Fa/Fa) Zucker rats. Am. J. Physiol. Regul. Integr. Comp. Physiol. (1998) 275, R1353–1357. Plata-Salaman, C. R., Peloso, E. and Satinoff, E.

19. Levels of tumour necrosis factor and soluble TNF receptors during malaria fever episodes in the community. Trans. R. Soc. Trop. Med. Hyg. (1998) 92, pp50–53. McGuire, W., Alessandro, U., Stephens, S., Olaleye, B. O., Langerock, P., Greenwood, B. M. and Kwiatkowski, D.

20. Tumour necrosis factor-alpha as a target of melanocortin in haemorrhagic shock, in the anaesthetised rat. British J. Pharmacol. (1998) 124, pp1587–1590. Altavilla, D., Cainazzo, M. M., Squadrito, F., Guarini, S., Bertolini, A. and Bazzani, C.

21. Significance of TNF in haemorrhage-related haemodynamic alterations, organ injury and mortality in rats. Bahrami, S., Yao, Y. M., Leichtfried, G., Redl, H., Marzi, I. And Schlag, G. Am.J.Physiol. Heart. Circ. Physiol. (1997), 272, pp41–45.

22. Pentoxifylline reduces plasma tumour necrosis factor alpha concentration in premature infants with sepsis. Eur. J. Pediatrics (1996) 155, pp404–409. Lauterbach, R. and Zembala, M.

What is claimed is:

1. A hydrazine compound, being a compound of the formula

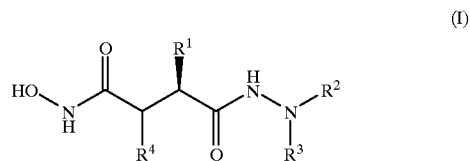

(I)

wherein

R$^1$ is lower alkyl, lower alkenyl, lower cycloalkyl, lower cycloalkyl-lower alkyl, aryl or aryl-lower alkyl;

R$^2$ is an acyl group derived from an α-, β-, γ- or δ-(arnino, hydroxy or thiol)-carboxylic acid, or an acyl group derived from an α-, β-, γ- or δ-(amino, hydroxy or thiol)carboxylic acid in which the amino, hydroxy or thiol group is lower alkylated or the amino group is acylated, sulphonylated or amidated, wherein any functional group present in a side-chain is protected or unprotected; or Het(CH$_2$)$_m$CO—;

R$^3$ is hydrogen, lower alkyl, halo-lower alkyl, cyano-lower alkyl, amino-lower alkyl, hydroxy-lower alkyl, lower alkoxy-lower alkyl, lower alkoxycarbonyl-lower alkyl, lower cycloalkyl-lower alkyl, aryl-lower alkyl, heterocyclyl-lower alkyl, heterocyclylcarbonyl-lower alkyl, lower alkenyl, lower alkynyl, lower cycloalkyl, aryl-lower alkenyl, aryl or heterocyclyl;

R$^4$ is lower cycloalky or lower cycloalkyl-lower alkyl,

Het is heterocyclyl; and m is 0,1,2,3 or 4;

wherein each heterocyclyl or heteroaryl group is independently unsubstituted or substituted by halogen, lower alkyl, lower alkoxy, oxo, thioxo, or imino;

or a mixture containing said compound and one or more optical isomers thereof, or a pharmaceutically acceptable salt of said compound or said mixture.

2. The hydrazine compound of claim 1, wherein R$^2$ is an acyl group derived from an α- or β-(amino, hydroxy or thiol)carboxylic acid, or an acyl group derived from an α- or β-(amino, hydroxy or thiol)carboxylic acid in which the amino, hydroxy or thiol group is lower alkylated or the amino group is acylated, sulphonylated or amidated, wherein any functional group present in a side-chain is protected or unprotected; or Het(CH$_2$)$_m$CO— in which m is 0, 1 or 2.

3. The hydrazine compound of claim 1, wherein R$^1$ is lower alkyl or lower cycloalkyl-lower alkyl.

4. The hydrazine compound of claim 3, wherein R$^1$ is isobutyl, cyclobutylmethyl or cyclopentylmethyl.

5. The hydrazine compound of claim 1, wherein $R^2$ is an acyl group derived from an α-aminocarboxylic acid or from an α-hydroxycarboxylic acid.

6. The hydrazine compound of claim 1, wherein $R^2$ is Het(CH$_2$)$_m$CO—.

7. The hydrazine compound of claim 6, wherein m is 0, 1 or 2.

8. The hydrazine compound of claim 1, wherein $R^3$ is lower alkyl, halo-lower alkyl, lower cycloalkyl-lower alkyl, aryl-lower alkyl, aryl or heterocyclyl.

9. The hydrazine compound of claim 8, wherein $R^3$ is lower alkyl.

10. The hydrazine compound of claim 9, wherein $R^3$ is isobutyl.

11. A hydrazine compound, being a compound of the formula

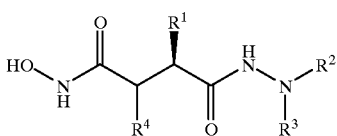

(I)

wherein
$R^1$ is lower alkyl, lower alkenyl, lower cycloalkyl, lower cycloalkyl-lower alkyl, aryl or aryl-lower alkyl;
$R^2$ is an acyl group derived from an α-, β-, γ- or δ-(amino, hydroxy or thiol)carboxylic acid, or an acyl group derived from an α-, β-, γ- or δ-(amino, hydroxy or thiol)carboxylic acid in which the amino, hydroxy or thiol group is lower alkylated or the amino group is acylated, sulphonylated or amidated, wherein any functional group present in a side-chain is protected or unprotected; or Het(CH$_2$)$_m$CO—;
$R^3$ is hydrogen, lower alkyl, halo-lower alkyl, cyano-lower alkyl, amino-lower alkyl, hydroxy-lower alkyl, lower alkoxy-lower alkyl, lower alkoxycarbonyl-lower alkyl, lower cycloalkyl-lower alkyl, aryl-lower alkyl, heterocyclyl-lower alkyl, heterocyclylcarbonyl-lower alkyl, lower alkenyl, lower alkynyl, lower cycloalkyl, aryl-lower alkenyl, aryl or heterocyclyl;
$R^4$ is —CH$_2$—CH=CH—Ph in which Ph is unsubstituted phenyl;
Het is heterocyclyl; and
m is 0, 1, 2, 3 or 4;
wherein each heterocyclyl or heteroaryl group is independently unsubstituted or substituted by halogen, lower alkyl, lower alkoxy, oxo, thioxo, or imino;
or a mixture containing said compound and one or more optical isomers thereof, or a pharmaceutically acceptable salt of said compound or said mixture.

12. The hydrazine compound of claim 11, (E)-2'-(D-Alanyl)-2(R)-[1(S)-(hydroxycarbamoyl)-4-phenyl-3-butenyl]-2'-isobutyl-4-methylvalerohydrazide or a pharmaceutically acceptable salt thereof.

13. The hydrazine compound of claim 11, (E)-2(R)-[1(S)-(Hydroxycarbamoyl)-4-phenyl-3-butenyl]-2'-(2(R)-hydroxypropionyl)-2'-isobutyl-4-methylvalerohydrazide or a pharmaceutically acceptable salt thereof.

14. The hydrazine compound of claim 11, (E)-2(R)-[1(S)-(Hydroxycarbamoyl)-4-phenyl-3-butenyl]-2'-[2-(1-imidazolyl)acetyl]-2'-isobutyl-4-methylvalerohydrazide or a pharmaceutically acceptable salt thereof.

15. The hydrazine compound of claim 11, (E)-2(R)-[1(S)-(Hydroxycarbamoyl)-4-phenyl-3-butenyl]-2'-isobutyl-4-methyl-2'-[(4-piperidinyl)carbonyl]valerohydrazide, or a pharmaceutically acceptable salt thereof.

16. A compound of the formula

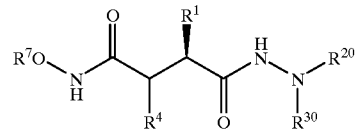

(II)

wherein
$R^1$ is lower alkyl, lower alkenyl, lower cycloalkyl, lower cycloalkyl-lower alkyl, aryl or aryl-lower alkyl;
$R^4$ is lower cycloalkyl or lower cycloalkyl-lower alkyl,
$R^7$ is a hydroxy protecting group;
$R^{20}$ is a protected or unprotected acyl group derived from an α-, β-, γ- or δ-(amino, hydroxy or thiol)carboxylic acid, or an acyl group derived from an α-, β-, γ- or δ-(amino, hydroxy or thiol)carboxylic acid in which the amino, hydroxy or thiol group is lower alkylated or the amino group is acylated, sulphonylated or amidated, wherein any functional group present in a side-chain thereof is protected or unprotected; or Het(CH$_2$)$_m$CO—;
$R^{30}$ is hydrogen, lower alkyl, halo-lower alkyl, cyano-lower alkyl, amino-lower alkyl, hydroxy-lower alkyl, lower alkoxy-lower alkyl, lower alkoxycarbonyl-lower alkyl, lower cycloalkyl-lower alkyl, aryl-lower alkyl, heterocyclyl-lower alkyl, heterocyclylcarbonyl-lower alkyl, lower alkenyl, lower alkynyl, lower cycloalkyl, aryl-lower alkenyl, aryl or heterocyclyl, provided that any amino or hydroxy group present therein is protected or unprotected.

17. The compound of claim 16, wherein $R^7$ is tetrahydropyranyl, benzyl, 4-methoxybenzyl or tri(lower alkyl)silyl.

18. A process for producing a hydrazine compound of the formula

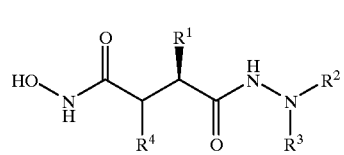

(I)

wherein
$R^1$ is lower alkyl, lower alkenyl, lower cycloalkyl, lower cycloalkyl-lower alkyl, aryl or aryl-lower alkyl;
$R^2$ is an acyl group derived from an α-, β-, γ- or δ-(amino, hydroxy or thiol)carboxylic acid, or an acyl group derived from an α-, β-, γ- or δ-(amino, hydroxy or thiol)carboxylic acid in which the amino, hydroxy or thiol group is lower alkylated or the amino group is acylated, sulphonylated or amidated, wherein any functional group present in a side-chain is protected or unprotected; or Het(CH$_2$)$_m$CO—;
$R^3$ is hydrogen, lower alkyl, halo-lower alkyl, cyano-lower alkyl, amino-lower alkyl, hydroxy-lower alkyl, lower alkoxy-lower alkyl, lower alkoxycarbonyl-lower alkyl, lower cycloalkyl-lower alkyl, aryl-lower alkyl, heterocyclyl-lower alkyl, heterocyclylcarbonyl-lower alkyl, lower alkenyl, lower alkynyl, lower cycloalkyl, aryl-lower alkenyl, aryl or heterocyclyl;

$R^4$ is lower cycloalkyl, or lower cycloalkyl-lower alkyl,
Het is heterocyclyl; and
m wherein each heterocyclyl or heteroaryl group is independently unsubstituted or substituted by halogen, lower alkyl, lower alkoxy, oxo, thioxo, or imino; or a mixture containing the compound of formula I and one or more optical isomers thereof, or a pharmaceutically acceptable salt of said compound or said mixture;
which process comprises cleaving off the protecting group denoted by $R^7$ and, as required, any protecting group(s) present in $R^{20}$ and or $R^{30}$ from a protected hydrazine derivative which comprises a compound of the formula

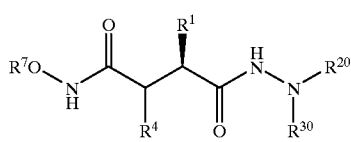

(II)

wherein
$R^7$ is a hydroxy protecting group;
$R^{20}$ has the same significance as $R^2$ provided that in the case of an acyl group the amino, hydroxy or thiol group (when not lower alkylated, acylated, sulphonylated or amidated as specified under $R^2$) is protected or unprotected and any functional group present in a side-chain is protected or unprotected; and
$R^{30}$ has the same significance as $R^3$ provided that any amino or hydroxy group present is protected or unprotected.
or a mixture containing the compound of formula II and one or more optical isomers thereof, or a pharmaceutically acceptable salt of said compound or said mixture, 19. The process of claim 18, further comprising converting the hydrazine compound into a pharmaceutically acceptable salt thereof.

20. A compound of the formula

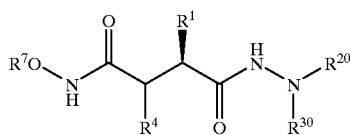

(II)

wherein
$R^1$ is lower alkyl, lower alkenyl, lower cycloalkyl, lower cycloalkyl-lower alkyl, aryl or aryl-lower alkyl;
$R^4$ is —$CH_2$—CH=CH—Ph in which Ph is unsubstituted phenyl;
$R^7$ is a hydroxy protecting group;
$R^{20}$ is a protected or unprotected acyl group derived from an α-, β-, γ- or δ-(amino, hydroxy or thiol)carboxylic acid, or an acyl group derived from an α-, β-, γ- or δ-(amino, hydroxy or thiol)carboxylic acid in which the amino, hydroxy or thiol group is lower alkylated or the amino group is acylated, sulphonylated or amidated, wherein any functional group present in a side-chain thereof is protected or unprotected; or Het($CH_2$)$_m$CO—;
$R^{30}$ is hydrogen, lower alkyl, halo-lower alkyl, cyano-lower alkyl, amino-lower alkyl, hydroxy-lower alkyl, lower alkoxy-lower alkyl, lower alkoxycarbonyl-lower alkyl, lower cycloalkyl-lower alkyl, aryl-lower alkyl, heterocyclyl-lower alkyl, heterocyclylcarbonyl-lower alkyl, lower alkenyl, lower alkynyl, lower cycloalkyl, aryl-lower alkenyl, aryl or heterocyclyl, provided that any amino or hydroxy group present therein is protected or unprotected.

21. A process for producing a hydrazine compound of the formula

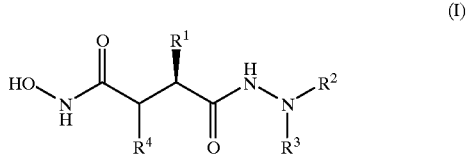

(I)

wherein
$R^1$ is lower alkyl, lower alkenyl, lower cycloalkyl, lower cycloalkyl-lower alkyl, aryl or aryl-lower alkyl;
$R^2$ is an acyl group derived from an α-, β-, γ- or δ-(amino, hydroxy or thiol)carboxylic acid, or an acyl group derived from an α-, β-, γ- or δ-(amino, hydroxy or thiol)carboxylic acid in which the amino, hydroxy or thiol group is lower alkylated or the amino group is acylated, sulphonylated or amidated, wherein any functional group present in a side-chain is protected or unprotected; or Het($CH_2$)$_m$CO—;
$R^3$ is hydrogen, lower alkyl, halo-lower alkyl, cyano-lower alkyl, amino-lower alkyl, hydroxy-lower alkyl, lower alkoxy-lower alkyl, lower alkoxycarbonyl-lower alkyl, lower cycloalkyl-lower alkyl, aryl-lower alkyl, heterocyclyl-lower alkyl, heterocyclylcarbonyl-lower alkyl, lower alkenyl, lower alkynyl, lower cycloalkyl, aryl-lower alkenyl, aryl or heterocyclyl;
$R^4$ is —$CH_2$—CH=CH—Ph in which Ph is unsubstituted phenyl;
Het is heterocyclyl;
m is 0, 1, 2, 3 or 4;
wherein each heterocyclyl or heteroaryl group is independently unsubstituted or substituted by halogen, lower alkyl, lower alkoxy, oxo, thioxo, or imino;
or a mixture containing the compound of formula I and one or more optical isomers thereof, or a pharmaceutically acceptable salt of said compound or said mixture;
which process comprises cleaving off the protecting group denoted by $R^7$ and, as required, any protecting group(s) present in $R^{20}$ and or $R^{30}$ from a protected hydrazine derivative which comprises a compound of the formula

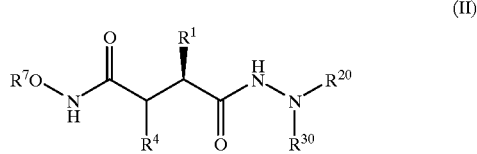

(II)

wherein
$R^7$ is a hydroxy protecting group;
$R^{20}$ has the same significance as $R^2$ provided that in the case of an acyl group the amino, hydroxy or thiol group (when not lower alkylated, acylated, sulphonylated or amidated as specified under $R^2$) is protected or unprotected and any functional group present in a side-chain is protected or unprotected; and $R^{30}$ has the same significance as $R^3$ provided that any amino or hydroxy group present is protected or unprotected,
or a mixture containing the compound of formula II and one or more optical isomers thereof, or a pharmaceutically acceptable salt of said compound or said mixture.

22. The process of claim 21, furer comprising converting the hydrazine compound into a pharmaceutically acceptable salt thereof.

* * * * *

UNITED STATES PATENT AND TRADEMARK OFFICE
CERTIFICATE OF CORRECTION

PATENT NO.     : 6,239,151 B1
DATED          : May 29, 2001
INVENTOR(S)    : Broadhurst et al.

It is certified that error appears in the above-identified patent and that said Letters Patent is hereby corrected as shown below:

<u>Column 106,</u>
Line 46, delete "cycloaky" and insert -- cycloalkyl --;

<u>Column 112,</u>
Line 1, delete "furer" and insert -- further --.

Signed and Sealed this

Twenty-sixth Day of February, 2002

Attest:

JAMES E. ROGAN
*Attesting Officer*     *Director of the United States Patent and Trademark Office*